United States Patent
Wang et al.

(10) Patent No.: US 8,450,361 B2
(45) Date of Patent: May 28, 2013

(54) SUBSTITUTED INDOLE AND AZAINDOLE OXOACETYL PIPERAZINAMIDE DERIVATIVES

(75) Inventors: Tao Wang, Farmington, CT (US); Zhongxing Zhang, Madison, CT (US); Zhiwei Yin, Glastonbury, CT (US); John F. Kadow, Wallingford, CT (US); Nicholas A. Meanwell, East Hampton, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/198,197

(22) Filed: Aug. 4, 2011

(65) Prior Publication Data

US 2012/0202775 A1    Aug. 9, 2012

Related U.S. Application Data

(60) Provisional application No. 61/371,202, filed on Aug. 6, 2010.

(51) Int. Cl.
| | |
|---|---|
| *A61K 31/4025* | (2006.01) |
| *A61K 31/498* | (2006.01) |
| *A61K 31/4439* | (2006.01) |
| *C07D 209/40* | (2006.01) |
| *C07D 403/06* | (2006.01) |
| *C07D 401/06* | (2006.01) |

(52) U.S. Cl.
USPC ...... 514/414; 514/254.09; 514/323; 548/468; 544/373; 546/201

(58) Field of Classification Search
USPC ............... 514/254.09, 323; 544/373; 546/201
See application file for complete search history.

(56) References Cited

U.S. PATENT DOCUMENTS

| | | | |
|---|---|---|---|
| 5,413,999 A | 5/1995 | Vacca et al. | |
| 6,469,006 B1 | 10/2002 | Blair et al. | |

(Continued)

FOREIGN PATENT DOCUMENTS

| | | |
|---|---|---|
| EP | 0 484 071 | 5/1992 |
| WO | WO 03/103607 | 12/2003 |

(Continued)

OTHER PUBLICATIONS

Blair, W.S. et al., "HIV-1 entry—an expanding portal for drug discovery", Drug Discovery Today, vol. 5, No. 5, pp. 183-194 (2000).

(Continued)

*Primary Examiner* — Wu-Cheng Winston Shen
*Assistant Examiner* — Karen Cheng
(74) *Attorney, Agent, or Firm* — John F. Levis

(57) ABSTRACT

Compounds having drug and bio-affecting properties are described herein, including their properties, pharmaceutical compositions and methods of use. In particular, tricyclic aryl or heteroaryl piperazine diamide derivatives that possess unique antiviral activity are set forth. These compounds are useful for the treatment of HIV and AIDS. The compounds herein have the general Formula I:

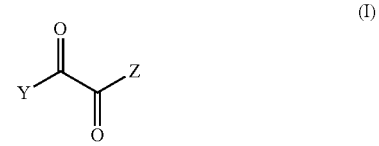

wherein:
Y is selected from the group of indole or azaindole systems:

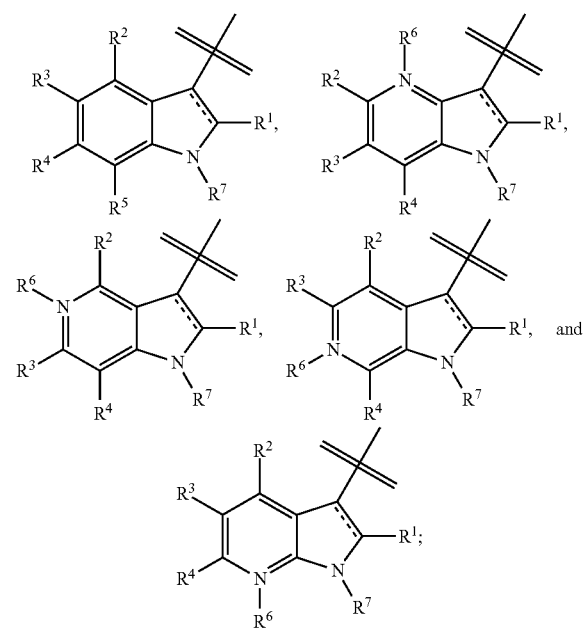

and Z is selected from the group of:

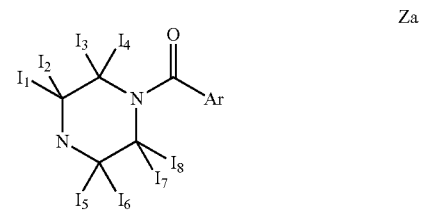

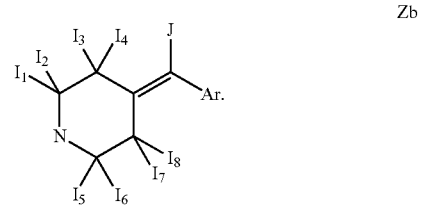

4 Claims, No Drawings

U.S. PATENT DOCUMENTS

| | | | |
|---|---|---|---|
| 6,573,262 | B2 | 6/2003 | Wallace et al. |
| 7,348,337 | B2 | 3/2008 | Wang et al. |
| 7,501,420 | B2 | 3/2009 | Wang et al. |
| 7,745,625 | B2 | 6/2010 | Ueda et al. |
| 7,776,863 | B2 | 8/2010 | Lin et al. |
| 7,807,676 | B2 | 10/2010 | Wang et al. |
| 2003/0069245 | A1* | 4/2003 | Wallace et al. ............ 514/245 |
| 2003/0207910 | A1* | 11/2003 | Wang et al. ............ 514/300 |
| 2005/0215543 | A1 | 9/2005 | Lin et al. |
| 2005/0215544 | A1 | 9/2005 | Lin et al. |

FOREIGN PATENT DOCUMENTS

| | | |
|---|---|---|
| WO | WO 2005/016344 | 2/2005 |
| WO | WO 2005/121094 | 12/2005 |

OTHER PUBLICATIONS

Hotoda, H., "Small-molecule inhibitors of HIV-1 entry via chemokine receptors", Drugs of the Future, vol. 24, No. 12, pp. 1355-1362 (1999).

Meanwell, N.A. et al., "Inhibitors of HIV-1 attachment. Part 2: An initial survey of indole substitution patterns", Bioorganic & Medicinal Chemistry Letters, vol. 19, pp. 1977-1981 (2009).

Meanwell, N.A. et al., "Inhibitors of the entry of HIV into host cells", Current Opinion in Drug Discovery & Development, vol. 6, No. 4, pp. 451-461 (2003).

Sodroski, J.G., "HIV-1 Entry Inhibitors in the Side Pocket: Minireview", Cell, vol. 99, pp. 243-246 (1999).

Wang, J. et al., "Modification and structure-activity relationship of a small molecule HIV-1 inhibitor targeting the viral envelope glycoprotein gp120", Org. Biomol. Chem., vol. 3, pp. 1781-1786 (2005).

Wang, T. et al., "Discovery of 4-Benzoyl-1-[(4-methoxy-1*H*-pyrrolo[2,3-*b*]pyridin-3-yl)oxoacetyl]-2-(*R*)-methylpiperazine (BMS-378806): A Novel HIV-1 Attachment Inhibitor that Interferes with CD4-gp120 Interactions", Journal of Medicinal Chemistry, vol. 46, No. 20, pp. 4236-4239 (2003).

Wang, T. et al., "Inhibitors of Human Immunodeficiency Virus Type 1 (HIV-1) Attachment. 5. An Evolution from Indole to Azaindoles Leading to the Discovery of 1-(4-Benzoylpiperazin-1-yl)-2-(4,7-dimethoxy-1*H*-pyrrolo[2,3-*c*]pyridin-3-yl)ethane-1,2-dione (BMS-488043), a Drug Candidate that Demonstrates Antiviral Activity in HIV-1-Infected Subjects", Journal of Medicinal Chemistry, vol. 52, No. 23, pp. 7778-7787 (2009).

* cited by examiner

SUBSTITUTED INDOLE AND AZAINDOLE OXOACETYL PIPERAZINAMIDE DERIVATIVES

CROSS REFERENCE TO RELATED APPLICATION

This non-provisional application claims the benefit of U.S. Provisional Application Ser. No. 61/371,202 filed Aug. 6, 2010.

FIELD OF THE INVENTION

This invention provides compounds having drug and bio-affecting properties, their pharmaceutical compositions and methods of use. In particular, the invention is directed to indole and azaindole piperazine diamide derivatives that possess unique antiviral activity. More particularly, the present invention relates to compounds useful for the treatment of HIV and AIDS.

BACKGROUND OF THE INVENTION

HIV-1 (human immunodeficiency virus-1) infection remains a major medical problem, with an estimated 35 million people infected worldwide at the end of 2008. The number of cases of HIV and AIDS (acquired immunodeficiency syndrome) has risen rapidly. By 2008, several million new infections were reported, and as many as 2 million people have died annually from AIDS. Currently available drugs for the treatment of HIV include many nucleoside reverse transcriptase (RT) inhibitors, non-nucleoside reverse transcriptase inhibitors, and protease inhibitors, including combination products such as Truvada®, Atripla®, and Kaletra®.

Some newer drugs include a fusion inhibitor, a CCR5 inhibitor, and an integrase inhibitor. Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and/or more favorable pharmacokinetic as well as safety profiles are needed to provide more treatment options.

The properties of a class of HIV entry inhibitors called HIV attachment inhibitors have been improved in an effort to obtain compounds with maximized utility and efficacy as antiviral agents. A disclosure describing indoles of which the structure shown below for BMS-705 is representative has been published as US 20030069245.

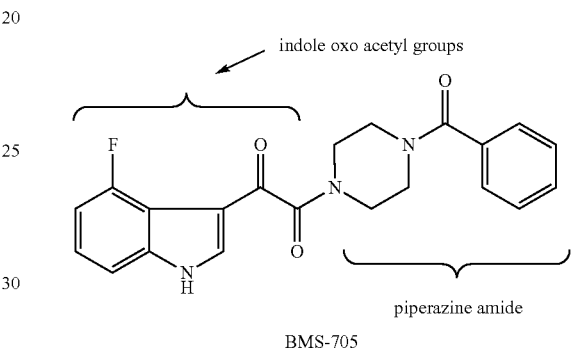

BMS-705

Two other compounds, referred to in the literature as BMS-806 and BMS-043 have been described in both the academic and patent art:

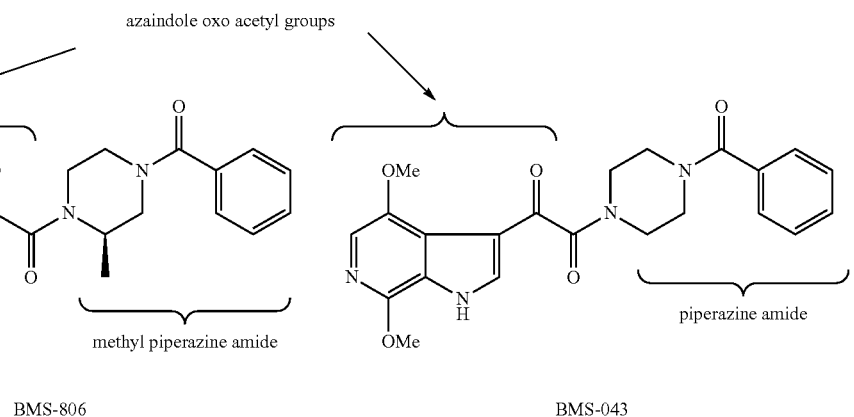

BMS-806

BMS-043

Some description of their properties in human clinical trials has been disclosed in the literature.

It should be noted that in all three of these structures, a piperazine amide (In these three structures a piperazine phenyl amide) is present and this group is directly attached to an oxoacetyl moiety. The oxoacetyl group is attached at the 3-position of 4-Fluoro indole in BMS-705 and to the 3 position of substituted azaindoles in BMS-806 and BMS-043.

In an effort to obtain improved anti-HIV compounds, later publications described in part, modified substitution patterns on the indoles and azaindoles. Examples of such effort include: (1) novel substituted indoleoxoacetic piperazine derivatives, (2) substituted piperazinyloxoacetylindole derivatives, and (3) substituted azaindoleoxoacetic piperazine derivatives.

Replacement of these groups with other heteroaromatics or substituted heteroaromatics or bicyclic hydrocarbons was also shown to be feasible. Examples include: (1) indole, azaindole and related heterocyclic amidopiperazine derivatives; (2) bicyclo 4.4.0 antiviral derivatives; and (3) diazaindole derivatives.

A select few replacements for the piperazine amide portion of the molecules have also been described in the art and among these examples are (1) some piperidine alkenes; (2) some pyrrolidine amides; (3) some N-aryl or heteroaryl piperazines; (4) some piperazinyl ureas; and (5) some carboline containing compounds.

Method(s) for preparing prodrugs for this class of compounds are described in Prodrugs of piperazine and Substituted Piperidine Antiviral Agents (Ueda et al., US 20050209246A1 or WO2005090367A1).

A published PCT patent application WO2003103607A1 sets forth an assay useful for assaying some HIV inhibitors.

Several published patent applications describe combination studies with piperazine benzamide inhibitors, for example, US20050215543 (WO2005102328A1), US20050215544 (WO2005102391A1), and US20050215545 (WO2005102392A2).

A publication on new compounds in this class of attachment inhibitors (Jinsong Wang et. al. Org. Biol. Chem. 2005, 3, 1781-1786.) and a patent application (WO2005/016344) on some more remotely related compounds have also appeared.

Published patent applications WO2005/016344 and WO2005/121094 also describe piperazine derivatives which are HIV inhibitors. It is believed that the compounds described in these applications are structurally distinct from the compounds of the present disclosure.

The compounds hereinafter described, as well as compositions containing same, and their use to inhibit HIV infection have not been described in the art it is believed, and would be useful for the treatment of HIV.

SUMMARY OF THE INVENTION

The present disclosure is directed to compounds of Formula I, including pharmaceutically acceptable salts and/or solvates (e.g., hydrates) thereof, their pharmaceutical formulations, and their use in patients suffering from or susceptible to a virus such as HIV. The compounds of Formula I and their pharmaceutically acceptable salts are effective antiviral agents, particularly as inhibitors of HIV. They are useful for the treatment of HIV and AIDS.

A first embodiment of the invention are compounds of Formula I, including pharmaceutically acceptable salts thereof:

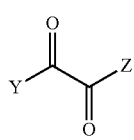

wherein:
Y is selected from the group consisting of indole or azaindole systems:

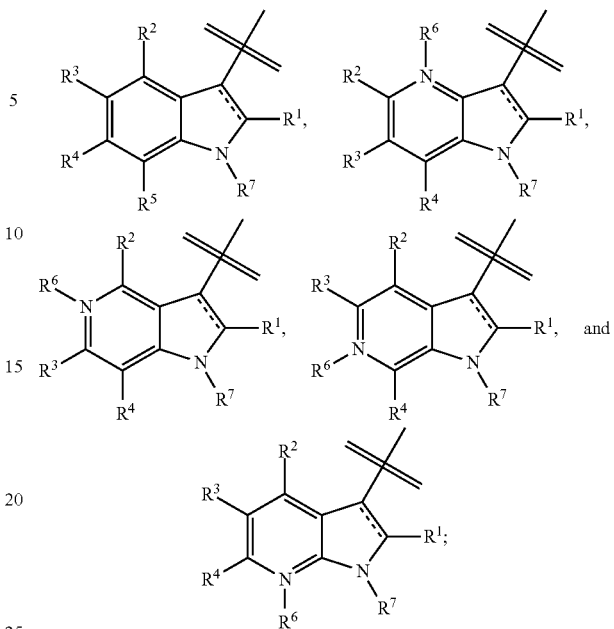

wherein one of $R^1$, $R^2$, $R^3$, $R^4$, and $R^5$ is selected from $NA^1A^2$, and the rest of $R^1$, $R^2$, $R^3$, $R^4$, and $R^5$ are independently selected from the group consisting of hydrogen, halogen, cyano, nitro, $COOR^8$, $XR^9$, $COR^{10}$, $CONR^{11}R^{12}$ and B;

$R^6$ is O or does not exist;

$A^1$ and $A^2$ are independently selected from $SO_2D^1$, $SO_2ND^2D^3$, $COD^4$, $COCOD^4$, $COOD^4$, $COND^5D^6$, $COCOND^5D^6$, $COCOOD^4$, $C(=ND^7)D^8$, $C(=ND^9)ND^{10}D^{11}$;

$A^1$ and $A^2$ can either never connect with each other, or can conjoin to form a ring structure;

$D^1$, $D^2$, $D^3$, $D^4$, $D^5$, $D^6$, $D^7$, $D^8$, $D^9$, $D^{10}$, and $D^{11}$ are each independently selected from the group consisting of H, $C_1$-$C_{50}$ alkyl, $C_3$-$C_{50}$ cycloalkyl, $C_4$-$C_{50}$ bicycloalkyl, $C_5$-$C_{50}$ tricycloalkyl, $C_6$-$C_{50}$ tetracycloalkyl, $C_3$-$C_{50}$ alkenyl, $C_4$-$C_{50}$ cycloalkenyl, $C_5$-$C_{50}$ bicycloalkenyl, $C_7$-$C_{50}$ tricycloalkenyl, $C_9$-$C_{50}$ tetracycloalkyl, phenyl, aryl, heteroaryl, $C_1$-$C_{50}$ amide, $C_3$-$C_{50}$ cyclic amide, $C_1$-$C_{50}$ amine, $C_3$-$C_{50}$ cyclic amine, $C_2$-$C_{50}$ ester, $C_3$-$C_{50}$ cyclic ester, $C_2$-$C_{50}$ ether, $C_3$-$C_{50}$ cyclic ether, $C_1$-$C_{50}$ sulfonamide, $C_3$-$C_{50}$ cyclic sulfonamide, $C_2$-$C_{50}$ sulfone, $C_3$-$C_{50}$ cyclic sulfone, $C_2$-$C_{50}$ sulfamide, $C_3$-$C_{50}$ cyclic sulfamide, $C_2$-$C_{50}$ acyl sulfamide, $C_3$-$C_{50}$ acyl sulfamide, $C_2$-$C_{50}$ urea, $C_3$-$C_{50}$ cyclic urea, $C_2$-$C_{50}$ amidine, $C_3$-$C_{50}$ cyclic amidine, $C_2$-$C_{50}$ guanidine, and $C_3$-$C_{50}$ cyclic guanidine; and wherein aryl or heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl, triazolyl, naphthalenyl, quinolinyl, isoquinolinyl, quinoxalinyl, indolyl, azaindolyl, indazolyl, azaindazolyl, benzoisoxazolyl, azabenzoisoxazolyl, benzoisothiazole, and azabenzothiazolyl; provided the carbon atoms which comprise the carbon-carbon double bond of said $C_3$-$C_{20}$ alkenyl or the carbon-carbon triple bond of said $C_3$-$C_{20}$ alkynyl are not the point of attachment to the nitrogen to which $D^2$, $D^3$, $D^5$, $D^6$, $D^7$, $D^9$, $D^{10}$, and $D^{11}$ is attached;

wherein said $C_1$-$C_{50}$ alkyl, $C_3$-$C_{50}$ cycloalkyl, $C_3$-$C_{50}$ alkenyl, $C_4$-$C_{50}$ cycloalkenyl, aryl, phenyl, heteroaryl, $C_3$-$C_{50}$ amide and $C_3$-$C_{50}$ ether is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic;

$R^7$ is $(CH_2)_n R^{13}$ and n=0-6;

$R^{13}$ is selected from the group consisting of H, $(C_{1-6})$alkyl, —C(O)—$(C_{1-6})$alkyl, C(O)-aryl and $CONR^{14}R^{15}$;

$R^{14}$ and $R^{15}$ are each independently H, $(C_{1-6})$alkyl, aryl or heteroaryl;

— represents a carbon-carbon bond or does not exist;

B is selected from the group consisting of $(C_{1-6})$alkyl, $(C_{3-6})$cycloalkyl, $C(O)NR^{16}R^{17}$, phenyl and heteroaryl; wherein said $(C_{1-6})$alkyl, phenyl and heteroaryl are independently optionally substituted with one to three same or different halogens or from one to three same or different substituents selected from E; and wherein heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl;

E is selected from the group consisting of $(C_{1-6})$alkyl, $(C_{3-6})$cycloalkyl cyano, phenyl, heteroaryl, heteroalicyclic, hydroxy, $(C_{1-6})$alkoxy, halogen, benzyl, —$NR^{18}C(O)$—$(C_{1-6})$alkyl, —$NR^{19}R^{20}$, morpholino, nitro, —$S(C_{1-6})$alkyl, —SPh, $NR^{21}S(O)_2$—$R^{22}$, piperazinyl, N-Me piperazinyl, C(O)H, $(CH2)_n COOR^{23}$ and —$CONR^{24}R^{25}$; wherein said $(C_{1-6})$alkyl, heteroaryl, or phenyl is optionally substituted with one to three same or different halogens or one to three methyl groups; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; heteroalicyclic is selected from the group consisting of aziridine, azetidine, pyrrolidine, piperazine, N-methyl piperazine, piperidine, tetrahydrofuran, tetrahydropyran, azepine and morpholine;

$R^8$, $R^9$, $R^{10}$, $R^{11}$, and $R^{12}$ are selected from the group consisting of hydrogen and $(C_{1-6})$alkyl; $(C_{1-6})$alkyl is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic;

X is selected from the group consisting of $NR^{26}$, O and S;

$R^{16}$, $R^{17}$, $R^{18}$, $R^{19}$, $R^{20}$, $R^{21}$, $R^{22}$, $R^{23}$, $R^{24}$, $R^{25}$, and $R^{26}$ are independently selected from the group consisting of hydrogen, $(C_{1-6})$alkyl, $(C_{1-6})$alkoxy, phenyl and heteroaryl; wherein said $(C_{1-6})$alkyl, phenyl, and heteroaryl are independently optionally substituted with one to three same or different group L or $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

L is selected from the group consisting of $(C_{1-6})$alkyl, phenyl, heteroaryl, hydroxy, $(C_{1-6})$alkoxy, halogen, benzyl, —$NR^{27}C(O)$—$(C_{1-6})$alkyl, —$NR^{28}R^{29}$, morpholino, nitro, —$S(C_{1-6})$alkyl, —SPh, $NR^{30}S(O)_2$—$R^{31}$, piperazinyl, N-Me piperazinyl, $(CH2)_n COOR^{32}$ and —$CONR^{33}R^{34}$; wherein said $(C_{1-6})$alkyl, heteroaryl, or phenyl is optionally substituted with one to three same or different halogens, amino, or methyl groups; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; and $R^{27}$, $R^{28}$, $R^{29}$, $R^{30}$, $R^{31}$, $R^{32}$, $R^{33}$, and $R^{34}$ are independently selected from the group consisting of hydrogen, $(C_{1-6})$alkyl, $(C_{1-6})$alkoxy, phenyl and heteroaryl; wherein said $(C_{1-6})$alkyl, phenyl, and heteroaryl are independently optionally substituted with one to three same or different $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

Z is selected from the group consisting of:

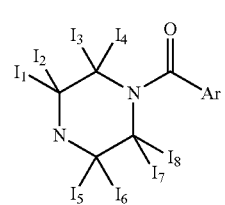

Za

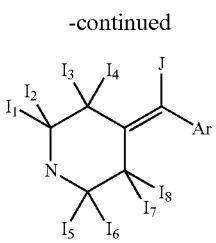

J is selected from the group consisting of hydrogen, $(C_{1-6})$ alkyl, $(C_{1-6})$alkynyl, $(C_{3-6})$ cycloalkyl, halogen, cyano, —CONG$^1$G$^2$, —SO2G$^3$, COG$^4$, COOG$^5$, tetrahydrofuryl, pyrrolidinyl, phenyl and heteroaryl; wherein said $(C_{1-6})$alkyl, $(C_{1-6})$alkynyl, phenyl and heteroaryl are each independently optionally substituted with one to three same or different members selected from the group J-1; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

J-1 is selected from the group consisting of $(C_{1-6})$alkyl, $(C_{3-6})$cycloalkyl, cyano, trimethylsilyl, phenyl, heteroaryl, heteroalicyclic, hydroxy, $(C_{1-6})$alkoxy, halogen, benzyl, —NG$^6$C(O)—$(C_{1-6})$alkyl, —NG$^7$G$^8$, —C(O)NG$^9$G$^{10}$, morpholino, nitro, —S$(C_{1-6})$alkyl, —SPh, NG$^{11}$S(O)$_2$-G$^{12}$, piperazinyl, N-Me piperazinyl, (CH2)$_n$COOG$^{13}$ and —CONG$^{14}$G$^{15}$; wherein said $(C_{1-6})$alkyl, heteroaryl, or phenyl is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; heteroalicyclic is selected from the group consisting of aziridine, azetidine, pyrrolidine, piperazine, N-methyl piperazine, piperidine, tetrahydrofuran, tetrahydropyran, azepine and morpholine;

G$^1$, G$^2$, G$^9$, G$^{10}$, G$^{14}$ and G$^{15}$ are each independently selected from the group consisting of H, C$_1$-C$_6$ alkyl, C$_3$-C$_6$ cycloalkyl, C$_3$-C$_6$ alkenyl, C$_4$-C$_6$ cycloalkenyl and C$_3$-C$_6$ alkynyl; provided the carbon atoms which comprise the carbon-carbon double bond of said C$_3$-C$_6$ alkenyl or the carbon-carbon triple bond of said C$_3$-C$_6$ alkynyl are not the point of attachment to the nitrogen to which G$^1$, G$^2$, G$^9$, G$^{10}$, G$^{14}$ and G$^{15}$ is attached; wherein said heteroaryl, or phenyl is optionally substituted with one to three same or different of the following functionalities: $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic;

G$^3$, G$^4$ and G$^{12}$ are each independently selected from the group consisting of H, C$_1$-C$_6$ alkyl, C$_{1-6}$ alkyl substituted with one to three halogen atoms, C$_3$-C$_6$ cycloalkyl, C$_2$-C$_6$ alkenyl, C$_4$-C$_6$ cycloalkenyl, and C$_3$-C$_6$ alkynyl; provided the carbon atoms which comprise the carbon-carbon triple bond of said C$_3$-C$_6$ alkynyl are not the point of attachment to the oxygen or sulfur to which G$^3$, G$^4$ and G$^{12}$ is attached; wherein said $(C_{1-6})$alkyl, heteroaryl, or phenyl is optionally substituted with one to three same or different of the following functionalities: $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic;

G$^5$ and G$^{13}$ are each independently selected from the group consisting of H, C$_1$-C$_6$ alkyl, C$_{1-6}$ alkyl substituted with one to three halogen atoms, C$_3$-C$_6$ cycloalkyl, C$_2$-C$_6$ alkenyl, C$_4$-C$_6$ cycloalkenyl, and C$_3$-C$_6$ alkynyl; provided the carbon atoms which comprise the carbon-carbon triple bond of said C$_3$-C$_6$ alkynyl are not the point of attachment to the oxygen or sulfur to which G$^5$ and G$^{13}$ is attached; wherein said $(C_{1-6})$alkyl, heteroaryl, or phenyl is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic;

G$^6$ and G$^{11}$ are each independently selected from the group consisting of H, OH, C$_1$-C$_6$ alkyl, C$_3$-C$_6$ cycloalkyl, C$_3$-C$_6$ alkenyl, C$_5$-C$_6$ cycloalkenyl, C$_3$-C$_6$ alkynyl and C(O)R$^{34}$; provided the carbon atoms which comprise the carbon-carbon double bond of said C$_3$-C$_6$ alkenyl, C$_4$-C$_6$ cycloalkenyl, or the carbon-carbon triple bond of said C$_3$-C$_6$ alkynyl are not the point of attachment to the nitrogen to G$^6$ and G$^{11}$ is attached; wherein said $(C_{1-6})$alkyl, heteroaryl, or phenyl is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic;

G$^7$ and G$^8$ are each independently selected from the group consisting of H, OH, C$_1$-C$_6$ alkyl, C$_3$-C$_6$ cycloalkyl, C$_3$-C$_6$ alkenyl, C$_5$-C$_6$ cycloalkenyl, C$_3$-C$_6$ alkynyl and C(O)G$^{16}$; provided the carbon atoms which comprise the carbon-carbon double bond of said C$_3$-C$_6$ alkenyl, C$_4$-C$_6$ cycloalkenyl, or the carbon-carbon triple bond of said C$_3$-C$_6$ alkynyl are not the point of attachment to the nitrogen to G$^7$ and G$^8$ is attached; wherein said $(C_{1-6})$alkyl, heteroaryl, or phenyl is optionally substituted with one to five same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic;

$G^{16}$ is independently selected from the group consisting of H, OH, $C_1$-$C_6$ alkyl, $C_3$-$C_6$ cycloalkyl, $C_3$-$C_6$ alkenyl, $C_5$-$C_6$ cycloalkenyl and $C_3$-$C_6$ alkynyl; provided the carbon atoms which comprise the carbon-carbon double bond of said $C_3$-$C_6$ alkenyl, $C_4$-$C_6$ cycloalkenyl, or the carbon-carbon triple bond of said $C_3$-$C_6$ alkynyl are not the point of attachment to the nitrogen to $G^{16}$ is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic;

Ar is selected from the group consisting of phenyl and heteroaryl; wherein said phenyl and heteroaryl are each independently optionally substituted with one to three same or different members selected from the group Ar-1; and heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl;

Ar-1 is selected from the group consisting of $(C_{1-6})$alkyl, $(C_{3-6})$cycloalkyl, cyano, phenyl, aryl, heteroaryl, heteroalicyclic, hydroxy, $(C_{1-6})$alkoxy, halogen, primary amine, secondary amine, tertiary amine, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic; wherein said $(C_{1-6})$alkyl, $(C_{1-6})$alkyl, $(C_{3-6})$cycloalkyl is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic;

$I_1$, $I_2$, $I_3$, $I_4$, $I_5$, $I_6$, $I_7$ and $I_8$ are each independently selected from the group consisting of H and $(C_{1-6})$alkyl; wherein $(C_{1-6})$alkyl is optionally substituted with one to three same or different halogen, amino, alkoxy, OH, CN or $NO_2$;

Another embodiment of the present invention is a method for treating mammals infected with a virus, especially wherein said virus is HIV, comprising administering to said mammal an antiviral effective amount of a compound of Formula I, and one or more pharmaceutically acceptable carriers, excipients or diluents; optionally the compound of Formula I can be administered in combination with an antiviral effective amount of another AIDS treatment agent selected from the group consisting of: (a) an AIDS antiviral agent; (b) an anti-infective agent; (c) an immunomodulator; and (d) HIV entry inhibitors.

Another embodiment of the present invention is a pharmaceutical composition comprising an antiviral effective amount of a compound of Formula I and one or more pharmaceutically acceptable carriers, excipients, diluents, and optionally in combination with an antiviral effective amount of another AIDS treatment agent selected from the group consisting of: (a) an AIDS antiviral agent; (b) an anti-infective agent; (c) an immunomodulator; and (d) HIV entry inhibitors.

The present invention is directed to these, as well as other important ends, hereinafter described.

DETAILED DESCRIPTION OF THE EMBODIMENTS

Since the compounds of the present invention may possess asymmetric centers and therefore occur as mixtures of diastereomers and enantiomers, the present invention includes the individual diastereoisomeric and enantiomeric forms of the compounds of Formula I in addition to the mixtures thereof.

DEFINITIONS

Unless otherwise specifically set forth elsewhere in the application, one or more of the following terms may be used herein, and shall have the following meanings:

The term "$C_{1-6}$ alkyl" as used herein means straight or branched chain alkyl groups such as methyl, ethyl, propyl, isopropyl, butyl, isobutyl, t-butyl, amyl, hexyl and the like.

"Halogen" refers to chlorine, bromine, iodine or fluorine.

"H" or "Hydrogen" refers to hydrogen, including its isotopes such as deuterium.

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl, diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —NR$^x$R$^y$, wherein R$^x$ and R$^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —NR$^x$R$^y$, wherein R$^x$ and R$^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo-methanesulfonamido, trihalomethanesulfonyl, silyl, guanyl, guanidino, ureido, phosphonyl, amino and —$^x$R$^y$ with R$^x$ and R$^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a Z$_3$CC(=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —CZ$_3$, group wherein Z is a halogen group as defined herein.

A "trihalomethanesulfonyl" group refers to an Z$_3$CS(=O)$_2$— groups with Z as defined above.

A "trihalomethanesulfonamido" group refers to a Z$_3$CS(=O)$_2$NR$^x$— group with Z as defined above and R$^x$ being H or (C$_{1-6}$)alkyl.

A "sulfinyl" group refers to a —S(=O)—R" group, with R" being (C$_{1-6}$)alkyl.

A "sulfonyl" group refers to a —S(=O)$_2$R" group with R" being (C$_{1-6}$)alkyl.

A "S-sulfonamido" group refers to a —S(=O)$_2$NR$^X$R$^Y$, with R$^X$ and R$^Y$ independently being H or (C$_{1-6}$)alkyl.

A "N-Sulfonamido" group refers to a R"S(=O)$_2$NR$_x$— group, with R$_x$ being H or (C$_{1-6}$)alkyl;

A "O-carbamyl" group refers to a —OC(=O)NR$^X$R$^Y$ group, with R$^X$ and R$^Y$ independently being H or (C$_{1-6}$)alkyl.

A "N-carbamyl" group refers to a R$^x$OC(=O)NR$^y$ group, with R$^x$ and R$^y$ independently being H or (C$_{1-6}$)alkyl.

A "O-thiocarbamyl" group refers to a —OC(=S)NR$^x$R$^y$ group, with R$^x$ and R$^y$ independently being H or (C$_{1-6}$)alkyl.

A "N-thiocarbamyl" group refers to a R$^x$OC(=S)NR$^y$— group, with R$^x$ and R$^y$ independently being H or (C$_{1-6}$)alkyl.

An "amino" group refers to an —NH$_2$ group.

A "C-amido" group refers to a —C(=O)NR$^x$R$^y$ group, with R$^x$ and R$^y$ independently being H or (C$_{1-6}$)alkyl.

A "C-thioamido" group refers to a —C(=S)NR$^x$R$^y$ group, with R$^x$ and R$^y$ independently being H or (C$_{1-6}$)alkyl.

A "N-amido" group refers to a R$^x$C(=O)NR$^y$— group, with R$^x$ and R$^y$ independently being H or (C$_{1-6}$)alkyl.

An "ureido" group refers to a —NR$^x$C(=O)NR$^y$R$^{y2}$ group, with R$^x$, R$^y$, and R$^{y2}$ independently being H or (C$_{1-6}$) alkyl.

A "guanidino" group refers to a —R$^x$NC(=N)NR$^y$R$^{y2}$ group, with R$_x$, R$^y$, and R$^{y2}$ independently being H or (C$_{1-6}$) alkyl.

A "guanyl" group refers to a R$^x$R$^y$NC(=N)— group, with R$^x$ and R$^y$ independently being H or (C$_{1-6}$)alkyl.

A "cyano" group refers to a —CN group.

A "silyl" group refers to a —Si(R")$_3$, with R" being (C$_{1-6}$) alkyl or phenyl.

A "phosphonyl" group refers to a P(=O)(OR$^x$)$_2$ with R$^x$ being (C$_{1-6}$)alkyl.

A "hydrazino" group refers to a —NR$^x$NR$^y$R$^{y2}$ group, with R$^x$, R$^y$, and R$^{y2}$ independently being H or (C$_{1-6}$)alkyl.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Physiologically acceptable salts and prodrugs of compounds disclosed herein are within the scope of this disclosure. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris (hydroxymethyl)-aminomethane), or with bases such as piperidine or morpholine.

As described above, the present invention is directed to compounds of Formula I, including pharmaceutically acceptable salts thereof:

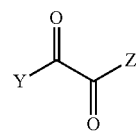

(I)

wherein:

Y is selected from the group consisting of indole or azaindole systems:

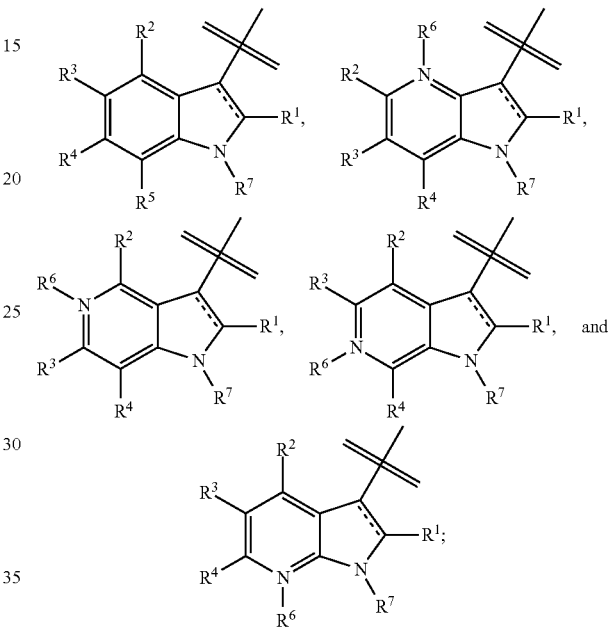

wherein one of R$^1$, R$^2$, R$^3$, R$^4$, and R$^5$ is selected from NA$^1$A$^2$, and the rest of R$^1$, R$^2$, R$^3$, R$^4$, and R$^5$ are independently selected from the group consisting of hydrogen, halogen, cyano, nitro, COOR$^8$, XR$^9$, COR$^{10}$, CONR$^{11}$R$^{12}$ and B;

R$^6$ is O or does not exist;

A$^1$ and A$^2$ are independently selected from SO$_2$D$^1$, SO$_2$ND$^2$D$^3$, COD$^4$, COCOD$^4$, COOD$^4$, COND$^5$D$^6$, COCOND$^5$D$^6$, COCOOD$^4$, C(=ND$^7$)D$^8$, C(=ND$^9$)ND$^{10}$D$^{11}$;

A$^1$ and A$^2$ can either never connect with each other, or can conjoin to form a ring structure;

D$^1$, D$^2$, D$^3$, D$^4$, D$^5$, D$^6$, D$^7$, D$^8$, D$^9$, D$^{10}$, and D$^{11}$ are each independently selected from the group consisting of H, C$_1$-C$_{50}$ alkyl, C$_3$-C$_{50}$ cycloalkyl, C$_4$-C$_{50}$ bicycloalkyl, C$_5$-C$_{50}$ tricycloalkyl, C$_6$-C$_{50}$ tetracycloalkyl, C$_3$-C$_{50}$ alkenyl, C$_4$-C$_{50}$ cycloalkenyl, C$_5$-C$_{50}$ bicycloalkenyl, C$_2$-C$_{50}$ tricycloalkenyl, C$_9$-C$_{50}$ tetracycloalkyl, phenyl, aryl, heteroaryl, C$_1$-C$_{50}$ amide, C$_3$-C$_{50}$ cyclic amide, C$_1$-C$_{50}$ amine, C$_3$-C$_{50}$ cyclic amine, C$_2$-C$_{50}$ ester, C$_3$-C$_{50}$ cyclic ester, C$_2$-C$_{50}$ ether, C$_3$-C$_{50}$ cyclic ether, C$_1$-C$_{50}$ sulfonamide, C$_3$-C$_{50}$ cyclic sulfonamide, C$_2$-C$_{50}$ sulfone, C$_3$-C$_{50}$ cyclic sulfone, C$_2$-C$_{50}$ sulfamide, C$_3$-C$_{50}$ cyclic sulfamide, C$_2$-C$_{50}$ acyl sulfamide, C$_3$-C$_{50}$ acyl sulfamide, C$_2$-C$_{50}$ urea, C$_3$-C$_{50}$ cyclic urea, C$_2$-C$_{50}$ amidine, C$_3$-C$_{50}$ cyclic amidine, C$_2$-C$_{50}$ guanidine, and C$_3$-C$_{50}$ cyclic guanidine; and wherein aryl or heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]

pyridin-2-yl, oxadiazolyl, thiadiazolyl, pyrazolyl, tetrazolyl, tetrazinyl, triazinyl, triazolyl, naphthalenyl, quinolinyl, isoquinolinyl, quinoxalinyl, indolyl, azaindolyl, indazolyl, azaindazolyl, benzoisoxazolyl, azabenzoisoxazolyl, benzoisothiazole, and azabenzothiazolyl; provided the carbon atoms which comprise the carbon-carbon double bond of said $C_3$-$C_{20}$ alkenyl or the carbon-carbon triple bond of said $C_3$-$C_{20}$ alkynyl are not the point of attachment to the nitrogen to which $D^2$, $D^3$, $D^5$, $D^6$, $D^7$, $D^9$, $D^{10}$, and $D^{11}$ is attached; wherein said $C_1$-$C_{50}$ alkyl, $C_3$-$C_{50}$ cycloalkyl, $C_3$-$C_{50}$ alkenyl, $C_4$-$C_{50}$ cycloalkenyl, aryl, phenyl, heteroaryl, $C_3$-$C_{50}$ amide and $C_3$-$C_{50}$ ether is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, and peroxide, among which ether, peroxide, thioether, secondary amine, tertiary amine, ammonium, ester, ketone, amide, amidine, oxime, hydrazine can be either acyclic or cyclic;

$R^7$ is $(CH_2)_n R^{13}$ and n=0-6;

$R^{13}$ is selected from the group consisting of H, $(C_{1-6})$alkyl, —C(O)—$(C_{1-6})$alkyl, C(O)-aryl and CONR$^{14}$R$^{15}$;

$R^{14}$ and $R^{15}$ are each independently H, $(C_{1-6})$alkyl, aryl or heteroaryl;

—represents a carbon-carbon bond or does not exist;

B is selected from the group consisting of $(C_{1-6})$alkyl, $(C_{3-6})$cycloalkyl, C(O)NR$^{16}$R$^{17}$, phenyl and heteroaryl; wherein said $(C_{1-6})$alkyl, phenyl and heteroaryl are independently optionally substituted with one to three same or different halogens or from one to three same or different substituents selected from E; heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl;

E is selected from the group consisting of $(C_{1-6})$alkyl, $(C_{3-6})$cycloalkyl cyano, phenyl, heteroaryl, heteroalicyclic, hydroxy, $(C_{1-6})$alkoxy, halogen, benzyl, —NR$^{18}$C(O)—$(C_{1-6})$alkyl, —NR$^{19}$R$^{20}$, morpholino, nitro, —S($C_{1-6}$)alkyl, —SPh, NR$^{21}$S(O)$_2$—R$^{22}$, piperazinyl, N-Me piperazinyl, C(O)H, (CH2)$_n$COOR$^{23}$ and —CONR$^{24}$R$^{25}$; wherein said $(C_{1-6})$alkyl, heteroaryl, or phenyl is optionally substituted with one to three same or different halogens or one to three methyl groups; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; heteroalicyclic is selected from the group consisting of aziridine, azetidine, pyrrolidine, piperazine, N-methyl piperazine, piperidine, tetrahydrofuran, tetrahydropyran, azepine and morpholine;

$R^8$, $R^9$, $R^{10}$, $R^{11}$ and $R^{12}$ are selected from the group consisting of hydrogen and $(C_{1-6})$alkyl; $(C_{1-6})$alkyl is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic;

X is selected from the group consisting of NR$^{26}$, O and S;

$R^{16}$, $R^{17}$, $R^{18}$, $R^{19}$, $R^{20}$, $R^{21}$, $R^{22}$, $R^{23}$, $R^{24}$, $R^{25}$, and $R^{26}$ are independently selected from the group consisting of hydrogen, $(C_{1-6})$alkyl, $(C_{1-6})$alkoxy, phenyl and heteroaryl; wherein said $(C_{1-6})$alkyl, phenyl, and heteroaryl are independently optionally substituted with one to three same or different group L or $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

L is selected from the group consisting of $(C_{1-6})$alkyl, phenyl, heteroaryl, hydroxy, $(C_{1-6})$alkoxy, halogen, benzyl, —NR$^{27}$C(O)—$(C_{1-6})$alkyl, —NR$^{28}$R$^{29}$, morpholino, nitro, —S($C_{1-6}$)alkyl, —SPh, NR$^{30}$S(O)$_2$—R$^{31}$, piperazinyl, N-Me piperazinyl, (CH2)$_n$COOR$^{32}$ and —CONR$^{33}$R$^{34}$; wherein said $(C_{1-6})$alkyl, heteroaryl, or phenyl is optionally substituted with one to three same or different halogens, amino, or methyl groups; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; and $R^{27}$, $R^{28}$, $R^{29}$, $R^{30}$, $R^{31}$, $R^{32}$, $R^{33}$, and $R^{34}$ are independently selected from the group consisting of hydrogen, $(C_{1-6})$alkyl, $(C_{1-6})$alkoxy, phenyl and heteroaryl; wherein said $(C_{1-6})$alkyl, phenyl, and heteroaryl are independently optionally substituted with one to three same or different $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, acyl sulfamide, sulfate, sulfuric acid, sulfamic acid, phosphate, phosphoric acid, boronic ester, boronic acid, squarate, squaric acid, oxime, hydrazine, peroxide, among which ether, peroxide, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

Z is selected from the group consisting of:

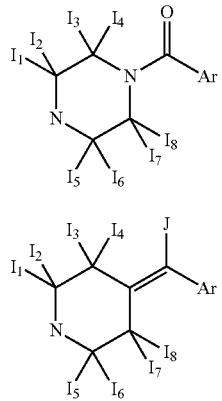

Za

Zb

J is selected from the group consisting of hydrogen, $(C_{1-6})$ alkyl, $(C_{1-6})$alkynyl, $(C_{3-6})$ cycloalkyl, halogen, cyano, —$CONG^1G^2$, —$SO2G^3$, $COG^4$, $COOG^5$, tetrahydrofuryl, pyrrolidinyl, phenyl and heteroaryl; wherein said $(C_{1-6})$alkyl, $(C_{1-6})$alkynyl, phenyl and heteroaryl are each independently optionally substituted with one to three same or different members selected from the group J-1; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

J-1 is selected from the group consisting of $(C_{1-6})$alkyl, $(C_{3-6})$cycloalkyl, cyano, trimethylsilyl, phenyl, heteroaryl, heteroalicyclic, hydroxy, $(C_{1-6})$alkoxy, halogen, benzyl, —$NG^6C(O)$—$(C_{1-6})$alkyl, —$NG^7G^8$, —$C(O)NG^9G^{10}$, morpholino, nitro, —$S(C_{1-6})$alkyl, —SPh, $NG^{11}S(O)_2$-$G^{12}$, piperazinyl, N-Me piperazinyl, $(CH2)_nCOOG^{13}$ and —$CONG^{14}G^{15}$; wherein said $(C_{1-6})$alkyl, heteroaryl, or phenyl is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; heteroalicyclic is selected from the group consisting of aziridine, azetidine, pyrrolidine, piperazine, N-methyl piperazine, piperidine, tetrahydrofuran, tetrahydropyran, azepine and morpholine;

$G^1$, $G^2$, $G^9$, $G^{10}$, $G^{14}$ and $G^{15}$ are each independently selected from the group consisting of H, $C_1$-$C_6$ alkyl, $C_3$-$C_6$ cycloalkyl, $C_3$-$C_6$ alkenyl, $C_4$-$C_6$ cycloalkenyl and $C_3$-$C_6$ alkynyl; provided the carbon atoms which comprise the carbon-carbon double bond of said $C_3$-$C_6$ alkenyl or the carbon-carbon triple bond of said $C_3$-$C_6$ alkynyl are not the point of attachment to the nitrogen to which $G^1$, $G^2$, $G^9$, $G^{10}$, $G^{14}$ and $G^{15}$ is attached; wherein said heteroaryl, or phenyl is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic;

$G^3$, $G^4$ and $G^{12}$ are each independently selected from the group consisting of H, $C_1$-$C_6$ alkyl, $C_{1-6}$ alkyl substituted with one to three halogen atoms, $C_3$-$C_6$ cycloalkyl, $C_2$-$C_6$ alkenyl, $C_4$-$C_6$ cycloalkenyl, and $C_3$-$C_6$ alkynyl; provided the carbon atoms which comprise the carbon-carbon triple bond of said $C_3$-$C_6$ alkynyl are not the point of attachment to the oxygen or sulfur to which $G^3$, $G^4$ and $G^{12}$ is attached; wherein said $(C_{1-6})$alkyl, heteroaryl, or phenyl is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic;

$G^5$ and $G^{13}$ are each independently selected from the group consisting of H, $C_1$-$C_6$ alkyl, $C_{1-6}$ alkyl substituted with one to three halogen atoms, $C_3$-$C_6$ cycloalkyl, $C_2$-$C_6$ alkenyl, $C_4$-$C_6$ cycloalkenyl, and $C_3$-$C_6$ alkynyl; provided the carbon atoms which comprise the carbon-carbon triple bond of said $C_3$-$C_6$ alkynyl are not the point of attachment to the oxygen or sulfur to which $G^5$ and $G^{13}$ is attached; wherein said $(C_{1-6})$alkyl, heteroaryl, or phenyl is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic;

$G^6$ and $G^{11}$ are each independently selected from the group consisting of H, OH, $C_1$-$C_6$ alkyl, $C_3$-$C_6$ cycloalkyl, $C_3$-$C_6$ alkenyl, $C_5$-$C_6$ cycloalkenyl, $C_3$-$C_6$ alkynyl and $C(O)R^{34}$; provided the carbon atoms which comprise the carbon-carbon double bond of said $C_3$-$C_6$ alkenyl, $C_4$-$C_6$ cycloalkenyl, or the carbon-carbon triple bond of said $C_3$-$C_6$ alkynyl are not the point of attachment to the nitrogen to $G^6$ and $G^{11}$ is attached; wherein said $(C_{1-6})$alkyl, heteroaryl, or phenyl is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic;

$G^7$ and $G^8$ are each independently selected from the group consisting of H, OH, $C_1$-$C_6$ alkyl, $C_3$-$C_6$ cycloalkyl, $C_3$-$C_6$ alkenyl, $C_5$-$C_6$ cycloalkenyl, $C_3$-$C_6$ alkynyl and $C(O)G^{16}$; provided the carbon atoms which comprise the carbon-carbon double bond of said $C_3$-$C_6$ alkenyl, $C_4$-$C_6$ cycloalkenyl, or the carbon-carbon triple bond of said $C_3$-$C_6$ alkynyl are not the point of attachment to the nitrogen to $G^7$ and $G^8$ is attached; wherein said $(C_{1-6})$alkyl, heteroaryl, or phenyl is optionally substituted with one to five same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic;

$G^{16}$ is independently selected from the group consisting of H, OH, $C_1$-$C_6$ alkyl, $C_3$-$C_6$ cycloalkyl, $C_3$-$C_6$ alkenyl, $C_5$-$C_6$ cycloalkenyl and $C_3$-$C_6$ alkynyl; provided the carbon atoms which comprise the carbon-carbon double bond of said $C_3$-$C_6$ alkenyl, $C_4$-$C_6$ cycloalkenyl, or the carbon-carbon triple bond of said $C_3$-$C_6$ alkynyl are not the point of attachment to the nitrogen to $G^{16}$ is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic;

Ar is selected from the group consisting of phenyl and heteroaryl; wherein said phenyl and heteroaryl are each independently optionally substituted with one to three same or different members selected from the group Ar-1; and heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl;

Ar-1 is selected from the group consisting of $(C_{1-6})$alkyl, $(C_{3-6})$cycloalkyl, cyano, phenyl, aryl, heteroaryl, heteroalicyclic, hydroxy, $(C_{1-6})$alkoxy, halogen, primary amine, secondary amine, tertiary amine, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic; wherein said $(C_{1-6})$alkyl, $(C_{1-6})$alkyl, $(C_{3-6})$cycloalkyl is optionally substituted with one to three same or different of the following functionalities: $(C_{1-6})$alkyl, $(C_{3-6})$cycloalkyl, cyano, phenyl, aryl, heteroaryl, heteroalicyclic, hydroxy, $(C_{1-6})$alkoxy, halogen, benzyl, primary amine, secondary amine, tertiary amine, ammonium, nitro, thiol, thioether, alcohol, ether, acid, aldehyde, ketone, amide, amidine, guanidine, sulfone, sulfonamide, sulfamide, oxime and hydrazine, among which ether, thioether, secondary amine, tertiary amine, ammonium, ester, ketone, amide, amidine, oxime, hydrazine can be either acyclic or cyclic; and $I_1, I_2, I_3, I_4, I_5, I_6, I_7$ and $I_8$ are each independently selected from the group consisting of H and $(C_{1-6})$alkyl; wherein $(C_{1-6})$alkyl is optionally substituted with one to three same or different halogen, amino, alkoxy, OH, CN or $NO_2$;

In a preferred embodiment, in the compound of Formula I $R^1$, $R^2$, and $R^3$ are each selected from the group consisting of hydrogen, halogen, $(C_1$-$C_3)$ alkyl, and $(C_1$-$C_3)$ alkoxy.

It is also preferred that in the compounds of Formula I, Y is the indole

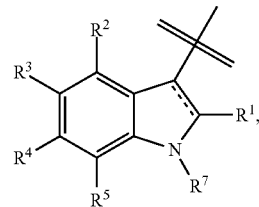

In this embodiment, it is also preferred that $R^5$ be selected from $NA^1A^2$.

In a further embodiment of the invention, it is preferred that Ar be phenyl or pyridine.

Especially preferred compounds of the invention include the following:

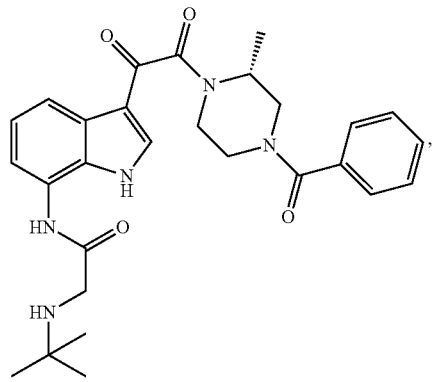

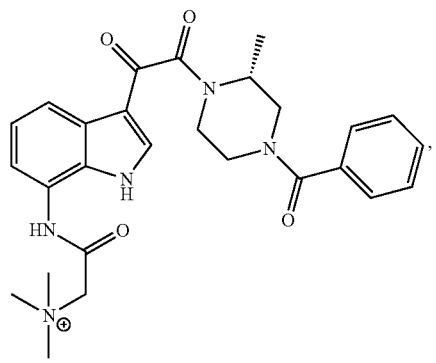

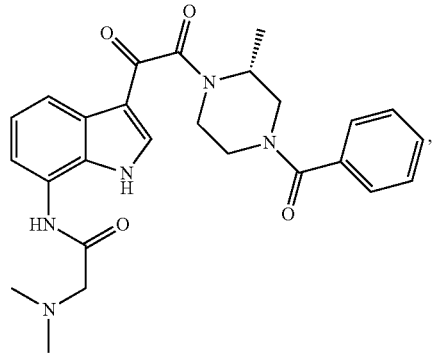

21
-continued
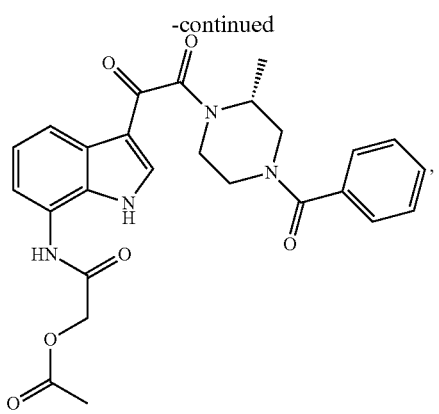
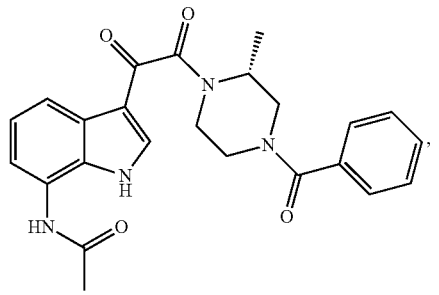
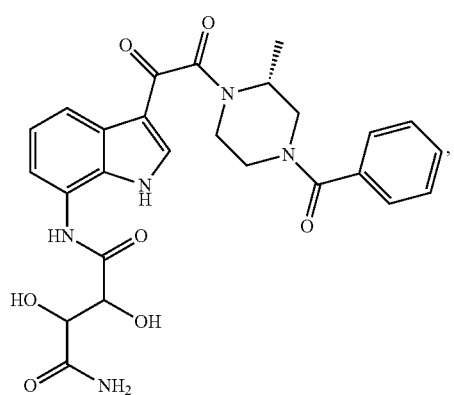
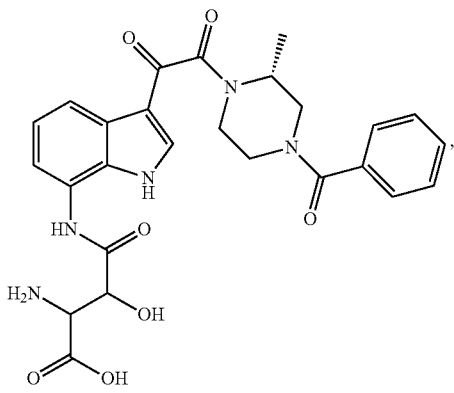
22
-continued
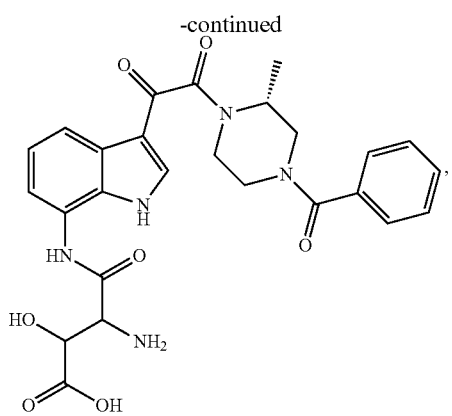
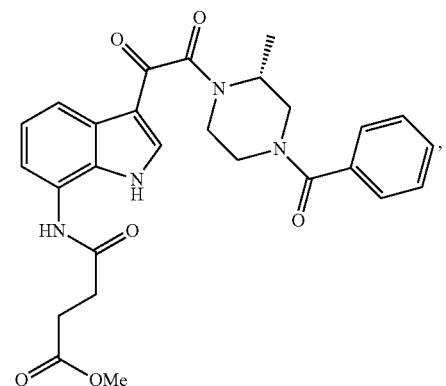
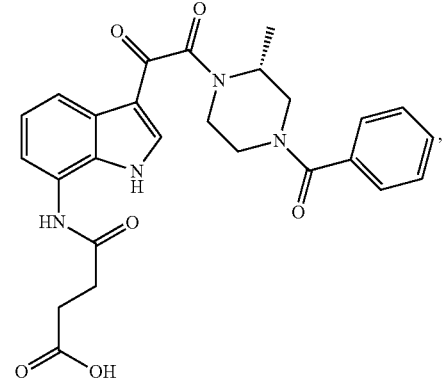
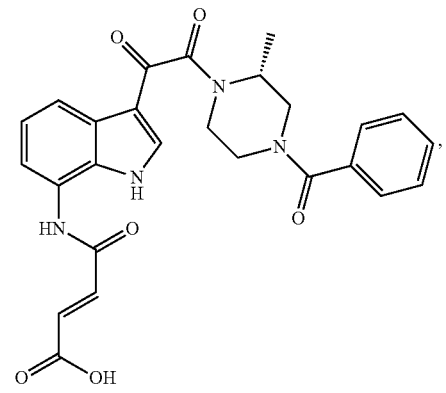

-continued
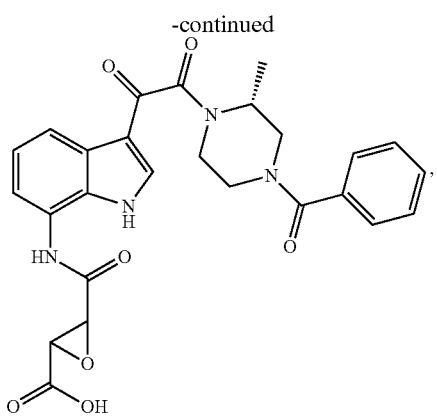
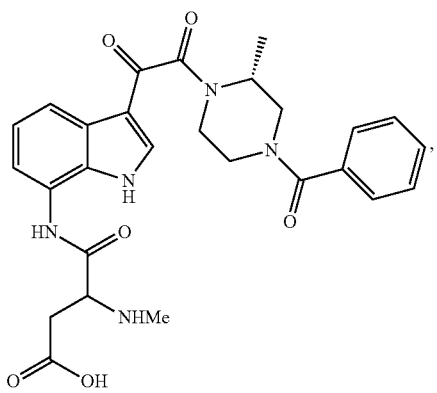
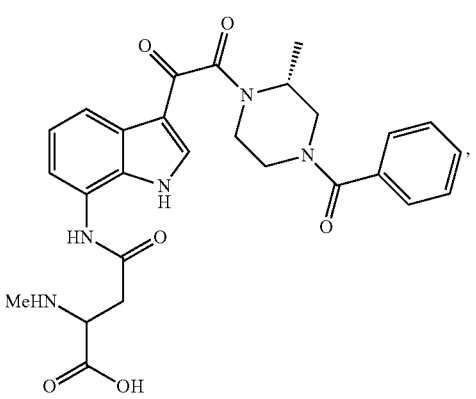
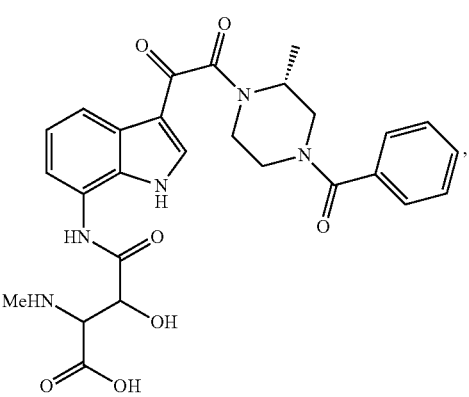
-continued
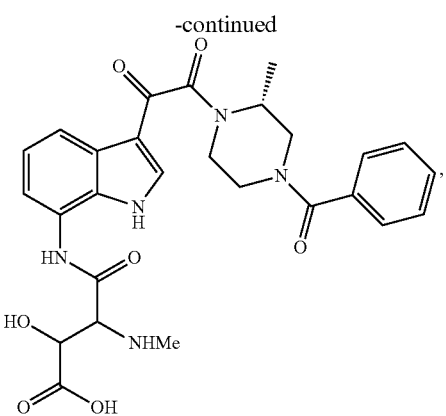
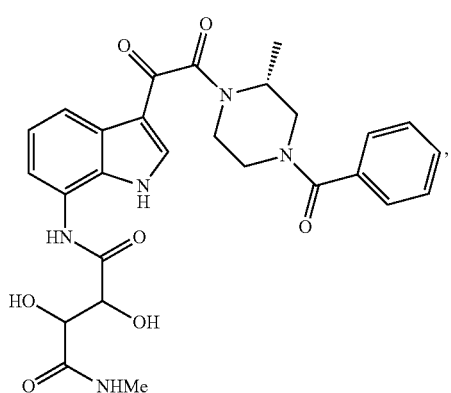
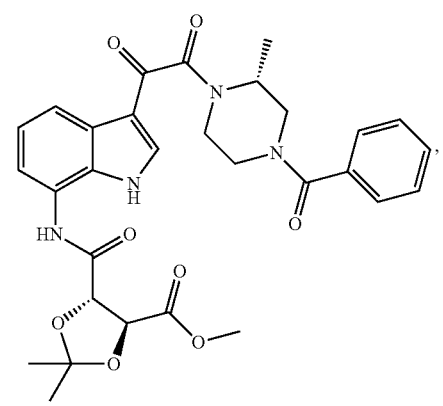
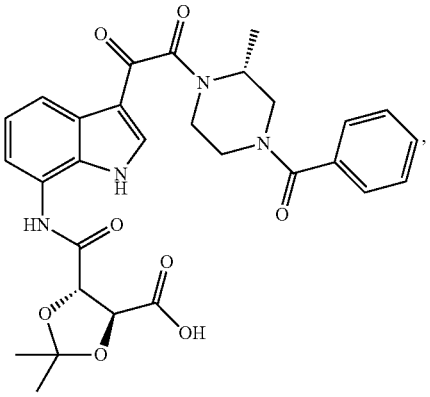

25
-continued
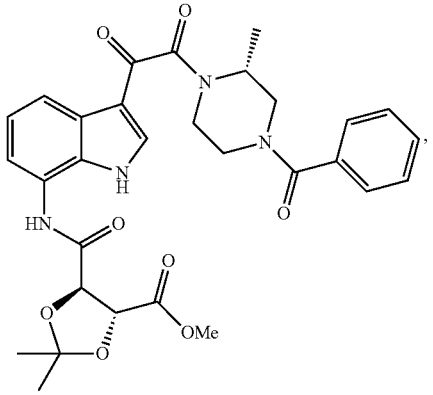
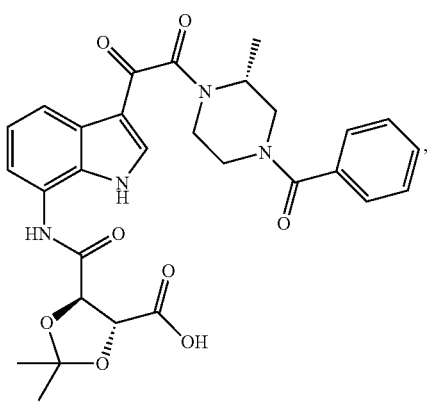
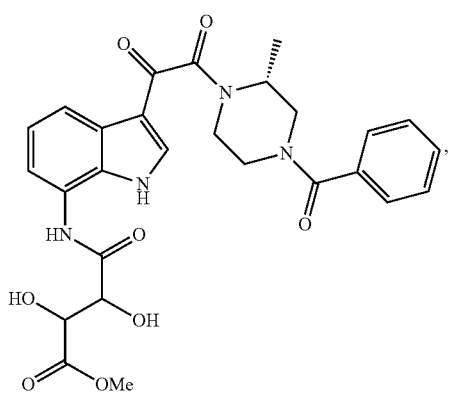
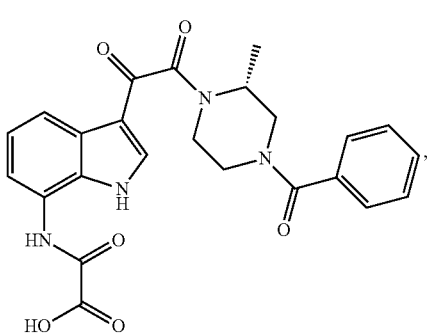
26
-continued
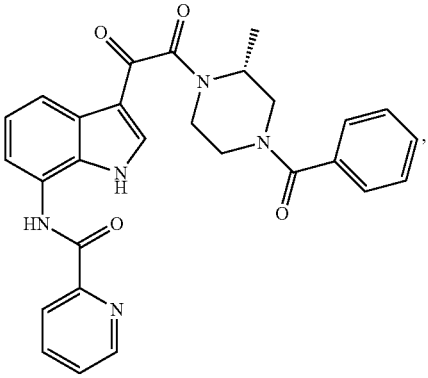
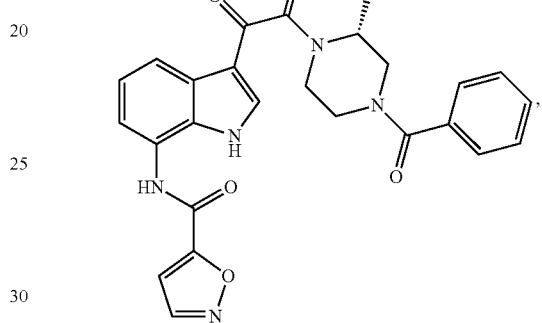
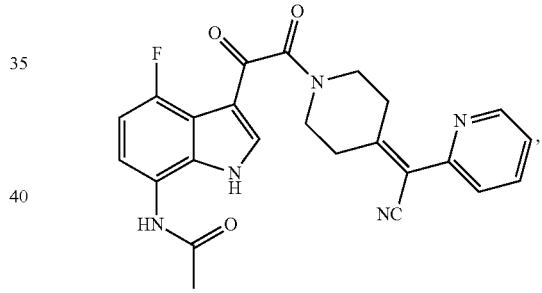
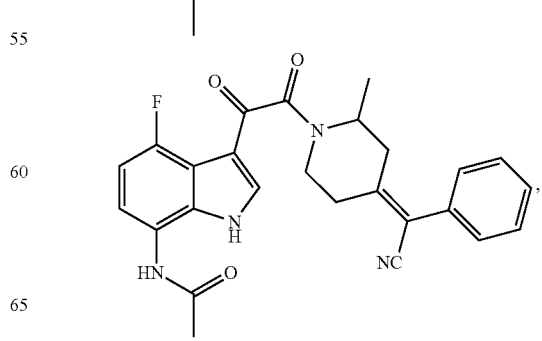

27
-continued
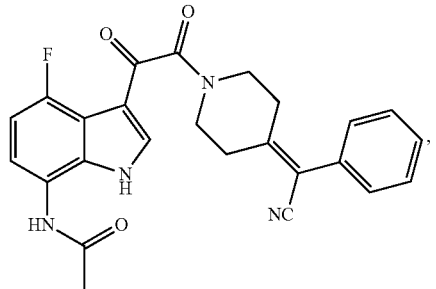
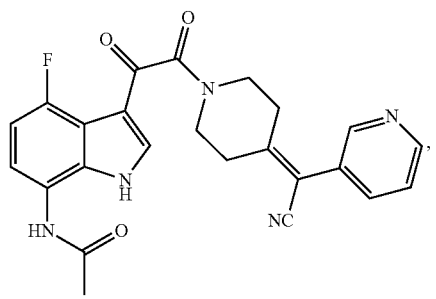
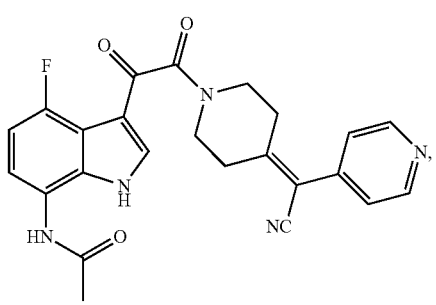
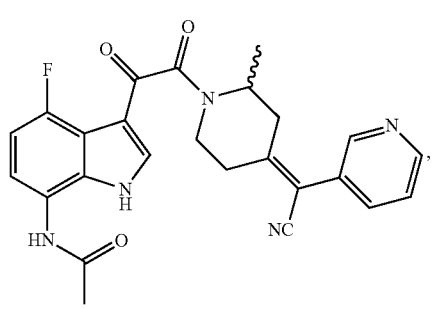
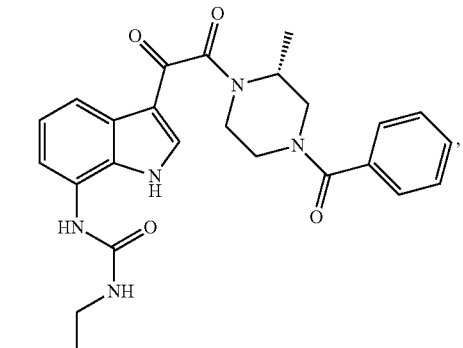
28
-continued
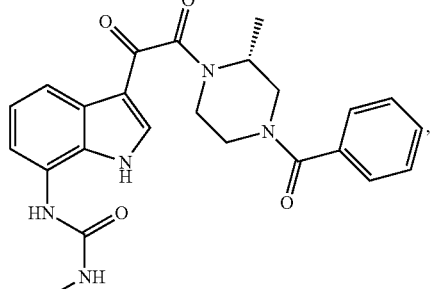
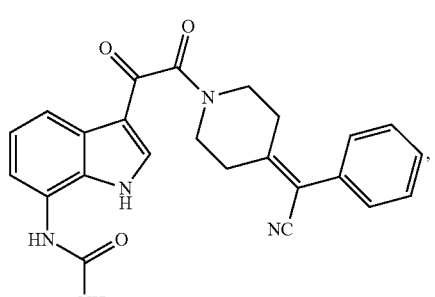
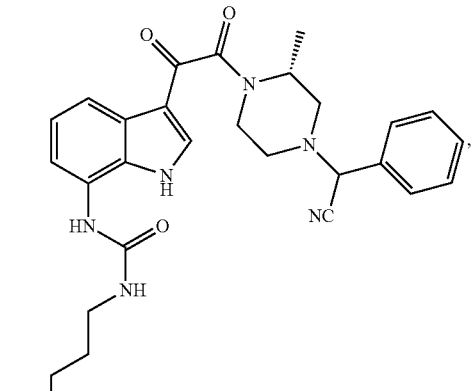

| 29 | 30 |
|---|---|
| -continued | -continued |
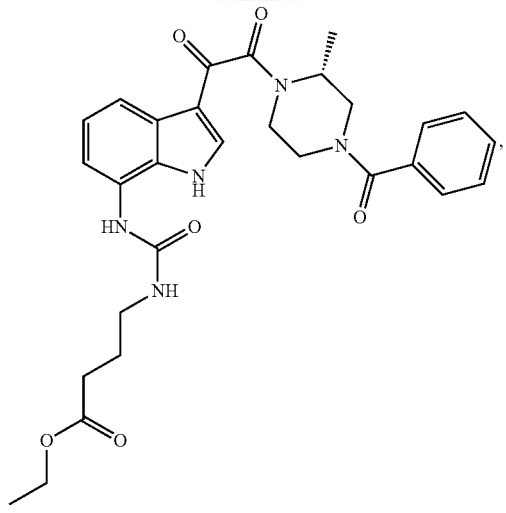
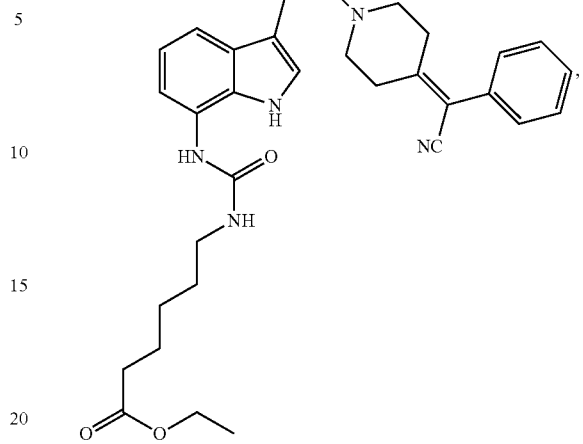
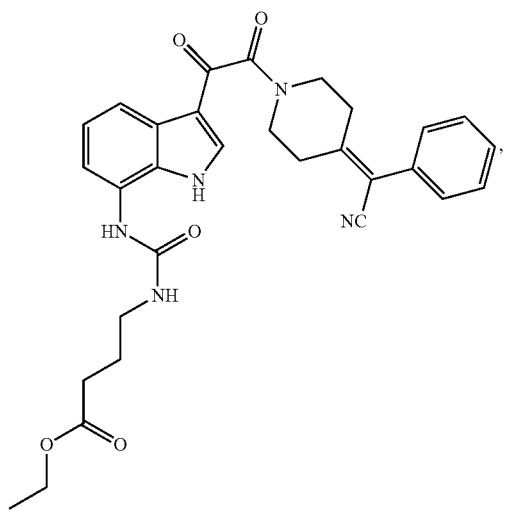
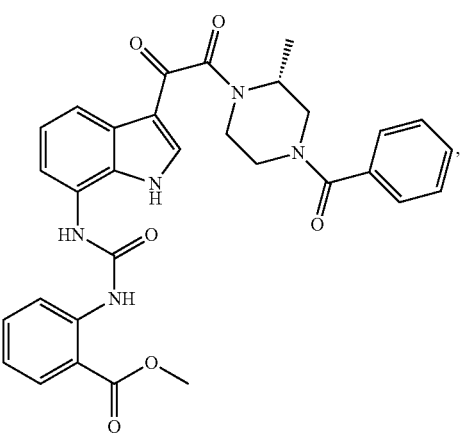
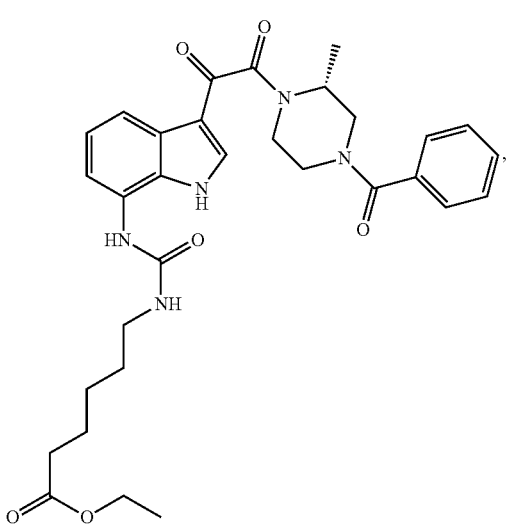
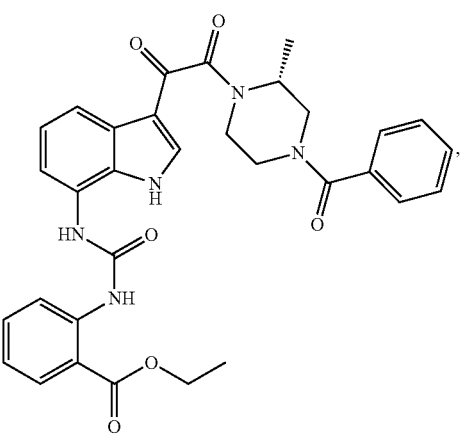

31
-continued
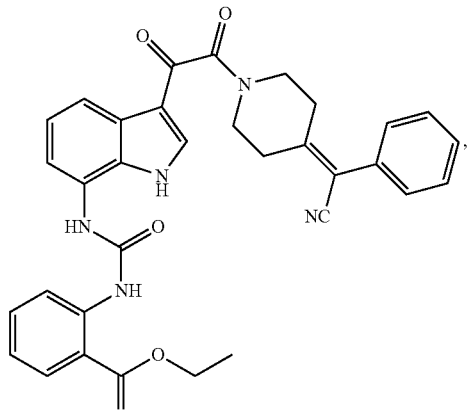
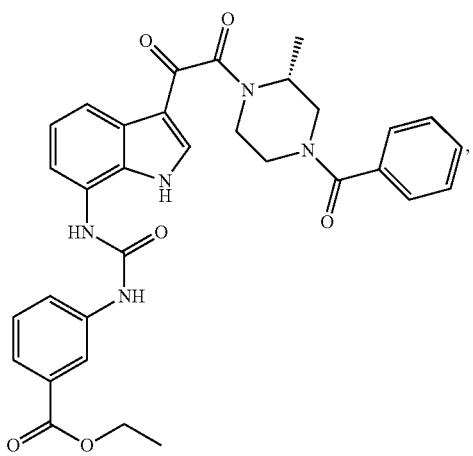
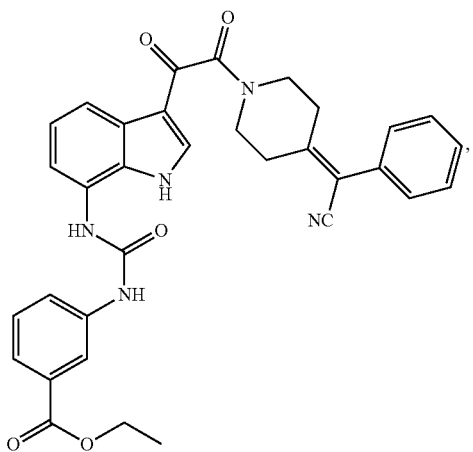
32
-continued
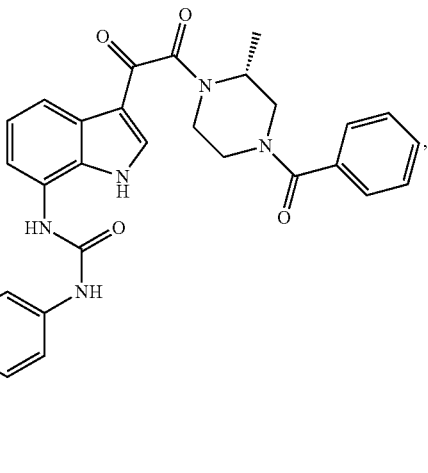
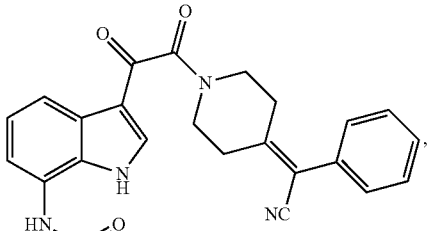
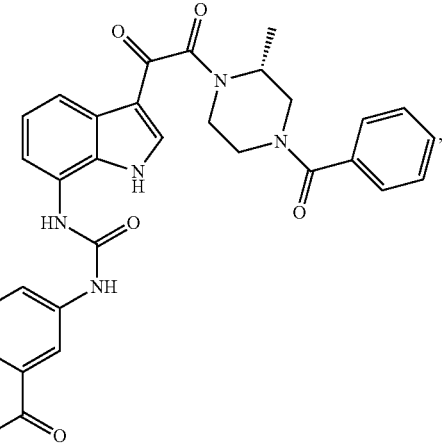

33
-continued
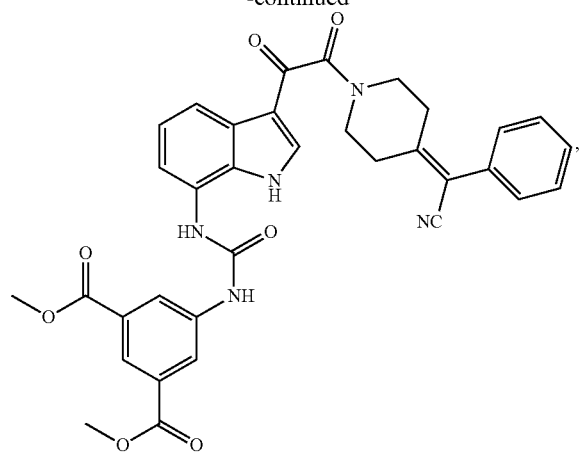
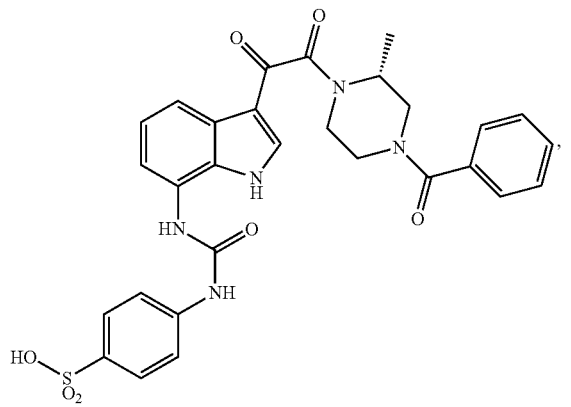
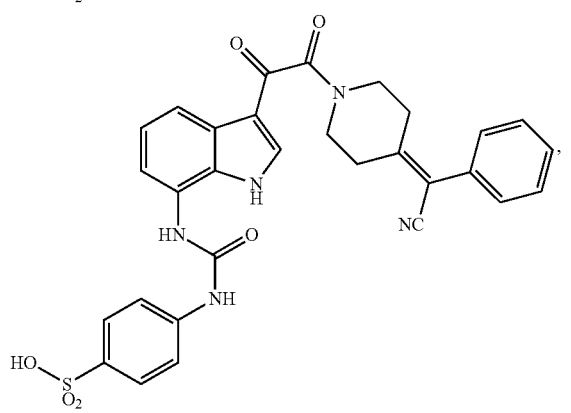
34
-continued
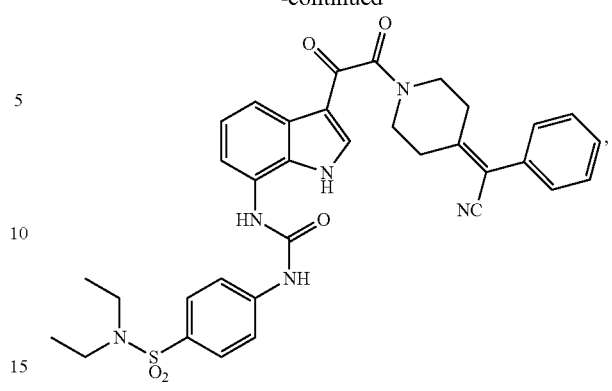
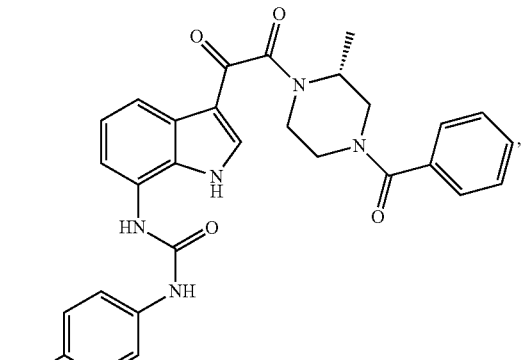
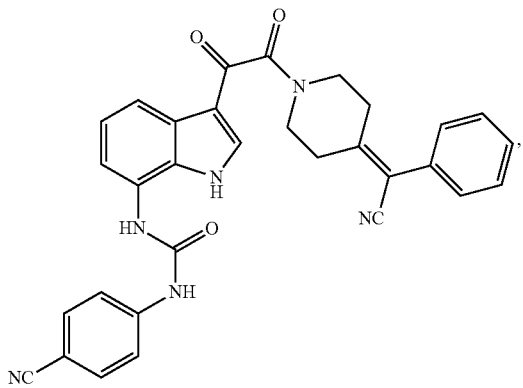
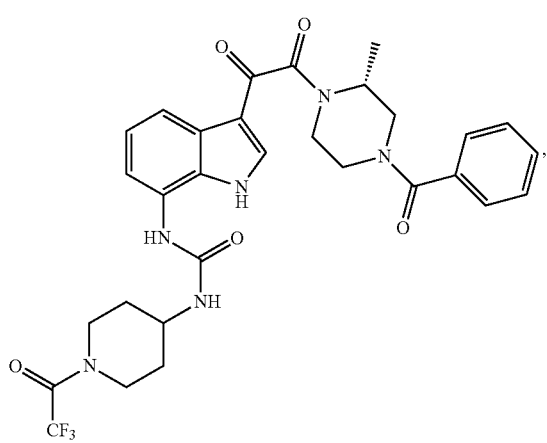

35
-continued
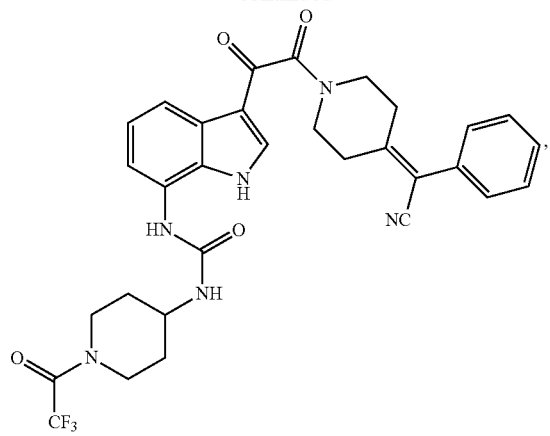
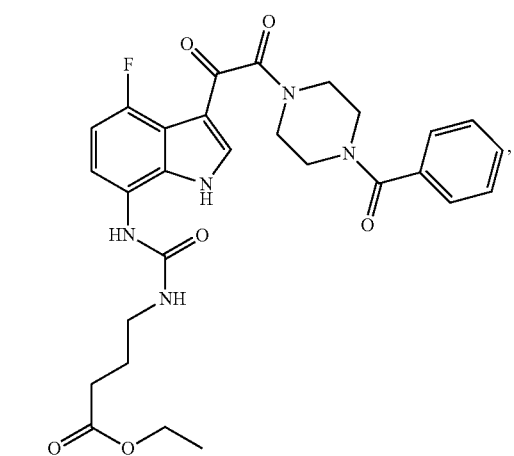
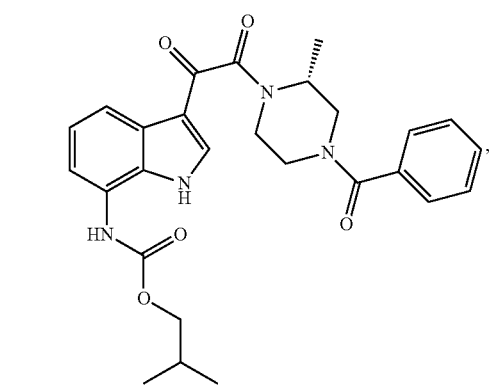
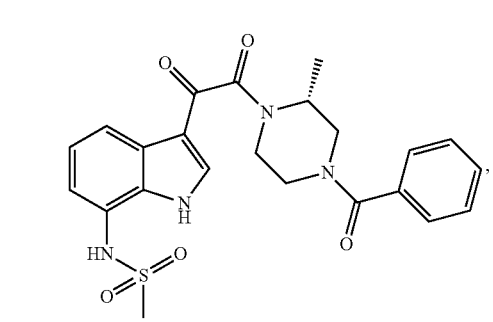
36
-continued
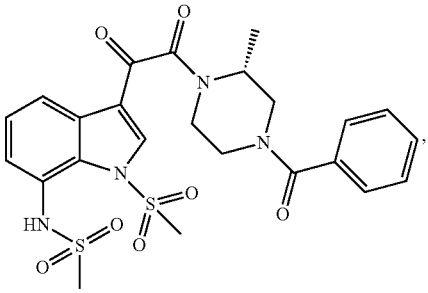
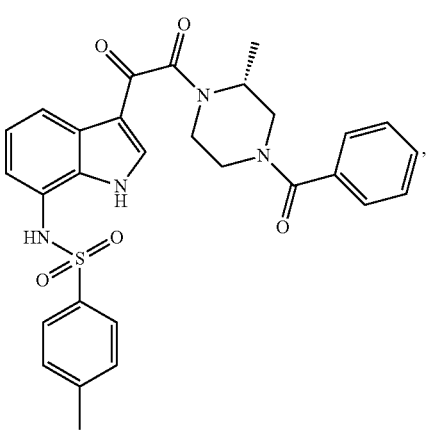
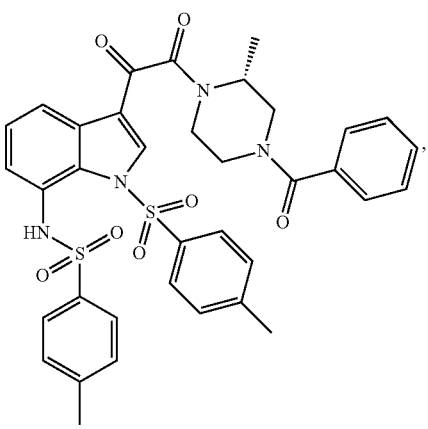
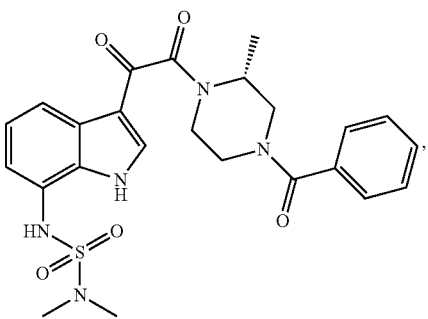

37
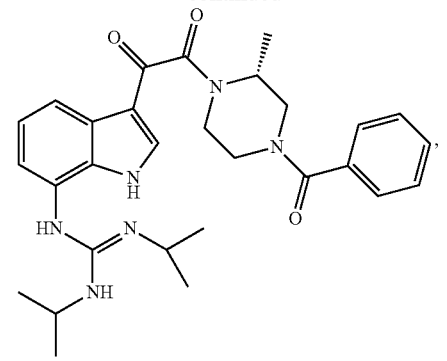
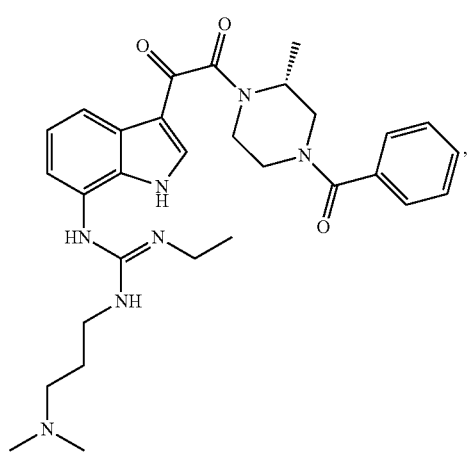
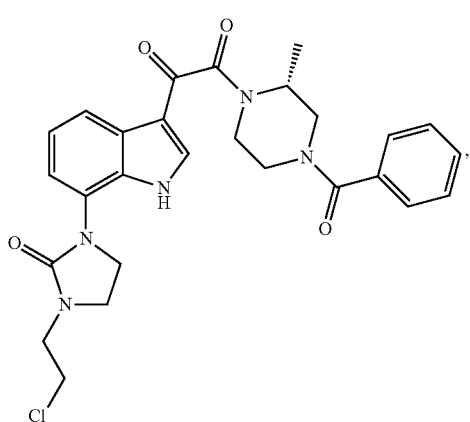
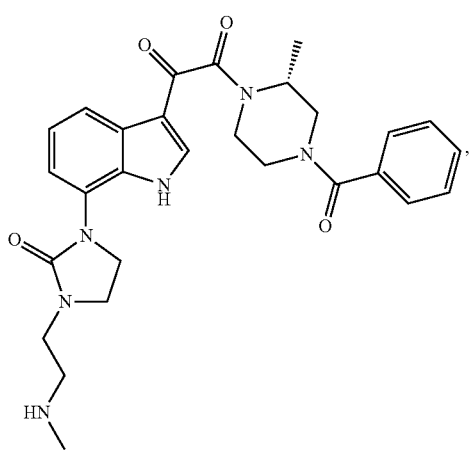
38
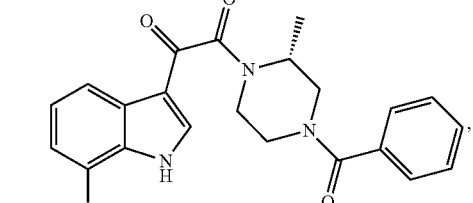
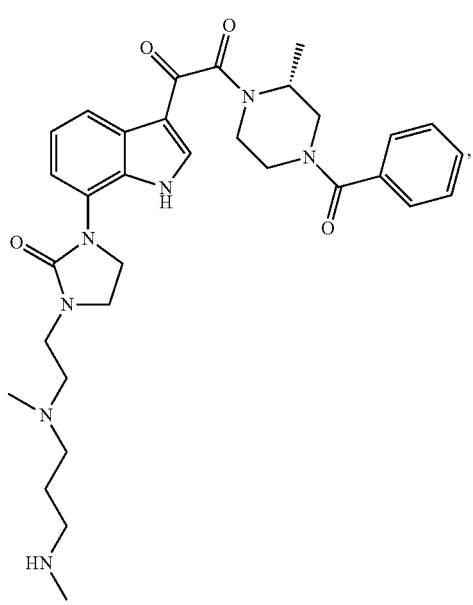
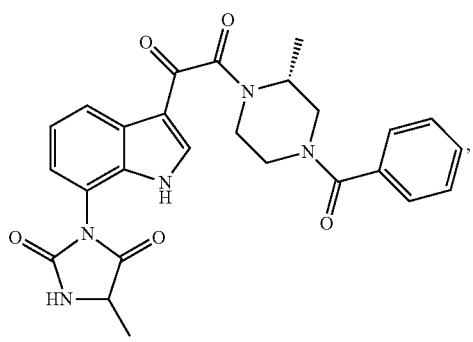

| 39 -continued | 40 -continued |
|---|---|
| 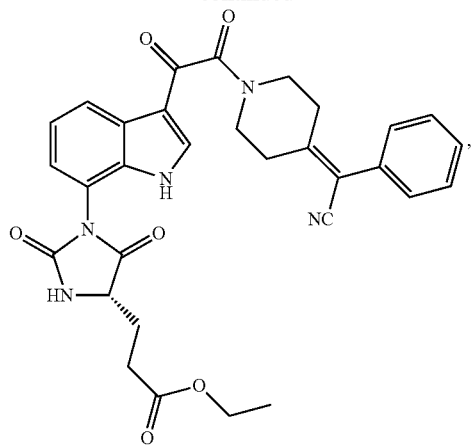 | 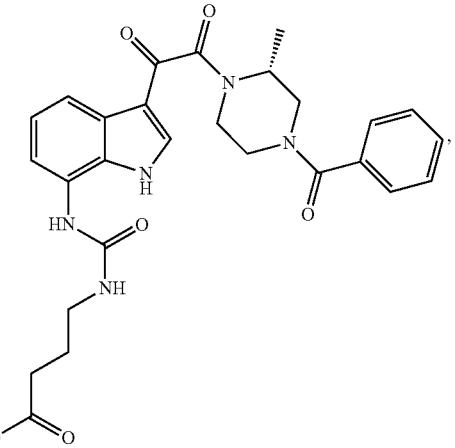 |
| 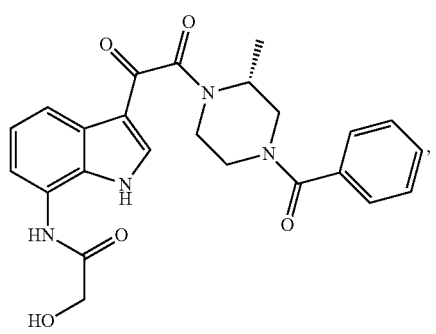 | 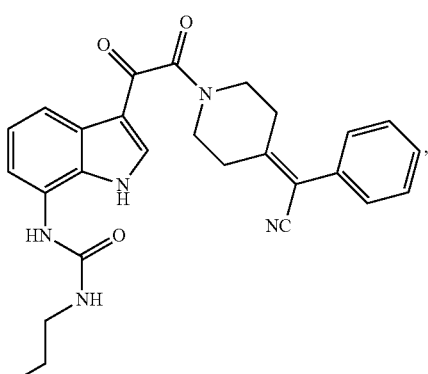 |
| 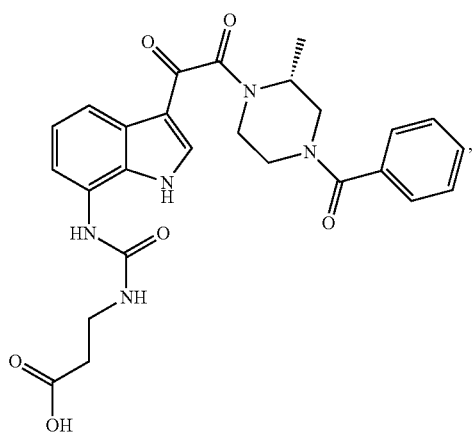 | |
| 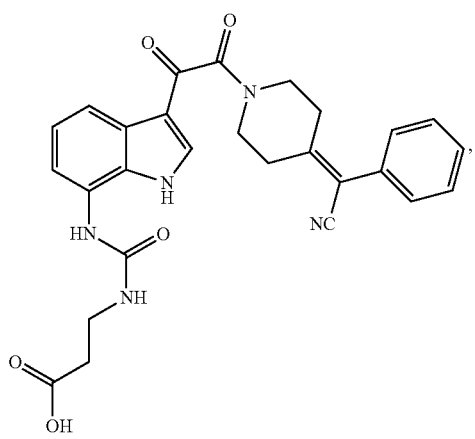 | 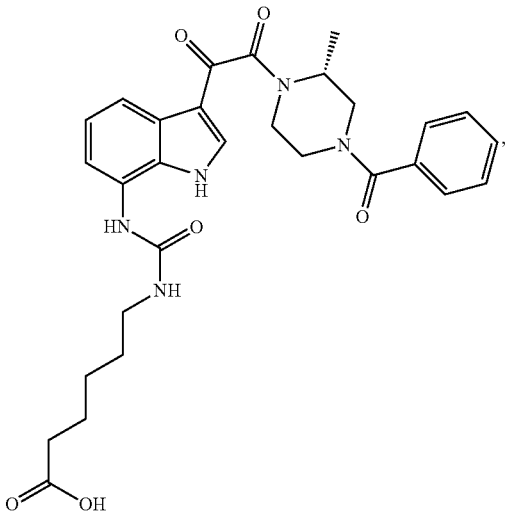 |

41
-continued
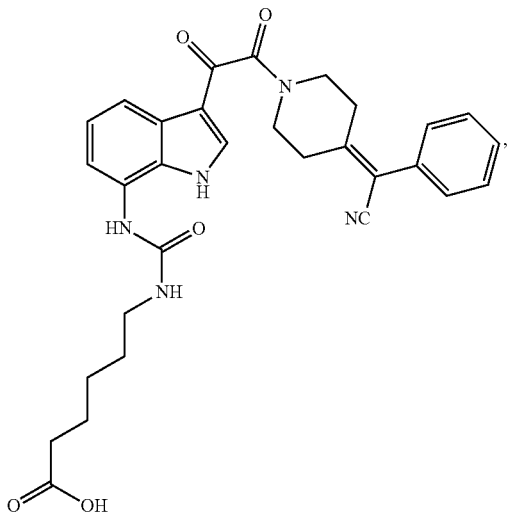
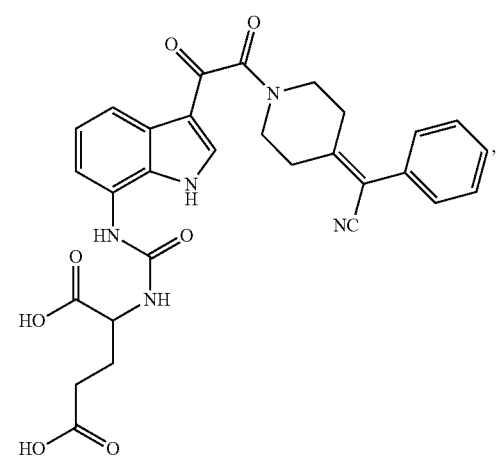
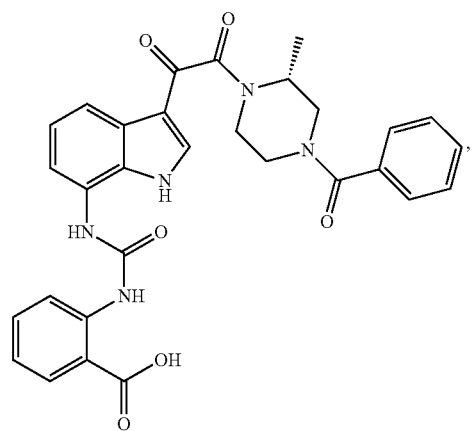
42
-continued
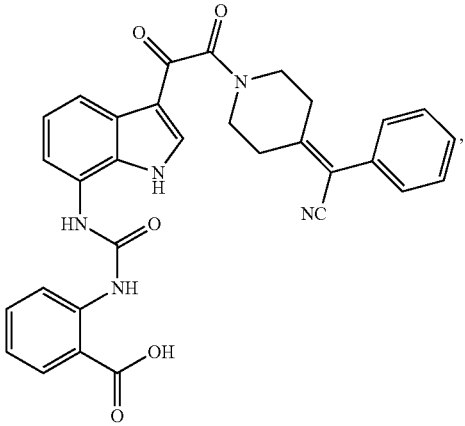
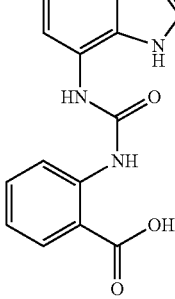
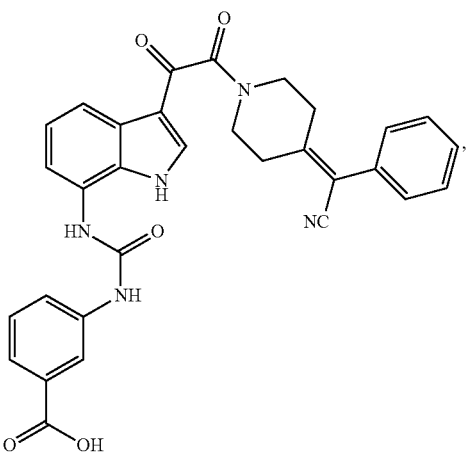

43
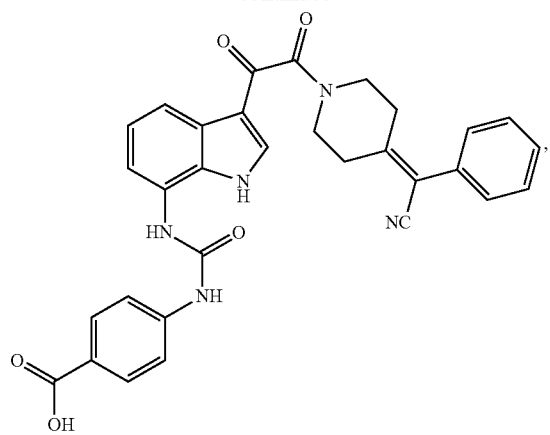
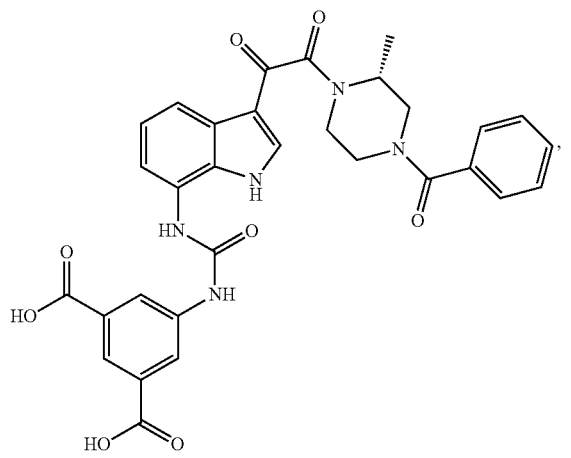
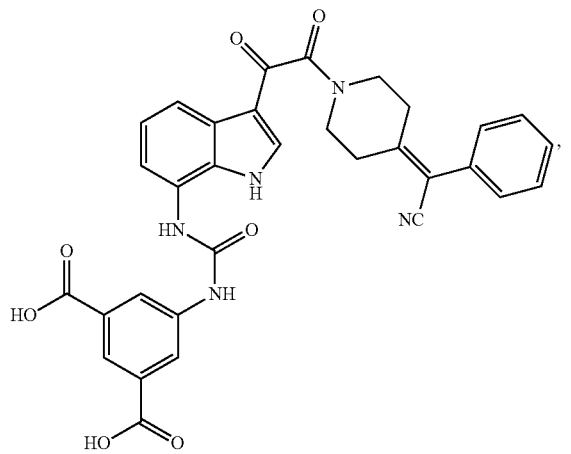
44
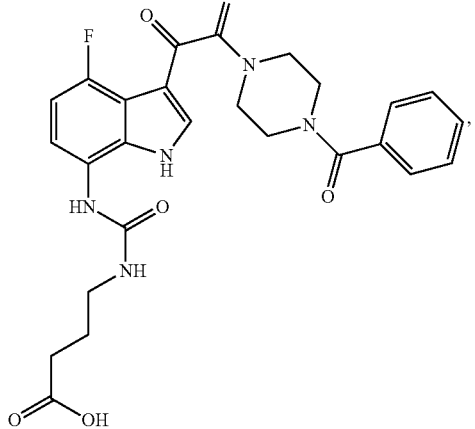
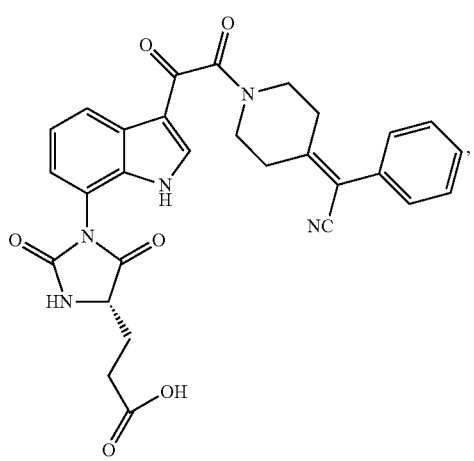
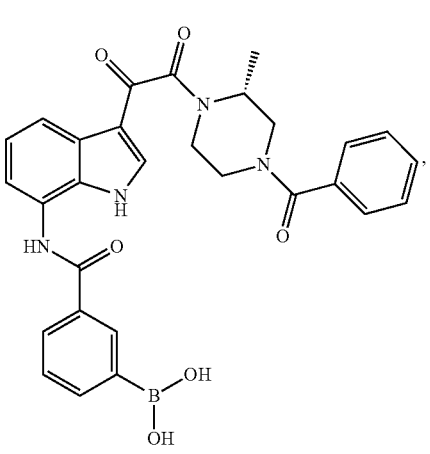

45
-continued
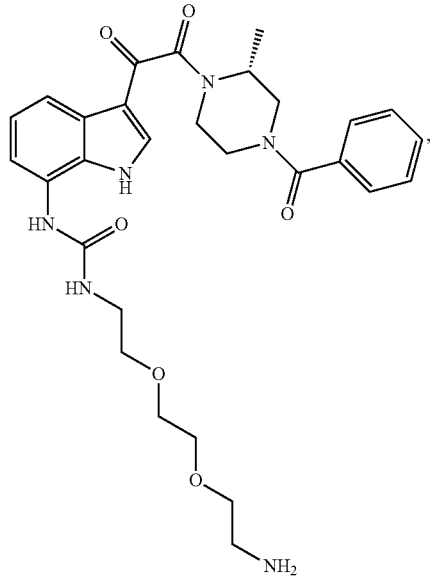
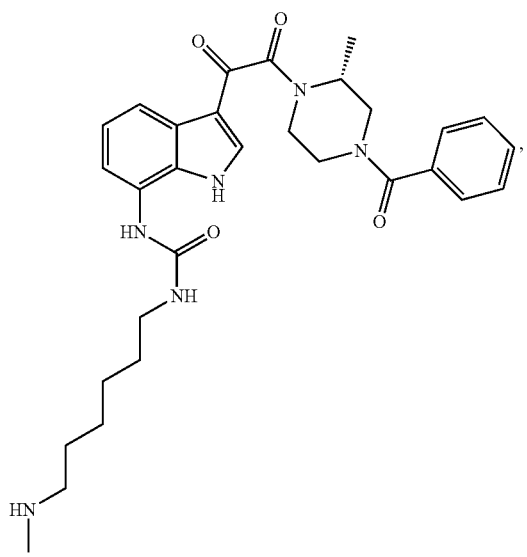
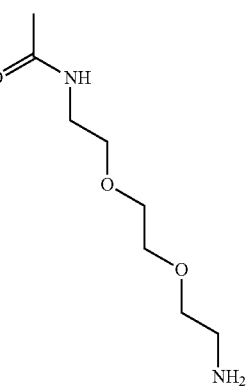
46
-continued
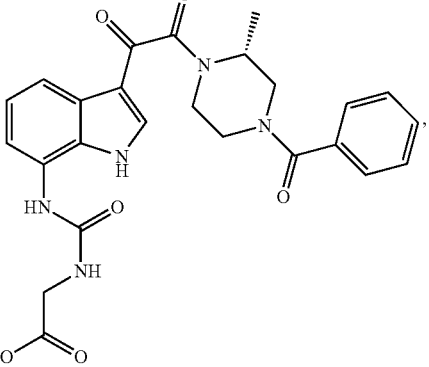
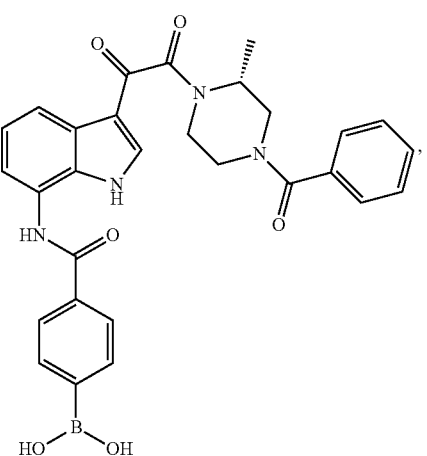
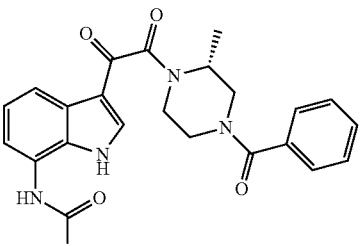
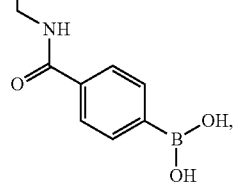

47
-continued
48
-continued
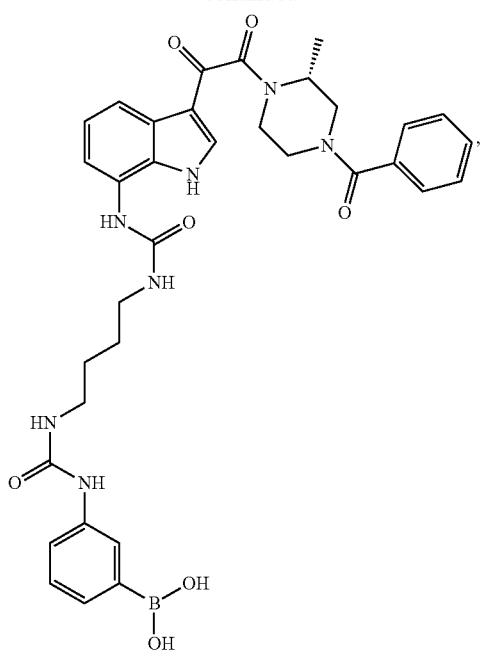
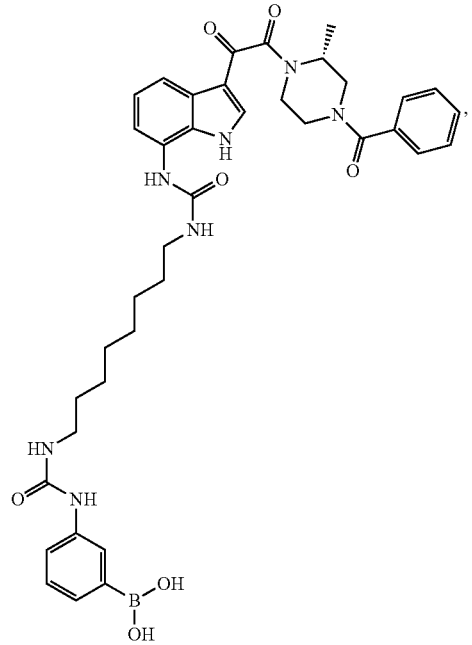

49
-continued
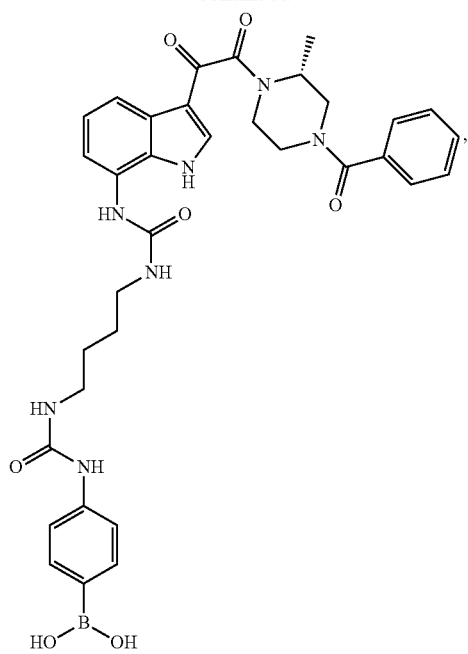
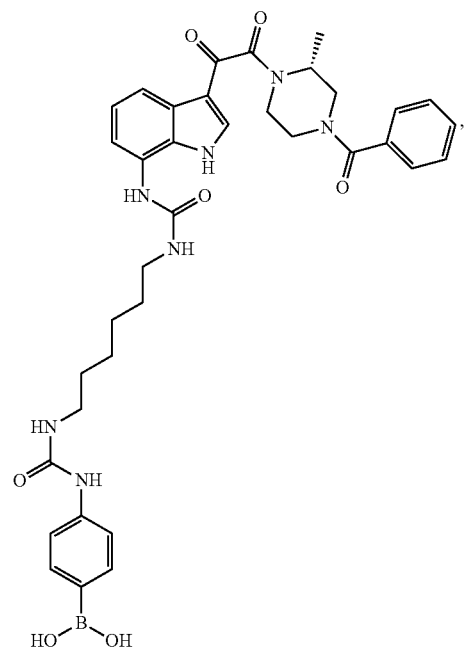
50
-continued
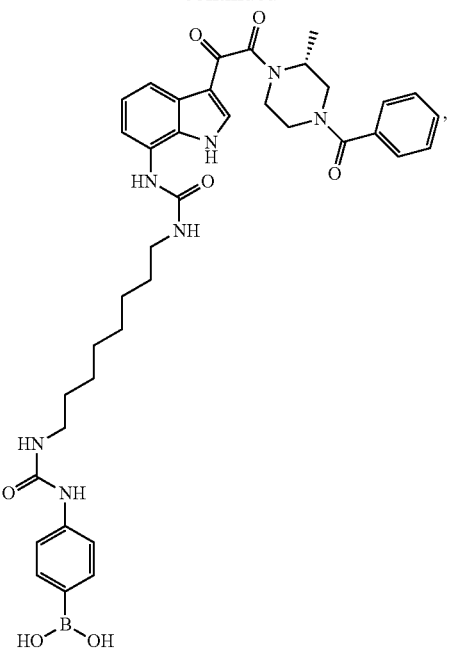
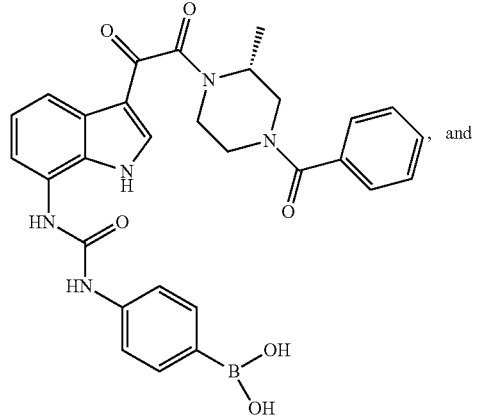
, and -continued
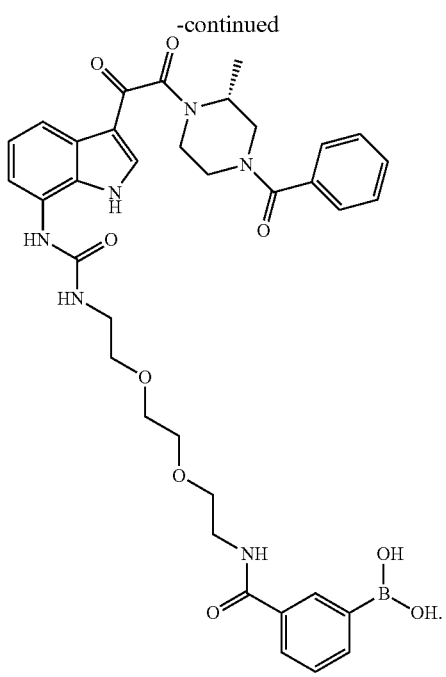
Of the foregoing, the following compounds are particularly preferred:
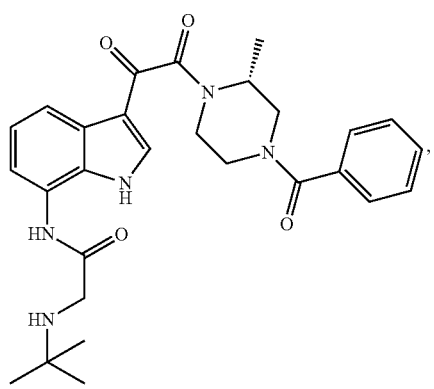
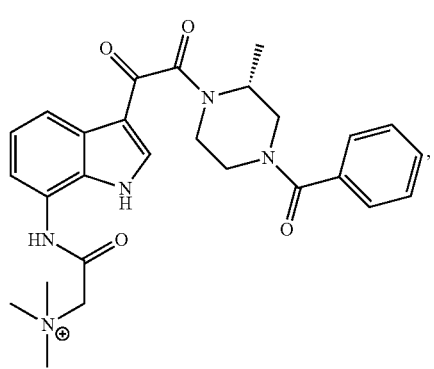
-continued
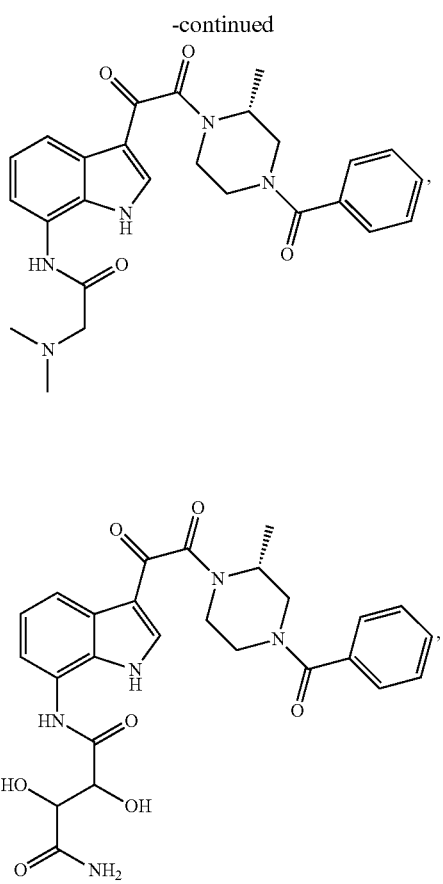
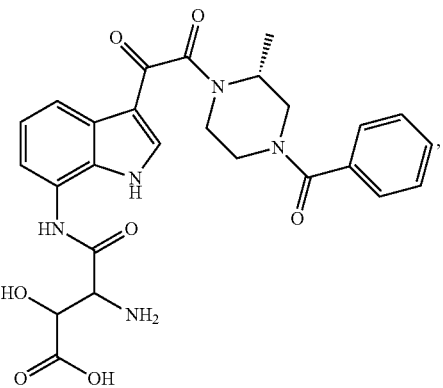
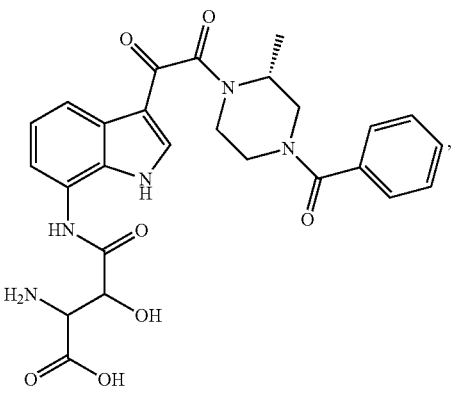

53
-continued
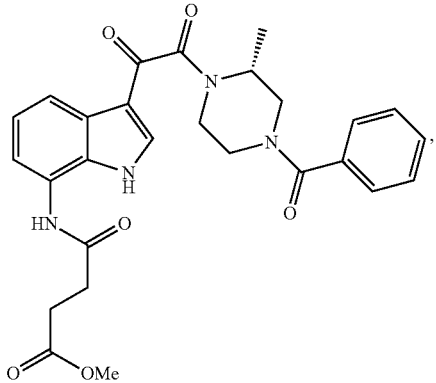
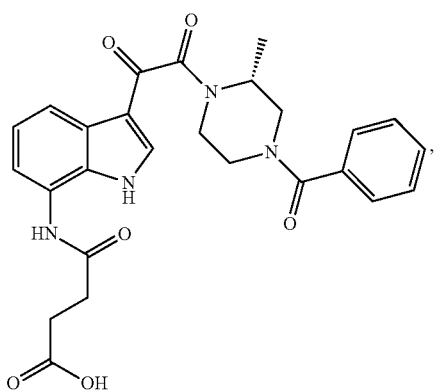
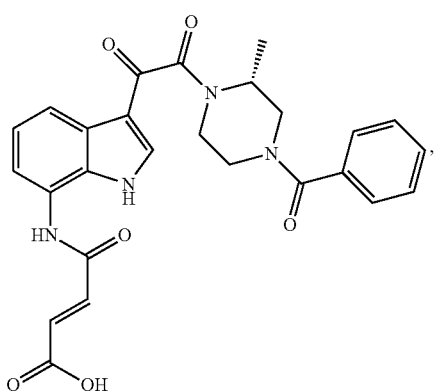
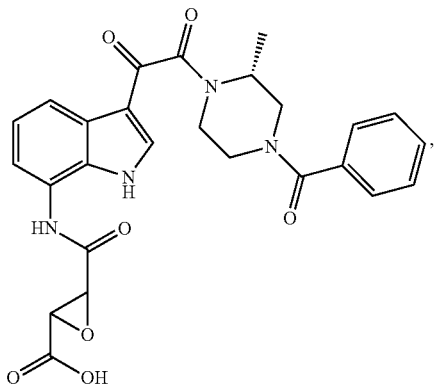
54
-continued
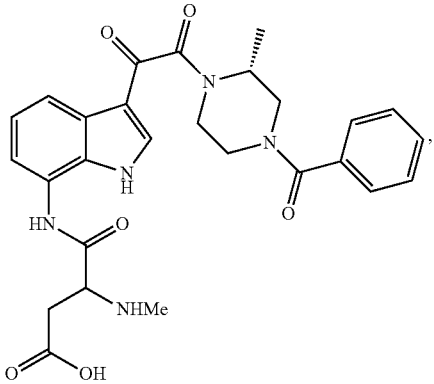
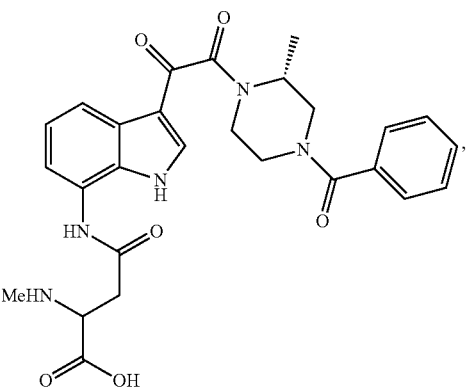
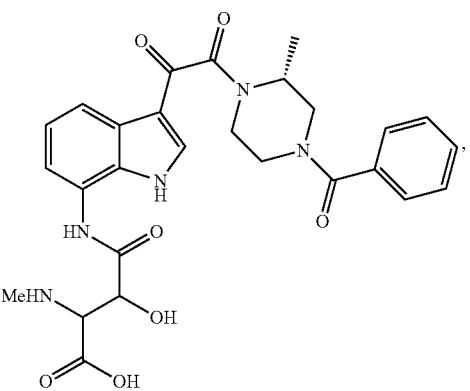
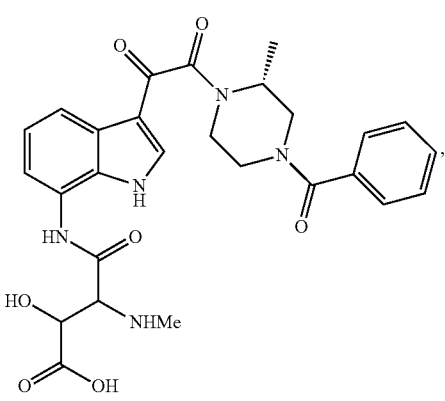

55 -continued
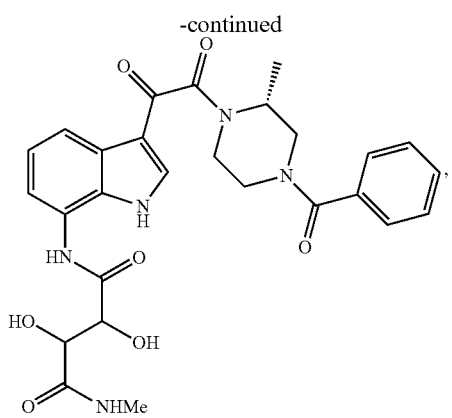
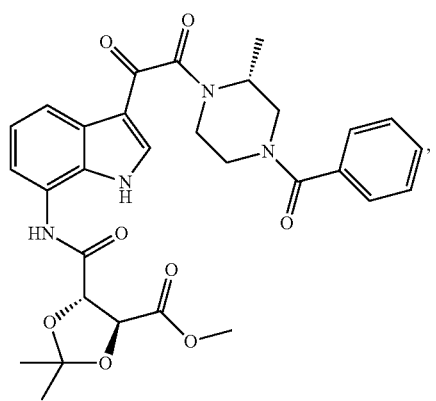
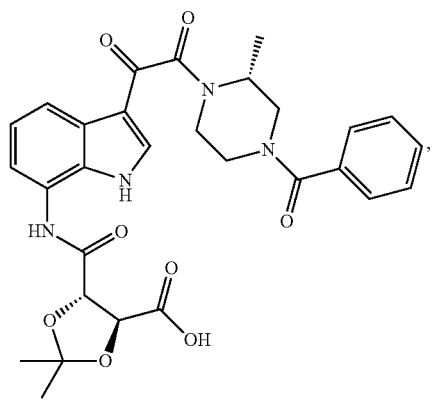
56 -continued
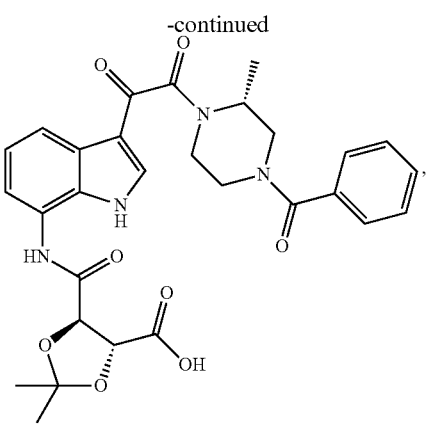
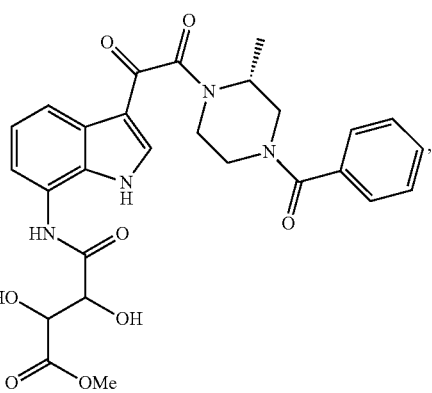
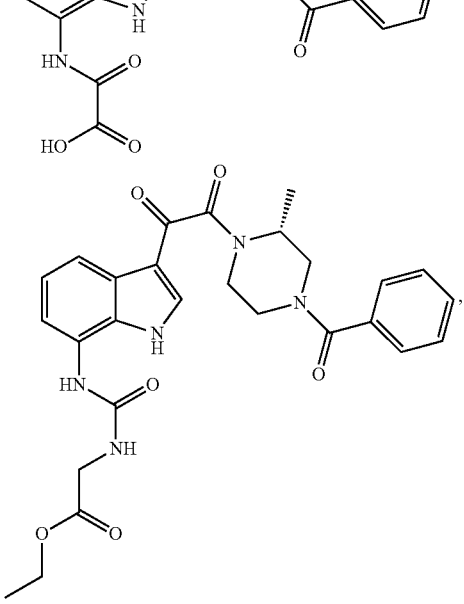

57
-continued
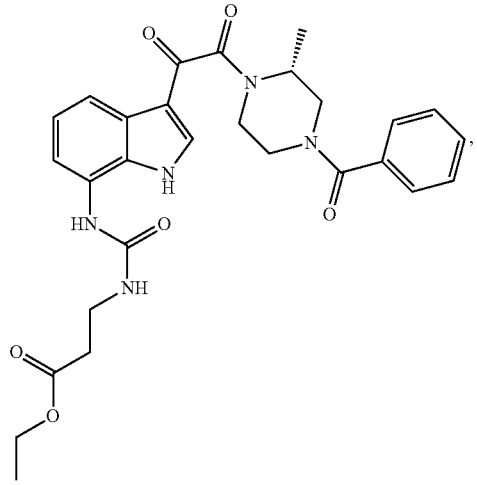
58
-continued
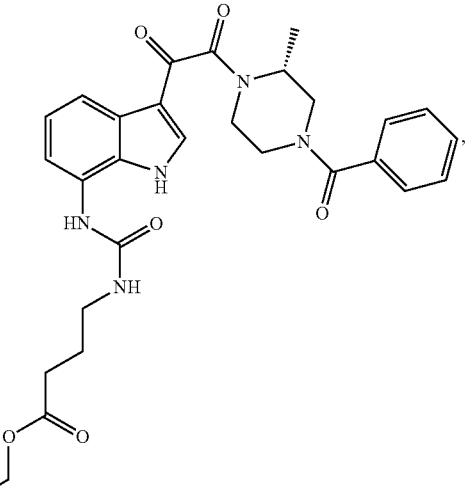
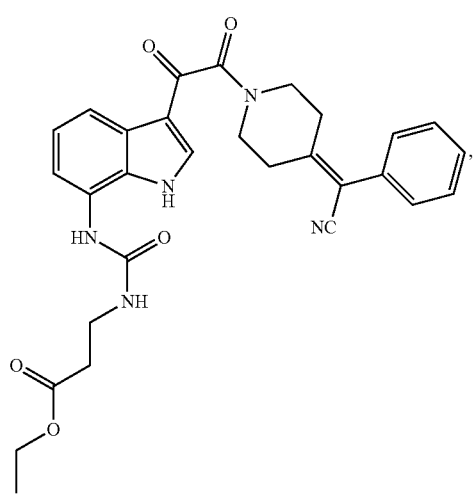
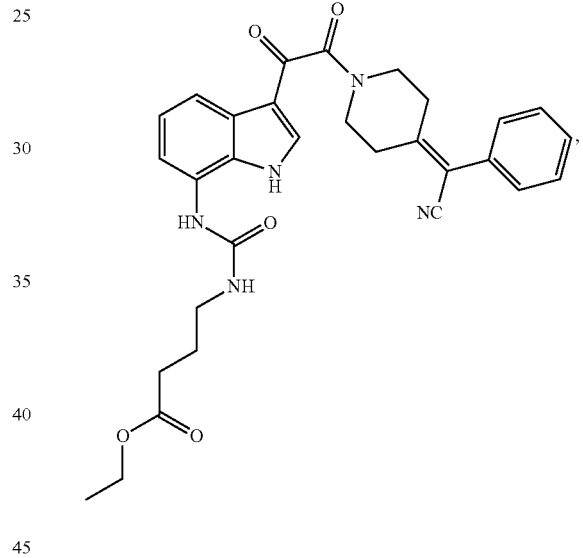
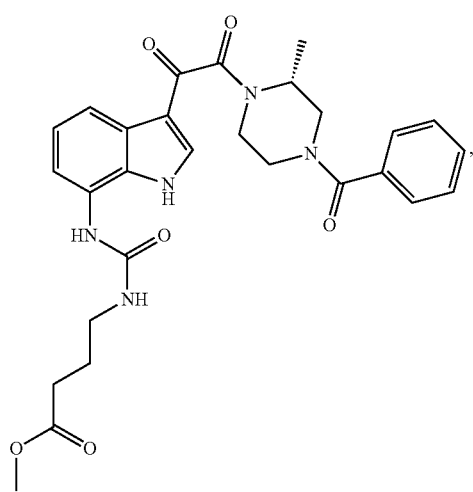
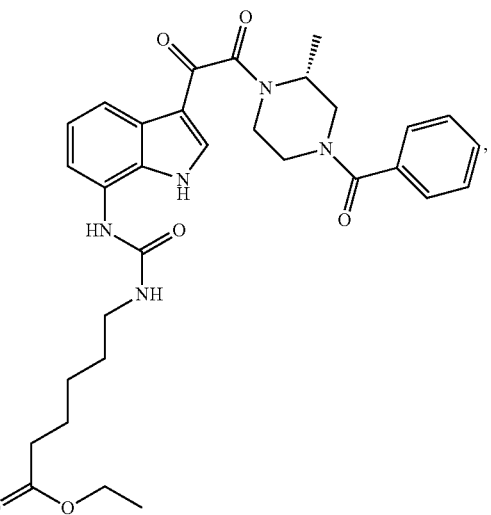

59
-continued
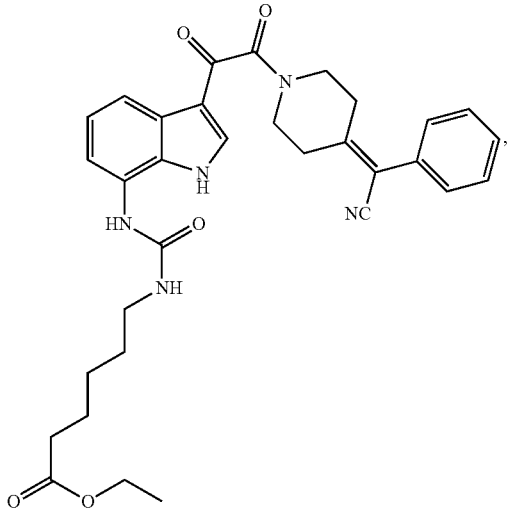
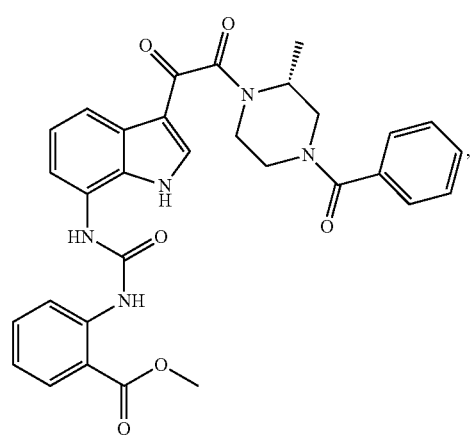
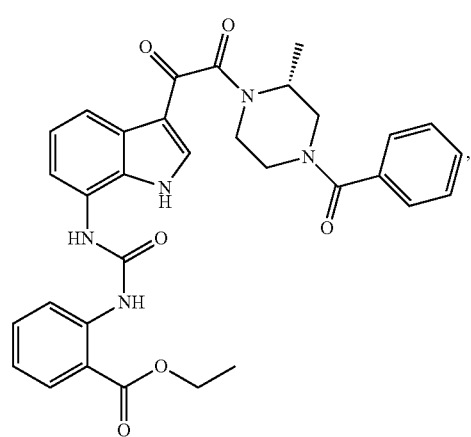
60
-continued
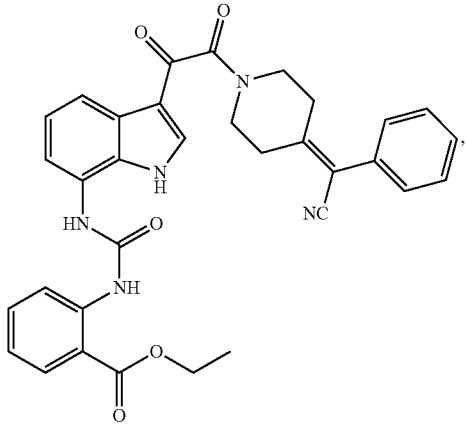
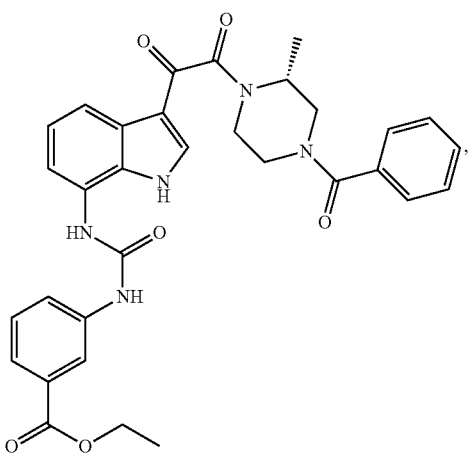
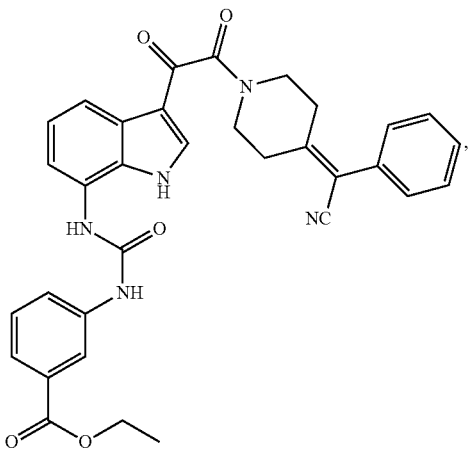

61
-continued
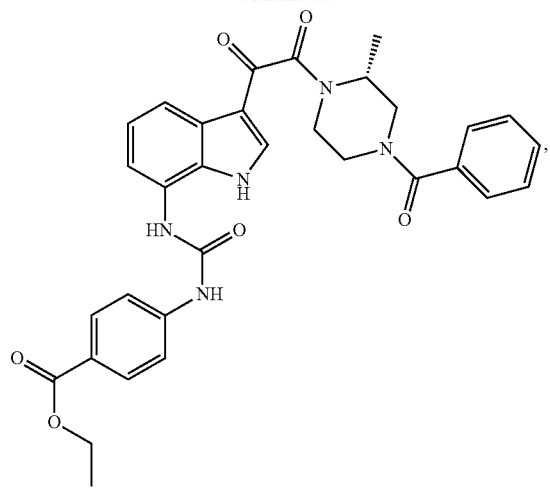
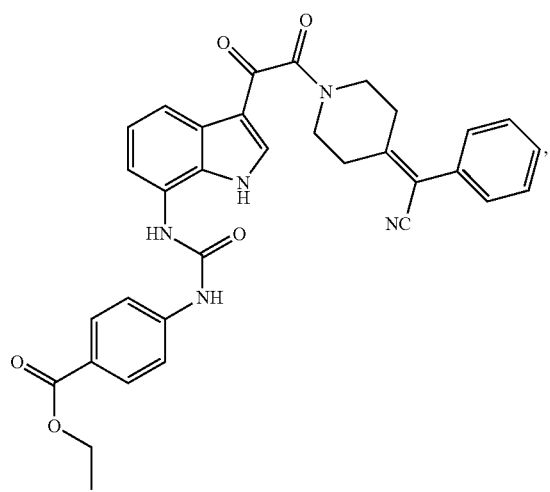
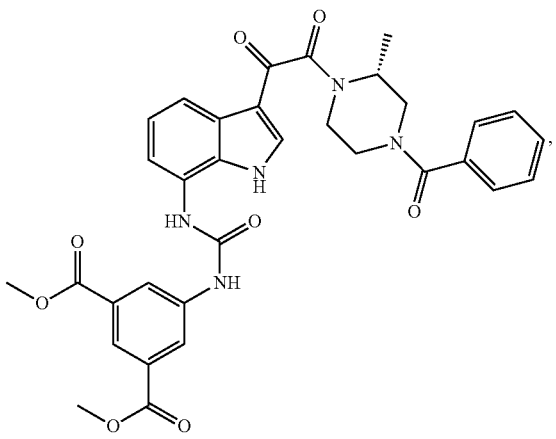
62
-continued
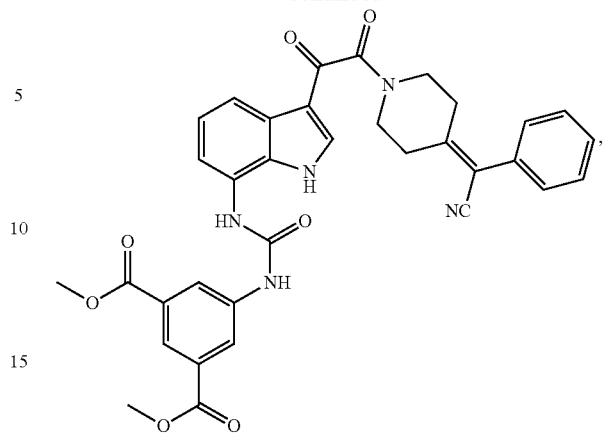
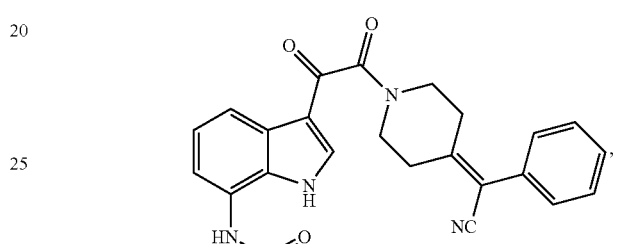
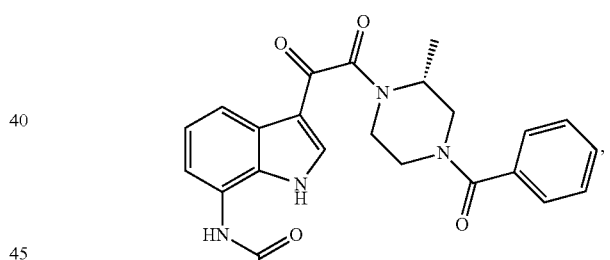
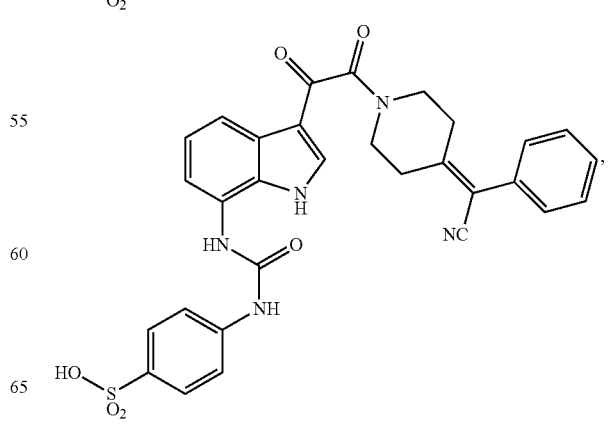

63
-continued
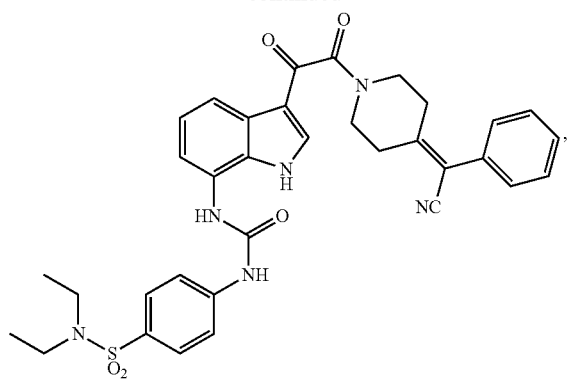
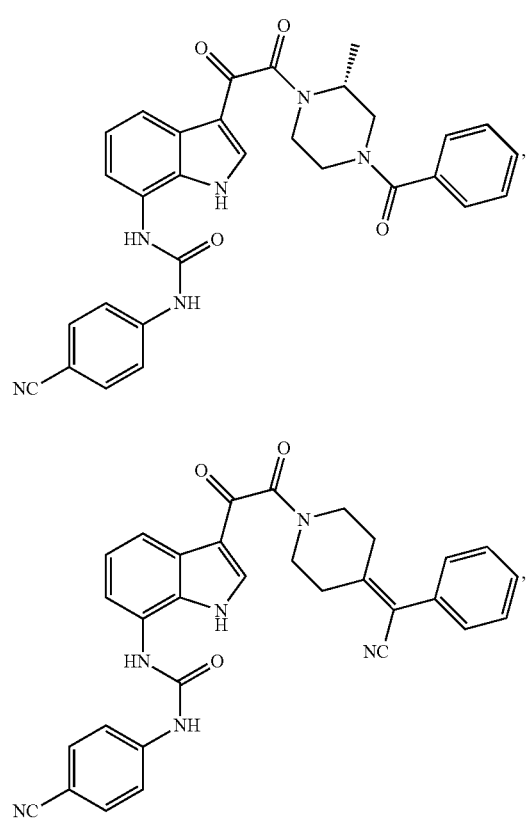
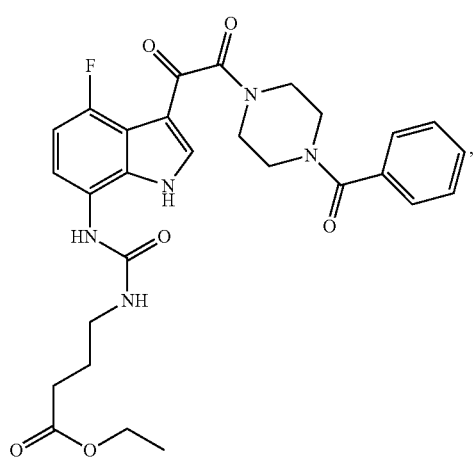
64
-continued
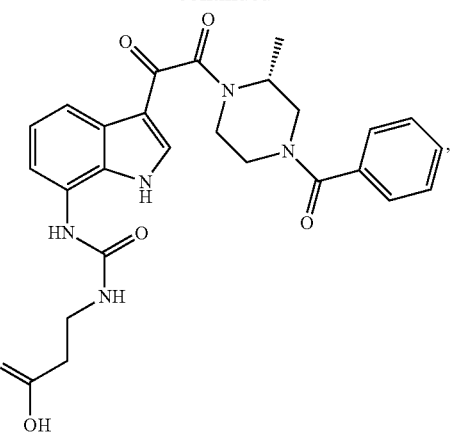
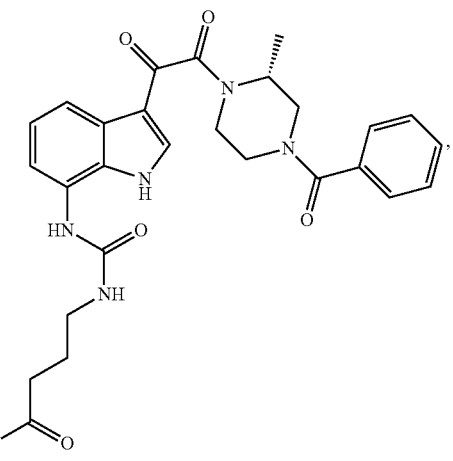

65
-continued
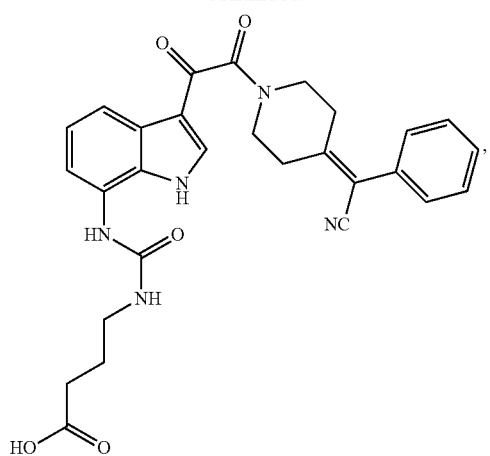
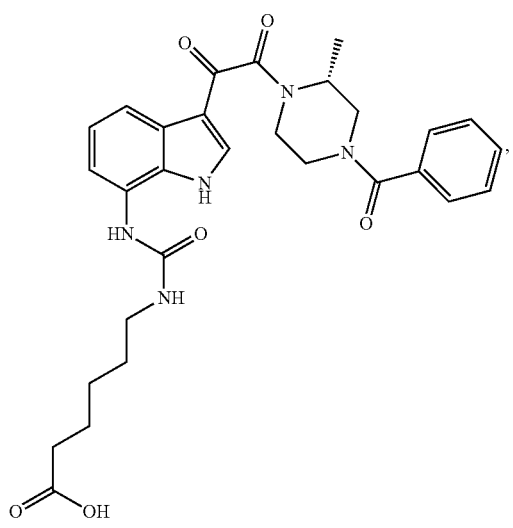
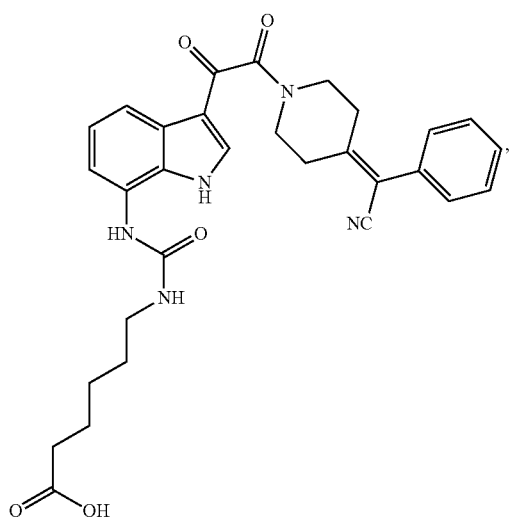
66
-continued
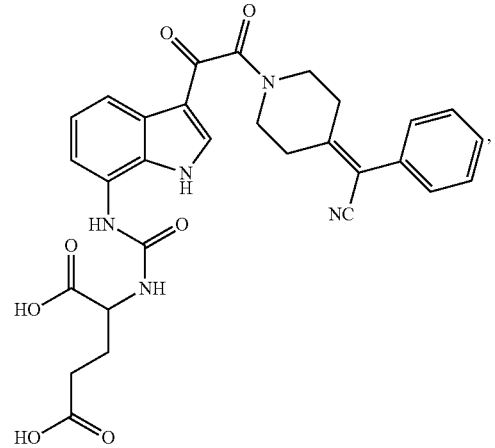
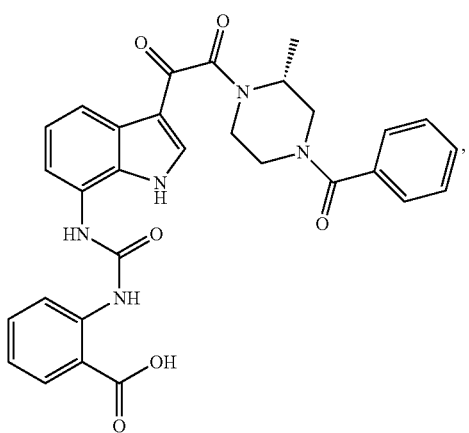
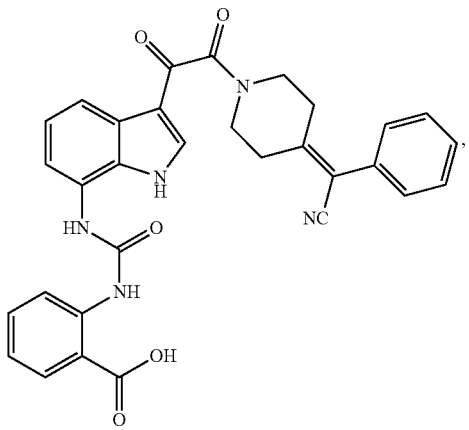

67
-continued
68
-continued
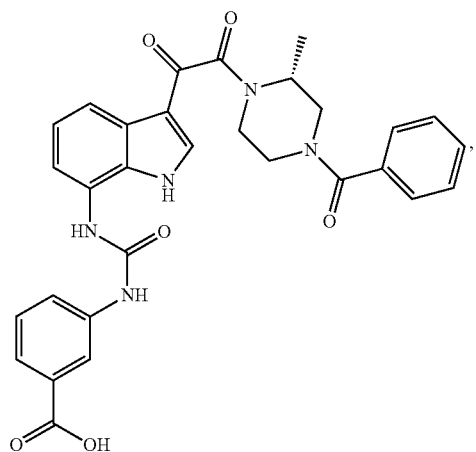
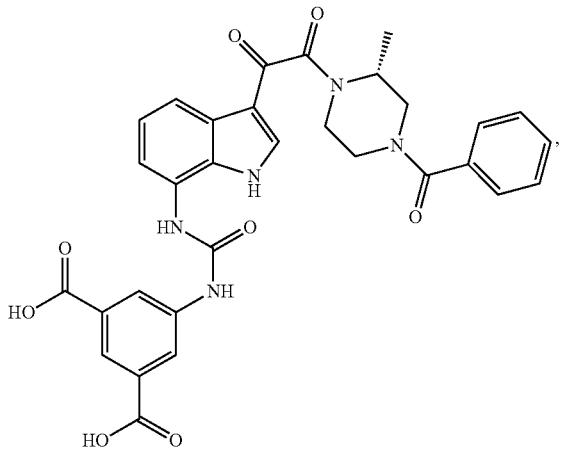
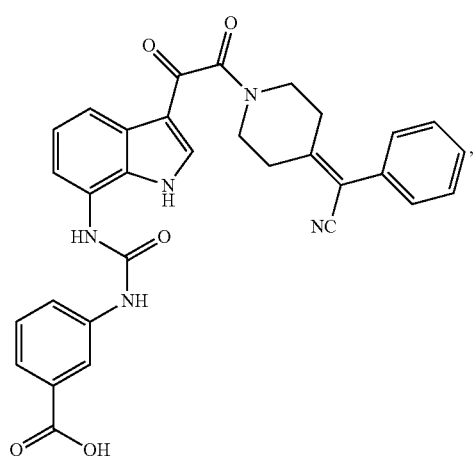
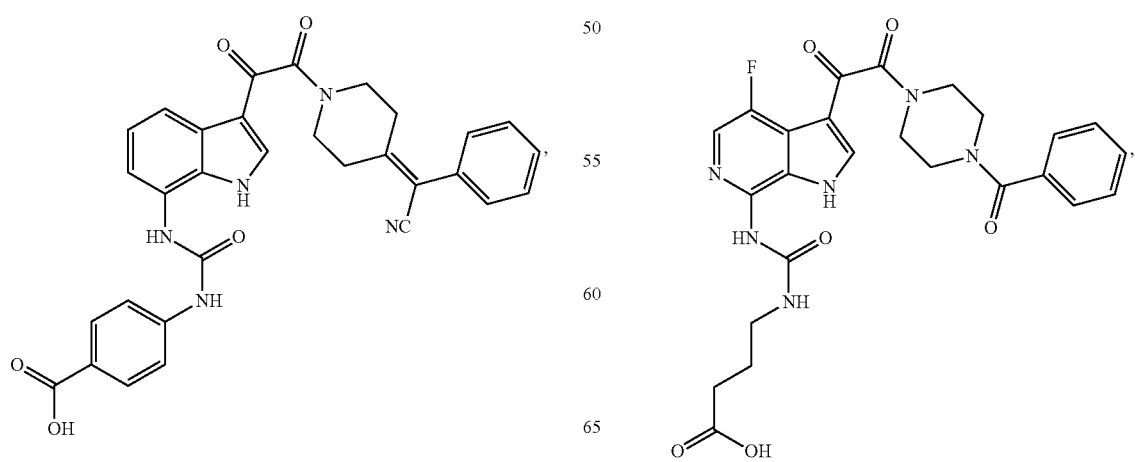

-continued

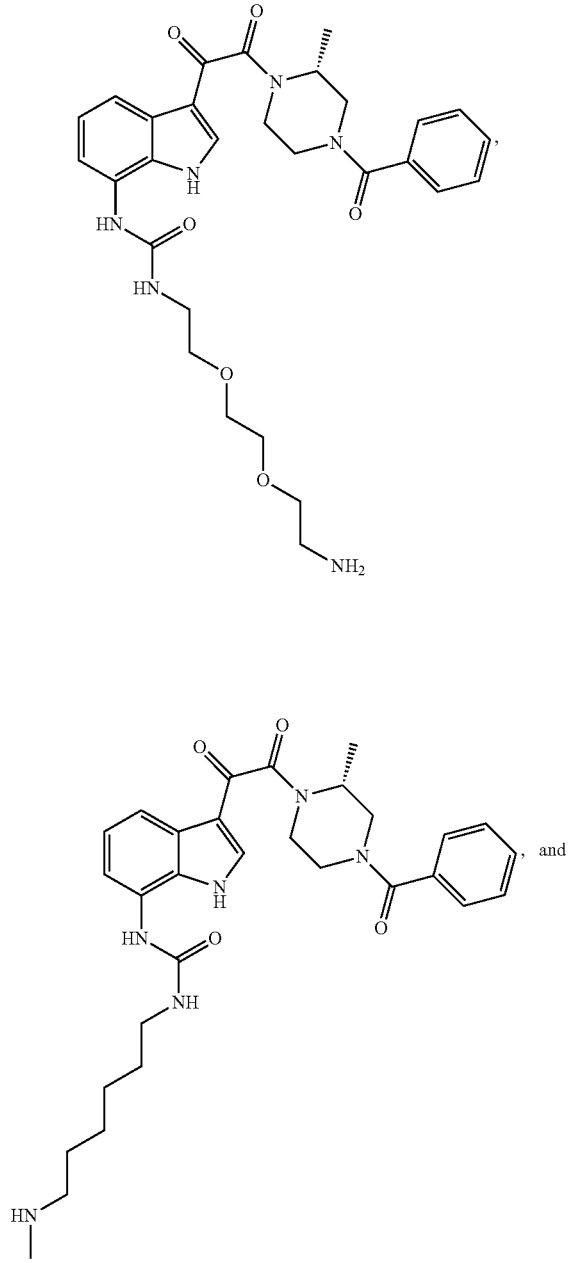

, and

-continued

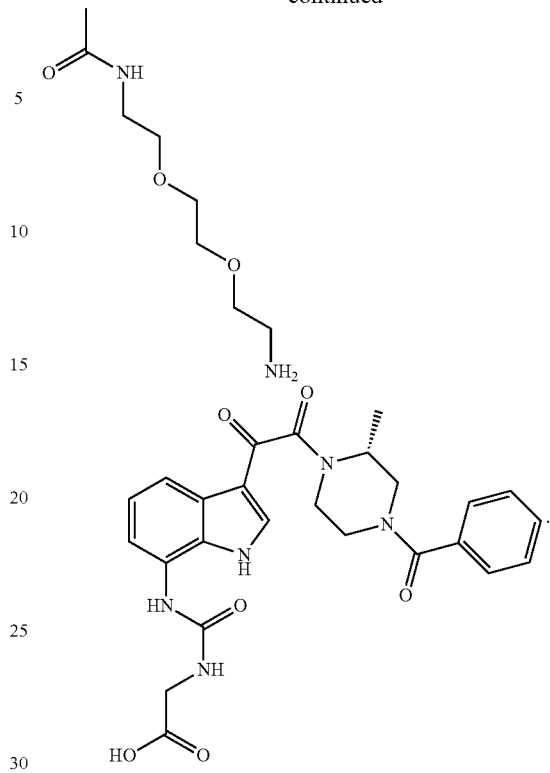

In the compositions and methods of the present invention, the term "antiviral effective amount" means the total amount of each active component of the composition or method that is sufficient to show a meaningful patient benefit, i.e., healing of acute conditions characterized by inhibition of the HIV infection. The terms "treat, treating, treatment" as used herein and in the claims means preventing or ameliorating diseases associated with HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously.

The present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table.

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |

-continued

| Drug Name | Manufacturer | Indication |
|---|---|---|
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec- J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, Sustiva ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |

-continued

| Drug Name | Manufacturer | Indication |
|---|---|---|
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV Infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) | Gilead | HIV infection, AIDS, (reverse transcriptase inhibitor) |
| Emtriva ® (Emtricitabine) (FTC) | Gilead | HIV infection, AIDS, (reverse transcriptase inhibitor) |

| Drug Name | Manufacturer | Indication |
|---|---|---|
| Combivir ® | GSK | HIV infection, AIDS, (reverse transcriptase inhibitor) |
| Abacavir succinate (or Ziagen ®) | GSK | HIV infection, AIDS, (reverse transcriptase inhibitor) |
| Reyataz ® (or atazanavir) | Bristol-Myers Squibb | HIV infection AIDs, protease inhibitor |
| Fuzeon ® (Enfuvirtide or T-20) | Roche/Trimeris | HIV infection AIDs, viral Fusion inhibitor |
| Lexiva ® (or Fosamprenavir calcium) | GSK/Vertex | HIV infection AIDs, viral protease inhibitor |
| Selzentry Maraviroc; (UK 427857) | Pfizer | HIV infection AIDs, (CCR5 antagonist, in development) |
| Trizivir ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| Truvada ® | Gilead | Combination of Tenofovir disoproxil fumarate salt (Viread ®) and Emtriva ® (Emtricitabine) |
| Integrase Inhibitor GS917/JTK-303 Elvitegravir | Gilead/Japan Tobacco | HIV Infection AIDs in development |
| Triple drug combination Atripla ® | Gilead/Bristol-Myers Squibb | Combination of Tenofovir disoproxil fumarate salt (Viread ®), Emtriva ® (Emtricitabine), and Sustiva ® (Efavirenz) |
| Festinavir ® | Oncolys BioPharma | HIV infection AIDs in development |
| CMX-157 Lipid conjugate of nucleotide tenofovir | Chimerix | HIV infection AIDs |
| GSK1349572 Integrase inhibitor | GSK | HIV infection AIDs |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4 + cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |

| Drug Name | Manufacturer | Indication |
|---|---|---|
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |

| Drug Name | Manufacturer | Indication |
|---|---|---|
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the invention herein may be used in combination with another class of agents for treating AIDS which are called HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells*. Meanwell, Nicholas A.; Kadow, John F. Current Opinion in Drug Discovery & Development (2003), 6(4), 451-461. Specifically the compounds can be utilized in combination with other attachment inhibitors, fusion inhibitors, and chemokine receptor antagonists aimed at either the CCR5 or CXCR4 coreceptor.

It will be understood that the scope of combinations of the compounds of this invention with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is Reyataz® (active ingredient Atazanavir). Typically a dose of 300 to 600 mg is administered once a day. This may be co-administered with a low dose of Ritonavir (50 to 500 mgs). Another preferred inhibitor of HIV protease is Kaletra®. Another useful inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

The compounds of the present invention may be administered orally, parenterally (including subcutaneous injections, intravenous, intramuscular, intrasternal injection or infusion techniques), by inhalation spray, or rectally or by other means available in the art, in dosage unit formulations containing conventional non-toxic pharmaceutically acceptable carriers, adjuvants and diluents.

Thus, in accordance with the present invention, there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically effective amount of a compound of the present disclosure.

The pharmaceutical composition may be in the form of orally administrable suspensions or tablets; nasal sprays, sterile injectable preparations, for example, as sterile injectable aqueous or oleaginous suspensions or suppositories.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein set forth can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Chemistry

Abbreviations

The following abbreviations, most of which are conventional abbreviations well known to those skilled in the art, are used throughout the description of the disclosure and the examples. Some of the abbreviations used are as follows:
h=hour(s)
rt=room temperature mol=mole(s)
mmol=millimole(s)
g=gram(s)
mg=milligram(s)
mL=milliliter(s)
TFA=trifluoroacetic Acid
DCE=1,2-Dichloroethane
$CH_2Cl_2$=dichloromethane
TPAP=tetrapropylammonium perruthenate
THF=tetrahydrofuran
DEPBT=3-(diethoxyphosphoryloxy)-1,2,3-benzotriazin-4(3H)-one
DMAP=4-dimethylaminopyridine
P-EDC=polymer supported 1-(3-dimethylaminopropyl)-3-ethylcarbodiimide
EDC=1-(3-dimethylaminopropyl)-3-ethylcarbodiimide
DMF=N,N-dimethylformamide
Hunig's Base=N,N-diisopropylethylamine
MCPBA=meta-chloroperbenzoic Acid
azaindole=1H-pyrrolo-pyridine
4-azaindole=1H-pyrrolo[3,2-b]pyridine
5-azaindole=1H-pyrrolo[3,2-c]pyridine
6-azaindole=1H-pyrrolo[2,3-c]pyridine
7-azaindole=1H-pyrrolo[2,3-b]pyridine
PMB=4-methoxybenzyl
DDQ=2,3-dichloro-5,6-dicyano-1,4-benzoquinone
OTf=trifluoromethanesulfonoxy
NMM=4-methylmorpholine
PIP-COPh=1-benzoylpiperazine
NaHMDS=sodium hexamethyldisilazide
EDAC=1-(3-dimethylaminopropyl)-3-ethylcarbodiimide
TMS=trimethylsilyl
DCM=dichloromethane
DCE=dichloroethane
MeOH=methanol
THF=tetrahydrofuran
EtOAc=ethyl acetate
LDA=lithium diisopropylamide
TMP-Li=2,2,6,6-tetramethylpiperidinyl lithium
DME=dimethoxyethane
DIBALH=diisobutylaluminum hydride
HOBT=1-hydroxybenzotriazole
CBZ=benzyloxycarbonyl
PCC=pyridinium chlorochromate The present invention comprises compounds of Formula I, their pharmaceutical formulations, and their use in patients suffering from or susceptible to HIV infection. The compounds of Formula I include pharmaceutically acceptable salts thereof. General procedures to construct compounds of Formula I and intermediates useful for their synthesis are described in the following Schemes.

Preparation of Compounds of Formula I

It should be noted that in many cases reactions are depicted for only one position of an intermediate, such as the C-7 position of an indole or azaindole, for example. It is to be understood that such reactions could be used at other positions, such as C-2, C-4, C-5 and C-6 position of indole or azaindole, of the various intermediates. Reaction conditions and methods given in the specific examples are broadly applicable to compounds with other substitution and other transformations in this application.

Schemes 1 through 12 describe general reaction schemes for preparing various compounds of Formula I. While these schemes are very general, other permutations such as carrying a precursor or precursors to substituents of template X through the reaction scheme and then converting it to a compound of Formula I in the last step are also contemplated methods of this invention. Non-limiting examples of such strategies follow in subsequent schemes.

I. Amide Formation

Standard conditions such as reacting amine with acyl halide (Scheme 1) carboxyl ester (Scheme 2) and carboxyl acid (Scheme 3) can be used to convert the ketone to the desired amide products. Some general references of these methodologies and directions for use are contained in "Comprehensive Organic Transformation" by Richard C. Larock, Wiley-VCH, New York, 1989, 972 (Carboxylic acids to amides), 979 (Acid halides to amides), 987 (Esters to amides).

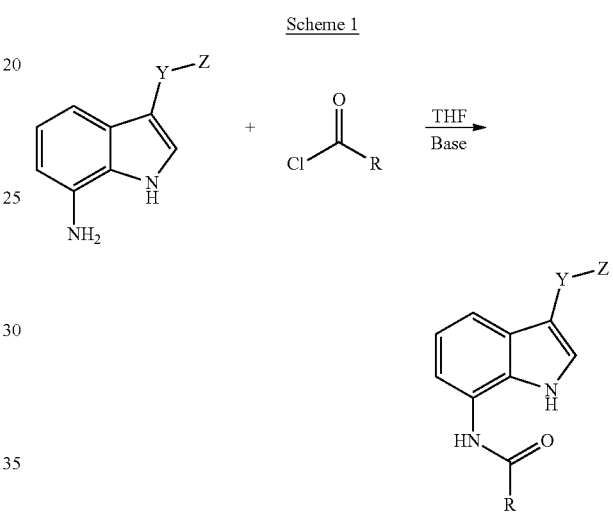

Scheme 1

Scheme 1 depicts a general method for forming an amide from an amine and acyl chloride. An appropriate base (from catalytic to an excess amount) selected from sodium hydride, potassium carbonate, triethylamine, DBU, pyridine, DMAP or di-isopropyl ethyl amine was added into a solution of amine and acyl chloride in an appropriate solvent selected from dichloromethane, chloroform, benzene, toluene, THF, diethyl ether, dioxane, acetone, N,N-dimethylformamide or pyridine at room temperature. Then reaction was carried out at either room temperature or evaluated temperature up to 150° C. over a period of time (30 minutes to 16 hours) to afford the structure of Formula I. Some selected references involving such reactions include a) *Indian J. Chem., Sect B* 1990, 29, 1077; 2) *Chem. Sci.* 1998, 53, 1216; 3) *Chem. Pharm. Bull.* 1992, 40, 1481; 4) *Chem. Heterocycl. Compd.* 2002, 38, 539.

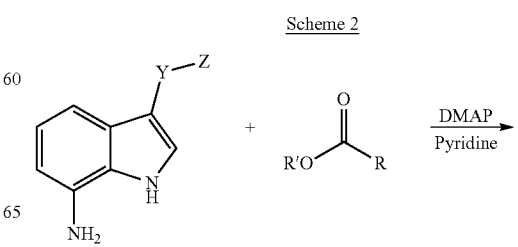

Scheme 2

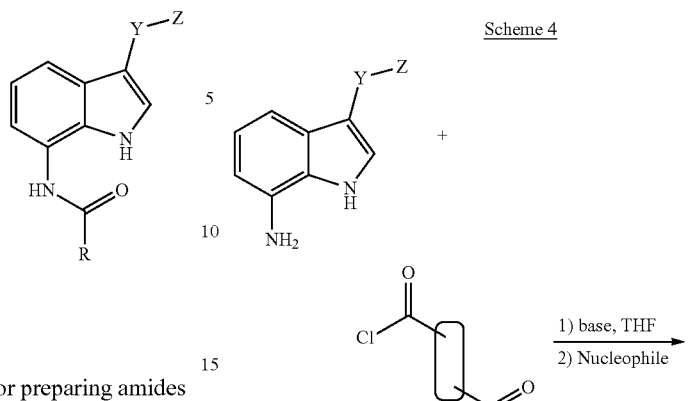

Scheme 2 describes a useful method for preparing amides in Formula I from anilines and esters. With pyridine as solvent and DMAP as base or catalyst, aniline reacted with ester to generate amide over 2 to 16 hours at 100 to 150° C.

Scheme 3

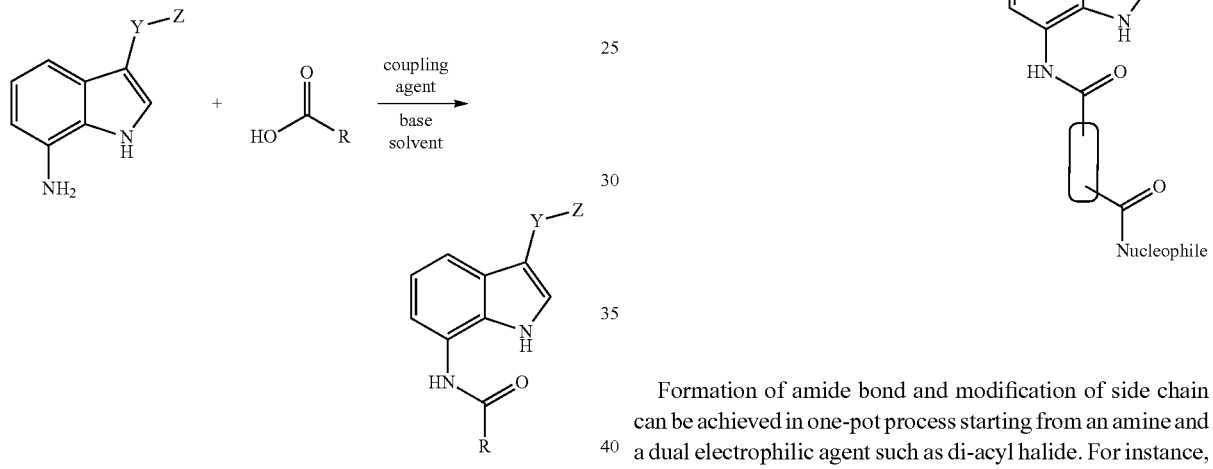

Alternatively, as shown in Scheme 3, an amine can be coupled with an acid using standard amide bond or peptide bond forming coupling reagents. Many reagents for amide bond couplings are known by an organic chemist skilled in the art and nearly all of these are applicable for realizing coupled amide products. The combination of EDAC and triethylamine in tetrahydrofuran or BOPCl and diisopropyl ethyl amine in chloroform have been utilized most frequently but DEPBT, or other coupling reagents such as PyBop could be utilized. Another useful coupling condition employs HATU ((a) J. Chem. Soc. Chem. Comm. 1994, 201; (b) J. Am. Chem. Soc. 1994, 116, 11580). Additionally, DEPBT (3-(diethoxyphosphoryloxy)-1,2,3-benzotriazin-4(3H)-one) and N,N-diisopropylethylamine, commonly known as Hunig's base, represents another efficient method to form the amide bond and provide compounds of Claim I. DEPBT is either purchased from Adrich or prepared according to the procedure described in Organic Lett., 1999, 1, 91. Typically an inert solvent such as DMF or THF is used but other aprotic solvents could be used.

Formation of amide bond and modification of side chain can be achieved in one-pot process starting from an amine and a dual electrophilic agent such as di-acyl halide. For instance, Scheme 4 elicits a tandem reaction involving the first amide bond formation between an aniline and an acyl chloride, followed by a reaction of the second acyl chloride with a nucleophile such as water, alcohol and amine Consequently, an amide with acid, ester or amide functional group on the side chain can be synthesized. An excess of appropriate base selected from sodium hydride, potassium carbonate, triethylamine, DBU, DMAP or di-isopropyl ethyl amine was added into a solution of amine and di acyl chloride in an appropriate solvent selected from dichloromethane, THF, diethyl ether, dioxane or N,N-dimethylformamide at room temperature. Then reaction was carried out at either room temperature or evaluated temperature up to 150° C. over a period of time (30 minutes to 16 hours). Then, an excessive amount of water, alcohol or amine was added into the reaction mixture to product the compound of Formula I.

Scheme 5 and 6 present another general route towards products of Claim I, exemplified by the formation of N-(4-fluoro-1H-indol-7-yl)acetamide derivatives. Being distinguished from the previous approaches described in Scheme 1-4, instead of modulating amino group in the final stage, this route starts from material with defined amine derived functional groups such as amides.

Scheme 5

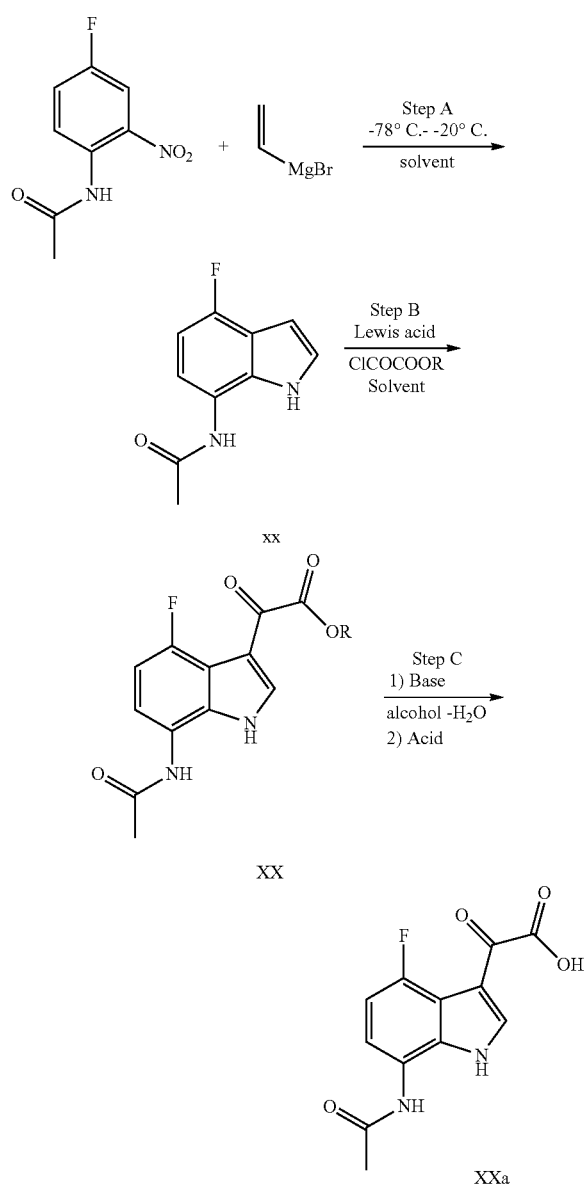

Step A in Scheme 5 depicts the synthesis of an indole intermediate, N-(4-fluoro-1H-indol-7-yl)acetamide, via the well known Bartoli reaction in which vinyl magnesium bromide reacts with an aryl or heteroaryl nitro group, such as N-(4-fluoro-2-Nitrophenyl)acetamide herein, to form a five-membered nitrogen containing ring as shown. Some references for the above transformation include: Bartoli et al. a) *Tetrahedron Lett.* 1989, 30, 2129. b) *J. Chem. Soc. Perkin Trans.* 1 1991, 2757. c) *J. Chem. Soc. Perkin Trans.* 1 1991, 657. d) *Synlett* 1999, 1594. e) *Synth. Commun.* 1991, 21, 611. In the preferred procedure, a solution of vinyl Magnesium bromide in THF (typically 1.0M but from 0.25 to 3.0M) is added dropwise to a solution of the nitro pyridine in THF at −78° under an inert atmosphere of either nitrogen or Argon. After addition is completed, the reaction temperature is allowed to warm to −20° and then is stirred for approximately 12 h before quenching with 20% aq ammonium chloride solution. The reaction is extracted with ethyl acetate and then worked up in a typical manner using a drying agent such as anhydrous magnesium sulfate or sodium sulfate. Products are generally purified using chromatography over Silica gel. Best results are generally achieved using freshly prepared vinyl Magnesium bromide. In some cases, vinyl Magnesium chloride may be substituted for vinyl Magnesium bromide.

Amino indoles or azaindoles may be prepared by methods described in the literature or may be available from commercial sources. Thus there are many methods in the literature for synthesizing amino indoles in addition to the Bartoli method depicted in step A of the scheme. Some alternative syntheses of amino indoles or aza indoles, but are not limited to, those described in the following references: (a) *Bioorg. Med. Chem. Lett.* 2000, 10, 1223; (b) *J. Org. Chem.* 1996, 61, 1155; (c) *Tetrahedron Lett.* 1995, 36, 2411: (d) *Org. Prep. Proced. Int.* 1995, 27, 576; (e) *Indian J. Chem., Sect. B: Org. Chem. Incl. Med. Chem.* 1997, 36, 185; (f) *J. Org. Chem.* 1983, 48, 5130; (g) *Heterocycles* 1981, 16, 1119; (h) Tetrahedron 1976, 32, 773; (i) *J. Am. Chem. Soc.* 1959, 81, 743, and references therein.

Intermediate XX can be prepared by reaction of amido indole or aza-indole, intermediate xx, with an excess of ClCOCOOMe or ClCOCOOEt in the presence of $AlCl_3$ (aluminum chloride) (*Khim. Geterotsikl. Soedin.*, 1987, 100). Typically an inert solvent such as $CH_2Cl_2$ is used but others such as THF, $Et_2O$, DCE, dioxane, benzene, or toluene may find applicability either alone or in mixtures. Other oxalate esters such as propyl, butyl or benzyl mono esters of oxalic acid could also suffice for either method shown above. More lipophilic esters ease isolation during aqueous extractions. Phenolic or substituted phenolic (such as pentafluorophenol) esters enable direct coupling of the H—Z group shown in Scheme 6, such as a piperazine, without activation. Lewis acid catalysts, such as tin tetrachloride, titanium IV chloride, and aluminum chloride are employed in Step B with aluminum chloride being most preferred. Alternatively, the indole or azaindole is treated with a Grignard reagent such as MeMgI (methyl magnesium iodide), methyl magnesium bromide or ethyl magnesium bromide and a zinc halide, such as $ZnCl_2$ (zinc chloride) or zinc bromide, followed by the addition of an oxalyl chloride mono ester, such as ClCOCOOMe (methyl chlorooxoacetate) or another ester as above, to afford the indole or aza-indole glyoxyl ester ((a) *J. Org. Chem.* 2002, 67, 6226; (b) *J. Med. Chem.* 2003, 46, 4236.). Oxalic acid esters such as methyl oxalate, ethyl oxalate or as above are used. Aprotic solvents such as dioxane, $CH_2Cl_2$, $Et_2O$, benzene, toluene, DCE, or the like may be used alone or in combination for this sequence. In addition to the oxalyl chloride mono esters, with or without Lewis acid, oxalyl chloride itself may be reacted with the indole or azaindole, and then further reacted with an appropriate amine, such as a piperazine derivative ((a) WO-00076521; (b) WO-00162255; (c) WO-00204440; (d) WO-02062423).

In step C (Scheme 5), hydrolysis of the ester, intermediate XX, affords a potassium salt of intermediate XXa, which is coupled with mono-benzoylated piperazine derivatives as shown in Scheme 6. Some typical conditions employ methanolic or ethanolic sodium hydroxide followed by careful acidification with aqueous hydrochloric acid of varying molarity but 1M HCl is preferred. The acidification is not utilized in many cases as described above for the preferred conditions. Lithium hydroxide, potassium hydroxide or potassium carbonate could also be employed and varying amounts of water could be added to the alcohols. Propanols or butanols could also be used as solvents. Elevated temperatures up to the boiling points of the solvents may be utilized if ambient temperatures do not suffice. Alternatively, the hydrolysis may be carried out in a non polar solvent such as CH₂Cl₂ or THF in the presence of Triton B. Temperatures of −78° C. to the boiling point of the solvent may be employed but −10° C. is preferred. Other conditions for ester hydrolysis are listed in "Comprehensive Organic Transformation" by Richard C. Larock, Wiley-VCH, New York, 1989, 981. And both these references and many of the conditions for ester hydrolysis are well known to chemists of average skill in the art.

The Alternative Procedures for Step B and C: Imidazolium Chloroaluminate

We found that ionic liquid 1-alkyl-3-alkylimidazolium chloroaluminate is generally useful in promoting the Friedel-Crafts type acylation of indoles and azaindoles. The ionic liquid is generated by mixing 1-alkyl-3-alkylimidazolium chloride with aluminum chloride at room temperature with vigorous stirring. 1:2 or 1:3 molar ratio of 1-alkyl-3-alkylimidazolium chloride to aluminum chloride is preferred. One particular useful imidazolium chloroaluminate for the acylation of azaindole with methyl or ethyl chlorooxoacetate is the 1-ethyl-3-methylimidazolium chloroaluminate. The reaction is typically performed at ambient temperature and the azaindoleglyoxyl ester can be isolated. More conveniently, we found that the glyoxyl ester can be hydrolyzed in situ at ambient temperature on prolonged reaction time (typically overnight) to give the corresponding glyoxyl acid for amide formation ((a) *Chem. Rev.* 1999, 99, 2071; (b) *Chem. Commun.* 1996, 2753; (c) WO 0015594; (d) *Tetrahedron Lett.* 2002, 43, 5793).

Scheme 6

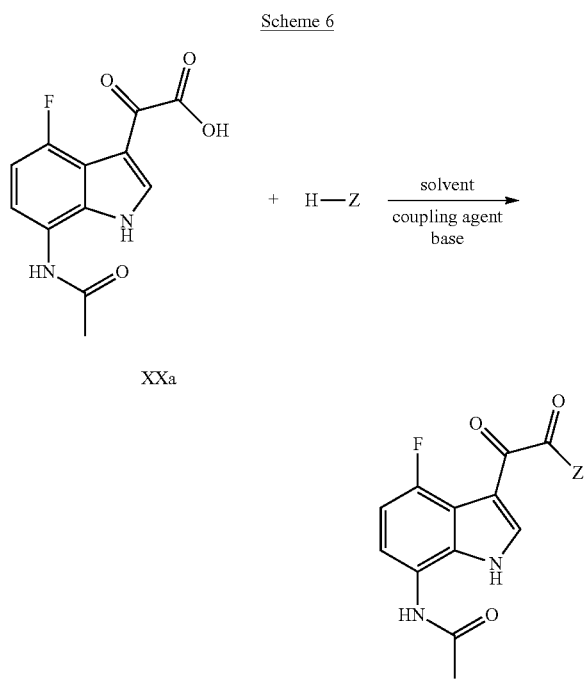

XXa

The acid or its salt intermediate can be coupled with an amine using standard amide bond or peptide bond forming coupling reagents. Many reagents for amide bond couplings are known by an organic chemist skilled in the art and nearly all of these are applicable for realizing coupled amide products. The combination of EDAC and triethylamine in tetrahydrofuran or BOPCl and diisopropyl ethyl amine in chloroform have been utilized most frequently but DEPBT, or other coupling reagents such as PyBop could be utilized. Another useful coupling condition employs HATU ((a) *J. Chem. Soc. Chem. Comm.* 1994, 201; (b) *J. Am. Chem. Soc.* 1994, 116, 11580). Additionally, DEPBT (3-(diethoxyphosphoryloxy)-1,2,3-benzotriazin-4(3H)-one) and N,N-diisopropylethylamine, commonly known as Hunig's base, represents another efficient method to form the amide bond and provide compounds of Claim I. DEPBT is either purchased from Adrich or prepared according to the procedure described in *Organic Lett.,* 1999, 1, 91. Typically an inert solvent such as DMF or THF is used but other aprotic solvents could be used.

II. Urea Formation

Scheme 7

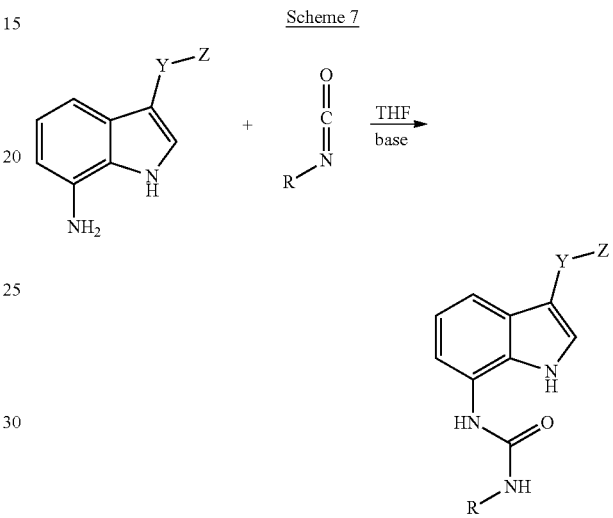

Scheme 7 illustrates a general method for forming a urea from an amine and isocyanide. An appropriate base (from catalytic to an excess amount) selected from sodium hydride, potassium carbonate, triethylamine, DBU, pyridine, DMAP or di-isopropyl ethyl amine was added into a solution of amine and isocyanide in an appropriate solvent selected from dioxane, dichloromethane, chloroform, benzene, toluene, xylene, THF, diethyl ether, petroleum ether, acetone, N,N-dimethylformamide or pyridine at room temperature. Then reaction was carried out at either room temperature or evaluated temperature up to 150° C. over a period of time (30 minutes to 16 hours) to afford the structure of Formula I. Selected references involving such transformations reaction include a) *Izv. Akad. Nauk., Ser. Khim.* 1995, 390; b) *Eur. J. Med. Chem.* 1994, 29, 963; c) *Liebigs Ann. Chem.* 1992, 159; d) *J. Prakt. Chem.* 1990, 332, 439; e) *J. Org. Chem.* 1965, 30, 2809; f) *J. Org. Chem.* 1961, 26, 5238; g) *Eur. J. Med. Chem.* 1998, 33, 83.

III. Carbamate Formation

Scheme 8

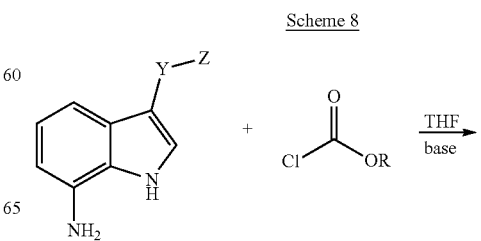

-continued

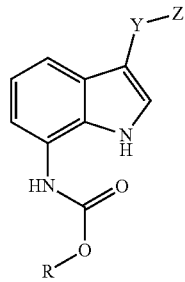

Scheme 8 describes a general method for forming a carbamate from an amine and chloro formate. An appropriate base (from catalytic to an excess amount) selected from sodium hydride, potassium carbonate, triethylamine, DBU, pyridine, DMAP or di-isopropyl ethyl amine was added into a solution of amine and chloro formate in an appropriate solvent selected from dioxane, dichloromethane, chloroform, benzene, toluene, xylene, THF, diethyl ether, petroleum ether, acetone, N,N-dimethylformamide or pyridine at room temperature. Then reaction was carried out at either room temperature or evaluated temperature up to 150° C. over a period of time (30 minutes to 16 hours) to afford the structure of Formula I. Selected references involving such transformations reaction include a) *Synth. Commun.* 1996, 26, 4253; b) *J. Med. Chem.* 1996, 39, 304; c) *Synlett.* 1995, 859; d) *Tetrahedron* 1995, 51, 5057; e) *J. Heterocycl. Chem.* 1990, 27, 1549; f) *J. Heterocycl. Chem.* 1985, 22, 1061; g) *Pharmazie* 2000, 55, 356.

IV. Sulfonamide and Sulfamide Formation

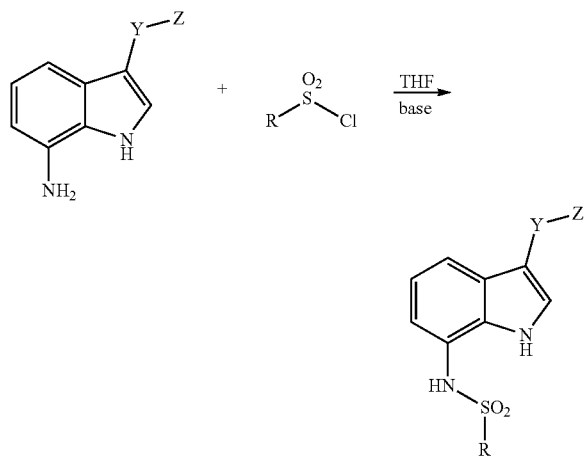

Scheme 9

Scheme 9 describes a general method for forming a sulfonamide or sulfamide from an amine and sulfonyl chloride or sulfamoyl chloride. An appropriate base (from catalytic to an excess amount) selected from sodium hydride, potassium carbonate, triethylamine, DBU, pyridine, DMAP or di-isopropyl ethyl amine was added into a solution of amine and sulfonyl chloride or sulfamoyl chloride in an appropriate solvent selected from dioxane, dichloromethane, chloroform, benzene, toluene, xylene, THF, diethyl ether, petroleum ether, acetone, N,N-dimethylformamide or pyridine at room temperature. Then reaction was carried out at either room temperature or evaluated temperature up to 150° C. over a period of time (30 minutes to 16 hours) to afford the structure of Formula I. Selected references involving such transformations reaction include a) *J. Med. Chem.* 1996, 39, 4116; b) *Farmaco* 1996, 51, 637; c) *Aust. J. Chem.* 1997, 50, 19; d) *Arch. Pharm.* 1996, 329, 161; e) *J. Org. Chem.* 1995, 60, 5969; f) *Arch. Pharm.* 1996, 329, 229; g) *J. Org. Chem.* 2000, 1263; h) *Tetrahedron* 2001, 57, 5009; i) *Bull. Soc. Chim. Fr.* 1945, 12, 954; j) *Helv. Chim. Acta.* 1942, 25, 1485; k) *Eur. J. Med. Chem.* 1997, 32, 901.

V. Guanidine Formation

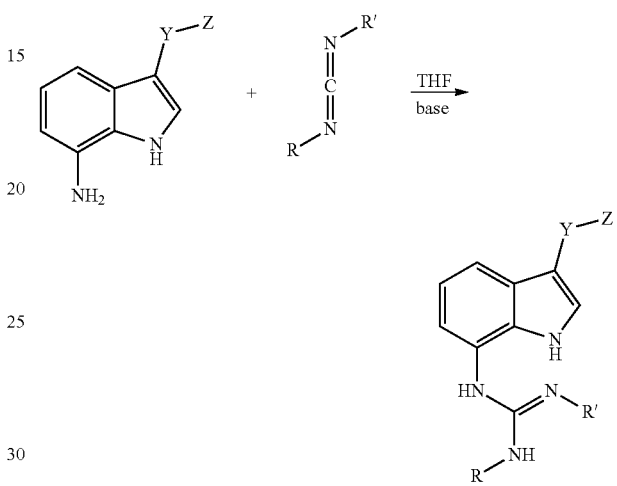

Scheme 7

Scheme 10 represents a general method for forming a urea from an amine and carbodiimide. An appropriate base (from catalytic to an excess amount) selected from sodium hydride, potassium carbonate, triethylamine, DBU, pyridine, DMAP or di-isopropyl ethyl amine was added into a solution of amine and carbodiimide in an appropriate solvent selected from dioxane, dichloromethane, chloroform, benzene, toluene, xylene, THF, diethyl ether, petroleum ether, acetone, N,N-dimethylformamide or pyridine at room temperature. Then reaction was carried out at either room temperature or evaluated temperature up to 150° C. over a period of time (30 minutes to 16 hours) to afford the structure of Formula I. Selected references involving such transformations reaction include: a) Yamamoto, N.; Isobe, M. *Chem. Lett.* 1994, 2299; b) Kurzer, F., et al. *Chem. Sci.* 1991, 46, 530-540; c) Molina, P.; Alajarin, M.; Sanchez-Andrada, P. *Tetrahedron Lett.* 1995, 36, 9405.

VI. Cyclic Urea Formation

Scheme 11 and 12 depicts specific examples of building cyclic ureas from 7-amino-indole derivatives. Behaving as a double-nucleophile, the amino group in 7-amino-indole compound can react with a double-electrophile to form the urea ring of Formula I. Very specifically, in THF, dioxane, ether or other aprotic organic solvents, with a base selected from sodium hydride, potassium carbonate, triethylamine, DBU, pyridine, DMAP or di-isopropyl ethyl amine, it reacts with bis(2-chloroethyl)carbamic chloride to afford a cyclic urea chloride (Scheme 11). Further reaction with nucleophiles allows conversion of the remaining chloride to other functional groups (e.g., hydroxyl, ester, ether, amine) (Scheme 12). Similarly, it forms a new ring with reagent isocyanato esters which possesses two different electrophilic centers (isocyanate and ester) (Scheme 13). Selected references involving such transformations reaction include: a) Ryczek, J. Pol. J. Chem. 1996, 70, 1518; b) Scicinski, J. J., et. al. Bioorg. Med. Chem. Lett. 1998, 8, 3609.

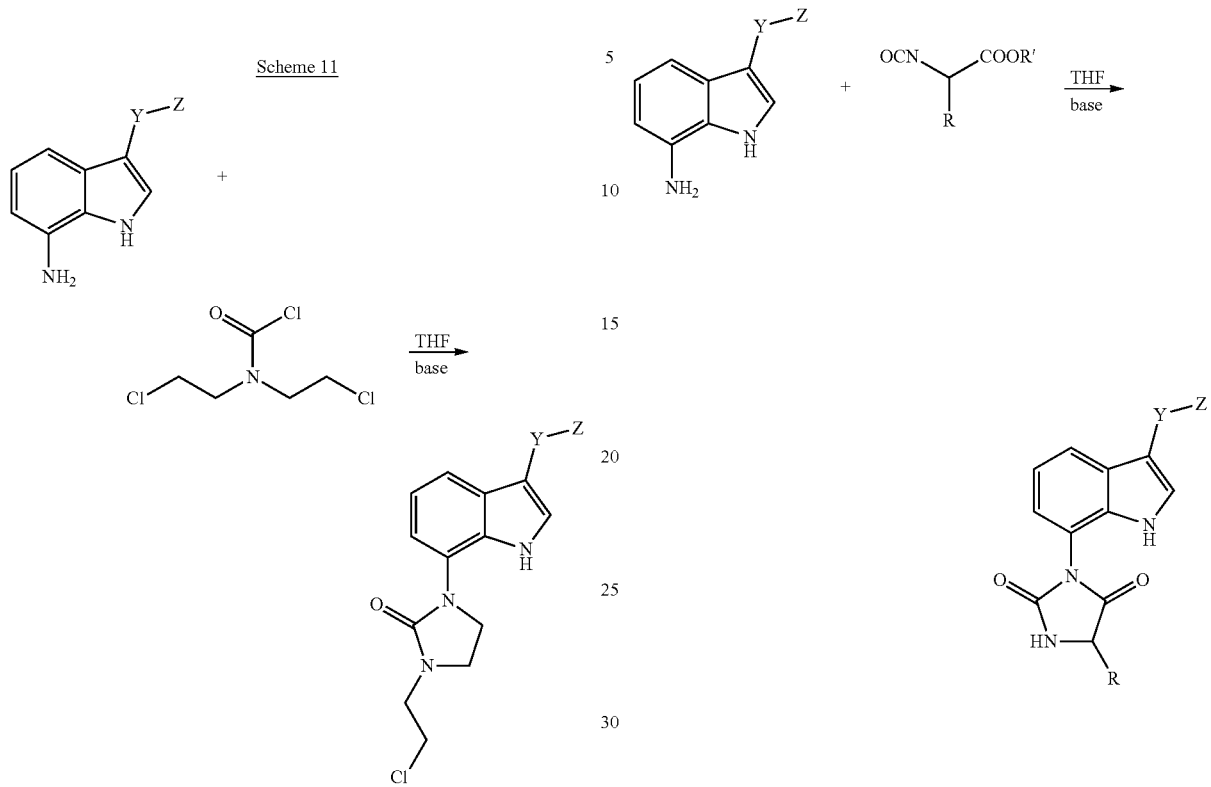

It should be noted that the above reactions are depicted for only C-& position of a starting indole system. It is to be understood that such reactions could be used at other positions of a variety of indole or azaindole systems during the construction of compounds of Formula I. Reaction conditions and methods given in the specific examples are broadly applicable to compounds with other substitution and to other transformations in this application.

EXAMPLES

Experimental Procedures

The following examples represent typical syntheses of the compounds of Formula I as described generally above. These examples are illustrative only and are not intended to limit the invention in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker DPX-300B or Varian Gemini 300 at 300 MHz as stated). The chemical shifts were reported in ppm on the δ scale relative to δTMS=0. The following internal references were used for the residual protons in the following solvents: CDCl$_3$ ($\delta_H$ 7.26), CD$_3$OD ($\delta_H$ 3.30), and DMSO-d6 ($\delta_H$ 2.50). Standard acronyms were employed to describe the multiplicity patterns: s (singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS Methods (i.e., Compound Identification)

Column A: XTERRA C18 S7 3.0×50 mm column

Column B: XTERRA 4.6×50 mm C18 5 um column

Column C: XTERRA MS C18 5 um 4.6×30 mm column

Column D: XTERRA MS C18 4.6×30 mm column

Column E: Phenomenex 5u C18 4.6×30 mm column

Column F: XTERRA 4.6×30 mm S5 column

Column G: Atlantis 4.6×30 mm 5u column

Column H: Phenomenex 4.6×50 mm C18 column

Column I: Phenomenex-Luna 4.6×50 mm S10 column

Gradient: 100% Solvent A/0% Solvent B to 0% Solvent A/100% Solvent B

Gradient time: 2 minutes

Hold time 1 minute

Flow rate: 5 ml/min

Detector Wavelength: 220 nm

Solvent System I

Solvent A: 10% MeOH/90% H$_2$O/0.1% Trifluoroacetic Acid

Solvent B: 10% H$_2$O/90% MeOH/0.1% Trifluoroacetic Acid

Solvent System II

Solvent A: 5% MeCN/95% H$_2$O/10 mm ammonium acetate

Solvent B: 95% MeCN/5% H$_2$O/10 mm ammonium acetate

All the LC-MS in the following sections, except which are specified using solvent system II, were obtained by using solvent system I.

Compounds purified by preparative HPLC were diluted in methanol (1.2 ml) and purified using the following methods on a Shimadzu LC-10A automated preparative HPLC system.

Preparative HPLC Method (i.e., Compound Purification)

Purification Method: Initial gradient (40% B, 60% A) ramp to final gradient (100% B, 0% A) over 20 minutes, hold for 3 minutes (100% B, 0% A)

Solvent A: 10% MeOH/90% H$_2$O/0.1% Trifluoroacetic Acid

Solvent B: 10% H$_2$O/90% MeOH/0.1% Trifluoroacetic Acid

Column: YMC C18 S5 20×100 mm column

Detector Wavelength: 220 nm

Typical Procedures and Characterization of Selected Examples:

Typical Procedure to Prepare Amino-Indole Procursors

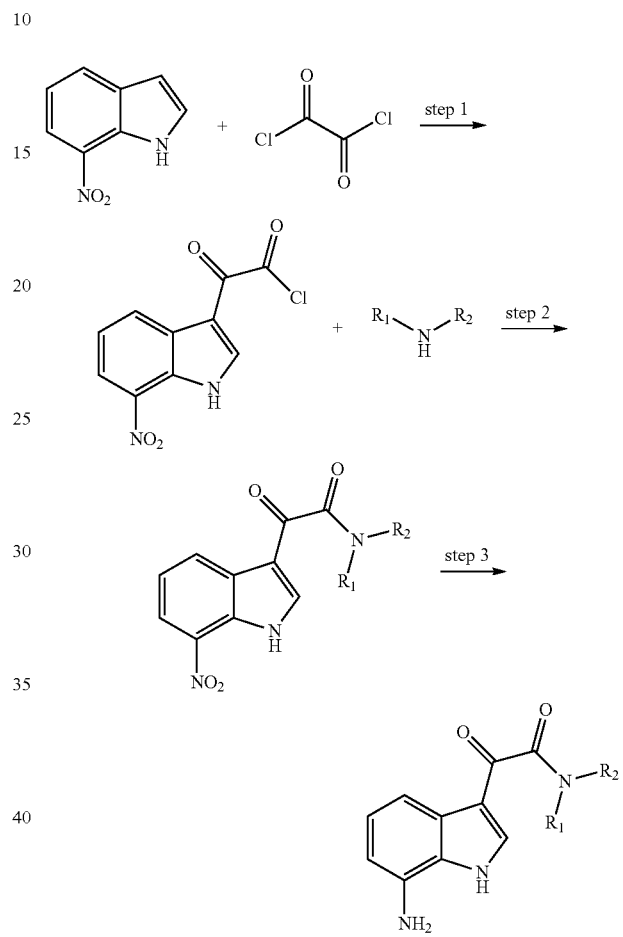

Step 1: 7-Nitro indole (1 eq.) and oxalyl dichloride (10 eq.) were mixed in ether or CH$_2$Cl$_2$. The reaction was stirred for 24 hours and 2-(7-nitro-1H-indol-3-yl)-2-oxoacetyl chloride precipitated from solution. Filtration offered yellow solid which was dried under vacuum and used in Step 2 without purification.

Step 2: iPr$_2$NEt (1-10 eq.) was added into a solution of 2-(7-nitro-1H-indol-3-yl)-2-oxoacetyl chloride from Step 1 and amine (1 eq.) in THF, dioxane or CH$_2$Cl$_2$. The reaction was stirred at room temperature for 24 hours, before being quenched with NaHCO$_3$ (equal volume to THF, dioxane or CH$_2$Cl$_2$ used). The aqueous phase was extracted with EtOAc (3× equal volume to THF, dioxane or CH$_2$Cl$_2$ used). The combined organic phase was dried over MgSO4, filtered and concentrated under vacuum to give a crude product, nitro indole 2-oxoacetyl amide, which was used without purification in the Step 3.

| Compd. Number | Structure | Amine | MS (M + H)+ Calcd. | MS (M + H)+ Observ. And Retention Time and NMR |
|---|---|---|---|---|
| In-A-1 | (structure) | (structure) | 421.2 | 421.2<br>1.67 min<br>(column I) |
| In-A-2 | (structure) | (structure) | 421.2 | 421.0<br>1.56 min<br>(column C) |
| In-A-3 | (structure) | (structure) | 415.1 | 415.0<br>1.72 min<br>(column C) |

Step 3: Reduction of nitro group to amine group used one of the following methods.

Method A: Nitro indole 2-oxoacetyl amide and catalytic amount of palladium on carbon (Pd—C) was mixed in EtOH. The mixture was hydrogenated using Parr reactor under hydrogen pressure of 40-50 psi at room temperature for 24 hours. Then, solid was removed via filtration and filtrate was concentrated under vacuum to give crude amino indole 2-oxoacetyl amide which could be used as was or purified by silica gel chromatography.

Method B: An excess of Fe (10-50 eq.) was added into the solution of nitro indole 2-oxoacetyl amide in saturated aqueous NH4Cl-EtOH (volume 1:1). The mixture was stirred at room temperature to 115° C. for 24 hours to 3 days. Solid was removed via filtration and solvents were removed under vacuum. Then, the residue was partitioned between water and EtOAc (equal volume to solvents used in reaction). The aqueous phase was extracted with EtOAc (3×e equal volume to solvents used in reaction). The combined organic phase was dried over MgSO4, filtered and concentrated under vacuum to give a crude amino indole 2-oxoacetyl amide which could be used as was or purified by silica gel chromatography.

| Compd. Number | Structure | Method | MS (M + H)+ Calcd. | MS (M + H)+ Observ. And Retention Time and NMR |
|---|---|---|---|---|
| In-B-1 | (structure) | B | 391.2 | 391.2<br>1.68 min<br>(column F) |

| Compd. Number | Structure | Method | MS (M + H)+ Calcd. | MS (M + H)+ Observ. And Retention Time and NMR |
|---|---|---|---|---|
| In-B-2 | 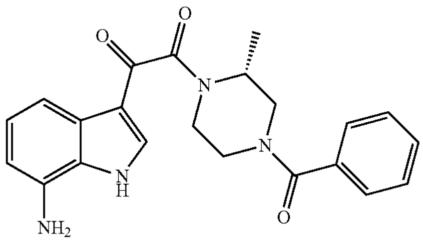 [SMILES: C[C@@H]1CN(C(=O)c2ccccc2)CCN1C(=O)C(=O)c1c[nH]c2c([N+](=O)[O-])cccc12] | A | 391.2 | 391.2 1.12 min (column C) |
| In-B-3 | 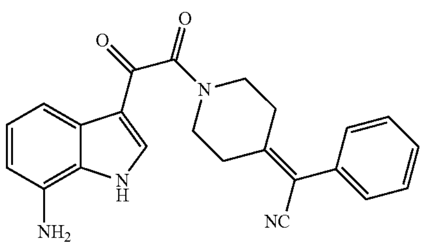 [SMILES: N#CC(=C1CCN(C(=O)C(=O)c2c[nH]c3c([N+](=O)[O-])cccc23)CC1)c1ccccc1] | B | 385.2 | 385.1 1.28 min (column C) |

Typical Procedure to Prepare Amide Derivatives from Amino-Indole Precursors

General Procedures:

Method A: An excess of triethyl amine or di-isopropyl ethyl amine was added into a solution of I-1-(7-amino-1H-indol-3-yl)-2-(4-benzoyl-2-methylpiperazin-1-yl)ethane-1,2-dione, amine-1 (1 eq.) and acyl chloride (1 to 5 eq.) in dry THF. After 16 hours, the reaction mixture was partitioned between saturated NaHCO₃ and EtOAc, and the aqueous phase was extracted with EtOAc. Then the combined organic layer was dried over MgSO₄ and concentrated to offer a residue which was purified using Shimadzu automated preparative HPLC System to afford the desired amide.

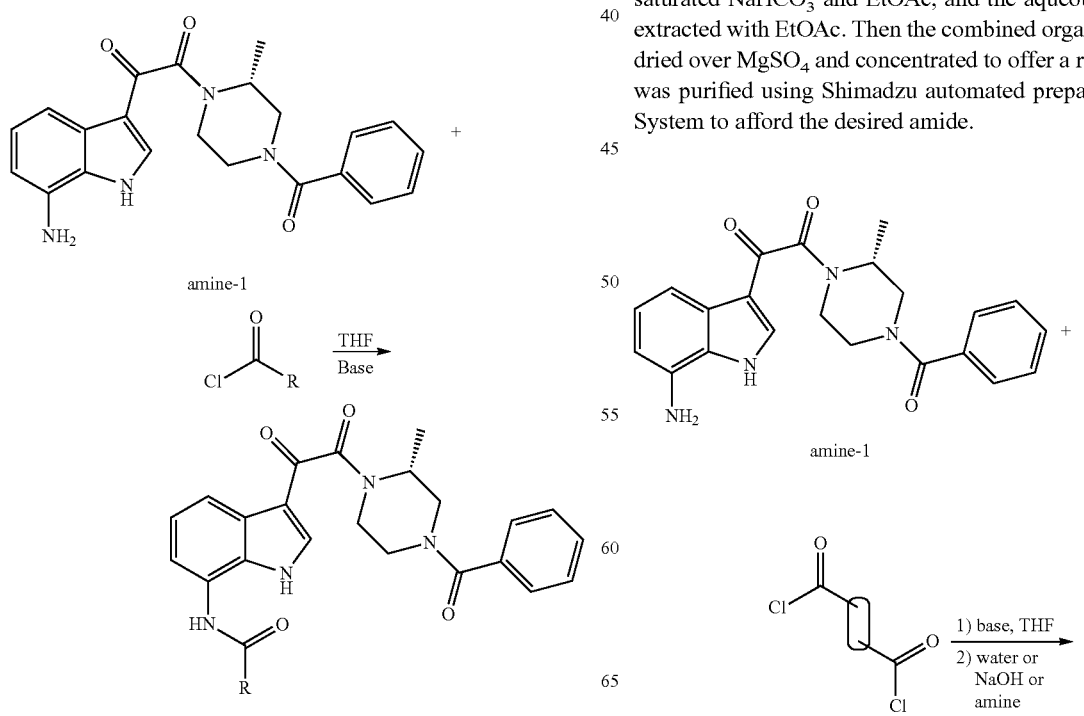

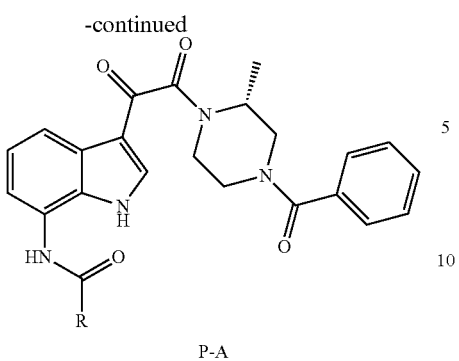

P-A

Method B: An excess of triethyl amine or di-isopropyl ethyl amine was added into a solution of I-1-(7-amino-1H-indol-3-yl)-2-(4-benzoyl-2-methylpiperazin-1-yl)ethane-1,2-dione, amine-1 (1 eq.) and acyl chloride (1 to 5 eq.) in dry THF. After 16 hours, NaOH or water or amine (primary or secondary) was added and reaction mixture was stirred for 16 hours. Then, the reaction mixture was partitioned between saturated NaHCO₃ and EtOAc, and the aqueous phase was extracted with EtOAc. Then the combined organic layer was dried over MgSO₄ and concentrated to offer a residue which was purified using Shimadzu automated preparative HPLC System to afford the desired amide.

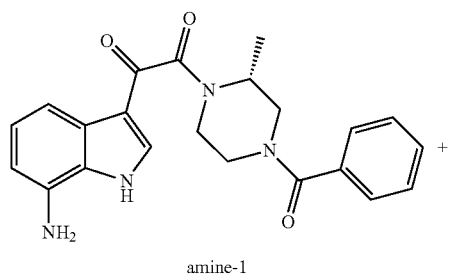

amine-1

+

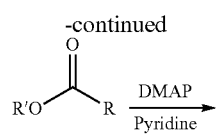

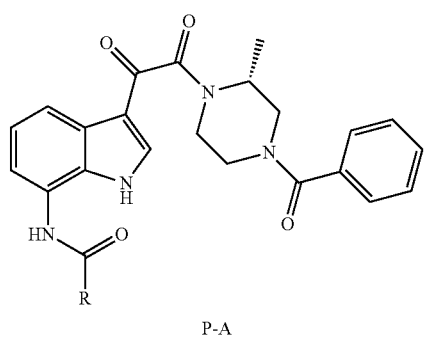

P-A

Method C: An excess of DMAP was added into a solution of I-1-(7-amino-1H-indol-3-yl)-2-(4-benzoyl-2-methylpiperazin-1-yl)ethane-1,2-dione, amine-1 (1 eq.) and ester (1 to 5 eq.) in dry pyridine and the reaction was heated to reflux. After 16 hours, the reaction mixture was cooled to room temperature and partitioned between saturated NaHCO₃ and EtOAc, and the aqueous phase was extracted with EtOAc. Then the combined organic layer was dried over MgSO₄ and concentrated to offer a residue which was purified using Shimadzu automated preparative HPLC System to afford the desired amide.

Characterization of the Compounds of Formula I:

TABLE A

| Compd. Number | Structure | Reagents Used Method Used | MS (M + H)$^+$ Calcd. | MS (M + H)$^+$ Observ. And Retention Time and NMR |
|---|---|---|---|---|
| P-A-1 | (structure) | (Cl-acyl chloride structure) Method A | 504.26 | 504.44 1.30 min (column A) |

TABLE A-continued

| Compd. Number | Structure | Reagents Used Method Used | MS (M + H)+ Calcd. | MS (M + H)+ Observ. And Retention Time and NMR |
|---|---|---|---|---|
| P-A-2 | 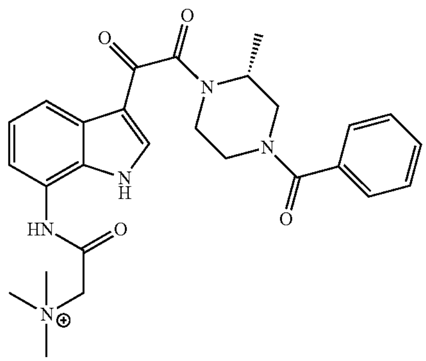 [SMILES: C[C@@H]1CN(C(=O)c2ccccc2)CCN1C(=O)C(=O)c1c[nH]c2c(NC(=O)C[N+](C)(C)C)cccc12] | Method A | 490.24 (M+) instead of (M + H)+ | 490.41 1.25 min (column A) |
| P-A-3 | 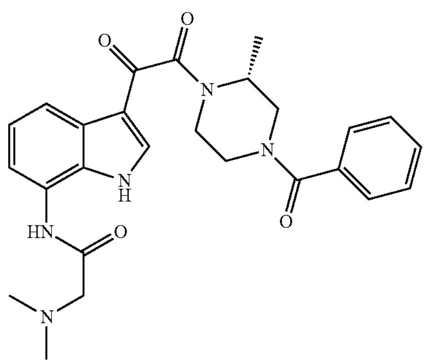 [SMILES: C[C@@H]1CN(C(=O)c2ccccc2)CCN1C(=O)C(=O)c1c[nH]c2c(NC(=O)CN(C)C)cccc12] | Method A | 476.23 | 476.31 1.32 min (column C) |
| P-A-4 | 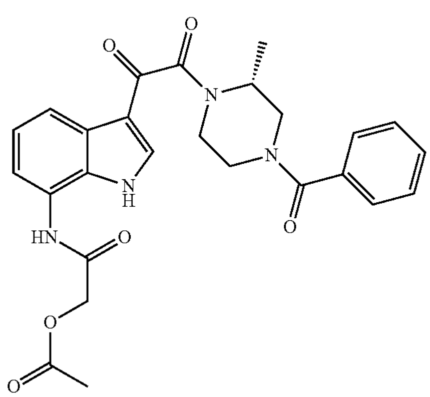 [SMILES: CC(=O)OCC(=O)Nc1cccc2c(C(=O)C(=O)N3CCN(C(=O)c4ccccc4)C[C@H]3C)c[nH]c12] | Method A | 491.19 | 491.38 1.42 min (column C) |
| P-A-5 | 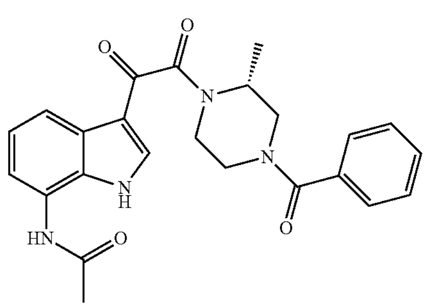 [SMILES: CC(=O)Nc1cccc2c(C(=O)C(=O)N3CCN(C(=O)c4ccccc4)C[C@H]3C)c[nH]c12] | Method A | 433.19 | 433.32 1.41 min (column C) |

TABLE A-continued
| Compd. Number | Structure | Reagents Used Method Used | MS (M + H)+ Calcd. | MS (M + H)+ Observ. And Retention Time and NMR |
|---|---|---|---|---|
| P-A-6 | 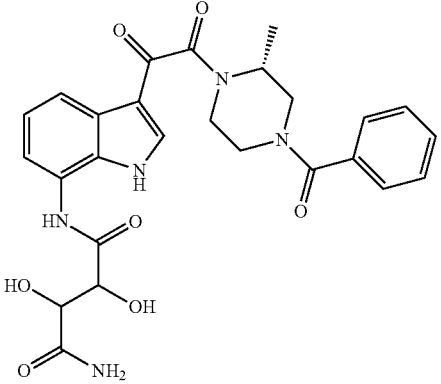 or/and 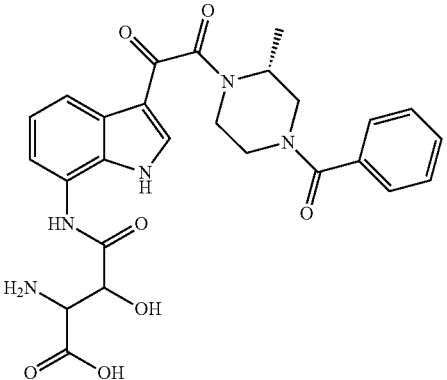 or/and 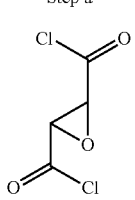 | Step a 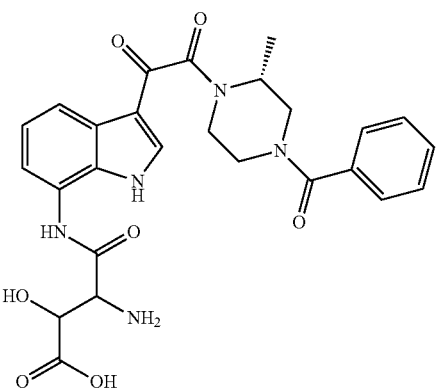 [SMILES: C[C@@H]1CN(C(=O)c2ccccc2)CCN1C(=O)C(=O)c1c[nH]c2c(NC(=O)C(N)C(O)C(=O)O)cccc12] Step b NH₃ in water Method B | 522.20 | 522.41 1.31 min (column C) |

TABLE A-continued

| Compd. Number | Structure | Reagents Used Method Used | MS (M + H)+ Calcd. | MS (M + H)+ Observ. And Retention Time and NMR |
|---|---|---|---|---|
| P-A-7 | 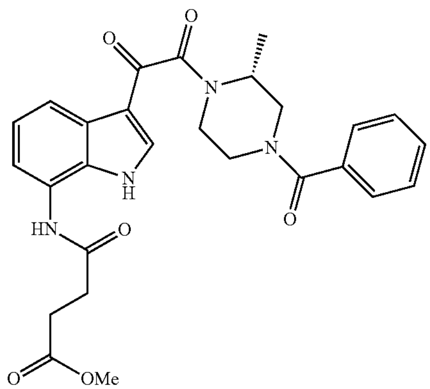 | Method A | 505.21 | 505.40 1.46 min (column C) |
| P-A-8 | 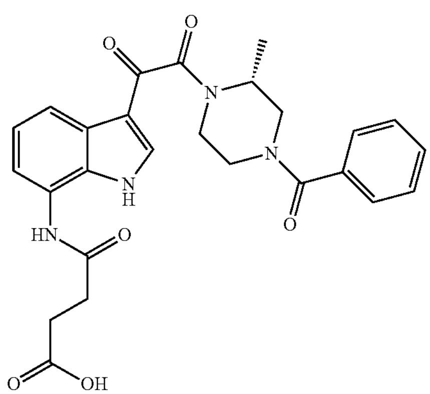 [SMILES: C[C@@H]1CN(C(=O)c2ccccc2)CCN1C(=O)C(=O)c1c[nH]c2c(NC(=O)CCC(=O)O)cccc12] | Method B | 491.19 | 491.31 1.44 min (column C) |
| P-A-9 | 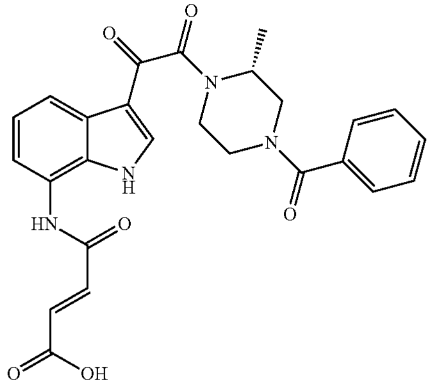 [SMILES: C[C@@H]1CN(C(=O)c2ccccc2)CCN1C(=O)C(=O)c1c[nH]c2c(NC(=O)/C=C/C(=O)O)cccc12] | Step a <br> Step b 1N NaOH Method B | 489.18 | 489.36 1.46 min (column C) |

TABLE A-continued

| Compd. Number | Structure | Reagents Used Method Used | MS (M + H)+ Calcd. | MS (M + H)+ Observ. And Retention Time and NMR |
|---|---|---|---|---|
| P-A-10 | 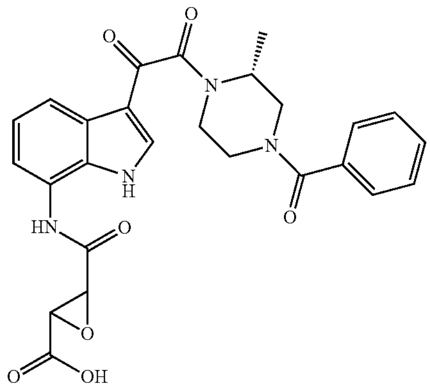 [SMILES: C[C@@H]1CN(C(=O)c2ccccc2)CCN1C(=O)C(=O)c1c[nH]c2c(NC(=O)C3OC3C(=O)O)cccc12] | Step a / Step b 1N NaOH Method B | 505.17 | 505.34 1.36 min (column C) |
| P-A-11 | 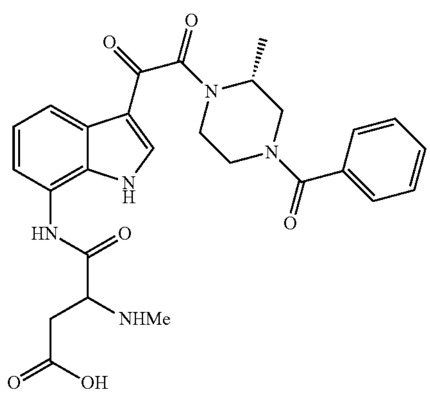 | Step a / Step b MeNH2 in water Method B | 520.22 | 520.41 1.35 min (column C) |

/ TABLE A-continued
| Compd. Number | Structure | Reagents Used Method Used | MS (M + H)+ Calcd. | MS (M + H)+ Observ. And Retention Time and NMR |
|---|---|---|---|---|
| P-A-12 | 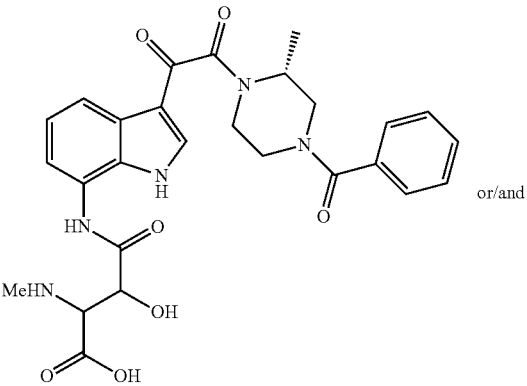 [SMILES: CNC(C(=O)O)C(O)C(=O)Nc1cccc2c(C(=O)C(=O)N3CCN(C(=O)c4ccccc4)C[C@H]3C)c[nH]c12] or/and 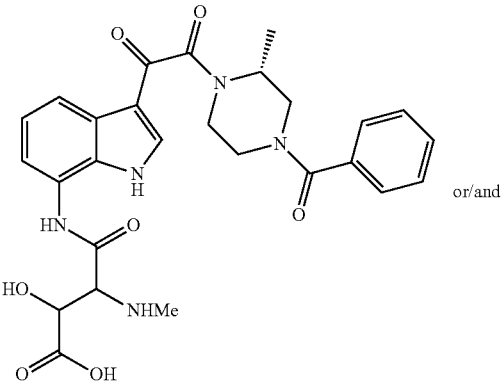 [SMILES: CNC(C(=O)Nc1cccc2c(C(=O)C(=O)N3CCN(C(=O)c4ccccc4)C[C@H]3C)c[nH]c12)C(O)C(=O)O] or/and 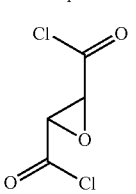 | Step a 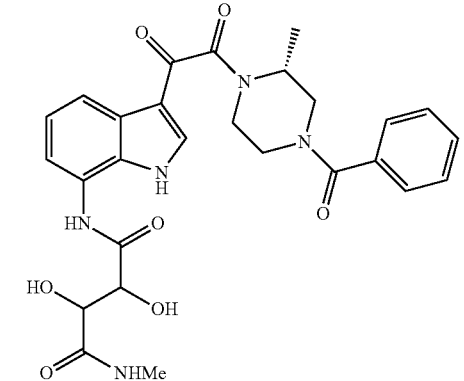 [SMILES: CNC(=O)C(O)C(O)C(=O)Nc1cccc2c(C(=O)C(=O)N3CCN(C(=O)c4ccccc4)C[C@H]3C)c[nH]c12] Step b MeNH₂ in water Method B | 536.21 | 536.44 1.38 min (column C) |

TABLE A-continued
| Compd. Number | Structure | Reagents Used Method Used | MS (M + H)+ Calcd. | MS (M + H)+ Observ. And Retention Time and NMR |
|---|---|---|---|---|
| P-A-13 | 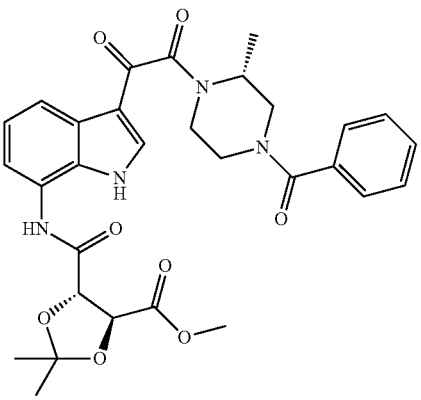 [SMILES: COC(=O)[C@H]1OC(C)(C)O[C@@H]1C(=O)Nc1cccc2c(C(=O)C(=O)N3CCN(C(=O)c4ccccc4)C[C@H]3C)c[nH]c12] | 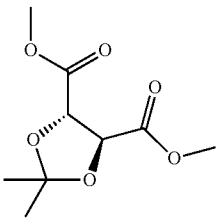<br>Method C | 577.23 | 577.35<br>1.56 min<br>(column C) |
| P-A-14 | 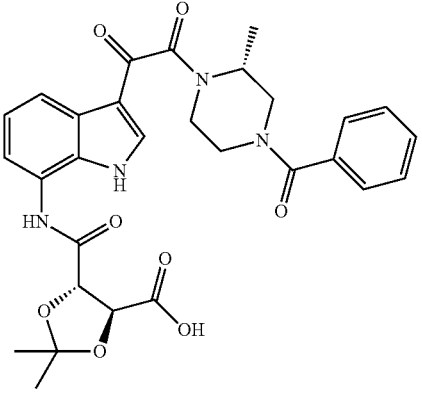 [SMILES: C[C@@H]1CN(C(=O)c2ccccc2)CCN1C(=O)C(=O)c1c[nH]c2c(NC(=O)[C@H]3OC(C)(C)O[C@@H]3C(=O)O)cccc12] | 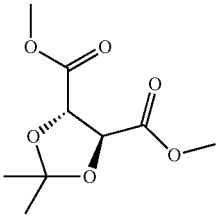<br>Method C | 563.21 | 563.34<br>1.51 min<br>(column C) |
| P-A-15 | 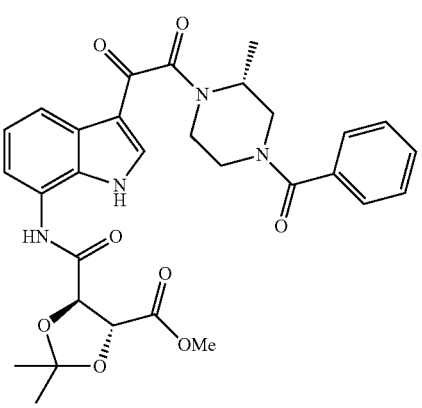 [SMILES: COC(=O)[C@@H]1OC(C)(C)O[C@H]1C(=O)Nc1cccc2c(C(=O)C(=O)N3CCN(C(=O)c4ccccc4)C[C@H]3C)c[nH]c12] | 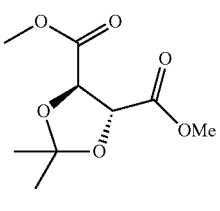<br>Method C | 577.23 | 577.42<br>1.58 min<br>(column C) |

TABLE A-continued
| Compd. Number | Structure | Reagents Used Method Used | MS (M + H)+ Calcd. | MS (M + H)+ Observ. And Retention Time and NMR |
|---|---|---|---|---|
| P-A-16 | 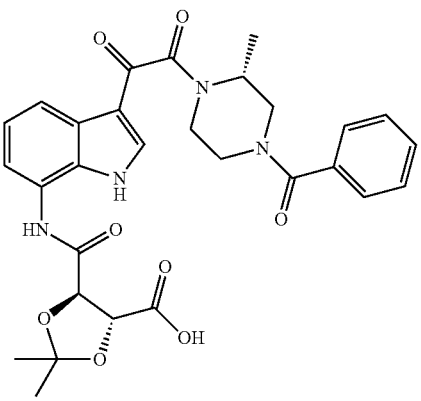 [SMILES: C[C@@H]1CN(C(=O)c2ccccc2)CCN1C(=O)C(=O)c1c[nH]c2c(NC(=O)[C@@H]3OC(C)(C)O[C@H]3C(=O)O)cccc12] | 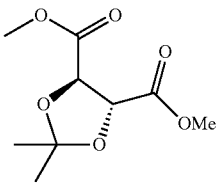<br>Method C | 563.21 | 563.38<br>1.52 min<br>(column C) |
| P-A-17 | 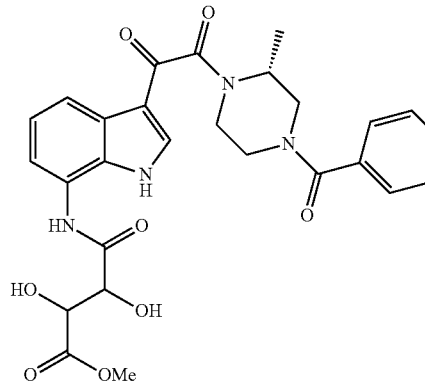 | 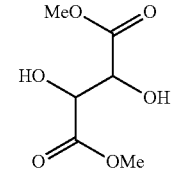 [SMILES: COC(=O)C(O)C(O)C(=O)OC]<br>Method C | 537.20 | 537.34<br>1.39 min<br>(column C) |
| P-A-18 | 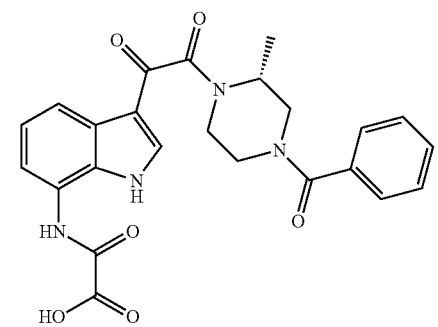 [SMILES: C[C@@H]1CN(C(=O)c2ccccc2)CCN1C(=O)C(=O)c1c[nH]c2c(NC(=O)C(=O)O)cccc12] | 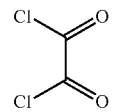<br>Method B | 463.16 | 463.31<br>1.39 min<br>(column C) |
| P-A-19 | 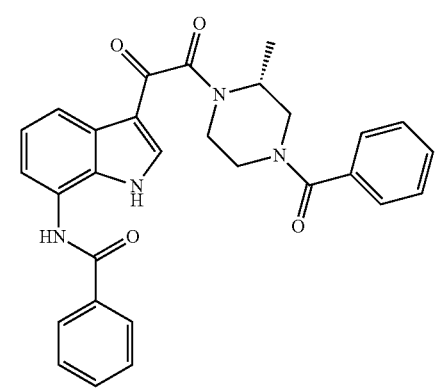 [SMILES: C[C@@H]1CN(C(=O)c2ccccc2)CCN1C(=O)C(=O)c1c[nH]c2c(NC(=O)c3ccccc3)cccc12] | 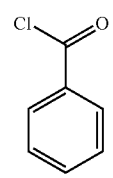<br>Method A | 495.20 | 495.39<br>1.59 min<br>(column C) |

TABLE A-continued

| Compd. Number | Structure | Reagents Used Method Used | MS (M + H)+ Calcd. | MS (M + H)+ Observ. And Retention Time and NMR |
|---|---|---|---|---|
| P-A-20 | 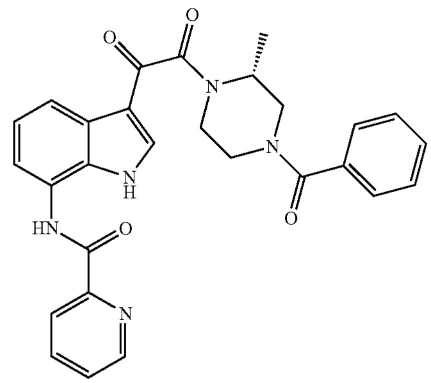 [SMILES: C[C@@H]1CN(C(=O)c2ccccc2)CCN1C(=O)C(=O)c1c[nH]c2c(NC(=O)c3ccccn3)cccc12] | pyridine-2-carbonyl chloride HCl<br><br>Method A | 496.20 | 496.33<br>1.61 min<br>(column C) |
| P-A-21 | 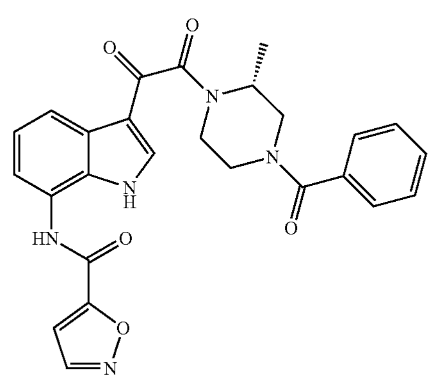 [SMILES: C[C@@H]1CN(C(=O)c2ccccc2)CCN1C(=O)C(=O)c1c[nH]c2c(NC(=O)c3ccno3)cccc12] | isoxazole-5-carbonyl chloride<br><br>Method A | 486.18 | 486.26<br>1.46 min<br>(column C) |

TABLE A-continued

| Compd. Number | Structure | Reagents Used Method Used | MS (M + H)+ Calcd. | MS (M + H)+ Observ. And Retention Time and NMR |
|---|---|---|---|---|
| P-A-22 | 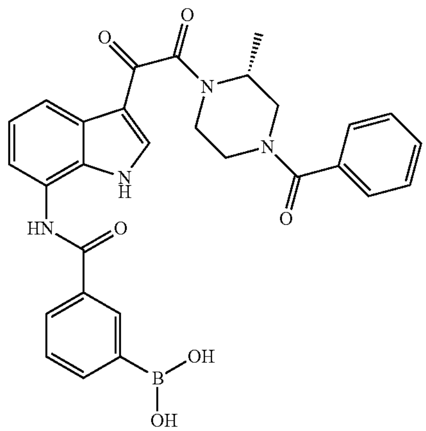 [SMILES: C[C@@H]1CN(C(=O)c2ccccc2)CCN1C(=O)C(=O)c1c[nH]c2c(NC(=O)c3cccc(B(O)O)c3)cccc12] | Method A | 539.21 | 539.24 1.99 in (column F) |
| P-A-23 | 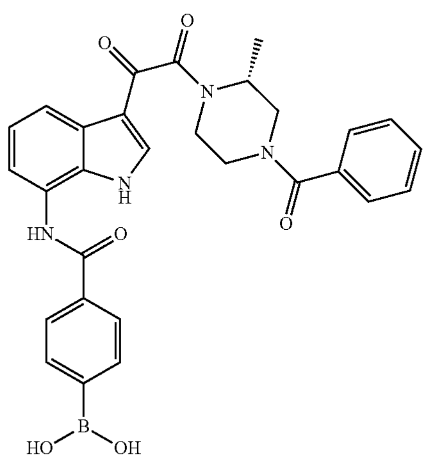 [SMILES: C[C@@H]1CN(C(=O)c2ccccc2)CCN1C(=O)C(=O)c1c[nH]c2c(NC(=O)c3ccc(B(O)O)cc3)cccc12] | Method A | 539.21 | 539.24 1.99 in (column F) |

Typical Procedure to Prepare Amide Derivatives from Amido-Indole Procusors

General Procedure:

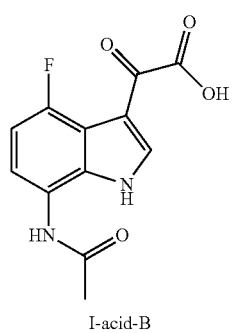

I-acid-B

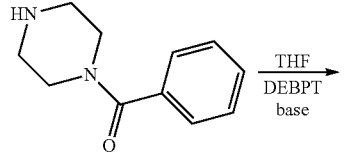

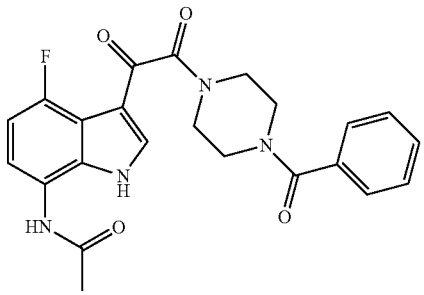

P-B

Indole 3-glyoxylic acid (1 eq.), benzoylpiperazine (1.2 eq.), 3-(diethoxyphosphoryloxy)-1,2,3-benzotriazin-4(3H)- one (DEPBT) (1.5 eq.) and triethyl amine or di-isopropyl ethyl amine (excess) were combined in DMF. The mixture was stirred at room temperature for 16 hours. DMF was removed via evaporation at reduced pressure and the residue was partitioned between ethyl acetate and saturated $NaHCO_3$ aqueous solution (2×400 ml). The aqueous layer was extracted with ethyl acetate. The organic phase combined and dried over anhydrous $MgSO_4$. Concentration in vacuo provided a crude product, which was purified using Shimadzu automated preparative HPLC System to afford the desired amide.

Characterization of the Compounds of Formula I:

TABLE B

| Compd. Number | Structure | Reagents Used | MS $(M + H)^+$ Calcd. | MS $(M + H)^+$ Observ. And Retention Time and NMR |
|---|---|---|---|---|
| P-B-1 | 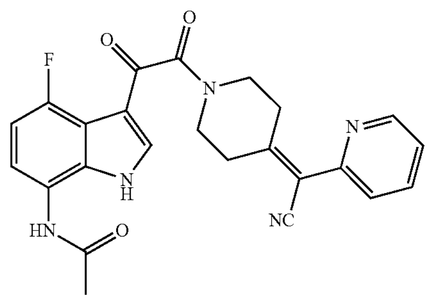 [SMILES: CC(=O)Nc1ccc(F)c2c(C(=O)C(=O)N3CCC(=C(C#N)c4ccccn4)CC3)c[nH]c12] | | 446.16 | 446.11 1.60 min (column F) |
| P-B-2 | 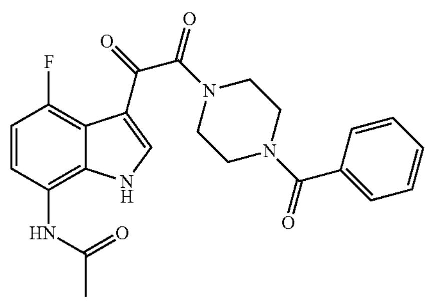 [SMILES: CC(=O)Nc1ccc(F)c2c(C(=O)C(=O)N3CCN(C(=O)c4ccccc4)CC3)c[nH]c12] | | 437.16 | 437.38 1.29 min (column E, solvent system II) |
| P-B-3 | 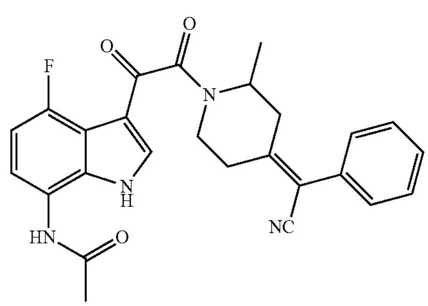 [SMILES: CC(=O)Nc1ccc(F)c2c(C(=O)C(=O)N3CC/C(=C(\C#N)c4ccccc4)CC3C)c[nH]c12] | | 459.18 | 459.42 1.23 min (column E, solvent system II) |
| P-B-4 | 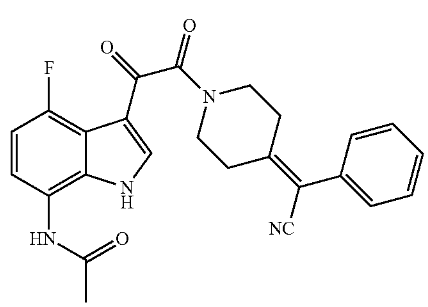 [SMILES: CC(=O)Nc1ccc(F)c2c(C(=O)C(=O)N3CCC(=C(C#N)c4ccccc4)CC3)c[nH]c12] | | 445.17 | 445.22 1.97 min (column G) NMR |

TABLE B-continued

| Compd. Number | Structure | Reagents Used | MS (M + H)+ Calcd. | MS (M + H)+ Observ. And Retention Time and NMR |
|---|---|---|---|---|
| P-B-5 | (4-fluoro-7-acetamido-indol-3-yl) glyoxyl piperidine with 4-(pyridin-3-yl)methylene cyano | piperidine with 4-(pyridin-3-yl)methylene cyano | 446.16 | 446.15 1.40 min (column F) |
| P-B-6 | (4-fluoro-7-acetamido-indol-3-yl) glyoxyl piperidine with 4-(pyridin-4-yl)methylene cyano | piperidine with 4-(pyridin-4-yl)methylene cyano | 446.16 | |
| P-B-7 | (4-fluoro-7-acetamido-indol-3-yl) glyoxyl piperidine with 4-(pyridin-3-yl)methylene cyano (chiral) | piperidine with 4-(pyridin-3-yl)methylene cyano (chiral) | 460.18 | 460.12 1.53 min (column F) |

Preparation of 1-acid-B

Step 1:

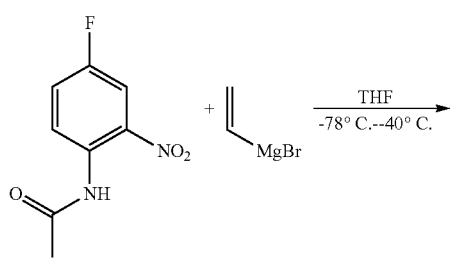

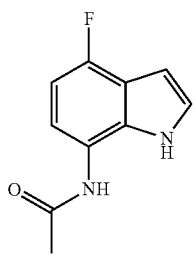

4-Fluoro-2-nitroacetanilide (1 eq.) was dissolved in dry THF. After the solution was cooled down to −78° C., an excess of vinyl magnesium bromide (3-4 eq.) was added. Then, the reaction was kept below −40° C. for two hours before quenched with 20% $NH_4Cl$. The aqueous phase was extracted with EtOAc. The combined organic layer was dried over $MgSO_4$. After filtration and concentration, the crude product was purified by silica gel column chromatography to afford N-(4-fluoro-1H-indol-7-yl)acetamide. MS m/z: (M+H)+ calc'd for $C_{10}H_{10}FN_2O$: 193.08. Found 193.09. HPLC retention time: 1.29 minutes (column E, solvent system II).

Step 2:

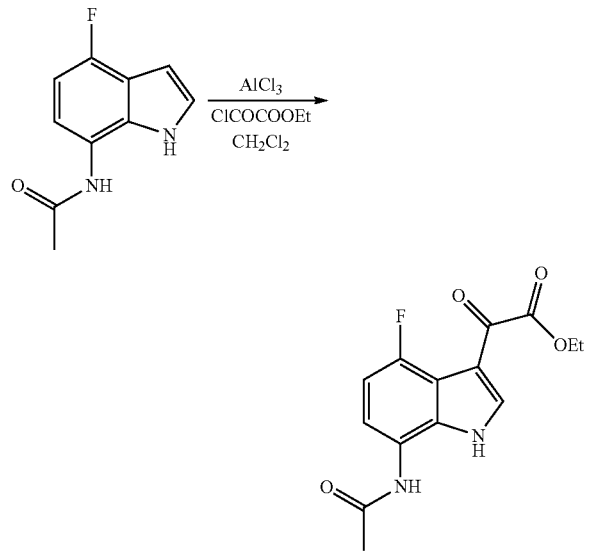

N-(4-fluoro-1H-indol-7-yl)acetamide (1 eq.) was added to a suspension of $AlCl_3$ (1 eq.) in $CH_2Cl_2$ (100 ml). After 15 min, a premixed suspension of $AlCl_3$ (2 eq.) and ClCOCOEt (2 eq.) in $CH_2Cl_2$ was added and stirring was continued at room temperature for 1 hour before iced saturated $NaHCO_3$ solution was added. The aqueous phase was extracted with EtOAc. The combined organic layer was dried over $MgSO_4$. After filtration and concentration, the crude product was purified by silica gel column chromatography to afford ethyl 2-(7-acetamido-4-fluoro-1H-indol-3-yl)-2-oxoacetate. MS m/z: (M+H)+ calc'd for $C_{14}H_{14}FN_2O_4$:293.09. Found 293.11. HPLC retention time: 0.98 minutes (column E, solvent system II). $^1$H NMR (300 MHz, $CD_3OD$) 8.32 (s, 1H), 7.16 (m, 1H), 6.94 (m, 1H), 4.43 (q, 2H, J=7.2 Hz), 2.24 (s, 3H), 1.39 (t, 3H, J=7.2 Hz).

Step 3:

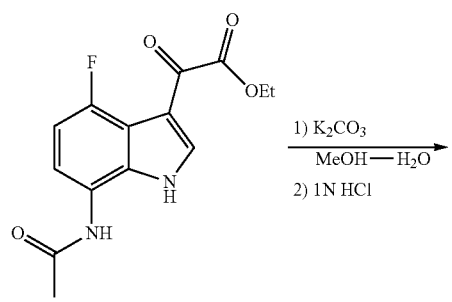

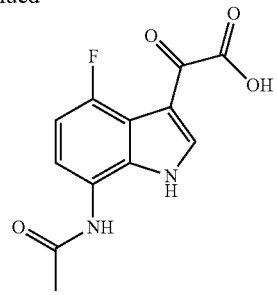

Ethyl 2-(7-acetamido-4-fluoro-1H-indol-3-yl)-2-oxoacetate (1 eq.) and $K_2CO_3$ (3 eq.) were dissolved in MeOH and $H_2O$ (volume ratio 2:1). After 16 hours, 1N HCl was added and pH was adjusted to 7. concentrated to offer a residue which was used in the further reactions without purification.

Typical Procedure to Prepare Urea Derivatives from Amino-Indole Precursors

General Procedure:

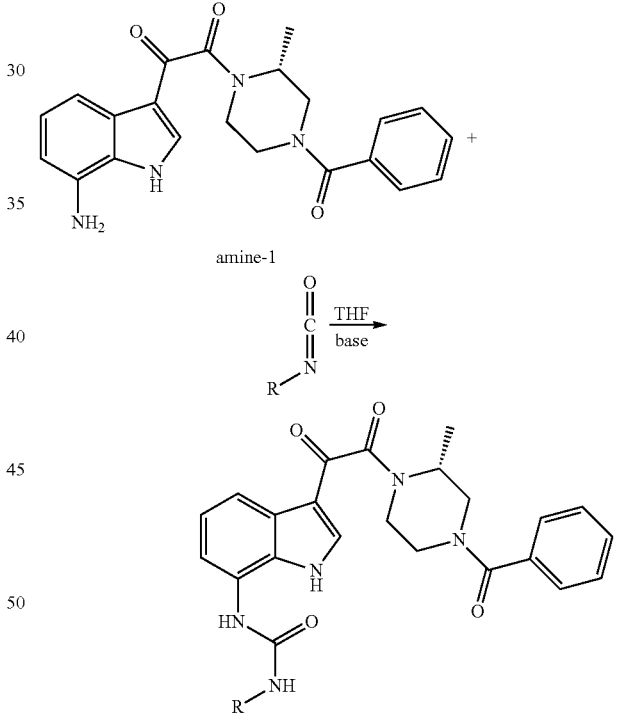

An excess of triethyl amine or di-isopropyl ethyl amine was added into a solution of I-1-(7-amino-1H-indol-3-yl)-2-(4-benzoyl-2-methylpiperazin-1-yl)ethane-1,2-dione, amine-1 (1 eq.) and isocyanate (1 to 5 eq.) in dry THF. After 16 hours, the reaction mixture was partitioned between saturated $NaHCO_3$ and EtOAc, and the aqueous phase was extracted with EtOAc. Then the combined organic layer was dried over $MgSO_4$ and concentrated to offer a residue which was purified using Shimadzu automated preparative HPLC System to afford the desired urea.

Characterization of the Compounds of Formula I:

TABLE C

| Compd. Number | Structure | Reagents Used | MS (M + H)+ Calcd. | MS (M + H)+ Observ. And Retention Time and NMR |
|---|---|---|---|---|
| P-C-1 | 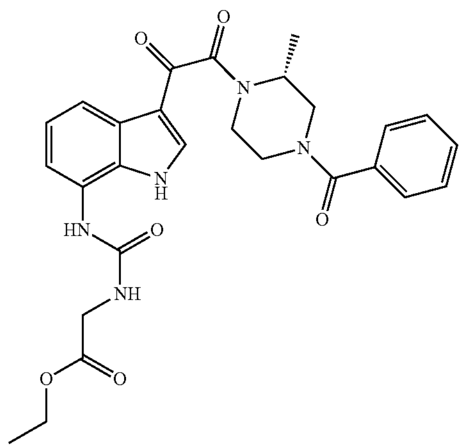 [SMILES: CCOC(=O)CNC(=O)Nc1cccc2c(C(=O)C(=O)N3CCN(C(=O)c4ccccc4)C[C@H]3C)c[nH]c12] | | 520.22 | 520.34 1.43 min (column E, solvent system II) |
| P-C-2 | 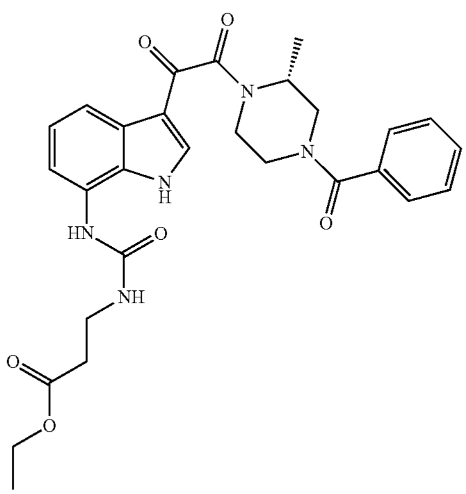 [SMILES: CCOC(=O)CCNC(=O)Nc1cccc2c(C(=O)C(=O)N3CCN(C(=O)c4ccccc4)C[C@H]3C)c[nH]c12] | | 534.24 | 534.39 1.05 min (column D, solvent system II) |
| P-C-3 | 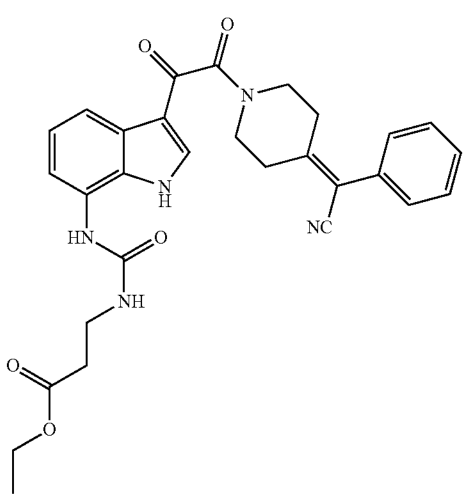 [SMILES: CCOC(=O)CCNC(=O)Nc1cccc2c(C(=O)C(=O)N3CCC(=C(C#N)c4ccccc4)CC3)c[nH]c12] | | 528.22 | 528.07 1.73 min (column B) |

TABLE C-continued
| Compd. Number | Structure | Reagents Used | MS (M + H)+ Calcd. | MS (M + H)+ Observ. And Retention Time and NMR |
|---|---|---|---|---|
| P-C-4 | 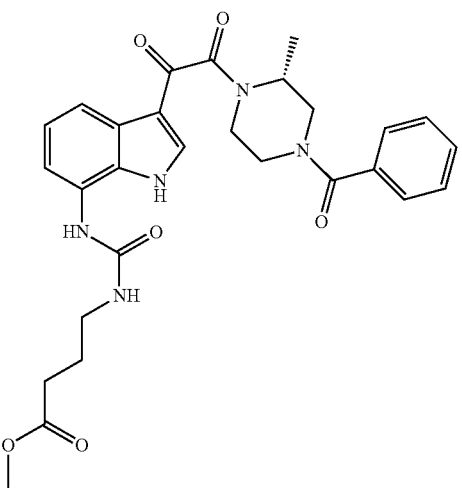 [SMILES: COC(=O)CCCNC(=O)Nc1cccc2c(C(=O)C(=O)N3CCN(C(=O)c4ccccc4)C[C@H]3C)c[nH]c12] | O=C=N-CH2CH2CH2-C(O)O-ethyl | 534.24 | 534.31 1.06 min (column D, solvent system II) |
| P-C-5 | 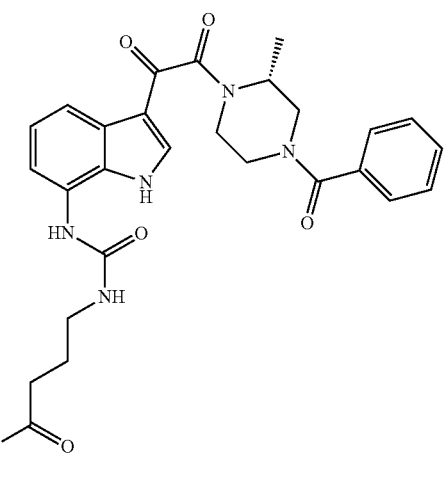 | O=C=N-CH2CH2CH2-C(O)O-ethyl | 548.25 | 548.36 1.17 min (column D, solvent system II) |
| P-C-6 | 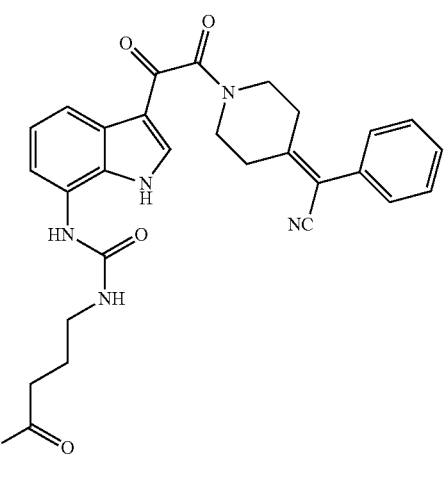 | O=C=N-CH2CH2CH2-C(O)O-ethyl | 542.24 | 542.08 1.76 min (column B) |

TABLE C-continued

| Compd. Number | Structure | Reagents Used | MS (M + H)+ Calcd. | MS (M + H)+ Observ. And Retention Time and NMR |
|---|---|---|---|---|
| P-C-7 | 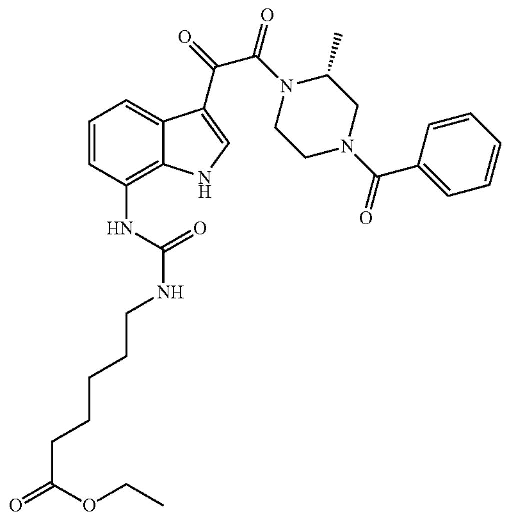 [SMILES: CCOC(=O)CCCCCNC(=O)Nc1cccc2c(C(=O)C(=O)N3CCN(C(=O)c4ccccc4)C[C@H]3C)c[nH]c12] | | 576.28 | 576.45 1.18 min (column D, solvent system II) |
| P-C-8 | 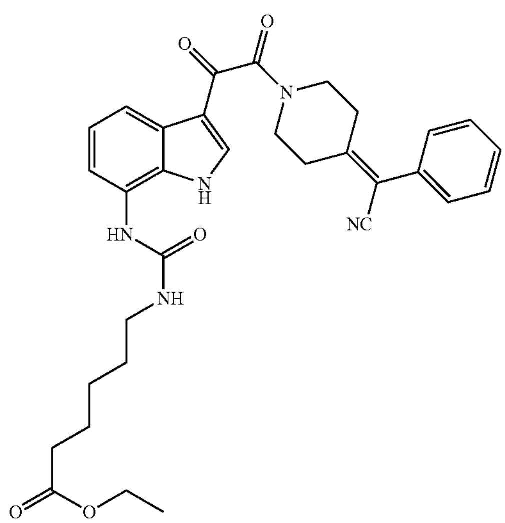 [SMILES: CCOC(=O)CCCCCNC(=O)Nc1cccc2c(C(=O)C(=O)N3CCC(=C(C#N)c4ccccc4)CC3)c[nH]c12] | | 570.27 | 570.10 1.89 min (column B) |
| P-C-9 | 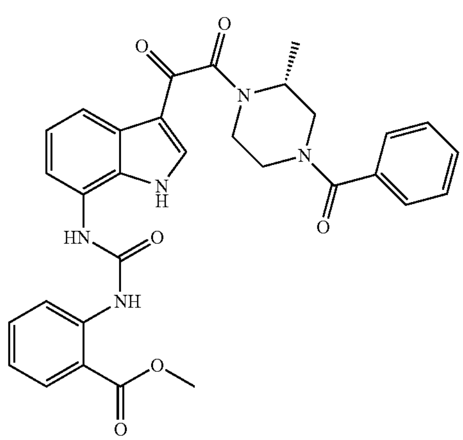 [SMILES: COC(=O)c1ccccc1NC(=O)Nc1cccc2c(C(=O)C(=O)N3CCN(C(=O)c4ccccc4)C[C@H]3C)c[nH]c12] | | 568.22 | 568.05 1.47 min (column D, solvent system II) |

TABLE C-continued
| Compd. Number | Structure | Reagents Used | MS (M + H)+ Calcd. | MS (M + H)+ Observ. And Retention Time and NMR |
|---|---|---|---|---|
| P-C-10 | 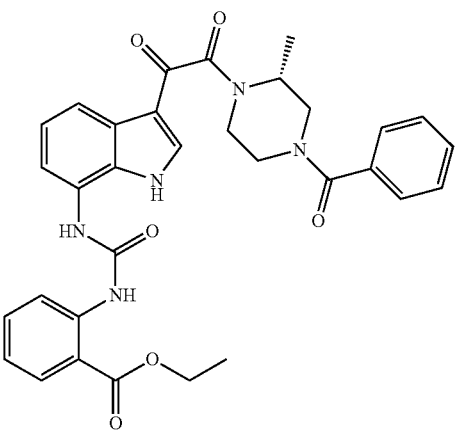 | 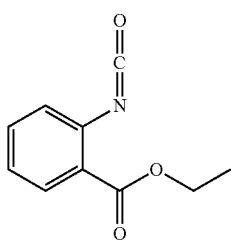 | 582.24 | 582.37 1.26 min (column D, solvent system II) |
| P-C-11 | 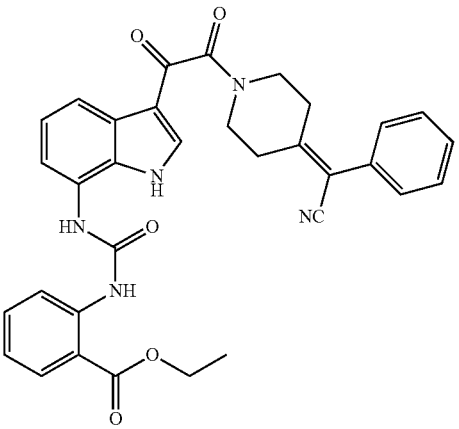 [SMILES: CCOC(=O)c1ccccc1NC(=O)Nc1cccc2c(C(=O)C(=O)N3CCC(=C(C#N)c4ccccc4)CC3)c[nH]c12] | 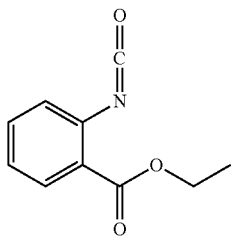 | 576.22 | 576.05 1.96 min (column B) |
| P-C-12 | 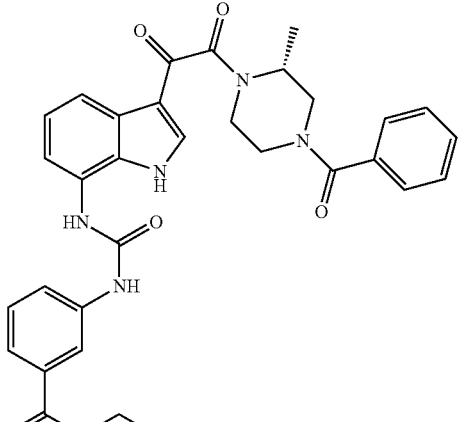 | 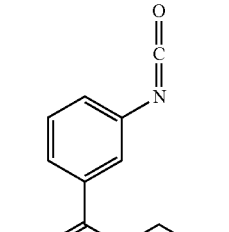 | 582.24 | 582.33 1.33 min (column D, solvent system II) |

TABLE C-continued
| Compd. Number | Structure | Reagents Used | MS (M + H)+ Calcd. | MS (M + H)+ Observ. And Retention Time and NMR |
|---|---|---|---|---|
| P-C-13 | 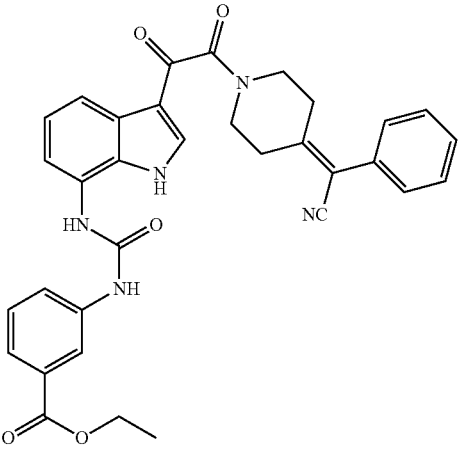 | 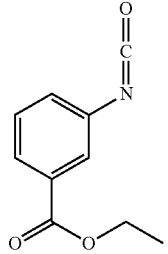 | 576.22 | 576.07 1.96 min (column B) |
| P-C-14 | 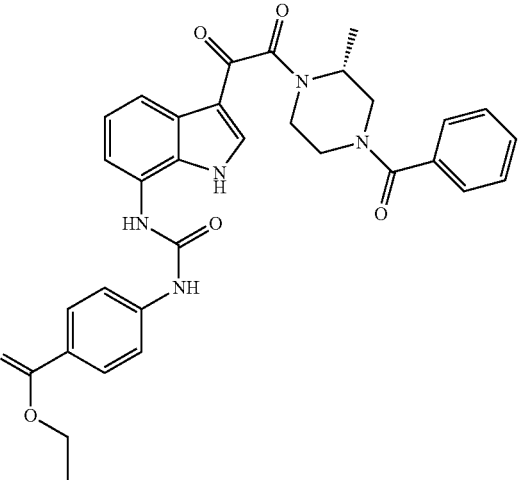 | 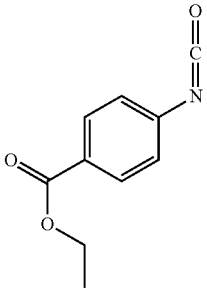 | 582.24 | 582.30 1.23 min (column D, solvent system II) |
| P-C-15 | 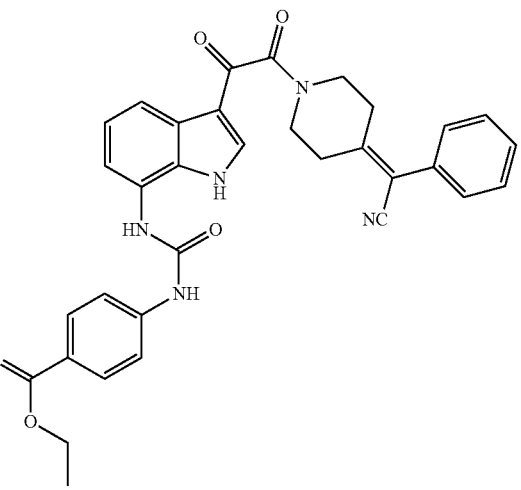 | 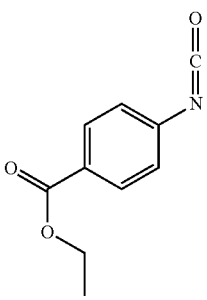 | 576.22 | 576.05 1.95 min (column B) |

TABLE C-continued

| Compd. Number | Structure | Reagents Used | MS (M + H)+ Calcd. | MS (M + H)+ Observ. And Retention Time and NMR |
|---|---|---|---|---|
| P-C-16 | 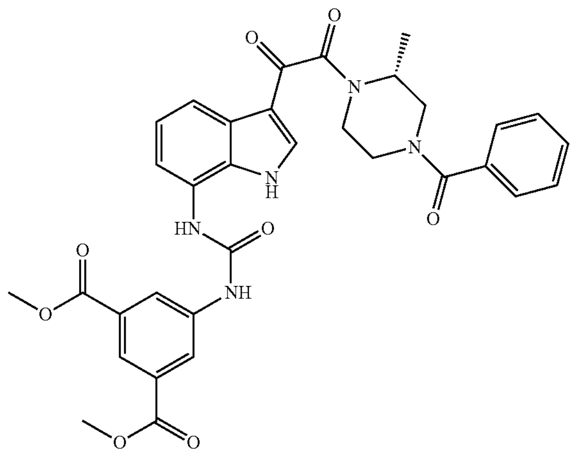 [SMILES: COC(=O)c1cc(NC(=O)Nc2cccc3c(C(=O)C(=O)N4CCN(C(=O)c5ccccc5)C[C@H]4C)c[nH]c23)cc(C(=O)OC)c1] | | 626.23 | 626.37 1.22 min (column D, solvent system II) |
| P-C-17 | 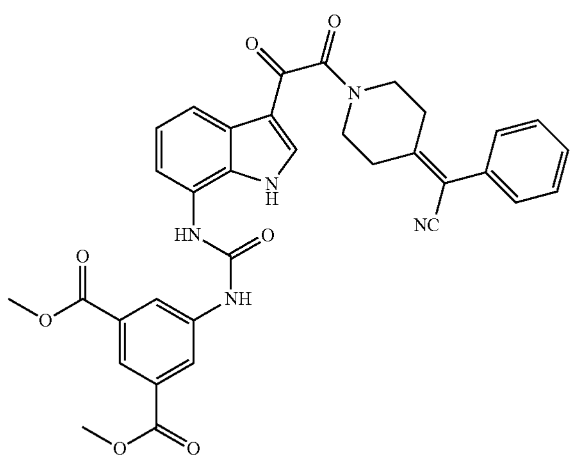 [SMILES: COC(=O)c1cc(NC(=O)Nc2cccc3c(C(=O)C(=O)N4CCC(=C(C#N)c5ccccc5)CC4)c[nH]c23)cc(C(=O)OC)c1] | | 620.21 | 620.02 1.97 min (column B) |
| P-C-18 | 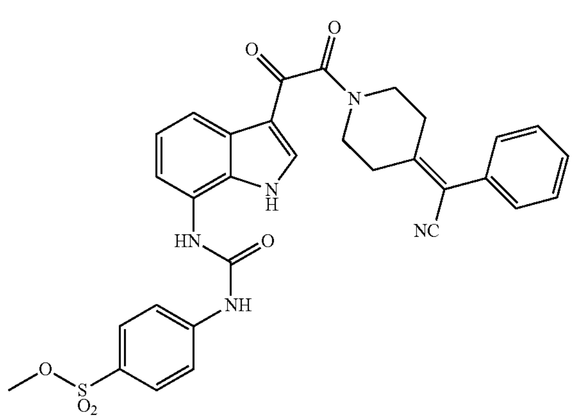 [SMILES: COS(=O)(=O)c1ccc(NC(=O)Nc2cccc3c(C(=O)C(=O)N4CCC(=C(C#N)c5ccccc5)CC4)c[nH]c23)cc1] | | 598.18 | 598.02 1.80 min (column B) |

TABLE C-continued
| Compd. Number | Structure | Reagents Used | MS (M + H)+ Calcd. | MS (M + H)+ Observ. And Retention Time and NMR |
|---|---|---|---|---|
| P-C-19 | 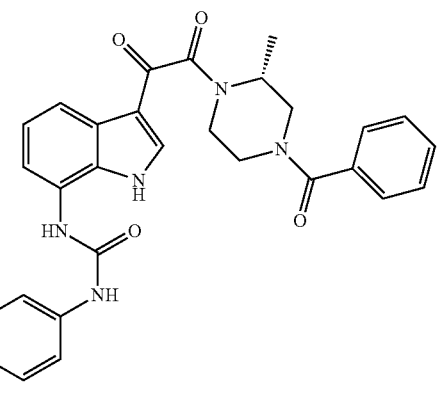 | 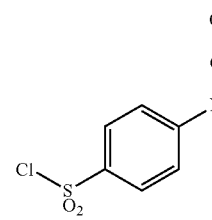 | 590.17 | 590.23 0.92 min (column D, solvent system II) |
| P-C-20 | 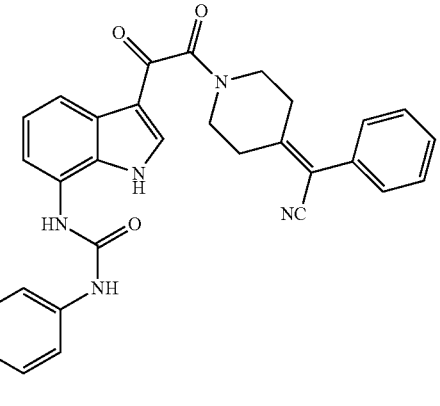 | 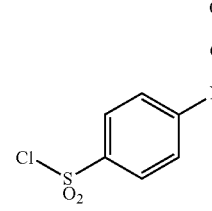 | 584.16 | 583.99 1.60 min (column B) |
| P-C-21 | 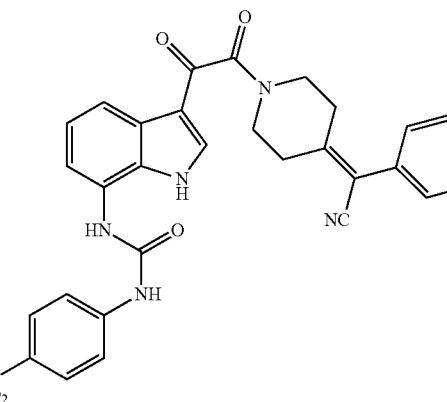 | 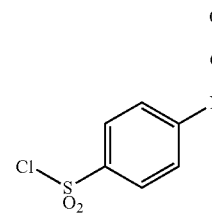 | 639.24 | 639.07 1.89 min (column B) | ns
TABLE C-continued
| Compd. Number | Structure | Reagents Used | MS (M + H)+ Calcd. | MS (M + H)+ Observ. And Retention Time and NMR |
|---|---|---|---|---|
| P-C-22 | 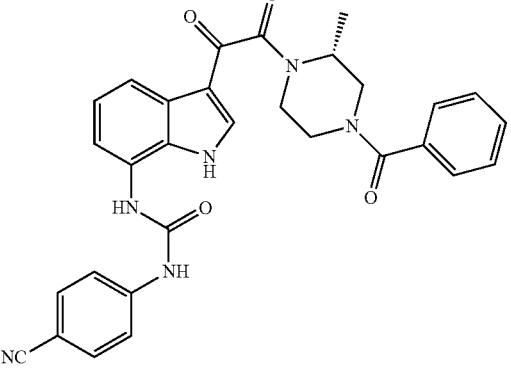 | 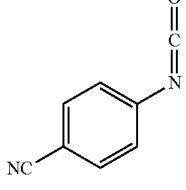 | 535.21 | 535.39 1.19 min (column D, solvent system II) |
| P-C-23 | 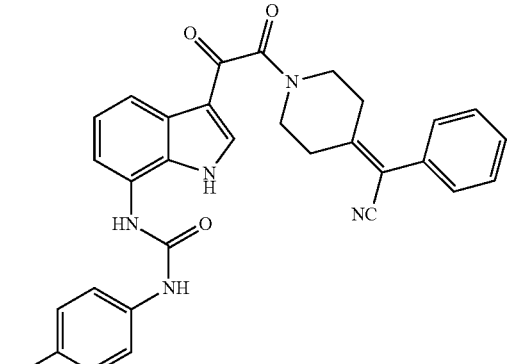 | 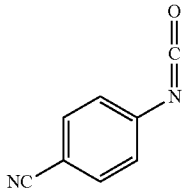 [SMILES: N#Cc1ccc(N=C=O)cc1] | 529.20 | 529.04 1.83 min (column B) |
| P-C-24 | 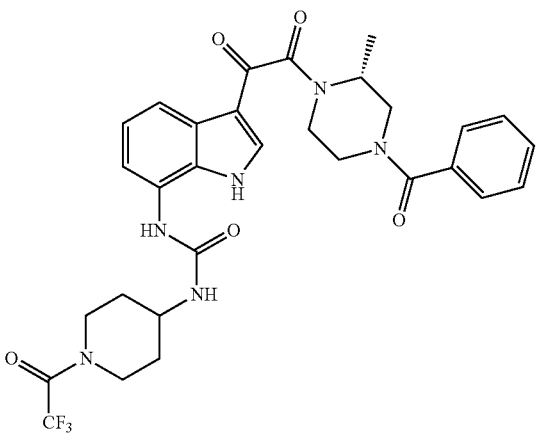 [SMILES: C[C@@H]1CN(C(=O)c2ccccc2)CCN1C(=O)C(=O)c1c[nH]c2c(NC(=O)NC3CCN(C(=O)C(F)(F)F)CC3)cccc12] | 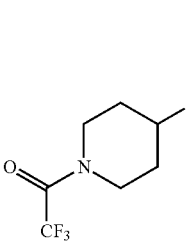 | 613.24 | 613.35 1.14 min (column D, solvent system II) |

TABLE C-continued
| Compd. Number | Structure | Reagents Used | MS (M + H)+ Calcd. | MS (M + H)+ Observ. And Retention Time and NMR |
|---|---|---|---|---|
| P-C-25 | 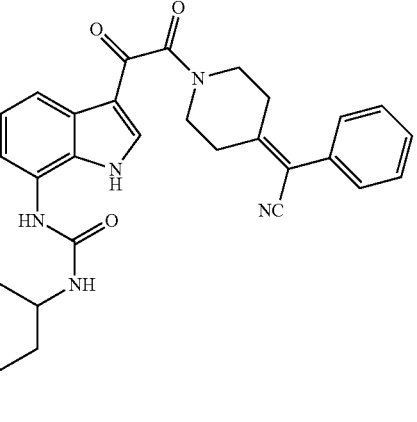 | 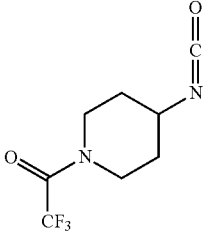 [SMILES: O=C=NC1CCN(C(=O)C(F)(F)F)CC1] | 607.23 | 607.06 1.81 min (column B) |
| P-C-26 | 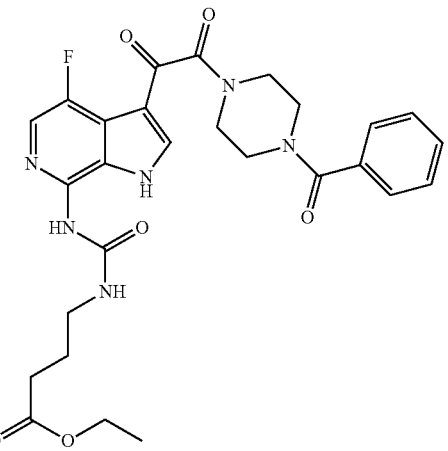 | 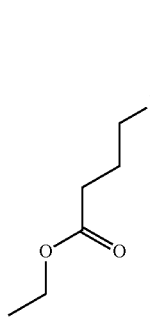 | 553.22 | 553.09 Rf = 1.64 min (column B) |
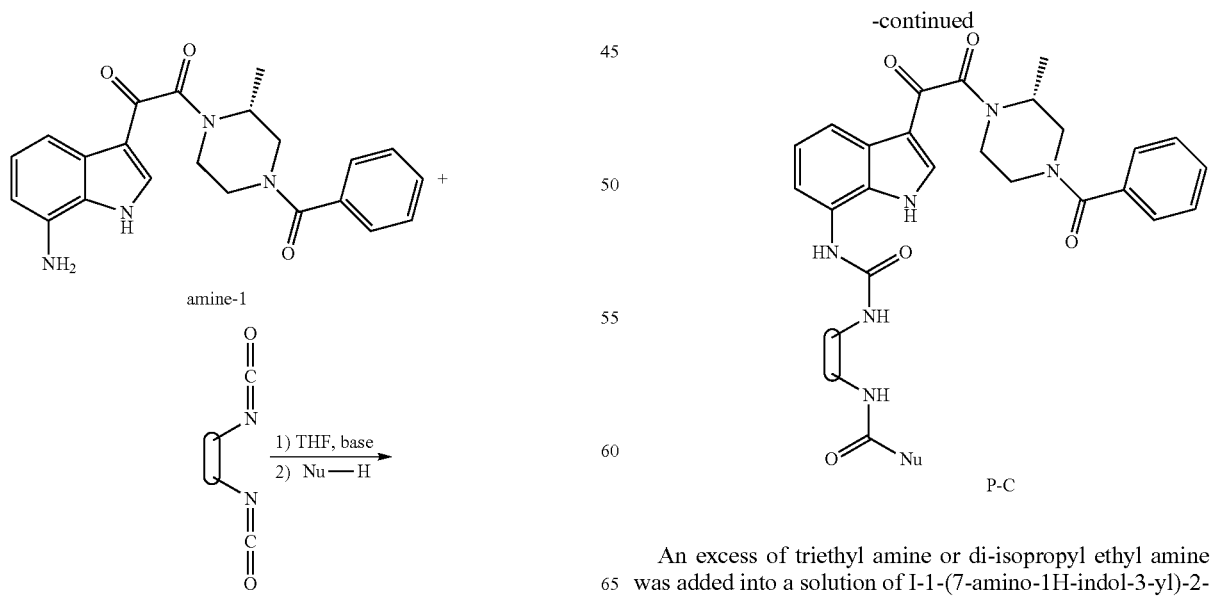
An excess of triethyl amine or di-isopropyl ethyl amine was added into a solution of I-1-(7-amino-1H-indol-3-yl)-2-(4-benzoyl-2-methylpiperazin-1-yl)ethane-1,2-dione, amine-1 (1 eq.) and bis-isocyanate (1 to 1.5 eq.) in dry THF.

After 16 hours, a nucleophile (2 to 5 eq.) such as alcohol or amine was added and the reaction mixture was stirred for another 14 hours. Then, the reaction mixture was partitioned between saturated NaHCO₃ and EtOAc, and the aqueous phase was extracted with EtOAc. Then the combined organic layer was dried over MgSO₄ and concentrated to offer a residue which was purified using Shimadzu automated preparative HPLC System to afford the desired urea.

| Compd. Number | Structure | Reagents Used | MS (M + H)⁺ Calcd. | MS (M + H)⁺ Observ. And Retention Time and NMR |
|---|---|---|---|---|
| P-C-101 | 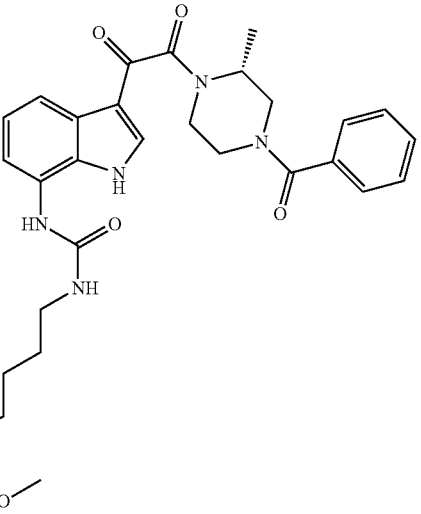 | 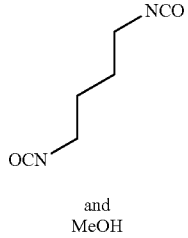 and MeOH | 563.26 | 563.27 1.97 min (column F) |
| P-C-102 | 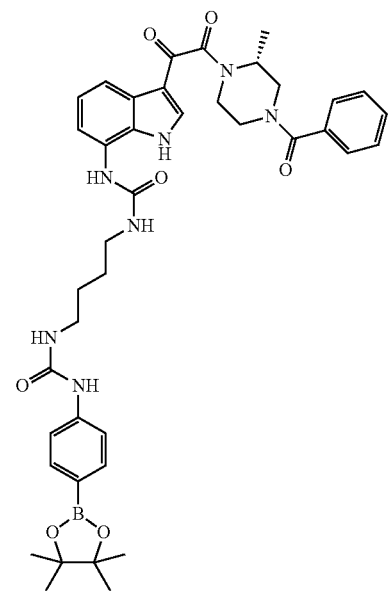 [SMILES: C[C@@H]1CN(C(=O)c2ccccc2)CCN1C(=O)C(=O)c1c[nH]c2c(NC(=O)NCCCCNC(=O)Nc3ccc(B4OC(C)(C)C(C)(C)O4)cc3)cccc12] | 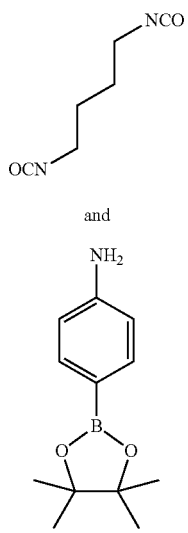 and | 750.37 | 750.35 2.20 min (column F) |

-continued
| Compd. Number | Structure | Reagents Used | MS (M + H)+ Calcd. | MS (M + H)+ Observ. And Retention Time and NMR |
|---|---|---|---|---|
| P-C-103 | 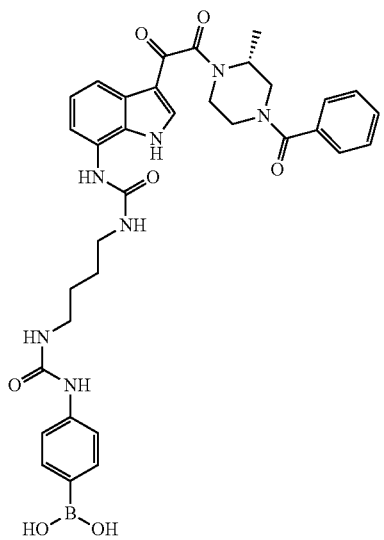 [SMILES: C[C@@H]1CN(C(=O)c2ccccc2)CCN1C(=O)C(=O)c1c[nH]c2c(NC(=O)NCCCCNC(=O)Nc3ccc(B(O)O)cc3)cccc12] | 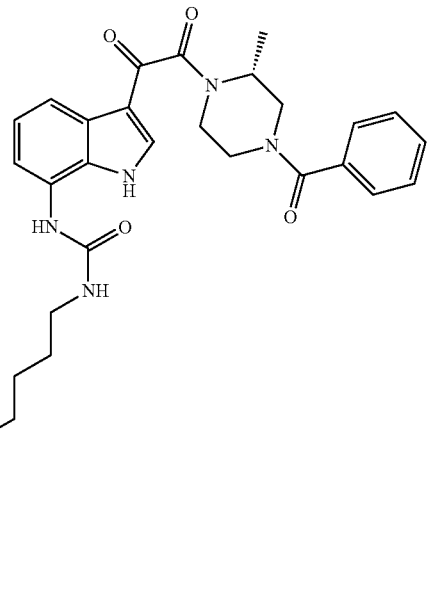 and 4-aminophenyl boronic acid pinacol ester | 668.3 | 668.34 2.04 min (column F) |
| P-C-104 | 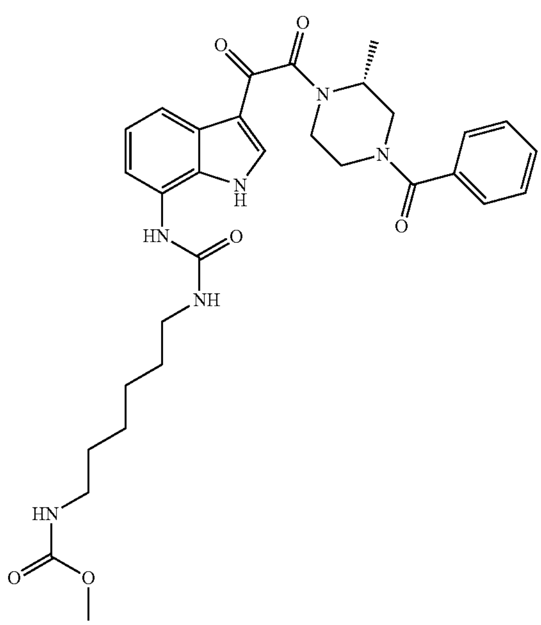 [SMILES: COC(=O)NCCCCCCNC(=O)Nc1cccc2c(C(=O)C(=O)N3CCN(C(=O)c4ccccc4)C[C@H]3C)c[nH]c12] | OCN-(CH2)6-NCO and MeOH | 591.29 | 591.28 1.98 min (column F) |

| Compd. Number | Structure | Reagents Used | MS (M + H)+ Calcd. | MS (M + H)+ Observ. And Retention Time and NMR |
|---|---|---|---|---|
| P-C-105 | 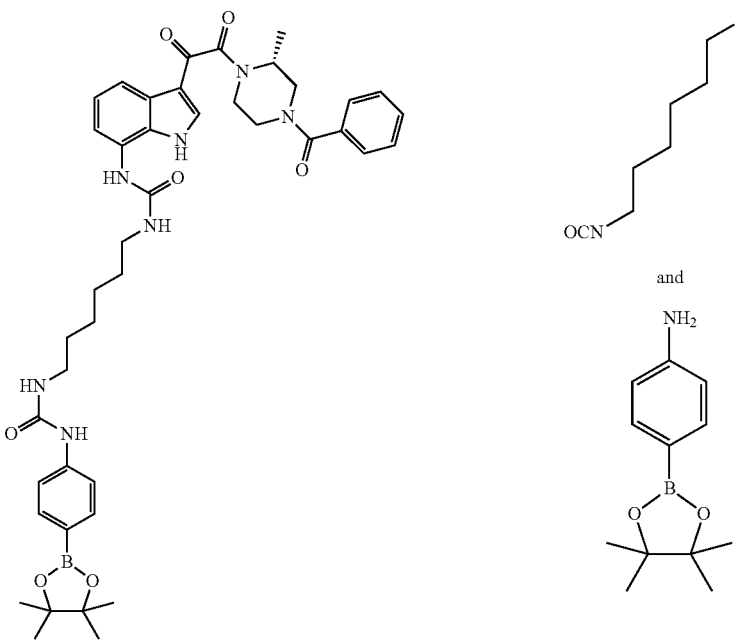 | | 778.41 | 778.43 2.28 min (column F) |
| P-C-106 | 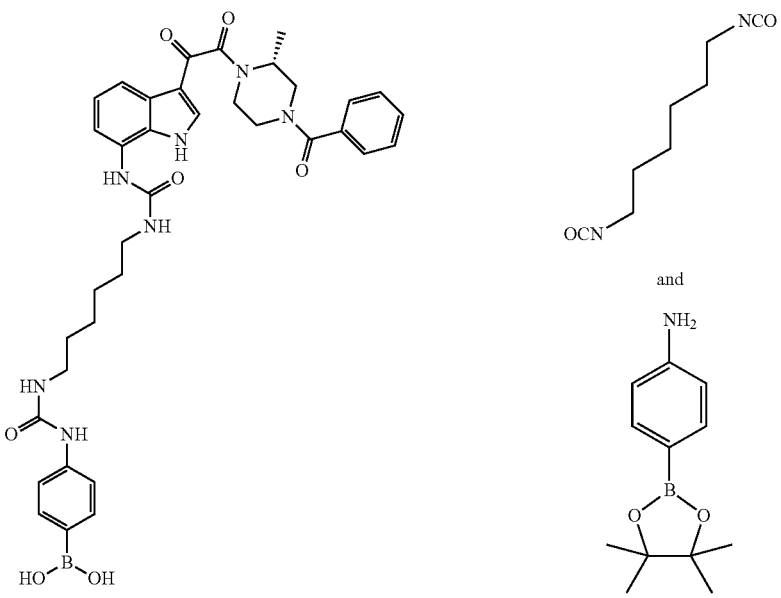 | | 696.33 | 696.37 2.12 min (column F) |

-continued
| Compd. Number | Structure | Reagents Used | MS (M + H)+ Calcd. | MS (M + H)+ Observ. And Retention Time and NMR |
|---|---|---|---|---|
| P-C-107 | 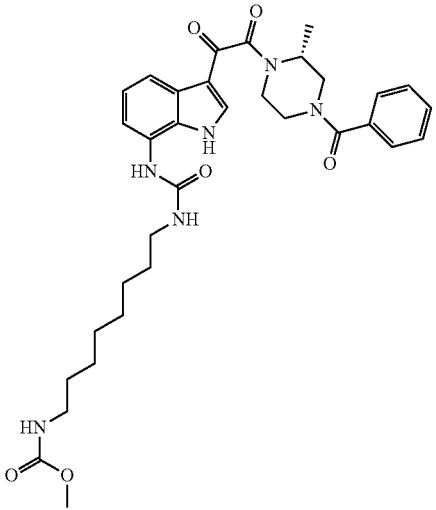 [SMILES: COC(=O)NCCCCCCCCNC(=O)Nc1cccc2c(C(=O)C(=O)N3CCN(C(=O)c4ccccc4)C[C@H]3C)c[nH]c12] |  and MeOH | 619.32 | 619.31 2.15 min (column F) |
| P-C-108 | 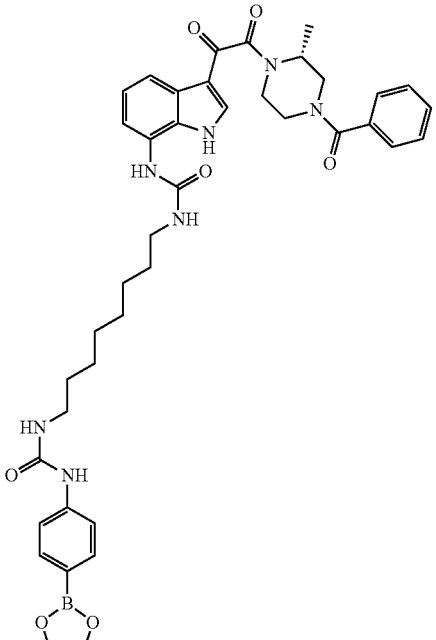 |  and 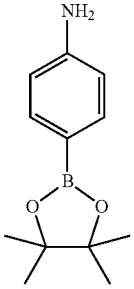 | 806.44 | 806.48 2.41 min (column F) |

-continued
| Compd. Number | Structure | Reagents Used | MS (M + H)+ Calcd. | MS (M + H)+ Observ. And Retention Time and NMR |
|---|---|---|---|---|
| P-C-109 | 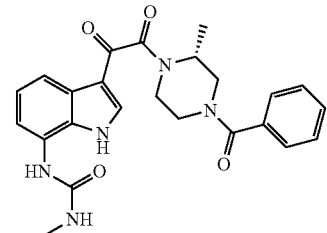 | 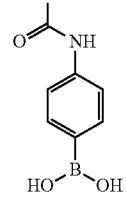 and  | 724.36 | 724.40 2.22 min (column F) |
| P-C-110 | 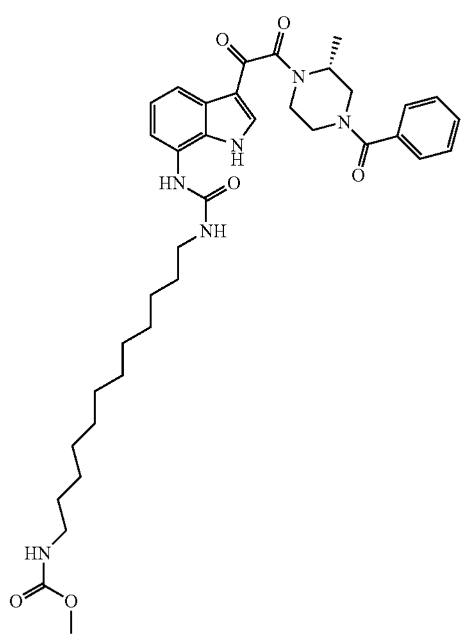 [SMILES: COC(=O)NCCCCCCCCCCCCNC(=O)Nc1cccc2c(C(=O)C(=O)N3CCN(C(=O)c4ccccc4)C[C@H]3C)c[nH]c12] |  and MeOH | 675.39 | 675.38 2.46 min (column F) |

-continued
| Compd. Number | Structure | Reagents Used | MS (M + H)+ Calcd. | MS (M + H)+ Observ. And Retention Time and NMR |
|---|---|---|---|---|
| P-C-111 | 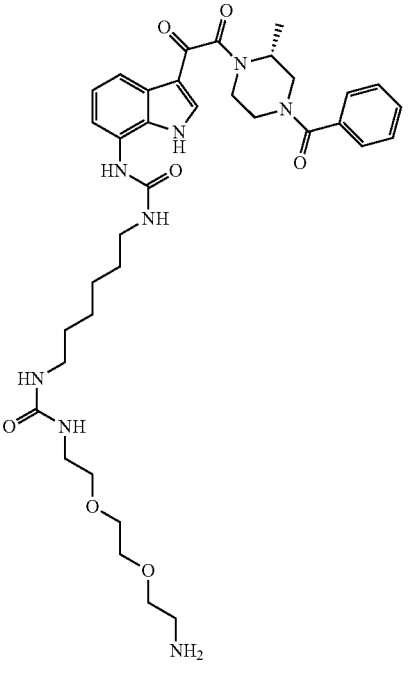 [SMILES: C[C@@H]1CN(C(=O)c2ccccc2)CCN1C(=O)C(=O)c1c[nH]c2c(NC(=O)NCCCCCCNC(=O)NCCOCCOCCN)cccc12] | 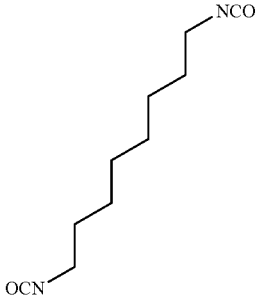 and 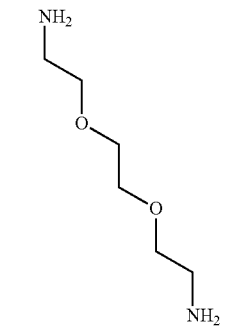 | 707.39 | 707.47 1.88 min (column F) |
| P-C-112 | 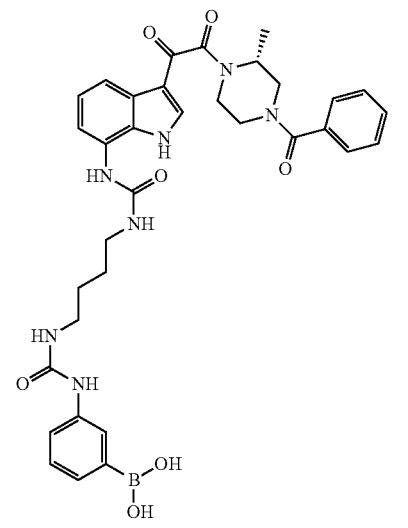 [SMILES: C[C@@H]1CN(C(=O)c2ccccc2)CCN1C(=O)C(=O)c1c[nH]c2c(NC(=O)NCCCCNC(=O)Nc3cccc(B(O)O)c3)cccc12] | 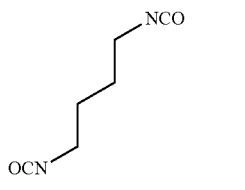 and 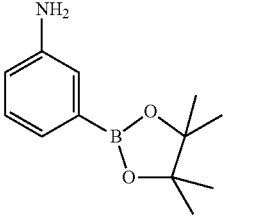 [SMILES: CC1(C)OB(c2cccc(N)c2)OC1(C)C] | 668.3 | 668.34 2.03 min (column F) |

-continued
| Compd. Number | Structure | Reagents Used | MS (M + H)+ Calcd. | MS (M + H)+ Observ. And Retention Time and NMR |
|---|---|---|---|---|
| P-C-113 | 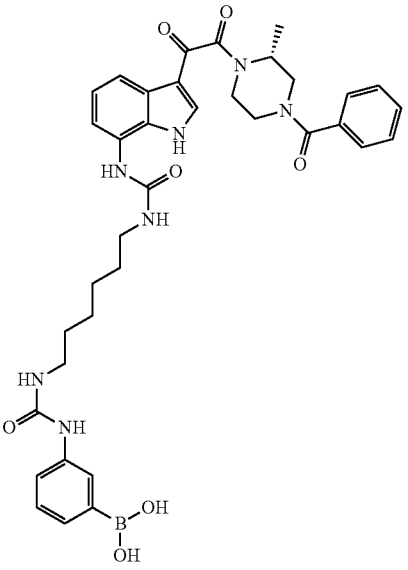 [SMILES: C[C@@H]1CN(C(=O)c2ccccc2)CCN1C(=O)C(=O)c1c[nH]c2c(NC(=O)NCCCCCCNC(=O)Nc3cccc(B(O)O)c3)cccc12] | 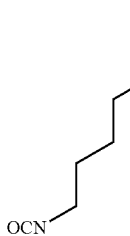 and 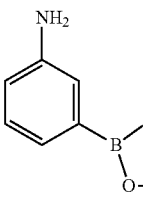 | 696.33 | 696.38 2.14 min (column F) |
| P-C-114 | 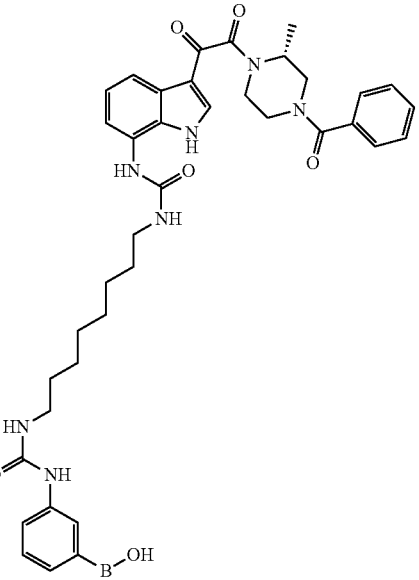 | 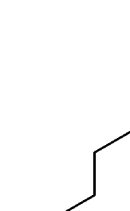 and 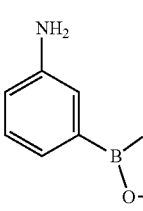 | 724.36 | 724.41 2.25 min (column F) |

-continued
| Compd. Number | Structure | Reagents Used | MS (M + H)+ Calcd. | MS (M + H)+ Observ. And Retention Time and NMR |
|---|---|---|---|---|
| P-C-115 | 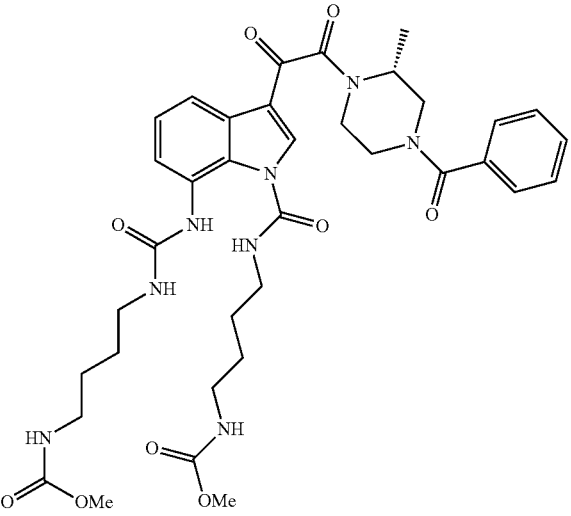 [SMILES: COC(=O)NCCCCNC(=O)Nc1cccc2c(C(=O)C(=O)N3CCN(C(=O)c4ccccc4)C[C@H]3C)cn(C(=O)NCCCCNC(=O)OC)c12] | 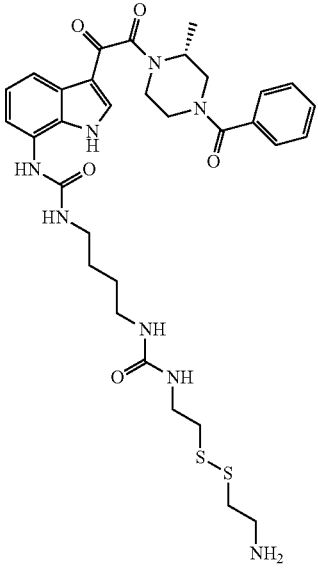 [SMILES: C[C@@H]1CN(C(=O)c2ccccc2)CCN1C(=O)C(=O)c1c[nH]c2c(NC(=O)NCCCCNC(=O)NCCSSCCN)cccc12]  and MeOH | 735.35 | 735.44 2.10 min (column F) |
| P-C-116 | 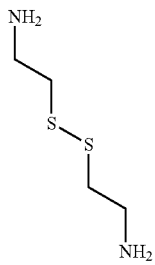 | OCN~~~NCO and H2N~~S-S~~NH2 | 638.28 | 683.30 1.91 min (column F) |

159

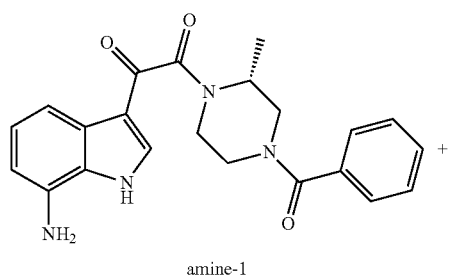

amine-1

160

-continued

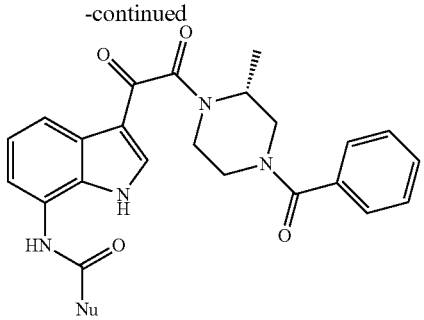

P-C

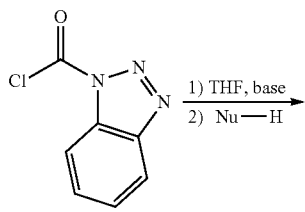

An excess of triethyl amine or di-isopropyl ethyl amine was added into a solution of I-1-(7-amino-1H-indol-3-yl)-2-(4-benzoyl-2-methylpiperazin-1-yl)ethane-1,2-dione, amine-1 (1 eq.) and 1H-benzo[d][1,2,3]triazole-1-carbonyl chloride (1 to 1.5 eq.) in dry THF. After 16 hours, a nucleophile (2 to 5 eq.) such as alcohol or amine was added and the reaction mixture was stirred for another 14 hours. Then, the reaction mixture was partitioned between saturated NaHCO$_3$ and EtOAc, and the aqueous phase was extracted with EtOAc. Then the combined organic layer was dried over MgSO$_4$ and concentrated to offer a residue which was purified using Shimadzu automated preparative HPLC System to afford the desired urea or carbamate.

| Compd. Number | Structure | Reagents Used | MS (M + H)$^+$ Calcd. | MS (M + H)$^+$ Observ. And Retention Time and NMR |
|---|---|---|---|---|
| P-C-201 | 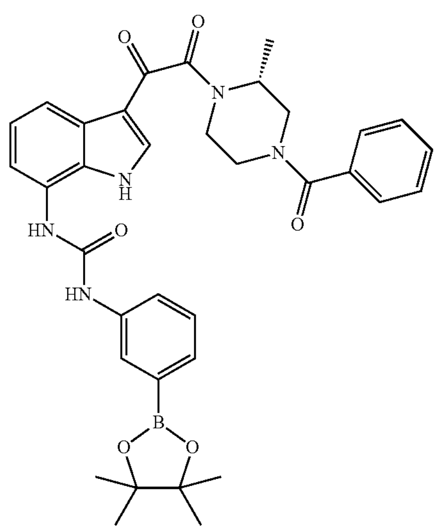 [SMILES: C[C@@H]1CN(C(=O)c2ccccc2)CCN1C(=O)C(=O)c1c[nH]c2c(NC(=O)Nc3cccc(B4OC(C)(C)C(C)(C)O4)c3)cccc12] | | 636.3 | 636.28 2.34 min (column F) |

| Compd. Number | Structure | Reagents Used | MS (M + H)+ Calcd. | MS (M + H)+ Observ. And Retention Time and NMR |
|---|---|---|---|---|
| P-C-202 | 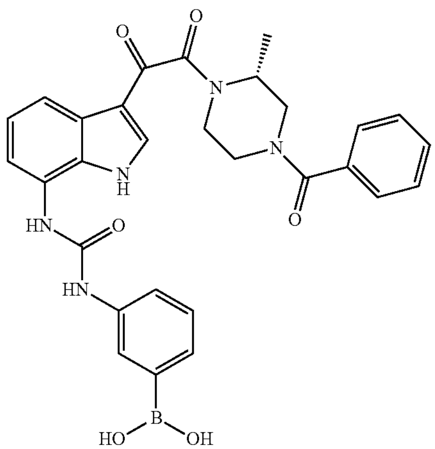 [SMILES: C[C@@H]1CN(C(=O)c2ccccc2)CCN1C(=O)C(=O)c1c[nH]c2c(NC(=O)Nc3cccc(B(O)O)c3)cccc12] | H₂N-C₆H₄-Bpin (3-) | 554.22 | 554.22 2.06 min (column F) |
| P-C-203 | 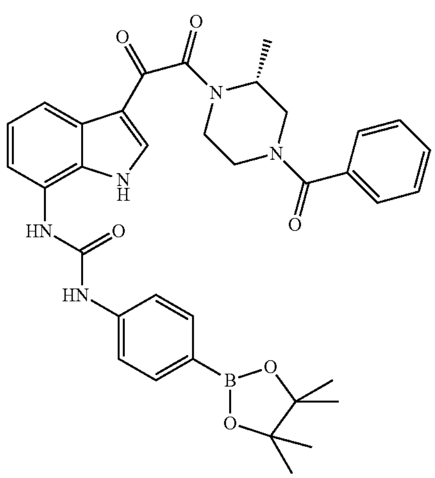 [SMILES: C[C@@H]1CN(C(=O)c2ccccc2)CCN1C(=O)C(=O)c1c[nH]c2c(NC(=O)Nc3ccc(B4OC(C)(C)C(C)(C)O4)cc3)cccc12] | NH₂-C₆H₄-Bpin (4-) | 636.3 | 636.25 2.32 min (column F) |
| P-C-204 | 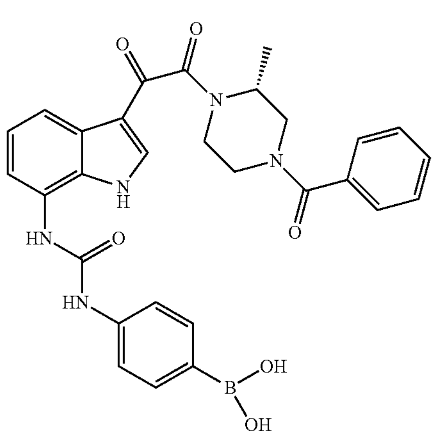 [SMILES: C[C@@H]1CN(C(=O)c2ccccc2)CCN1C(=O)C(=O)c1c[nH]c2c(NC(=O)Nc3ccc(B(O)O)cc3)cccc12] | NH₂-C₆H₄-B(OH)₂ (4-) | 554.22 | 554.23 2.07 min (column F) |

-continued

| Compd. Number | Structure | Reagents Used | MS (M + H)+ Calcd. | MS (M + H)+ Observ. And Retention Time and NMR |
|---|---|---|---|---|
| P-C-205 | 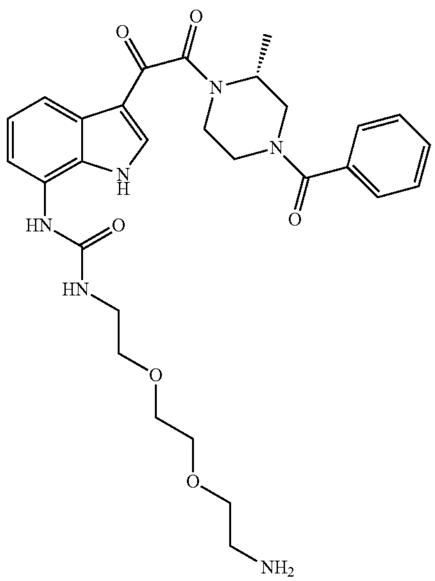 [SMILES: C[C@@H]1CN(C(=O)c2ccccc2)CCN1C(=O)C(=O)c1c[nH]c2c(NC(=O)NCCOCCOCCN)cccc12] | H₂N-CH₂CH₂-O-CH₂CH₂-O-CH₂CH₂-NH₂ | 565.28 | 565.31 1.69 min (column F) |
| P-C-206 | 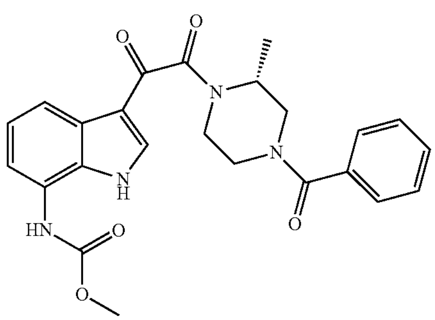 [SMILES: COC(=O)Nc1cccc2c(C(=O)C(=O)N3CCN(C(=O)c4ccccc4)C[C@H]3C)c[nH]c12] | MeOH | 449.18 | 449.19 1.91 min (column F) |
| P-C-207 | 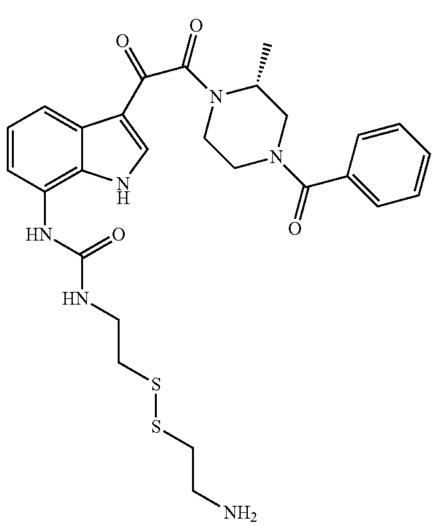 [SMILES: C[C@@H]1CN(C(=O)c2ccccc2)CCN1C(=O)C(=O)c1c[nH]c2c(NC(=O)NCCSSCCN)cccc12] | H₂N-CH₂CH₂-S-S-CH₂CH₂-NH₂ | 569.2 | 569.16 1.80 min (column F) |

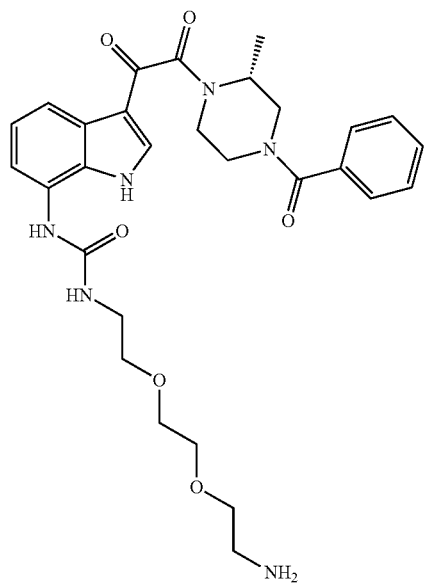

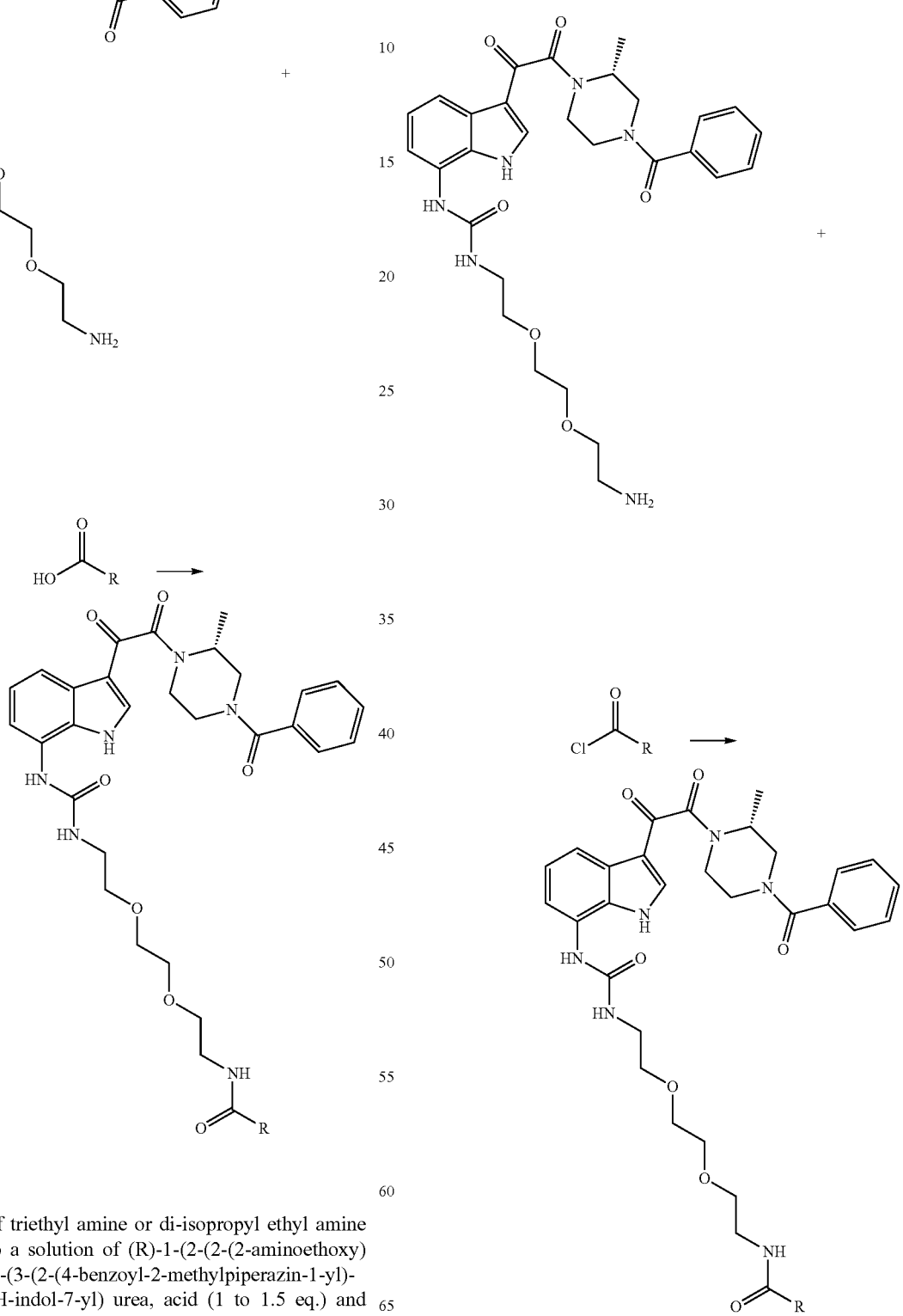

Na$_2$CO$_3$ solution and EtOAc, and the aqueous phase was extracted with EtOAc. Then the combined organic layer was dried over MgSO$_4$ and concentrated to offer a residue which was purified using Shimadzu automated preparative HPLC System to afford the desired amide.

An excess of triethyl amine or di-isopropyl ethyl amine was added into a solution of (R)-1-(2-(2-(2-aminoethoxy)ethoxy)ethyl)-3-(3-(2-(4-benzoyl-2-methylpiperazin-1-yl)-2-oxoacetyl)-1H-indol-7-yl) urea, acid (1 to 1.5 eq.) and TBTU (1 to 5 eq.) in dry THF or DMF. After 16 hours, the reaction mixture was partitioned between 10% aqueous An excess of triethyl amine or di-isopropyl ethyl amine was added into a solution of (R)-1-(2-(2-(2-aminoethoxy)ethoxy)ethyl)-3-(3-(2-(4-benzoyl-2-methylpiperazin-1-yl)-2-oxoacetyl)-1H-indol-7-yl)urea and acyl halide (1 to 1.5 eq.) in dry THF or DMF. After 16 hours, the reaction mixture was partitioned between 10% aqueous Na₂CO₃ solution or saturated aqueous NaHCO₃ solution and EtOAc, and the aqueous phase was extracted with EtOAc. Then the combined organic layer was dried over MgSO₄ and concentrated to offer a residue which was purified using Shimadzu automated preparative HPLC System to afford the desired amide.

| Compd. Number | Structure | RCOCl Used | MS (M + H)⁺ Calcd. | MS (M + H)⁺ Observ. |
|---|---|---|---|---|
| P-C-401 | 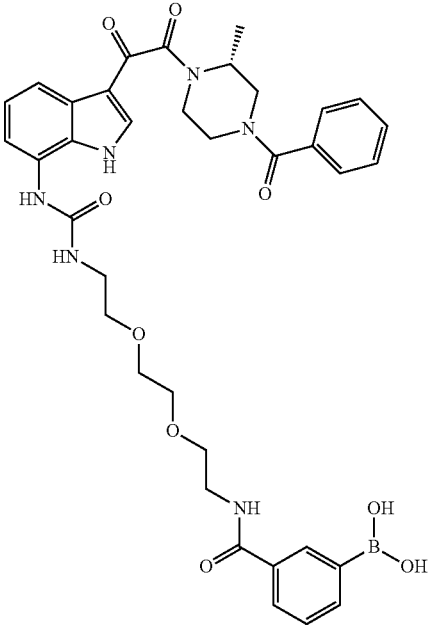 [SMILES: C[C@@H]1CN(C(=O)c2ccccc2)CCN1C(=O)C(=O)c1c[nH]c2c(NC(=O)NCCOCCOCCNC(=O)c3cccc(B(O)O)c3)cccc12] | 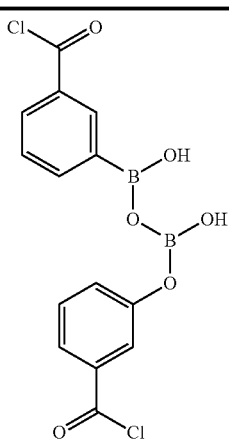 | 713.31 | 713.36 2.02 min (column F) |
| P-C-402 | 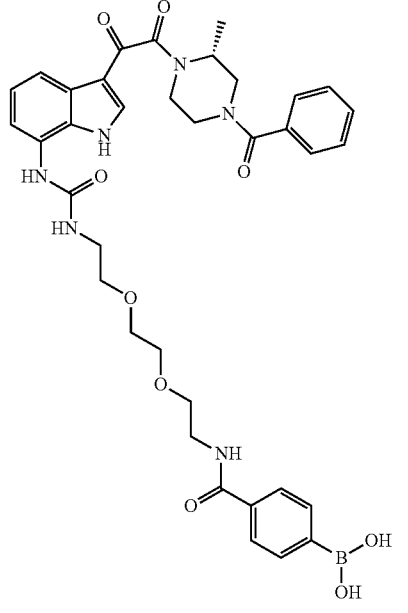 [SMILES: C[C@@H]1CN(C(=O)c2ccccc2)CCN1C(=O)C(=O)c1c[nH]c2c(NC(=O)NCCOCCOCCNC(=O)c3ccc(B(O)O)cc3)cccc12] | 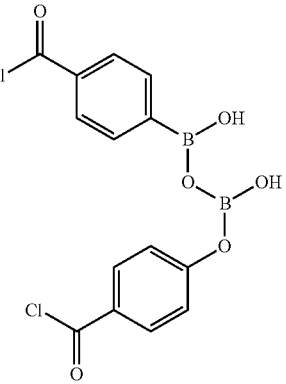 | 713.31 | 713.36 2.01 min (column F) |

169
Typical Procedure to Prepare Carbamate Derivatives from Amino-Indole Procusors General Procedure:

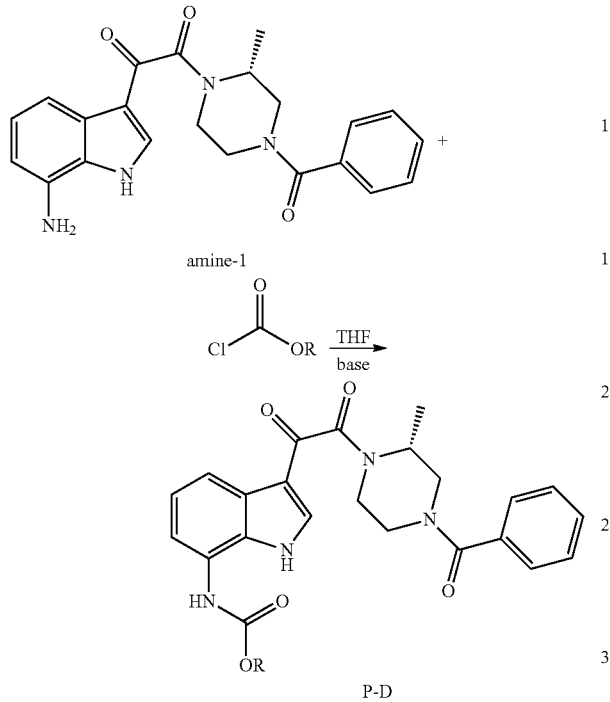

P-D

An excess of triethyl amine or di-isopropyl ethyl amine was added into a solution of I-1-(7-amino-1H-indol-3-yl)-2-(4-benzoyl-2-methylpiperazin-1-yl)ethane-1,2-dione, amine-1 (1 eq.) and alkoxyl chloroformate (1 to 5 eq.) in dry THF. After 16 hours, the reaction mixture was partitioned between saturated NaHCO$_3$ and EtOAc, and the aqueous phase was extracted with EtOAc. Then the combined organic layer was dried over MgSO$_4$ and concentrated to offer a residue which was purified using Shimadzu automated preparative HPLC System to afford the desired carbamate. Characterization of the Compounds of Formula I:

170
Typical Procedure to Prepare Sulfonamide and Sulfamide Derivatives from Amino-Indole Procusors General Procedure:

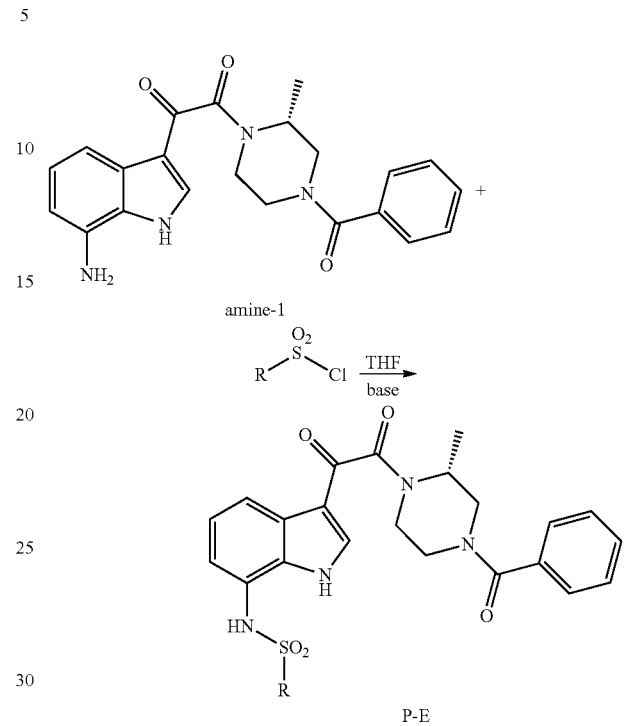

P-E

An excess of triethyl amine or di-isopropyl ethyl amine was added into a solution of I-1-(7-amino-1H-indol-3-yl)-2-(4-benzoyl-2-methylpiperazin-1-yl)ethane-1,2-dione, amine-1 (1 eq.) and sulfonyl chloride or sulfamoyl chloride (1 to 5 eq.) in dry THF. After 16 hours, the reaction mixture was partitioned between saturated NaHCO$_3$ and EtOAc, and the aqueous phase was extracted with EtOAc. Then the combined organic layer was dried over MgSO$_4$ and concentrated to offer a residue which was purified using Shimadzu automated preparative HPLC System to afford the desired sulfonamide or sulfamide.

TABLE D

| Compd. Number | Structure | Reagents Used | MS (M + H)$^+$ Calcd. | MS (M + H)$^+$ Observ. And Retention Time and NMR |
|---|---|---|---|---|
| P-D-1 | 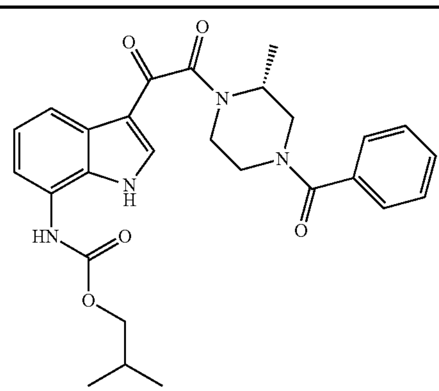 | | 491.23 | 491.33 1.66 min (column C) |

Characterization of the Compounds of Formula I:

TABLE E

| Compd. Number | Structure | Reagents Used | MS (M + H)+ Calcd. | MS (M + H)+ Observ. And Retention Time and NMR |
|---|---|---|---|---|
| P-E-1 | 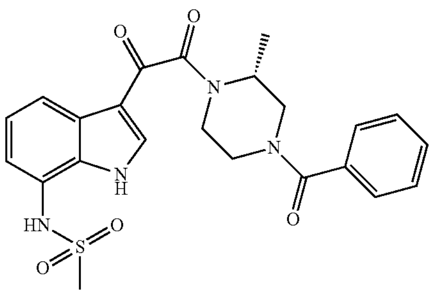 [SMILES: C[C@@H]1CN(C(=O)c2ccccc2)CCN1C(=O)C(=O)c1c[nH]c2c(NS(C)(=O)=O)cccc12] | | 469.15 | 469.26 1.44 min (column C) |
| P-E-2 | 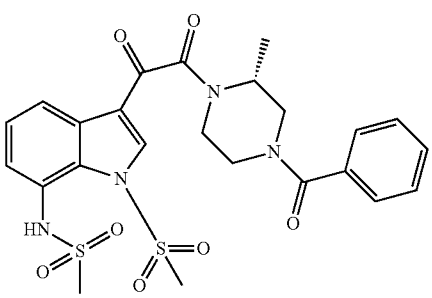 [SMILES: C[C@@H]1CN(C(=O)c2ccccc2)CCN1C(=O)C(=O)c1cn(S(C)(=O)=O)c2c(NS(C)(=O)=O)cccc12] | | 547.13 | 547.29 1.45 min (column C) |
| P-E-3 | 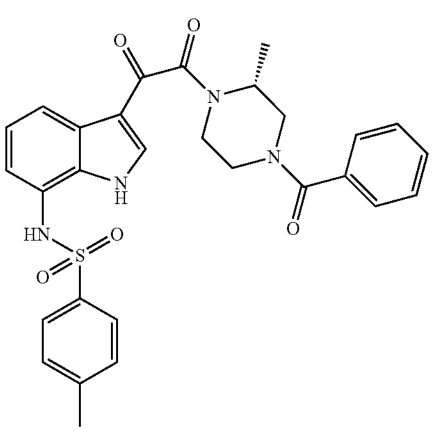 [SMILES: Cc1ccc(S(=O)(=O)Nc2cccc3c(C(=O)C(=O)N4CCN(C(=O)c5ccccc5)C[C@H]4C)c[nH]c23)cc1] | | 545.19 | 545.38 1.69 min (column C) |

TABLE E-continued

| Compd. Number | Structure | Reagents Used | MS (M + H)+ Calcd. | MS (M + H)+ Observ. And Retention Time and NMR |
|---|---|---|---|---|
| P-E-4 | 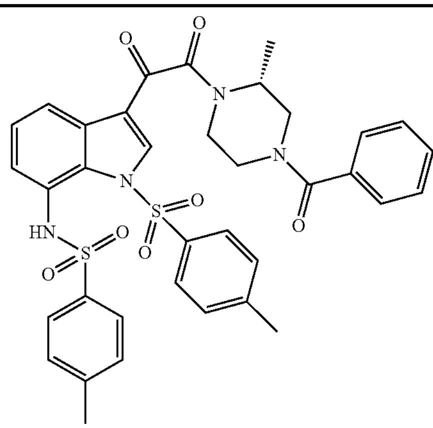 | | 699.19 | 699.41<br>1.94 min<br>(column C) |
| P-E-5 | 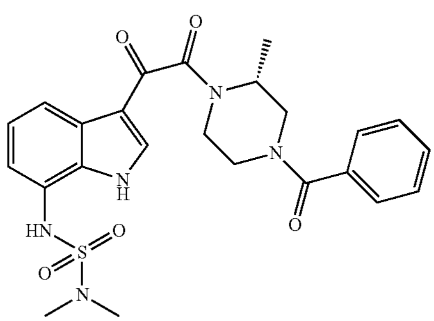 [SMILES: C[C@@H]1CN(C(=O)c2ccccc2)CCN1C(=O)C(=O)c1c[nH]c2c(NS(=O)(=O)N(C)C)cccc12] | | 498.18 | 498.29<br>1.51 min<br>(column C) |

Typical Procedure to Prepare Guanidine Derivatives from Amino-Indole Procusors

General Procedures:

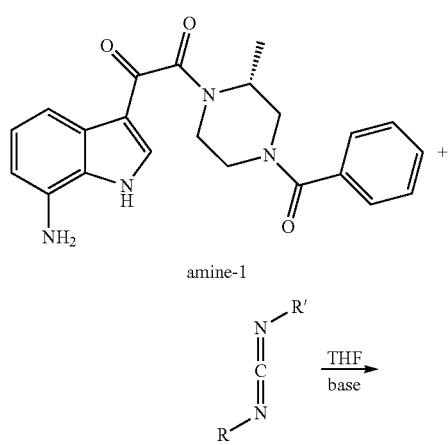

amine-1

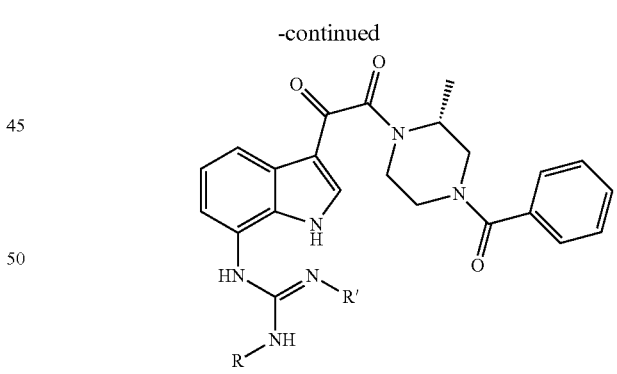

P-F

An excess of triethyl amine or di-isopropyl ethyl amine was added into a solution of I-1-(7-amino-1H-indol-3-yl)-2-(4-benzoyl-2-methylpiperazin-1-yl)ethane-1,2-dione, amine-1 (1 eq.) and carbodiimide (1 to 5 eq.) in dry THF. After 16 hours, the reaction mixture was partitioned between saturated NaHCO$_3$ and EtOAc, and the aqueous phase was extracted with EtOAc. Then the combined organic layer was dried over MgSO$_4$ and concentrated to offer a residue which was purified using Shimadzu automated preparative HPLC System to afford the desired guanidine.

Characterization of the Compounds of Formula I:

TABLE F

| Compd. Number | Structure | Reagents Used | MS (M + H)+ Calcd. | MS (M + H)+ Observ. And Retention Time and NMR |
|---|---|---|---|---|
| P-F-1 | 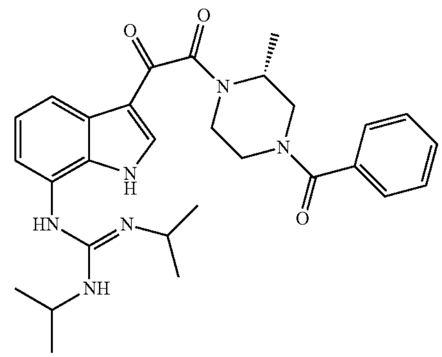 [SMILES: CC(C)/N=C(/Nc1cccc2c(C(=O)C(=O)N3CCN(C(=O)c4ccccc4)C[C@H]3C)c[nH]c12)NC(C)C] | | 571.29 | 517.43 1.45 min (column C) |
| P-F-2 | 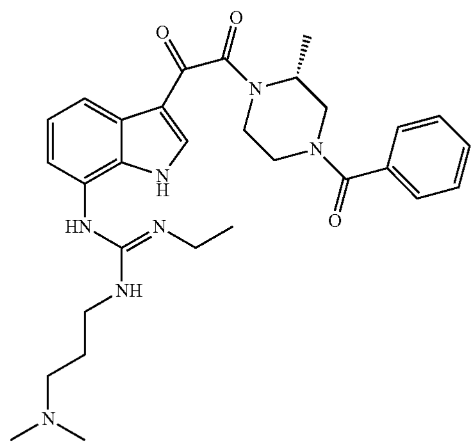 [SMILES: CC/N=C(\NCCCN(C)C)Nc1cccc2c(C(=O)C(=O)N3CCN(C(=O)c4ccccc4)C[C@H]3C)c[nH]c12] | | 546.32 | 546.46 1.33 min (column C) |

Typical Procedure to Prepare Cyclic Urea Derivatives from Amino-Indole Precursors General Procedures:
Step A:

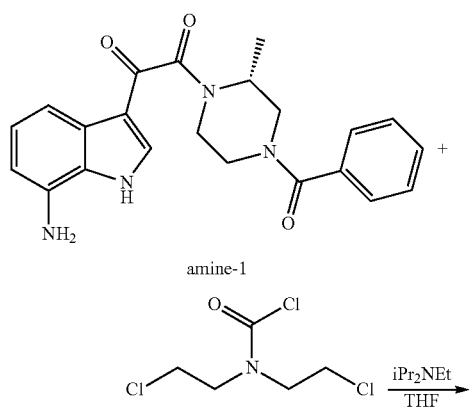

amine-1

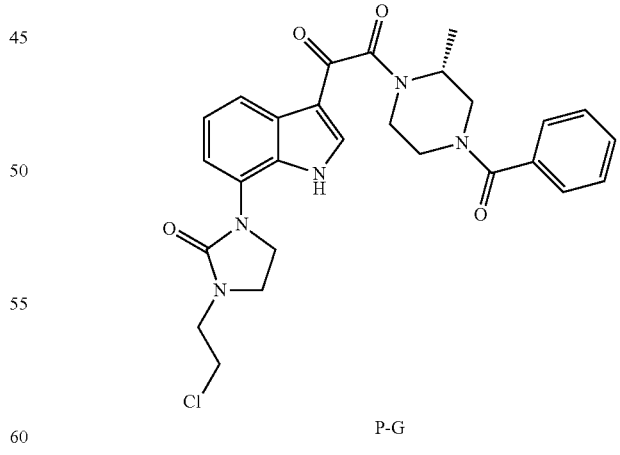

P-G

An excess of di-isopropyl ethyl amine was added into a solution of I-1-(7-amino-1H-indol-3-yl)-2-(4-benzoyl-2-methylpiperazin-1-yl)ethane-1,2-dione, amine-1 (300 mg) and bis(2-chloroethyl)carbamic chloride (157 mg) in dry THF. After 16 hours, the reaction mixture was partitioned between saturated NaHCO₃ and EtOAc, and the aqueous phase was extracted with EtOAc. Then the combined organic layer was dried over MgSO₄ and concentrated to offer a crude product chloride which was used in the further reactions without purification.

Characterization of the Compounds of Formula I:

TABLE G

| Compd. Number | Structure | MS (M + H)⁺ Calcd. | MS (M + H)⁺ Observ. And Retention Time and NMR |
|---|---|---|---|
| P-G-1 | 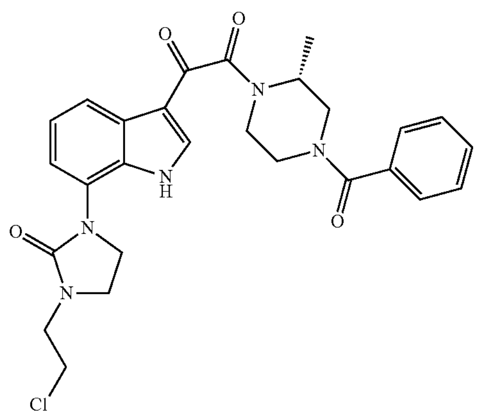 [SMILES: C[C@@H]1CN(C(=O)c2ccccc2)CCN1C(=O)C(=O)c1c[nH]c2c(N3CCN(CCCl)C3=O)cccc12] | 522.19 | 522.22 1.36 min (column C) |

Step B:

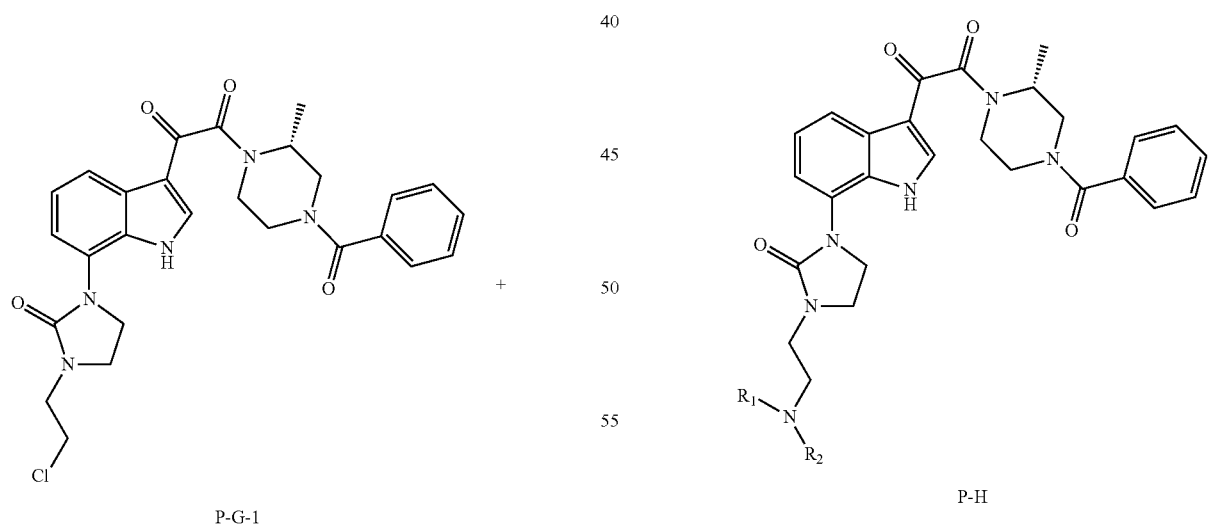

P-H

An excess of amine was added into a solution of the afore chloride in THF. After 16 hours, the reaction mixture was partitioned between saturated NaHCO₃ and EtOAc, and the aqueous phase was extracted with EtOAc. Then the combined organic layer was dried over MgSO₄ and concentrated to offer a residue which was purified using Shimadzu automated preparative HPLC System to afford the desired urea.

Characterization of the Compounds of Formula I:

TABLE H

| Compd. Number | Structure | Reagents Used | MS (M + H)+ Calcd. | MS (M + H)+ Observ. And Retention Time and NMR |
|---|---|---|---|---|
| P-H-1 | 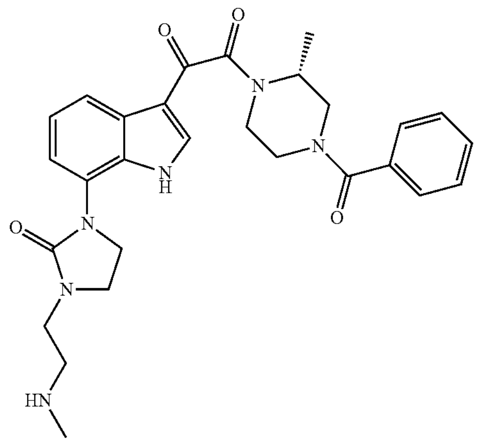 [SMILES: CNCCN1CCN(c2cccc3c(C(=O)C(=O)N4CCN(C(=O)c5ccccc5)C[C@H]4C)c[nH]c23)C1=O] | MeNH2 in water | 517.26 | 517.27 1.10 min (column C) |
| P-H-2 | 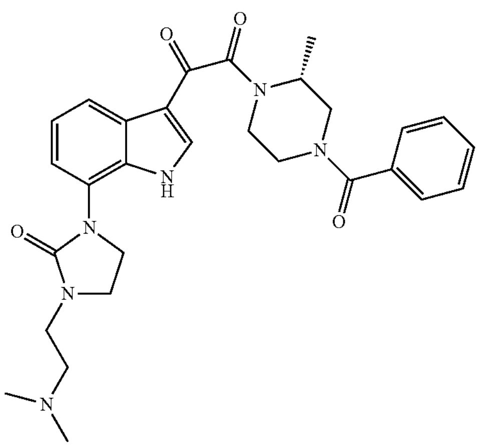 [SMILES: C[C@@H]1CN(C(=O)c2ccccc2)CCN1C(=O)C(=O)c1c[nH]c2c(N3CCN(CCN(C)C)C3=O)cccc12] | Me2NH in water | 531.27 | 531.30 1.36 min (column C) |

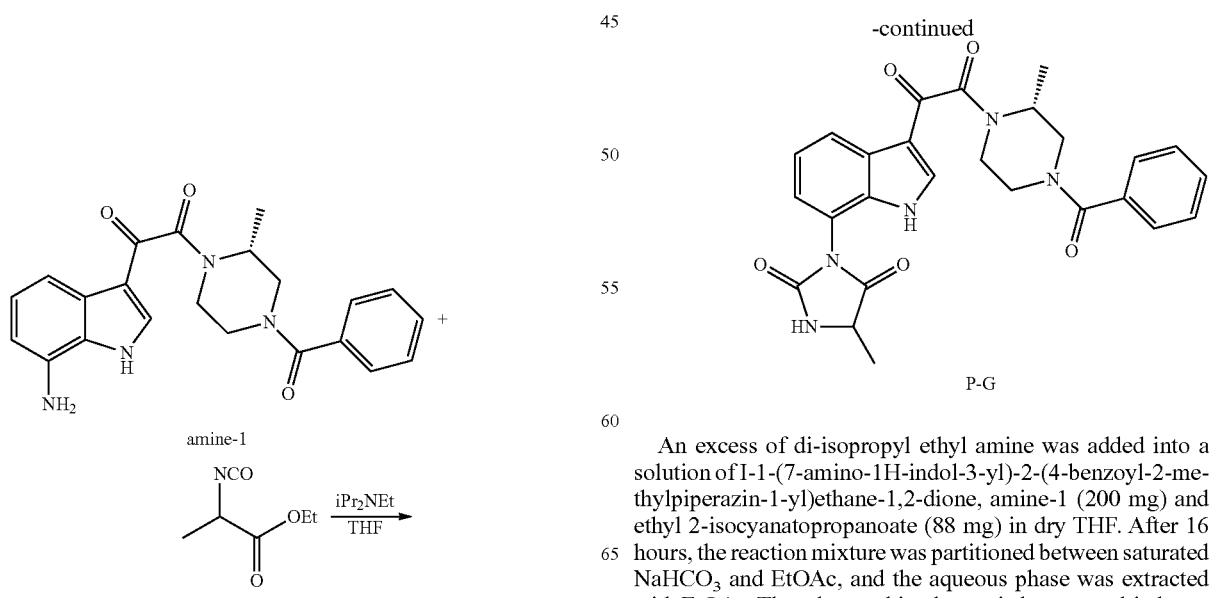

P-G

An excess of di-isopropyl ethyl amine was added into a solution of I-1-(7-amino-1H-indol-3-yl)-2-(4-benzoyl-2-methylpiperazin-1-yl)ethane-1,2-dione, amine-1 (200 mg) and ethyl 2-isocyanatopropanoate (88 mg) in dry THF. After 16 hours, the reaction mixture was partitioned between saturated NaHCO3 and EtOAc, and the aqueous phase was extracted with EtOAc. Then the combined organic layer was dried over MgSO₄ and concentrated to offer a residue which was purified using Shimadzu automated preparative HPLC System to afford the desired urea.

| Compd. Number | Structure | Reagents Used | MS (M + H)⁺ Calcd. | MS (M + H)⁺ Observ. And Retention Time and NMR |
|---|---|---|---|---|
| P-G-2 | 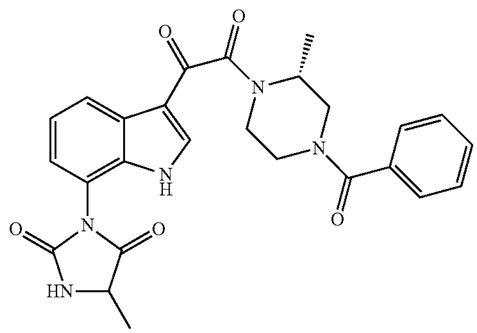 [SMILES: CC1NC(=O)N(c2cccc3c(C(=O)C(=O)N4CCN(C(=O)c5ccccc5)C[C@H]4C)c[nH]c23)C1=O] | | 488.19 | 488.34 Rf = 1.41 min (column C) |
| P-G-3 | 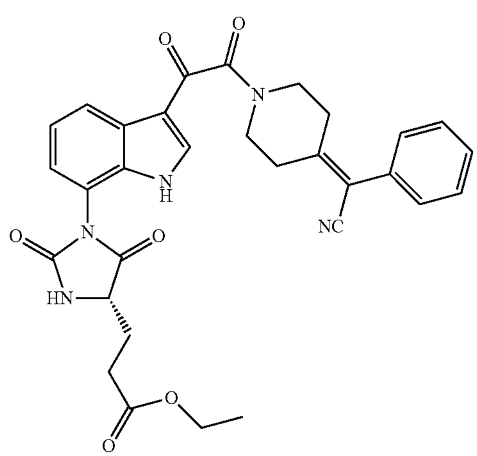 [SMILES: CCOC(=O)CC[C@@H]1NC(=O)N(c2cccc3c(C(=O)C(=O)N4CCC(=C(C#N)c5ccccc5)CC4)c[nH]c23)C1=O] | | 568.22 | 568.04 Rf = 1.77 min (column B) |

Typical Procedure of Hydrolysis of Ester to Acid and Alcohol

General Procedure:

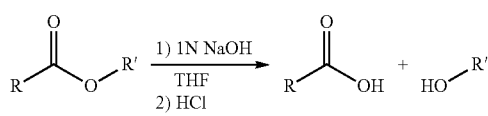

Ester was dissolved in a mixed solution of 1N NaOH and THF. After 16 hours, the reaction mixture was partitioned between saturated 1N HCl (to neutralize NaOH and acidify the reaction mixture) and EtOAc, and the aqueous phase was extracted with EtOAc. Then the combined organic layer was dried over MgSO₄ and concentrated to offer a residue which was purified using Shimadzu automated preparative HPLC System to afford the desired ester or alcohol.

| Compd. Number | Structure | Precursor | MS (M + H)+ Calcd. | MS (M + H)+ Observ. And Retention Time and NMR |
|---|---|---|---|---|
| P-I-1 | 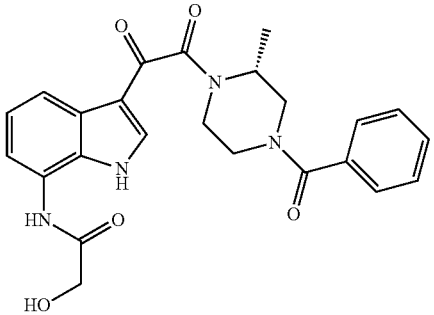 [SMILES: C[C@@H]1CN(C(=O)c2ccccc2)CCN1C(=O)C(=O)c1c[nH]c2c(NC(=O)CO)cccc12] | P-A-4 | 449.18 | 449.30<br>1.32 min<br>(column C) |
| P-I-2 | 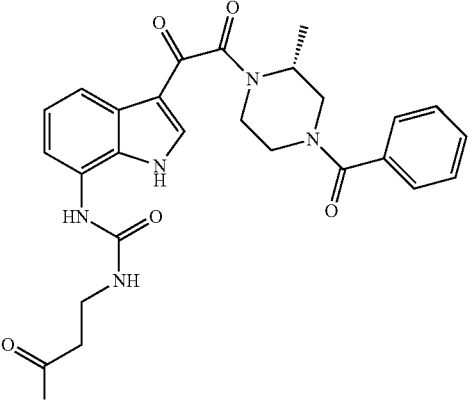 | P-C-2 | 506.20 | 506.27<br>0.84 min<br>(column D, solvent system II) |
| P-I-3 | 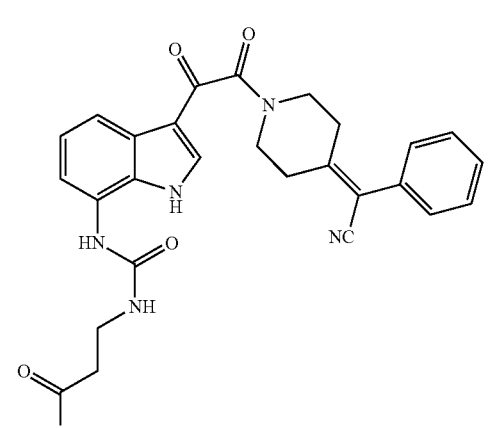 | P-C-3 | 500.19 | 500.03<br>1.63 min<br>(column B) |

-continued

| Compd. Number | Structure | Precursor | MS (M + H)+ Calcd. | MS (M + H)+ Observ. And Retention Time and NMR |
|---|---|---|---|---|
| P-I-4 | 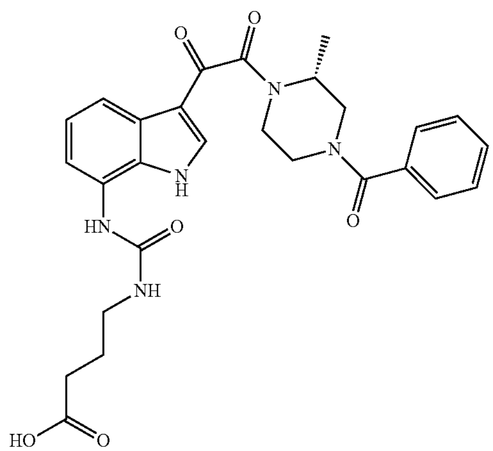 [SMILES: C[C@@H]1CN(C(=O)c2ccccc2)CCN1C(=O)C(=O)c1c[nH]c2c(NC(=O)NCCCC(=O)O)cccc12] | P-C-5 | 520.22 | 520.30 0.90 min (column D, solvent system II) |
| P-I-5 | 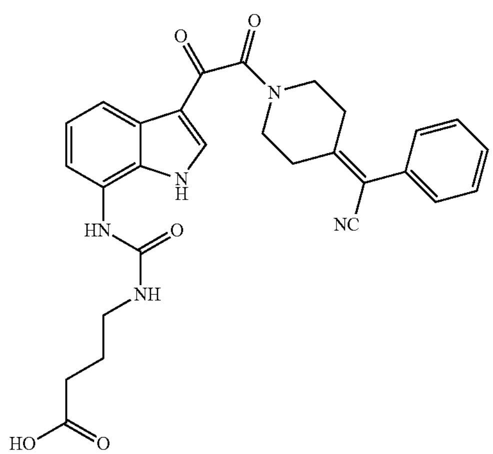 [SMILES: N#CC(=C1CCN(C(=O)C(=O)c2c[nH]c3c(NC(=O)NCCCC(=O)O)cccc23)CC1)c1ccccc1] | P-C-6 | 514.21 | 514.06 1.63 min (column B) |
| P-I-6 | 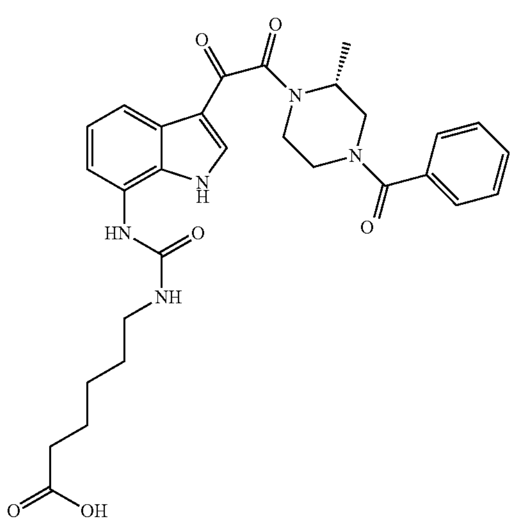 [SMILES: C[C@@H]1CN(C(=O)c2ccccc2)CCN1C(=O)C(=O)c1c[nH]c2c(NC(=O)NCCCCCC(=O)O)cccc12] | P-C-7 | 548.25 | 548.30 0.90 min (column D, solvent system II) |

-continued
| Compd. Number | Structure | Precursor | MS (M + H)+ Calcd. | MS (M + H)+ Observ. And Retention Time and NMR |
|---|---|---|---|---|
| P-I-7 | 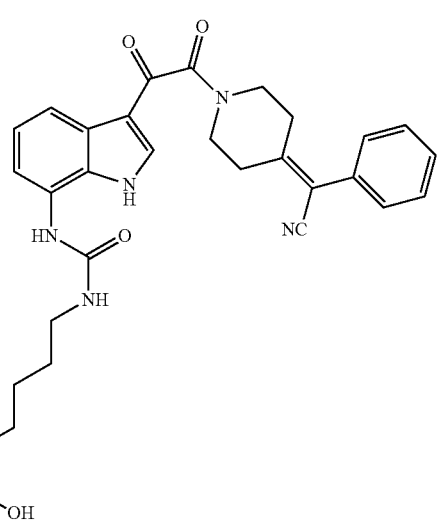 | P-C-8 | 542.24 | 542.11<br>1.66 min<br>(column B) |
| P-I-8 | 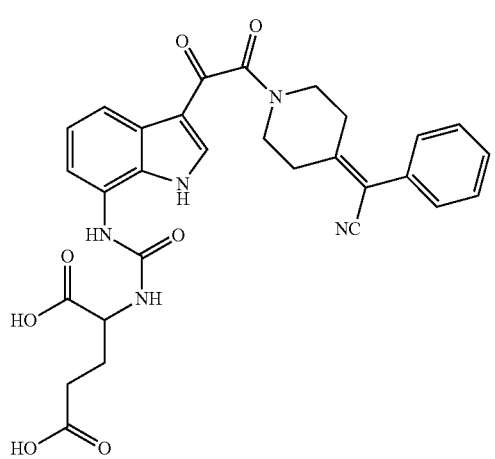 [SMILES: N#CC(=C1CCN(C(=O)C(=O)c2c[nH]c3c(NC(=O)NC(CCC(=O)O)C(=O)O)cccc23)CC1)c1ccccc1] | The corresponding dimethylester (not isolated) | 558.20 | 558.04<br>1.61 min<br>(column B) |
| P-I-9 | 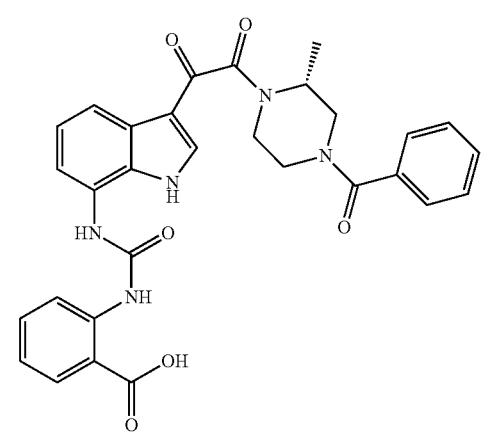 [SMILES: C[C@@H]1CN(C(=O)c2ccccc2)CCN1C(=O)C(=O)c1c[nH]c2c(NC(=O)Nc3ccccc3C(=O)O)cccc12] | P-C-10 | 554.57 | 554.29<br>0.92 min<br>(column D solvent system II) |

-continued

| Compd. Number | Structure | Precursor | MS (M + H)+ Calcd. | MS (M + H)+ Observ. And Retention Time and NMR |
|---|---|---|---|---|
| P-I-10 | 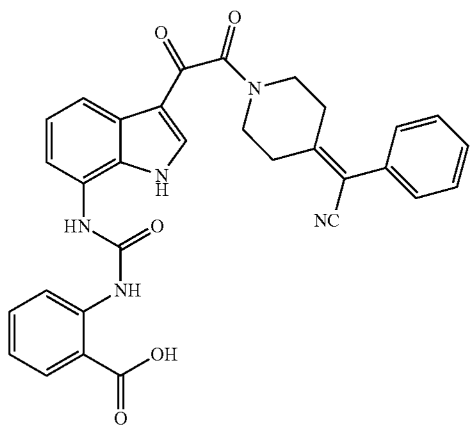 [SMILES: N#CC(=C1CCN(C(=O)C(=O)c2c[nH]c3c(NC(=O)Nc4ccccc4C(=O)O)cccc23)CC1)c1ccccc1] | P-C-11 | 548.19 | 548.04<br>1.78 min<br>(column B) |
| P-I-11 | 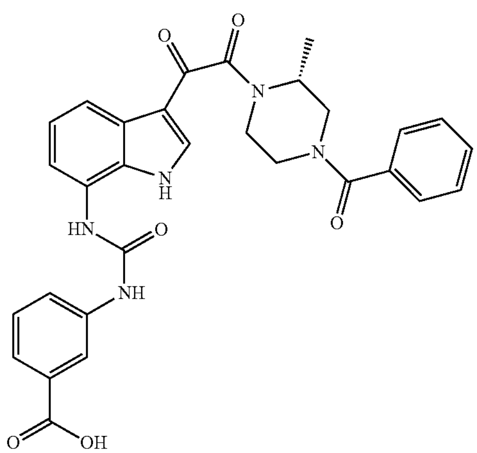 [SMILES: C[C@@H]1CN(C(=O)c2ccccc2)CCN1C(=O)C(=O)c1c[nH]c2c(NC(=O)Nc3cccc(C(=O)O)c3)cccc12] | P-C-12 | 554.20 | 554.31<br>0.84 min<br>(column D, solvent system II) |
| P-I-12 | 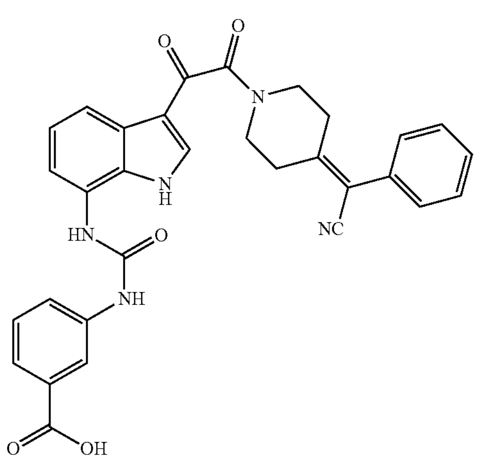 [SMILES: N#CC(=C1CCN(C(=O)C(=O)c2c[nH]c3c(NC(=O)Nc4cccc(C(=O)O)c4)cccc23)CC1)c1ccccc1] | P-C-13 | 548.19 | 548.05<br>1.82 min<br>(column B) |

-continued

| Compd. Number | Structure | Precursor | MS (M + H)+ Calcd. | MS (M + H)+ Observ. And Retention Time and NMR |
|---|---|---|---|---|
| P-I-13 | 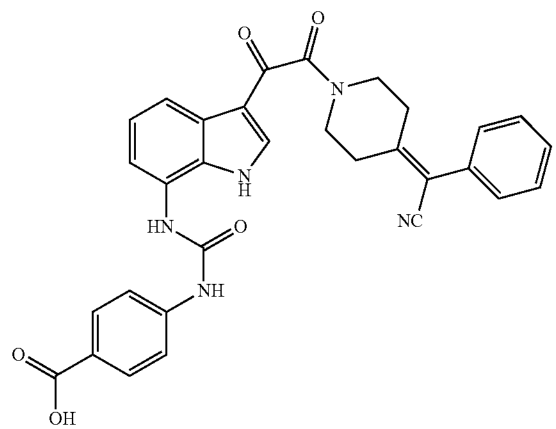 [SMILES: N#CC(=C1CCN(C(=O)C(=O)c2c[nH]c3c(NC(=O)Nc4ccc(C(=O)O)cc4)cccc23)CC1)c1ccccc1] | P-C-15 | 548.19 | 548.05<br>1.81 min<br>(column B) |
| P-I-14 | 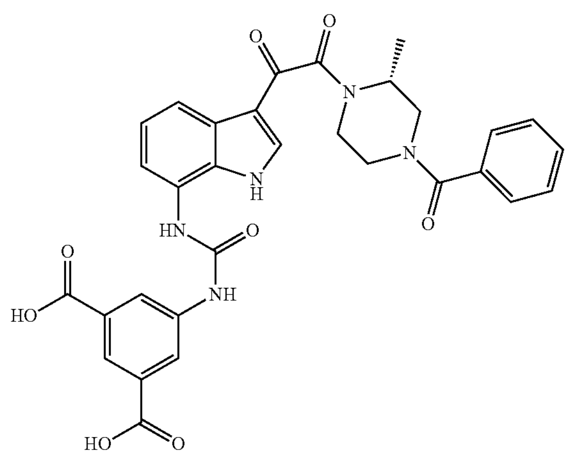 [SMILES: C[C@@H]1CN(C(=O)c2ccccc2)CCN1C(=O)C(=O)c1c[nH]c2c(NC(=O)Nc3cc(C(=O)O)cc(C(=O)O)c3)cccc12] | P-C-16 | 598.19 | 598.27<br>0.82 min<br>(column D, solvent system II) |
| P-I-15 | 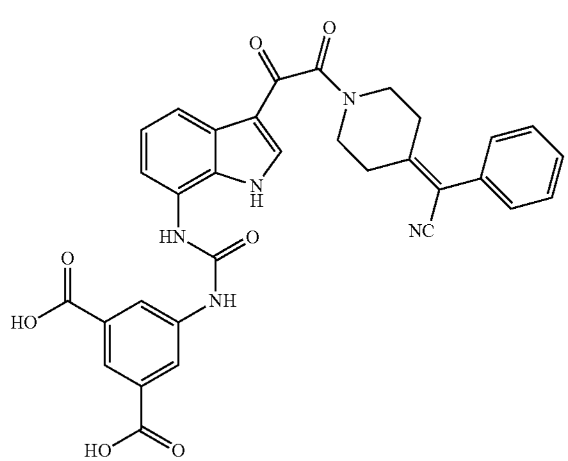 [SMILES: N#CC(=C1CCN(C(=O)C(=O)c2c[nH]c3c(NC(=O)Nc4cc(C(=O)O)cc(C(=O)O)c4)cccc23)CC1)c1ccccc1] | P-C-17 | 592.18 | 592.04<br>1.71 min<br>(column B) |

| Compd. Number | Structure | Precursor | MS (M + H)+ Calcd. | MS (M + H)+ Observ. And Retention Time and NMR |
|---|---|---|---|---|
| P-I-16 | 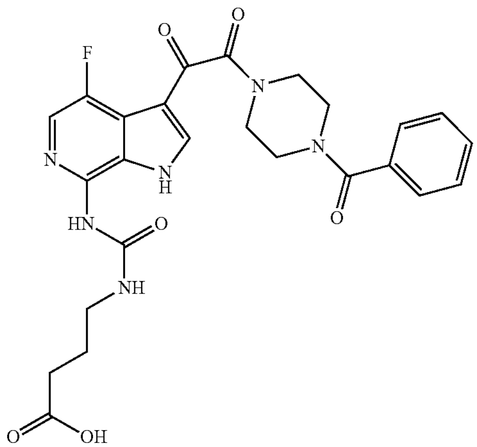 [SMILES: O=C(O)CCCNC(=O)Nc1ncc(F)c2c(C(=O)C(=O)N3CCN(C(=O)c4ccccc4)CC3)c[nH]c12] | P-C-26 | 525.19 | 525.05<br>Rf = 1.36 min<br>(Column B)<br>$^1$H NMR (500 MHz, CD$_3$OD) 8.32 (s, 1H), 7.83 (s, 1H), 7.43 (m, 5H), 4.00-3.20 (m, 10H), 2.40 (m, 2H), 1.92 (m, 2H). |
| P-I-17 | 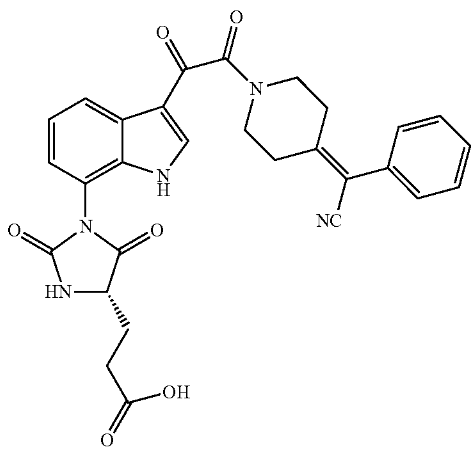 [SMILES: N#CC(=C1CCN(C(=O)C(=O)c2c[nH]c3c(N4C(=O)N[C@@H](CCC(=O)O)C4=O)cccc23)CC1)c1ccccc1] | P-G-3 | 540.19 | 540.03<br>Rf = 1.55 min<br>(column B) |
| P-I-18 | 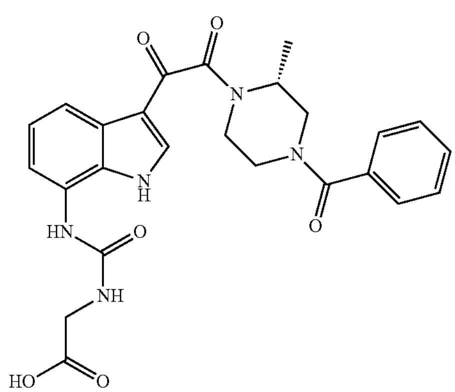 [SMILES: C[C@@H]1CN(C(=O)c2ccccc2)CCN1C(=O)C(=O)c1c[nH]c2c(NC(=O)NCC(=O)O)cccc12] | P-C-1 | 492.19 | 592.16<br>Rf = 1.92 min<br>(column I) |

Biology

"μM" means micromolar;
"mL" means milliliter;
"μl" means microliter;
"mg" means milligram;

The materials and experimental procedures used to obtain the results reported in Tables 1-2 are described below.

Cells:

Virus production—Human embryonic Kidney cell line, 293T, was propagated in Dulbecco's Modified Eagle Medium (Invitrogen, Carlsbad, Calif.) containing 10% fetal Bovine serum (FBS, Sigma, St. Louis, Mo.).

Virus infection—Human epithelial cell line, HeLa, expressing the HIV-1 receptor CD4 was propagated in Dulbecco's Modified Eagle Medium (Invitrogen, Carlsbad, Calif.) containing 10% fetal Bovine serum (FBS, Sigma, St. Louis, Mo.) and supplemented with 0.2 mg/mL Geneticin (Invitrogen, Carlsbad, Calif.).

Virus—Single-round infectious reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen et al, Ref 41). Transfections were performed using lipofectAMINE PLUS reagent as described by the manufacturer (Invitrogen, Carlsbad, Calif.).

Experiment

1. HeLa CD4 cells were plated in 96 well plates at a cell density of $1 \times 10^4$ cells per well in 100 µl Dulbecco's Modified Eagle Medium containing 10% fetal Bovine serum and incubated overnight.
2. Compound was added in a 2 µl dimethylsulfoxide solution, so that the final assay concentration would be $\leqq 10$ µM.
3. 100 µl of single-round infectious reporter virus in Dulbecco's Modified Eagle Medium was then added to the plated cells and compound at an approximate multiplicity of infection (MOI) of 0.01, resulting in a final volume of 200 µl per well.
4. Virally-infected cells were incubated at 37 degrees Celsius, in a $CO_2$ incubator, and harvested 72 h after infection.
5. Viral infection was monitored by measuring luciferase expression from viral DNA in the infected cells using a luciferase reporter gene assay kit, as described by the manufacturer (Roche Molecular Biochemicals, Indianapolis, Ind.). Infected cell supernatants were removed and 50 µl of lysis buffer was added per well. After 15 minutes, 50 µl of freshly-reconstituted luciferase assay reagent was added per well. Luciferase activity was then quantified by measuring luminescence using a Wallac microbeta scintillation counter.
6. The percent inhibition for each compound was calculated by quantifying the level of luciferase expression in cells infected in the presence of each compound as a percentage of that observed for cells infected in the absence of compound and subtracting such a determined value from 100.
7. An $EC_{50}$ provides a method for comparing the antiviral potency of the compounds of this invention. The effective concentration for fifty percent inhibition ($EC_{50}$) was calculated with the Microsoft Excel Xlfit curve fitting software. For each compound, curves were generated from percent inhibition calculated at 10 different concentrations by using a four parameter logistic model (model 205). The $EC_{50}$ data for the compounds is shown in Table 2. Table 1 is the key for the data in Table 2.

Results

TABLE 1

Biological Data Key for $EC_{50}s$

| Compounds with $EC_{50}s > 5$ µM | Compounds with $EC_{50}s > 1$ µM but $<5$ µM | Compounds with $EC_{50} < 1$ µM |
|---|---|---|
| Group C | Group B | Group A |

TABLE 2

| Compd. Number | Structure | $EC_{50}$ Group from Table 1 |
|---|---|---|
| P-A-1 | [structure] | A |
| P-A-2 | [structure] | A |

TABLE 2-continued
| Compd. Number | Structure | EC$_{50}$ Group from Table 1 |
|---|---|---|
| P-A-3 | 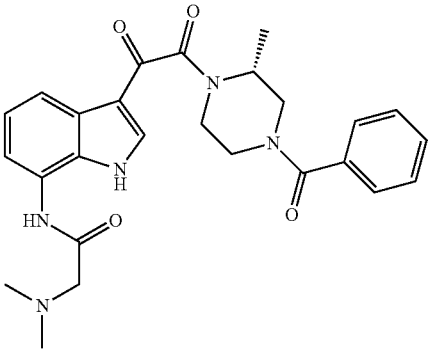 [SMILES: C[C@@H]1CN(C(=O)c2ccccc2)CCN1C(=O)C(=O)c1c[nH]c2c(NC(=O)CN(C)C)cccc12] | A |
| P-A-4 | 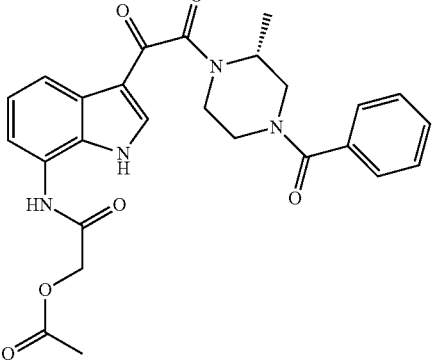 | A |
| P-A-5 | 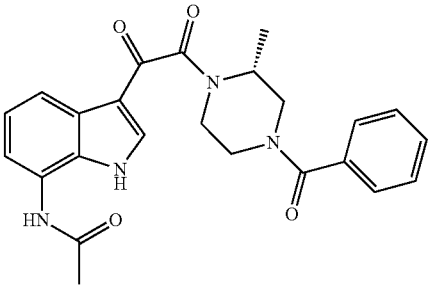 [SMILES: CC(=O)Nc1cccc2c(C(=O)C(=O)N3CCN(C(=O)c4ccccc4)C[C@H]3C)c[nH]c12] | A |

TABLE 2-continued
| Compd. Number | Structure | EC$_{50}$ Group from Table 1 |
|---|---|---|
| P-A-6 | 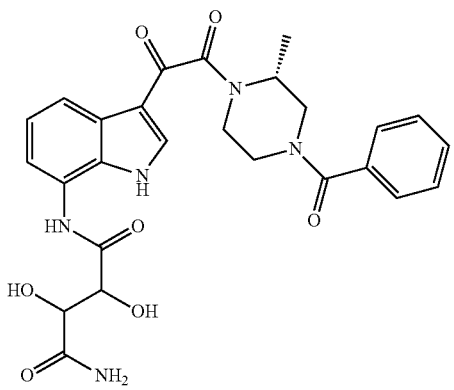 [SMILES: C[C@@H]1CN(C(=O)c2ccccc2)CCN1C(=O)C(=O)c1c[nH]c2c(NC(=O)C(O)C(O)C(N)=O)cccc12] or/and 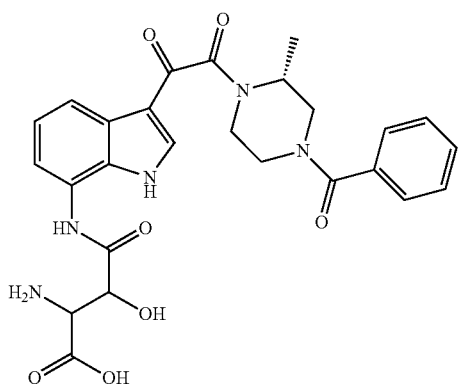 [SMILES: C[C@@H]1CN(C(=O)c2ccccc2)CCN1C(=O)C(=O)c1c[nH]c2c(NC(=O)C(O)C(N)C(=O)O)cccc12] or/and 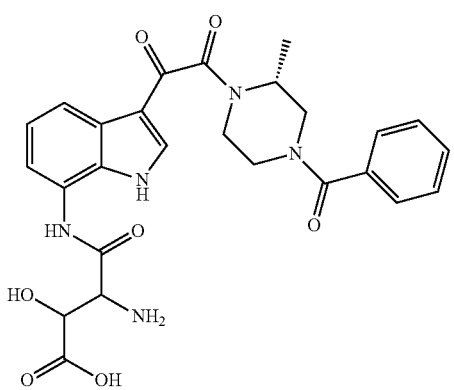 [SMILES: C[C@@H]1CN(C(=O)c2ccccc2)CCN1C(=O)C(=O)c1c[nH]c2c(NC(=O)C(N)C(O)C(=O)O)cccc12] | A |

TABLE 2-continued

| Compd. Number | Structure | EC$_{50}$ Group from Table 1 |
|---|---|---|
| P-A-7 | 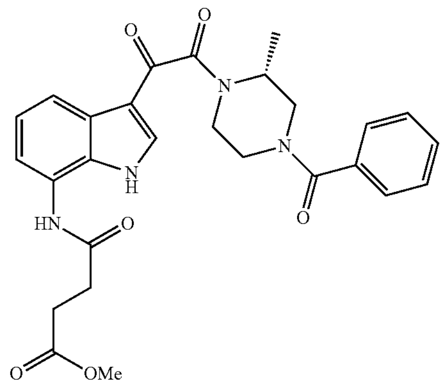 [SMILES: COC(=O)CCC(=O)Nc1cccc2c(C(=O)C(=O)N3CCN(C(=O)c4ccccc4)C[C@H]3C)c[nH]c12] | A |
| P-A-8 | 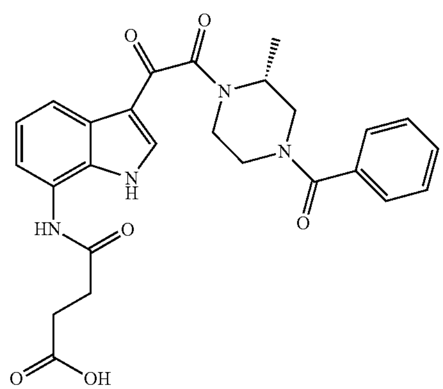 [SMILES: C[C@@H]1CN(C(=O)c2ccccc2)CCN1C(=O)C(=O)c1c[nH]c2c(NC(=O)CCC(=O)O)cccc12] | A |
| P-A-9 | 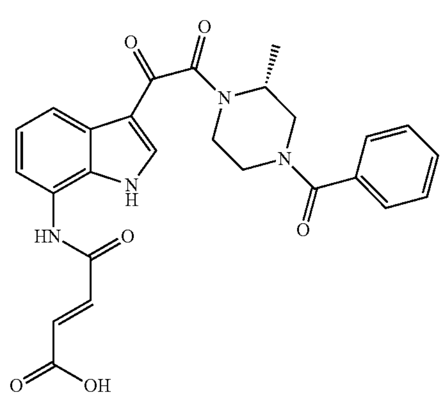 [SMILES: C[C@@H]1CN(C(=O)c2ccccc2)CCN1C(=O)C(=O)c1c[nH]c2c(NC(=O)/C=C/C(=O)O)cccc12] | A |

TABLE 2-continued
| Compd. Number | Structure | EC$_{50}$ Group from Table 1 |
|---|---|---|
| P-A-10 | 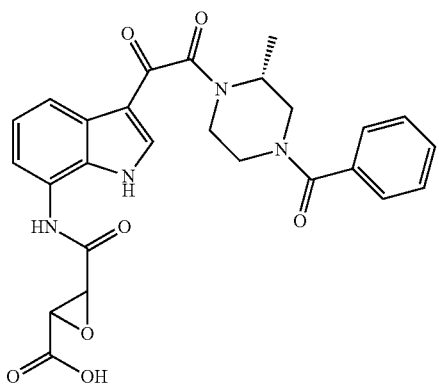 [SMILES: C[C@@H]1CN(C(=O)c2ccccc2)CCN1C(=O)C(=O)c1c[nH]c2c(NC(=O)C3OC3C(=O)O)cccc12] | A |
| P-A-11 | 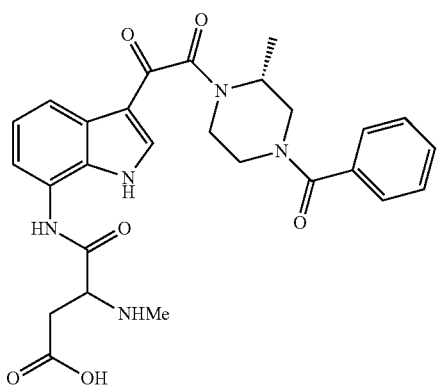 [SMILES: CNC(CC(=O)O)C(=O)Nc1cccc2c(C(=O)C(=O)N3CCN(C(=O)c4ccccc4)C[C@H]3C)c[nH]c12]
or/and
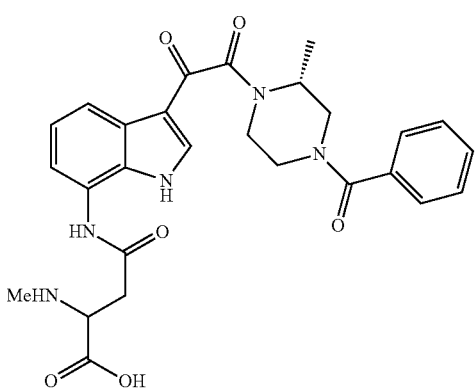 [SMILES: CNC(CC(=O)Nc1cccc2c(C(=O)C(=O)N3CCN(C(=O)c4ccccc4)C[C@H]3C)c[nH]c12)C(=O)O] | A |

TABLE 2-continued
| Compd. Number | Structure | EC$_{50}$ Group from Table 1 |
|---|---|---|
| P-A-12 | 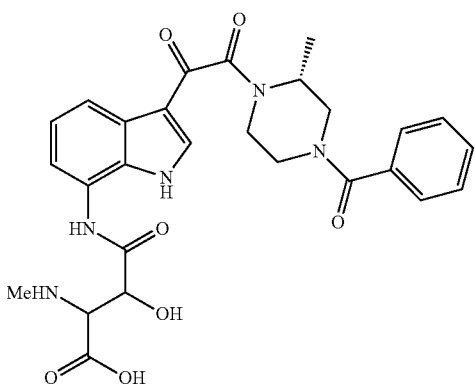 [SMILES: CNC(C(=O)O)C(O)C(=O)Nc1cccc2c(C(=O)C(=O)N3CCN(C(=O)c4ccccc4)C[C@H]3C)c[nH]c12]<br>or/and<br>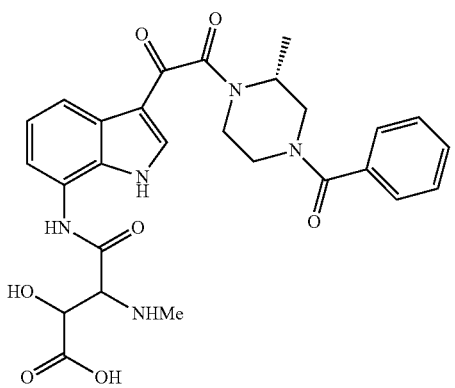 [SMILES: CNC(C(=O)Nc1cccc2c(C(=O)C(=O)N3CCN(C(=O)c4ccccc4)C[C@H]3C)c[nH]c12)C(O)C(=O)O]<br>or/and<br>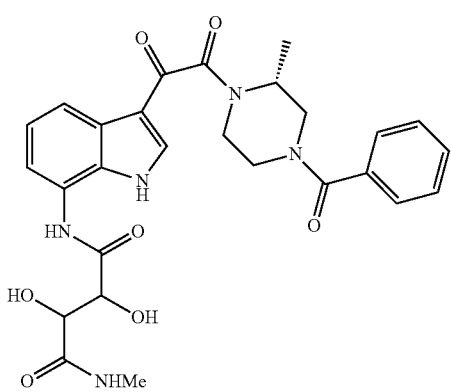 [SMILES: CNC(=O)C(O)C(O)C(=O)Nc1cccc2c(C(=O)C(=O)N3CCN(C(=O)c4ccccc4)C[C@H]3C)c[nH]c12] | A |

TABLE 2-continued

| Compd. Number | Structure | EC$_{50}$ Group from Table 1 |
|---|---|---|
| P-A-13 | 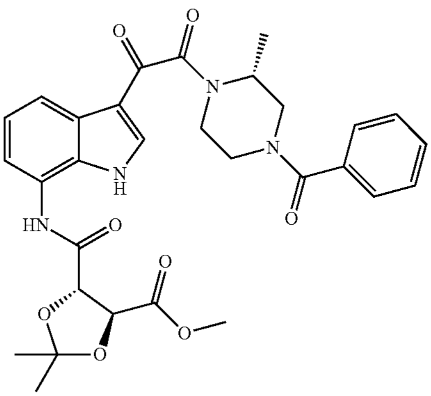 [SMILES: COC(=O)[C@H]1OC(C)(C)O[C@@H]1C(=O)Nc1cccc2c(C(=O)C(=O)N3CCN(C(=O)c4ccccc4)C[C@H]3C)c[nH]c12] | A |
| P-A-14 | 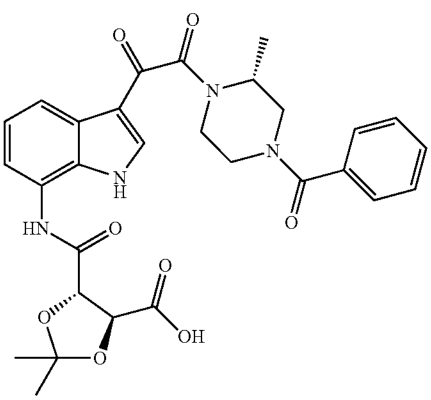 [SMILES: C[C@@H]1CN(C(=O)c2ccccc2)CCN1C(=O)C(=O)c1c[nH]c2c(NC(=O)[C@H]3OC(C)(C)O[C@@H]3C(=O)O)cccc12] | A |
| P-A-15 | 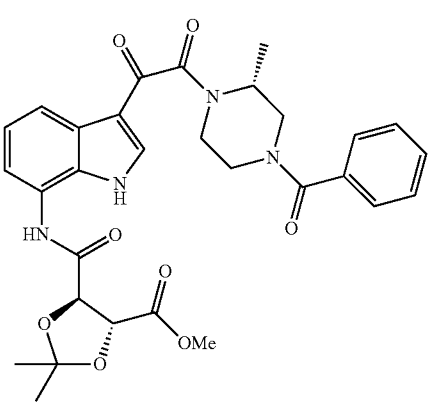 [SMILES: COC(=O)[C@@H]1OC(C)(C)O[C@H]1C(=O)Nc1cccc2c(C(=O)C(=O)N3CCN(C(=O)c4ccccc4)C[C@H]3C)c[nH]c12] | A |

TABLE 2-continued

| Compd. Number | Structure | EC$_{50}$ Group from Table 1 |
|---|---|---|
| P-A-16 | 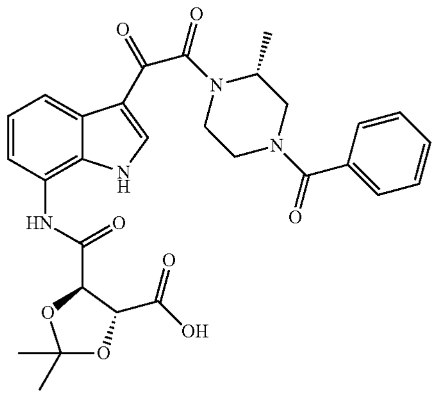 [SMILES: C[C@@H]1CN(C(=O)c2ccccc2)CCN1C(=O)C(=O)c1c[nH]c2c(NC(=O)[C@@H]3OC(C)(C)O[C@H]3C(=O)O)cccc12] | A |
| P-A-17 | 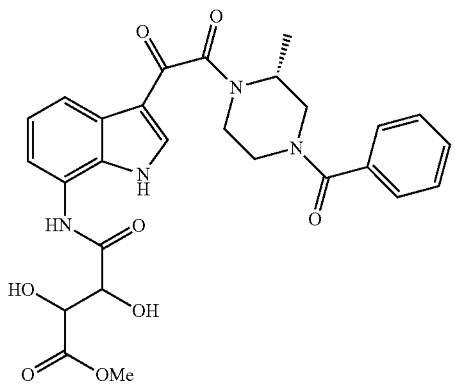 [SMILES: COC(=O)C(O)C(O)C(=O)Nc1cccc2c(C(=O)C(=O)N3CCN(C(=O)c4ccccc4)C[C@H]3C)c[nH]c12] | A |
| P-A-18 | 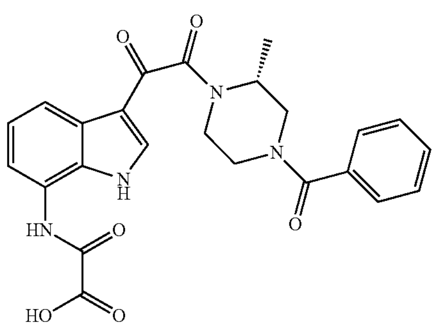 [SMILES: C[C@@H]1CN(C(=O)c2ccccc2)CCN1C(=O)C(=O)c1c[nH]c2c(NC(=O)C(=O)O)cccc12] | A |
| P-A-20 | 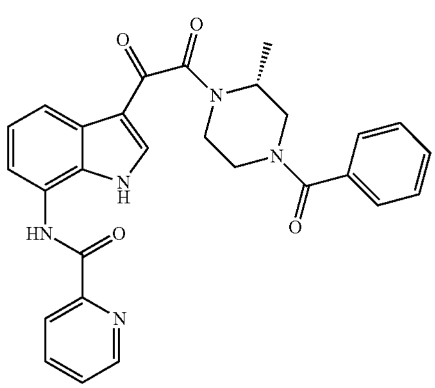 [SMILES: C[C@@H]1CN(C(=O)c2ccccc2)CCN1C(=O)C(=O)c1c[nH]c2c(NC(=O)c3ccccn3)cccc12] | A |

TABLE 2-continued

| Compd. Number | Structure | EC$_{50}$ Group from Table 1 |
|---|---|---|
| P-A-21 | 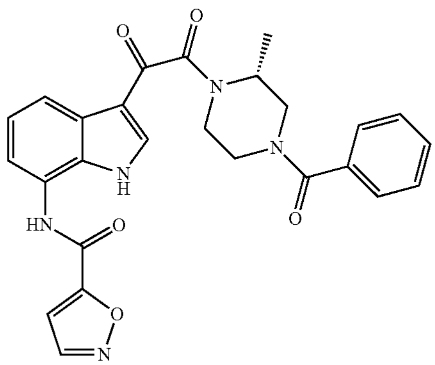 [SMILES: C[C@@H]1CN(C(=O)c2ccccc2)CCN1C(=O)C(=O)c1c[nH]c2c(NC(=O)c3ccno3)cccc12] | A |
| P-B-1 | 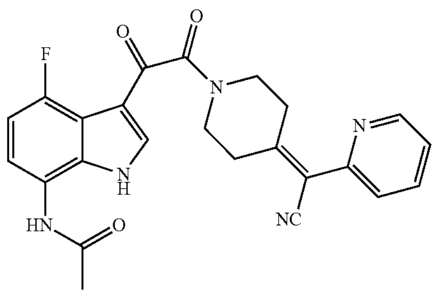 [SMILES: CC(=O)Nc1ccc(F)c2c(C(=O)C(=O)N3CCC(=C(C#N)c4ccccn4)CC3)c[nH]c12] | A |
| P-B-2 | 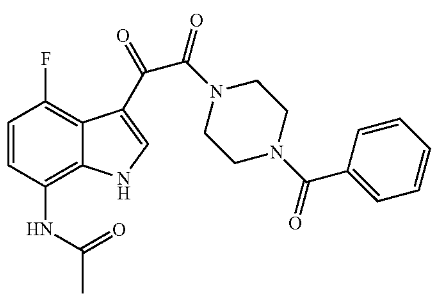 [SMILES: CC(=O)Nc1ccc(F)c2c(C(=O)C(=O)N3CCN(C(=O)c4ccccc4)CC3)c[nH]c12] | A |
| P-B-3 | 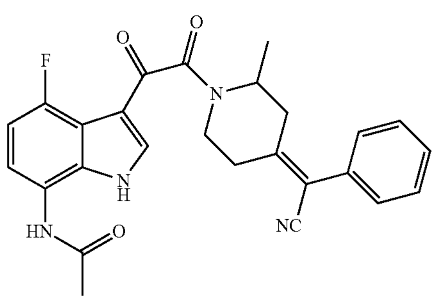 [SMILES: CC(=O)Nc1ccc(F)c2c(C(=O)C(=O)N3CC/C(=C(\C#N)c4ccccc4)CC3C)c[nH]c12] | A |
| P-B-4 | 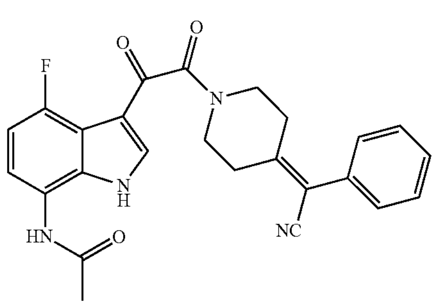 [SMILES: CC(=O)Nc1ccc(F)c2c(C(=O)C(=O)N3CCC(=C(C#N)c4ccccc4)CC3)c[nH]c12] | A |

TABLE 2-continued

| Compd. Number | Structure | EC$_{50}$ Group from Table 1 |
|---|---|---|
| P-B-5 | 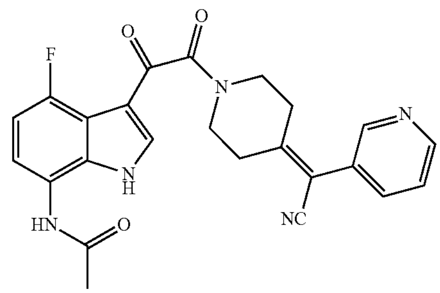 [SMILES: CC(=O)Nc1ccc(F)c2c(C(=O)C(=O)N3CCC(=C(C#N)c4cccnc4)CC3)c[nH]c12] | A |
| P-B-6 | 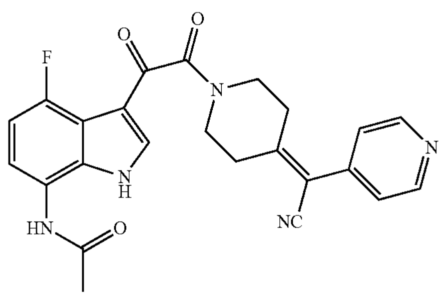 [SMILES: CC(=O)Nc1ccc(F)c2c(C(=O)C(=O)N3CCC(=C(C#N)c4ccncc4)CC3)c[nH]c12] | A |
| P-B-7 | 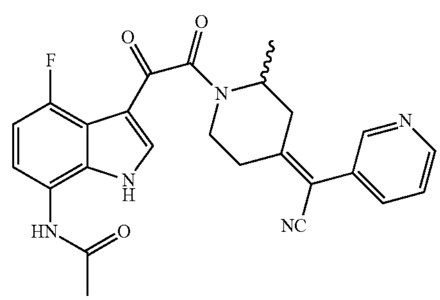 [SMILES: CC(=O)Nc1ccc(F)c2c(C(=O)C(=O)N3CC/C(=C(\C#N)c4cccnc4)CC3C)c[nH]c12] | A |
| P-C-1 | 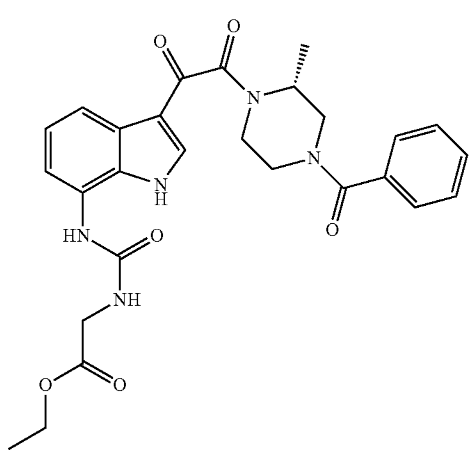 [SMILES: CCOC(=O)CNC(=O)Nc1cccc2c(C(=O)C(=O)N3CCN(C(=O)c4ccccc4)C[C@H]3C)c[nH]c12] | A |

TABLE 2-continued

| Compd. Number | Structure | EC$_{50}$ Group from Table 1 |
|---|---|---|
| P-C-2 | 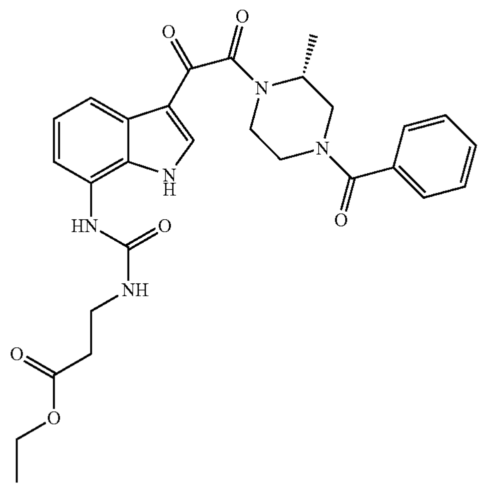 [SMILES: CCOC(=O)CCNC(=O)Nc1cccc2c(C(=O)C(=O)N3CCN(C(=O)c4ccccc4)C[C@H]3C)c[nH]c12] | A |
| P-C-3 | 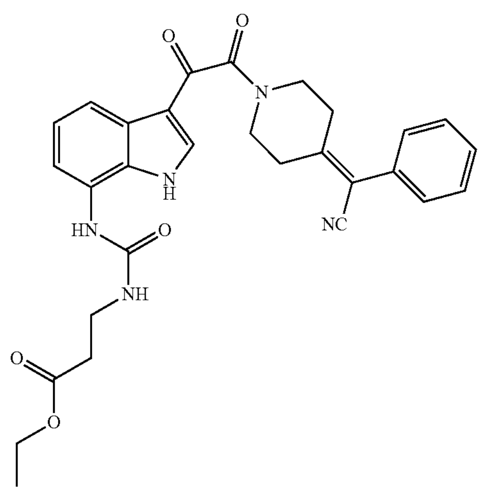 [SMILES: CCOC(=O)CCNC(=O)Nc1cccc2c(C(=O)C(=O)N3CCC(=C(C#N)c4ccccc4)CC3)c[nH]c12] | A |
| P-C-4 | 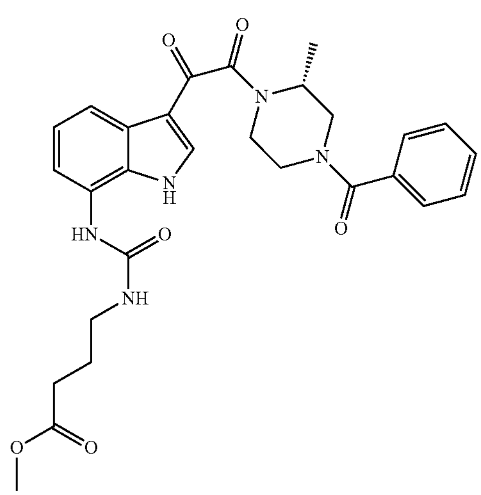 [SMILES: COC(=O)CCCNC(=O)Nc1cccc2c(C(=O)C(=O)N3CCN(C(=O)c4ccccc4)C[C@H]3C)c[nH]c12] | A |

TABLE 2-continued
| Compd. Number | Structure | EC$_{50}$ Group from Table 1 |
|---|---|---|
| P-C-5 | 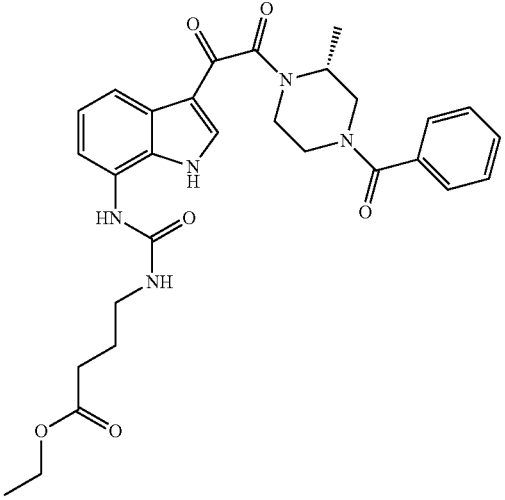 [SMILES: CCOC(=O)CCCNC(=O)Nc1cccc2c(C(=O)C(=O)N3CCN(C(=O)c4ccccc4)C[C@H]3C)c[nH]c12] | A |
| P-C-6 | 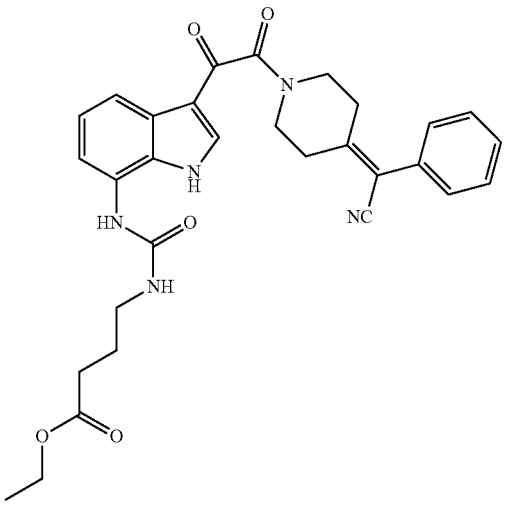 [SMILES: CCOC(=O)CCCNC(=O)Nc1cccc2c(C(=O)C(=O)N3CCC(=C(C#N)c4ccccc4)CC3)c[nH]c12] | A |
| P-C-7 | 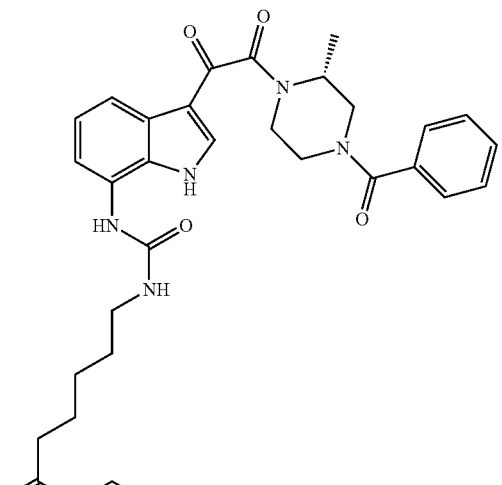 | A |

TABLE 2-continued
| Compd. Number | Structure | EC$_{50}$ Group from Table 1 |
|---|---|---|
| P-C-8 | 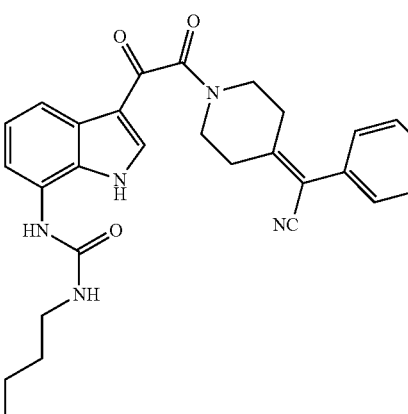 | A |
| P-C-9 | 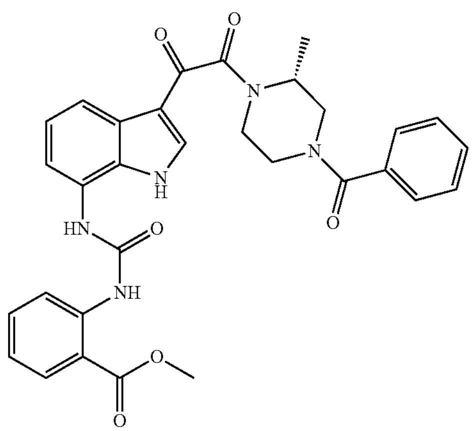 [SMILES: COC(=O)c1ccccc1NC(=O)Nc1cccc2c(C(=O)C(=O)N3CCN(C(=O)c4ccccc4)C[C@H]3C)c[nH]c12] | A |
| P-C-10 | 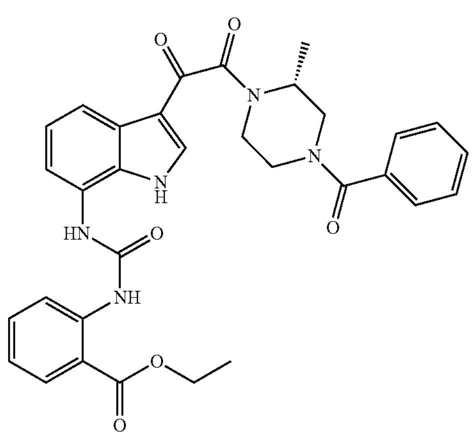 [SMILES: CCOC(=O)c1ccccc1NC(=O)Nc1cccc2c(C(=O)C(=O)N3CCN(C(=O)c4ccccc4)C[C@H]3C)c[nH]c12] | A |

TABLE 2-continued
| Compd. Number | Structure | $EC_{50}$ Group from Table 1 |
|---|---|---|
| P-C-11 | 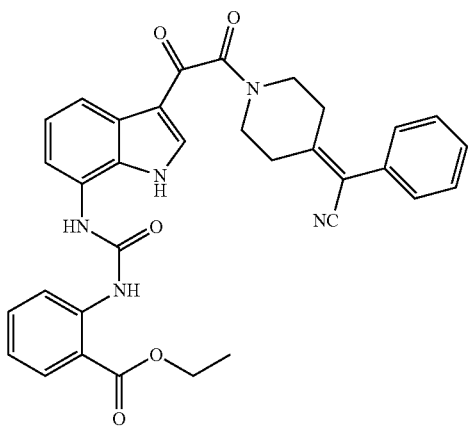 [SMILES: CCOC(=O)c1ccccc1NC(=O)Nc1cccc2c(C(=O)C(=O)N3CCC(=C(C#N)c4ccccc4)CC3)c[nH]c12] | A |
| P-C-12 | 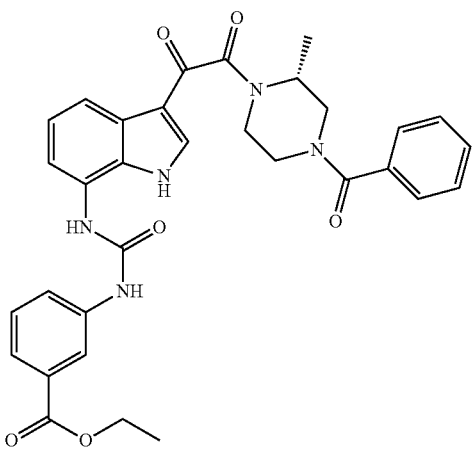 [SMILES: CCOC(=O)c1cccc(NC(=O)Nc2cccc3c(C(=O)C(=O)N4CCN(C(=O)c5ccccc5)C[C@H]4C)c[nH]c23)c1] | A |
| P-C-13 | 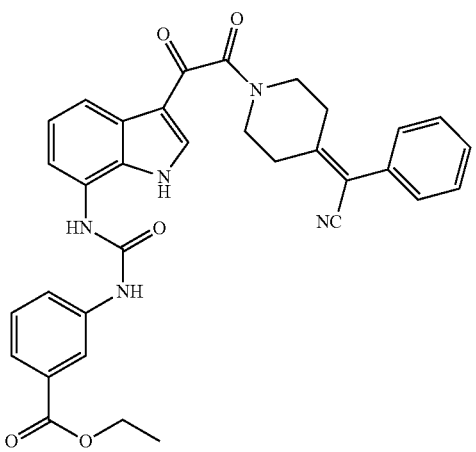 [SMILES: CCOC(=O)c1cccc(NC(=O)Nc2cccc3c(C(=O)C(=O)N4CCC(=C(C#N)c5ccccc5)CC4)c[nH]c23)c1] | A |

TABLE 2-continued
| Compd. Number | Structure | EC$_{50}$ Group from Table 1 |
|---|---|---|
| P-C-14 | 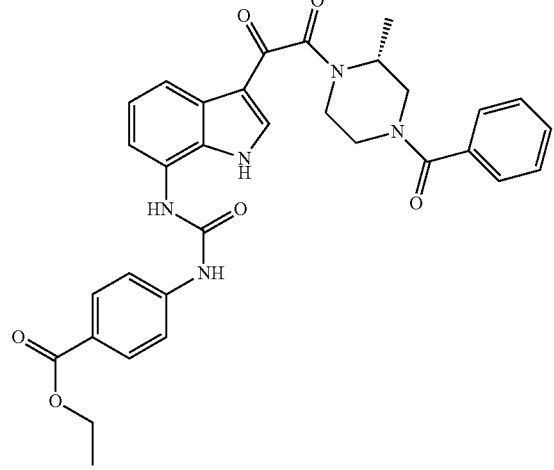 | A |
| P-C-15 | 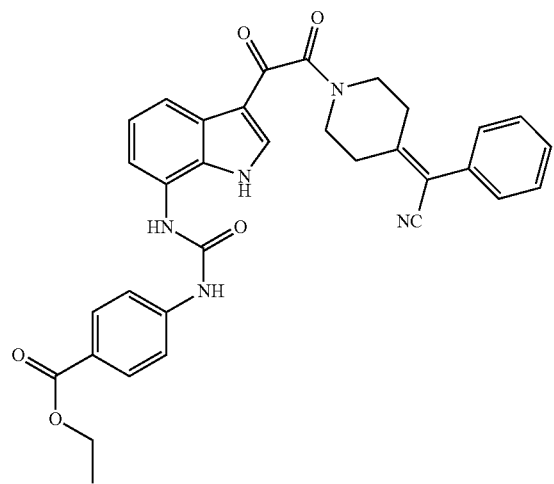 [SMILES: CCOC(=O)c1ccc(NC(=O)Nc2cccc3c(C(=O)C(=O)N4CCC(=C(C#N)c5ccccc5)CC4)c[nH]c23)cc1] | A |
| P-C-16 | 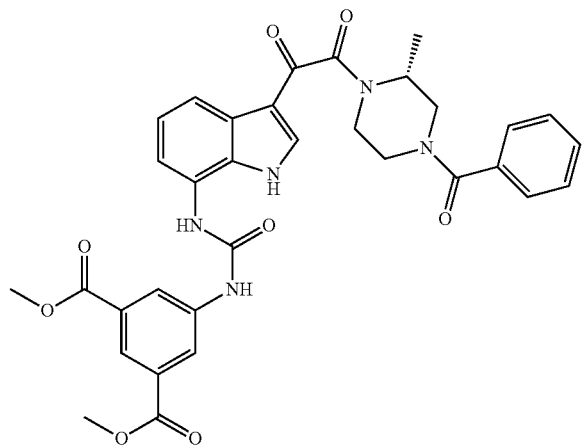 [SMILES: COC(=O)c1cc(NC(=O)Nc2cccc3c(C(=O)C(=O)N4CCN(C(=O)c5ccccc5)C[C@H]4C)c[nH]c23)cc(C(=O)OC)c1] | A |

TABLE 2-continued
| Compd. Number | Structure | $EC_{50}$ Group from Table 1 |
|---|---|---|
| P-C-17 | 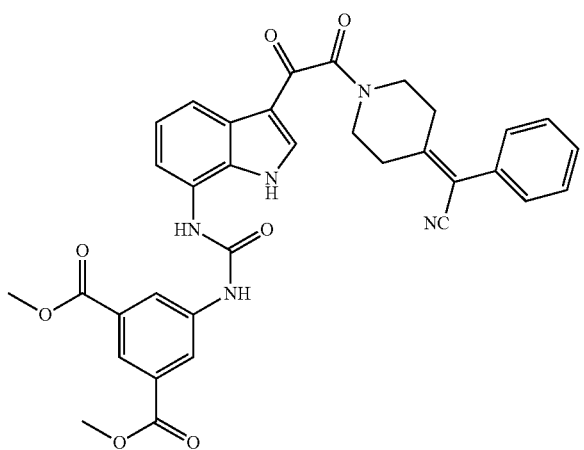 [SMILES: COC(=O)c1cc(NC(=O)Nc2cccc3c(C(=O)C(=O)N4CCC(=C(C#N)c5ccccc5)CC4)c[nH]c23)cc(C(=O)OC)c1] | A |
| P-C-18 | 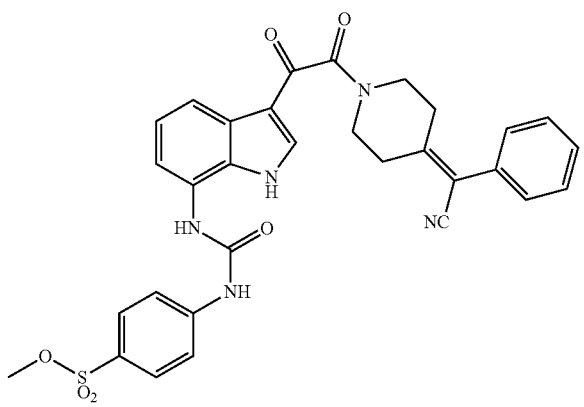 [SMILES: COS(=O)(=O)c1ccc(NC(=O)Nc2cccc3c(C(=O)C(=O)N4CCC(=C(C#N)c5ccccc5)CC4)c[nH]c23)cc1] | A |
| P-C-19 | 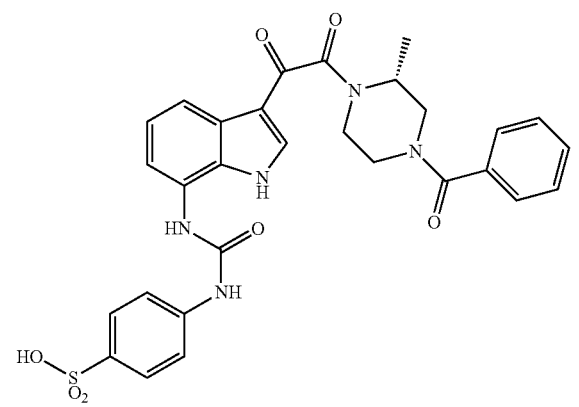 [SMILES: C[C@@H]1CN(C(=O)c2ccccc2)CCN1C(=O)C(=O)c1c[nH]c2c(NC(=O)Nc3ccc(S(=O)(=O)O)cc3)cccc12] | A |

TABLE 2-continued

| Compd. Number | Structure | EC$_{50}$ Group from Table 1 |
|---|---|---|
| P-C-20 | 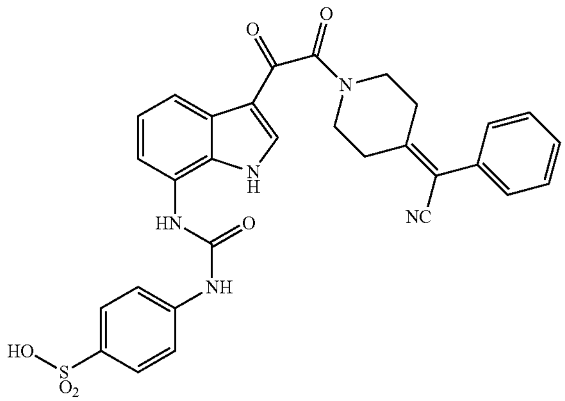 [SMILES: N#CC(=C1CCN(C(=O)C(=O)c2c[nH]c3c(NC(=O)Nc4ccc(S(=O)(=O)O)cc4)cccc23)CC1)c1ccccc1] | A |
| P-C-21 | 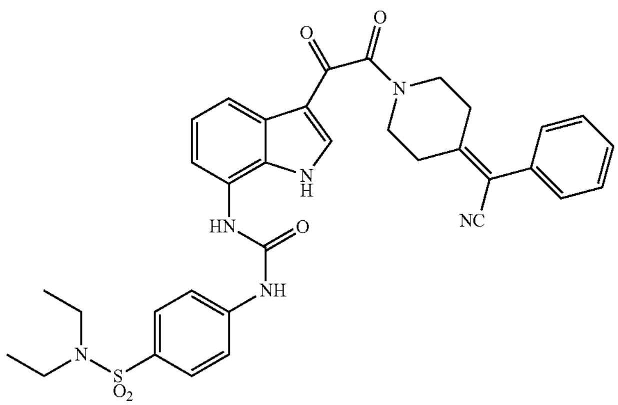 [SMILES: CCN(CC)S(=O)(=O)c1ccc(NC(=O)Nc2cccc3c(C(=O)C(=O)N4CCC(=C(C#N)c5ccccc5)CC4)c[nH]c23)cc1] | A |
| P-C-22 | 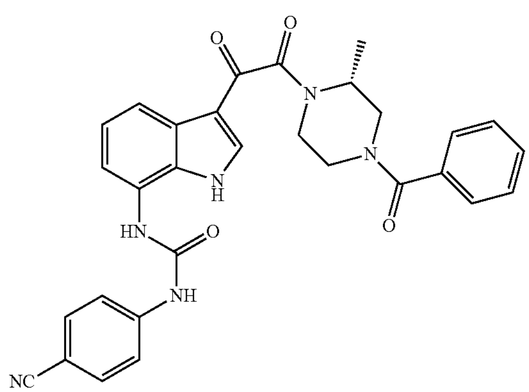 [SMILES: C[C@@H]1CN(C(=O)c2ccccc2)CCN1C(=O)C(=O)c1c[nH]c2c(NC(=O)Nc3ccc(C#N)cc3)cccc12] | A |
| P-C-23 | 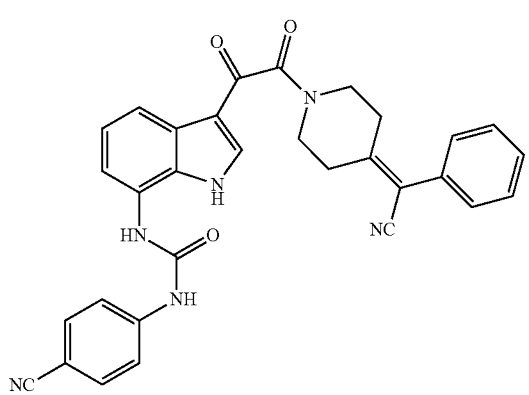 [SMILES: N#CC(=C1CCN(C(=O)C(=O)c2c[nH]c3c(NC(=O)Nc4ccc(C#N)cc4)cccc23)CC1)c1ccccc1] | A |

TABLE 2-continued
| Compd. Number | Structure | EC$_{50}$ Group from Table 1 |
|---|---|---|
| P-C-24 | 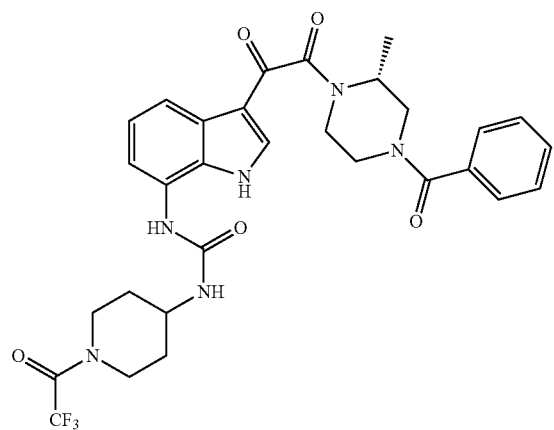 [SMILES: C[C@@H]1CN(C(=O)c2ccccc2)CCN1C(=O)C(=O)c1c[nH]c2c(NC(=O)NC3CCN(C(=O)C(F)(F)F)CC3)cccc12] | A |
| P-C-25 | 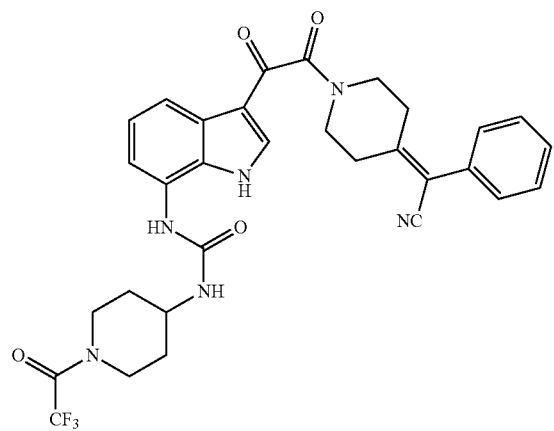 [SMILES: N#CC(=C1CCN(C(=O)C(=O)c2c[nH]c3c(NC(=O)NC4CCN(C(=O)C(F)(F)F)CC4)cccc23)CC1)c1ccccc1] | A |
| P-C-26 | 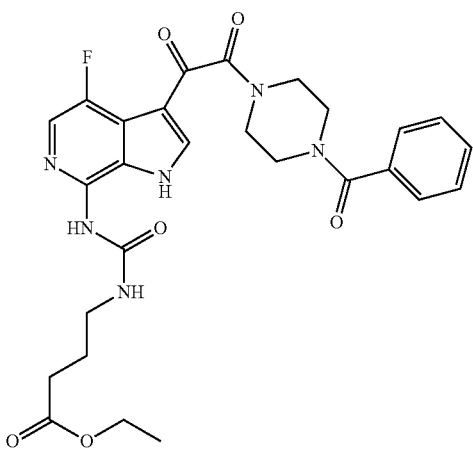 [SMILES: CCOC(=O)CCCNC(=O)Nc1ncc(F)c2c(C(=O)C(=O)N3CCN(C(=O)c4ccccc4)CC3)c[nH]c12] | A |

TABLE 2-continued
| Compd. Number | Structure | EC$_{50}$ Group from Table 1 |
|---|---|---|
| P-D-1 | 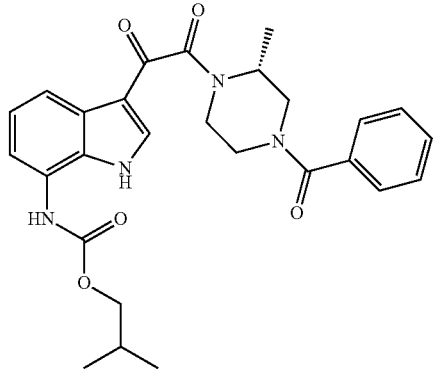 [SMILES: CC(C)COC(=O)Nc1cccc2c(C(=O)C(=O)N3CCN(C(=O)c4ccccc4)C[C@H]3C)c[nH]c12] | A |
| P-E-1 | 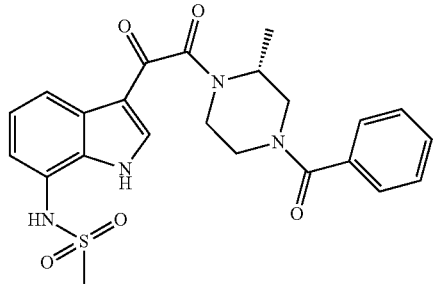 [SMILES: C[C@@H]1CN(C(=O)c2ccccc2)CCN1C(=O)C(=O)c1c[nH]c2c(NS(C)(=O)=O)cccc12] | A |
| P-E-2 | 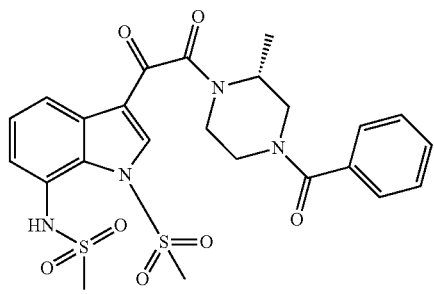 [SMILES: C[C@@H]1CN(C(=O)c2ccccc2)CCN1C(=O)C(=O)c1cn(S(C)(=O)=O)c2c(NS(C)(=O)=O)cccc12] | A |
| P-E-3 | 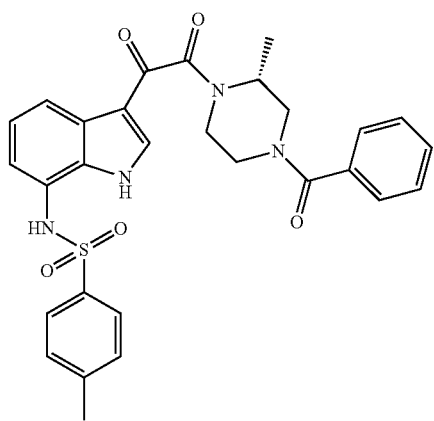 [SMILES: Cc1ccc(S(=O)(=O)Nc2cccc3c(C(=O)C(=O)N4CCN(C(=O)c5ccccc5)C[C@H]4C)c[nH]c23)cc1] | B |

TABLE 2-continued

| Compd. Number | Structure | EC$_{50}$ Group from Table 1 |
|---|---|---|
| P-E-4 | 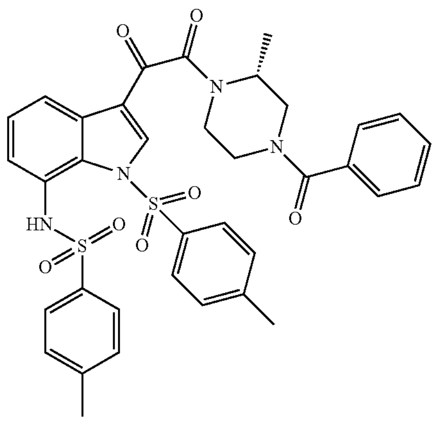 [SMILES: Cc1ccc(S(=O)(=O)Nc2cccc3c(C(=O)C(=O)N4CCN(C(=O)c5ccccc5)C[C@H]4C)cn(S(=O)(=O)c4ccc(C)cc4)c23)cc1] | A |
| P-E-5 | 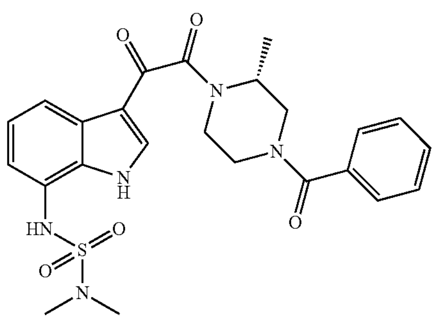 [SMILES: C[C@@H]1CN(C(=O)c2ccccc2)CCN1C(=O)C(=O)c1c[nH]c2c(NS(=O)(=O)N(C)C)cccc12] | A |
| P-F-1 | 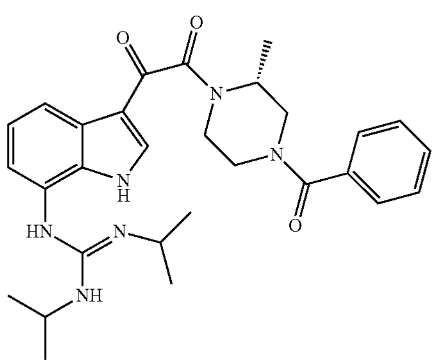 [SMILES: CC(C)/N=C(/Nc1cccc2c(C(=O)C(=O)N3CCN(C(=O)c4ccccc4)C[C@H]3C)c[nH]c12)NC(C)C] | A |
| P-F-2 | 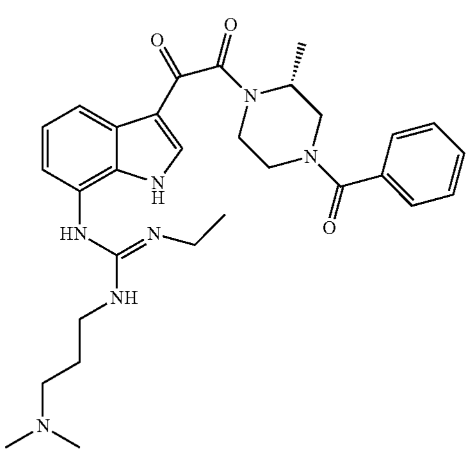 [SMILES: CC/N=C(\NCCCN(C)C)Nc1cccc2c(C(=O)C(=O)N3CCN(C(=O)c4ccccc4)C[C@H]3C)c[nH]c12] | A |

TABLE 2-continued
| Compd. Number | Structure | EC$_{50}$ Group from Table 1 |
|---|---|---|
| P-G-1 | 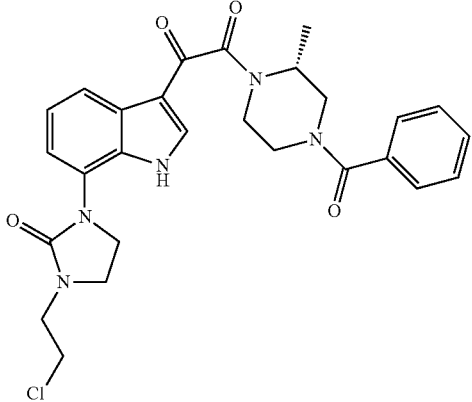 [SMILES: C[C@@H]1CN(C(=O)c2ccccc2)CCN1C(=O)C(=O)c1c[nH]c2c(N3CCN(CCCl)C3=O)cccc12] | A |
| P-H-1 | 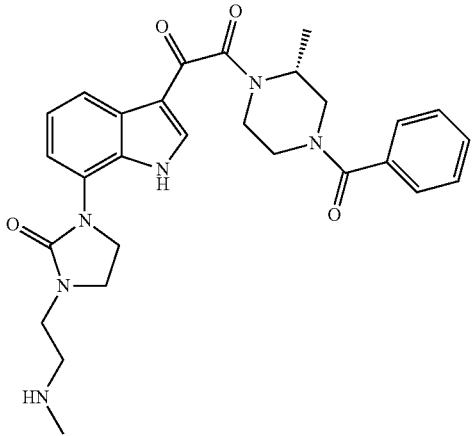 [SMILES: CNCCN1CCN(c2cccc3c(C(=O)C(=O)N4CCN(C(=O)c5ccccc5)C[C@H]4C)c[nH]c23)C1=O] | A |
| P-H-2 | 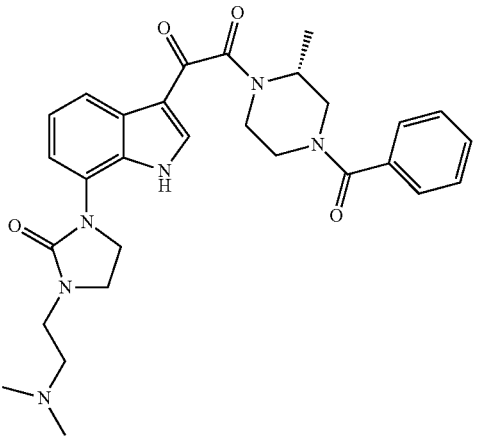 [SMILES: C[C@@H]1CN(C(=O)c2ccccc2)CCN1C(=O)C(=O)c1c[nH]c2c(N3CCN(CCN(C)C)C3=O)cccc12] | A |

TABLE 2-continued

| Compd. Number | Structure | EC$_{50}$ Group from Table 1 |
|---|---|---|
| P-H-3 | 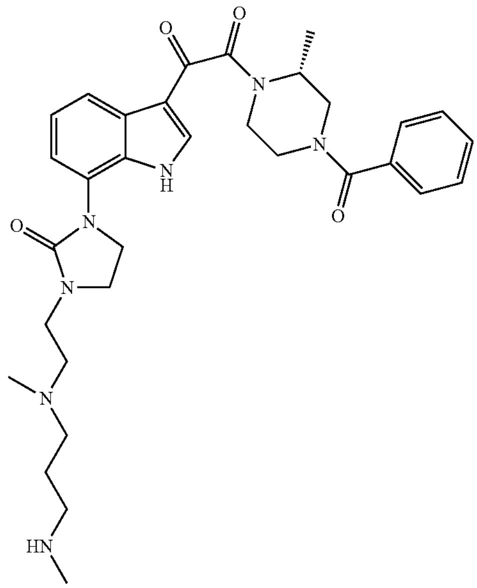 [SMILES: CNCCCN(C)CCN1CCN(c2cccc3c(C(=O)C(=O)N4CCN(C(=O)c5ccccc5)C[C@H]4C)c[nH]c23)C1=O] | A |
| P-G-2 | 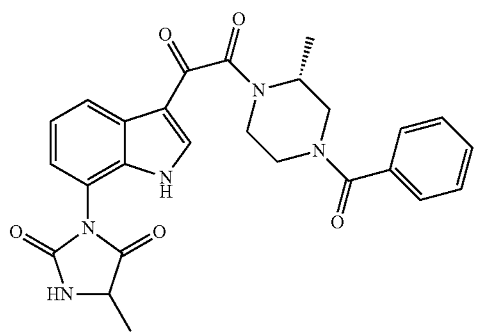 [SMILES: CC1NC(=O)N(c2cccc3c(C(=O)C(=O)N4CCN(C(=O)c5ccccc5)C[C@H]4C)c[nH]c23)C1=O] | A |
| P-G-3 | 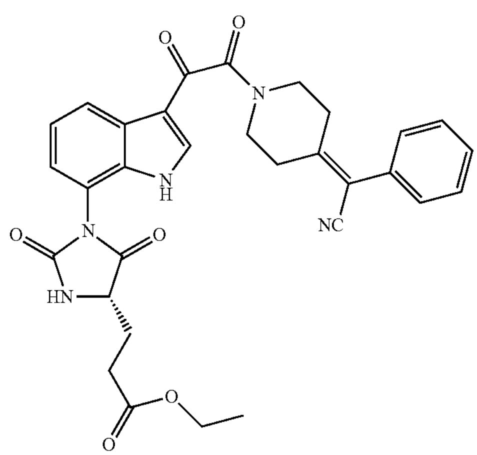 [SMILES: CCOC(=O)CC[C@@H]1NC(=O)N(c2cccc3c(C(=O)C(=O)N4CCC(=C(C#N)c5ccccc5)CC4)c[nH]c23)C1=O] | A |

TABLE 2-continued
| Compd. Number | Structure | EC$_{50}$ Group from Table 1 |
|---|---|---|
| P-I-1 | 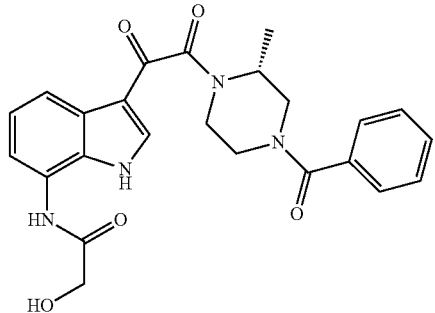 [SMILES: C[C@@H]1CN(C(=O)c2ccccc2)CCN1C(=O)C(=O)c1c[nH]c2c(NC(=O)CO)cccc12] | A |
| P-I-2 | 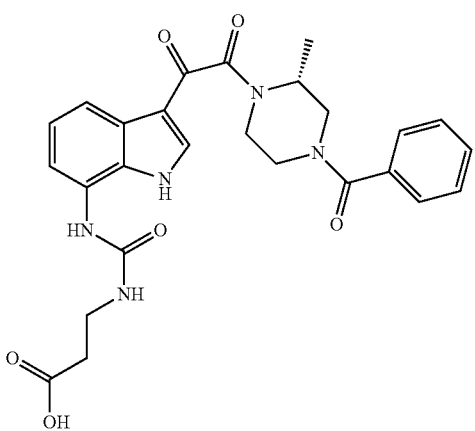 [SMILES: C[C@@H]1CN(C(=O)c2ccccc2)CCN1C(=O)C(=O)c1c[nH]c2c(NC(=O)NCCC(=O)O)cccc12] | A |
| P-I-3 | 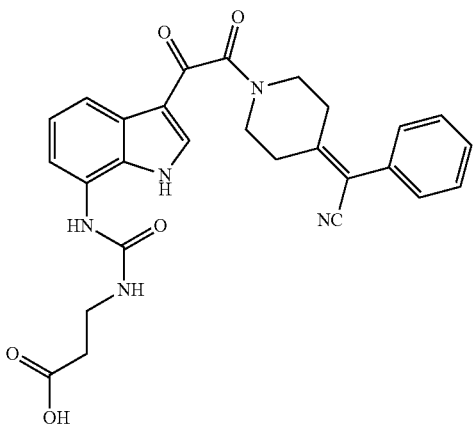 [SMILES: N#CC(=C1CCN(C(=O)C(=O)c2c[nH]c3c(NC(=O)NCCC(=O)O)cccc23)CC1)c1ccccc1] | A |

TABLE 2-continued

| Compd. Number | Structure | EC$_{50}$ Group from Table 1 |
|---|---|---|
| P-I-4 | 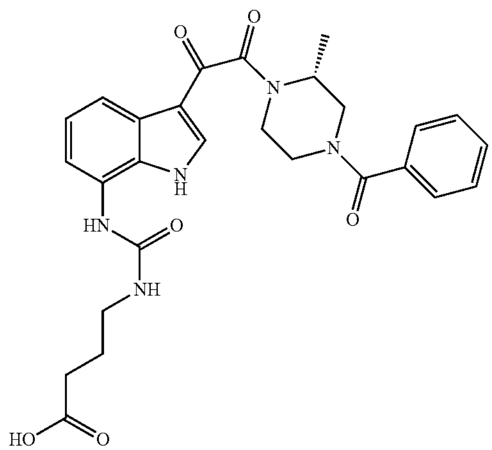 [SMILES: C[C@@H]1CN(C(=O)c2ccccc2)CCN1C(=O)C(=O)c1c[nH]c2c(NC(=O)NCCCC(=O)O)cccc12] | A |
| P-I-5 | 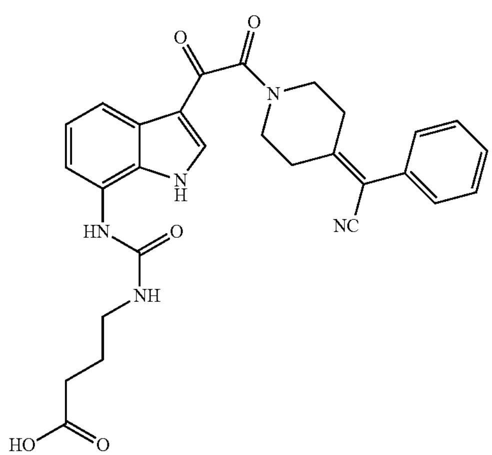 [SMILES: N#CC(=C1CCN(C(=O)C(=O)c2c[nH]c3c(NC(=O)NCCCC(=O)O)cccc23)CC1)c1ccccc1] | A |
| P-I-6 | 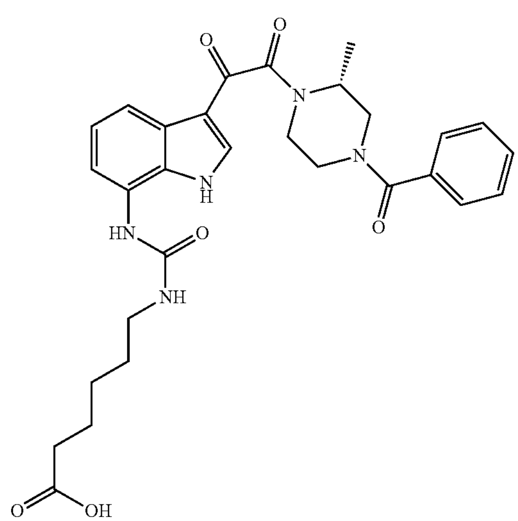 [SMILES: C[C@@H]1CN(C(=O)c2ccccc2)CCN1C(=O)C(=O)c1c[nH]c2c(NC(=O)NCCCCCC(=O)O)cccc12] | A |

TABLE 2-continued

| Compd. Number | Structure | EC$_{50}$ Group from Table 1 |
|---|---|---|
| P-I-7 | 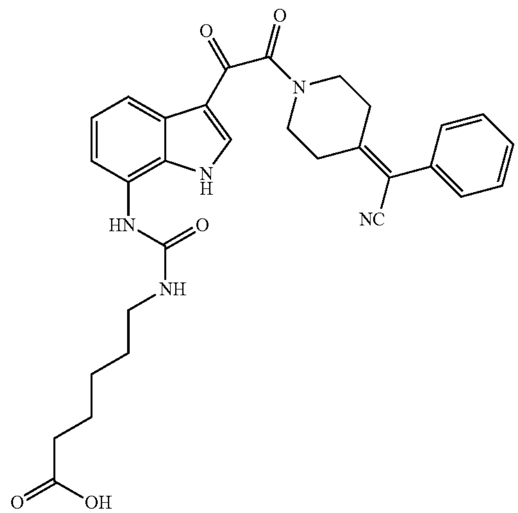 [SMILES: N#CC(=C1CCN(C(=O)C(=O)c2c[nH]c3c(NC(=O)NCCCCCC(=O)O)cccc23)CC1)c1ccccc1] | A |
| P-I-8 | 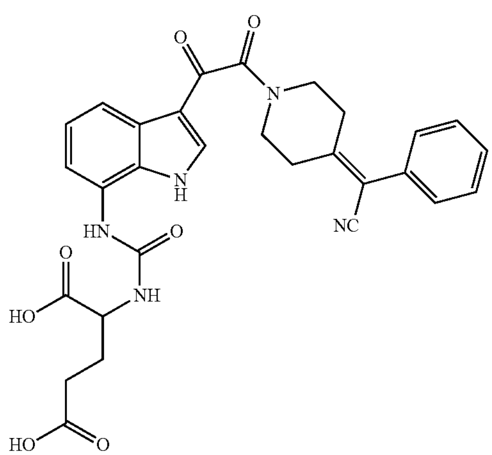 [SMILES: N#CC(=C1CCN(C(=O)C(=O)c2c[nH]c3c(NC(=O)NC(CCC(=O)O)C(=O)O)cccc23)CC1)c1ccccc1] | A |
| P-I-9 | 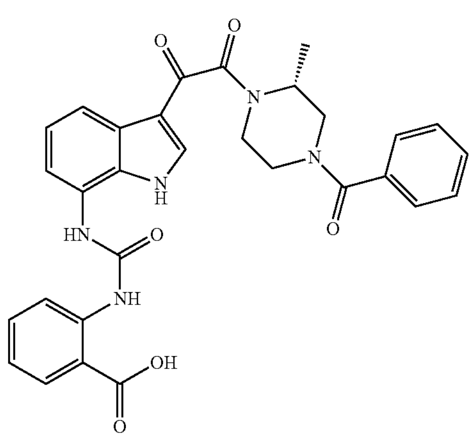 [SMILES: C[C@@H]1CN(C(=O)c2ccccc2)CCN1C(=O)C(=O)c1c[nH]c2c(NC(=O)Nc3ccccc3C(=O)O)cccc12] | A |

TABLE 2-continued
| Compd. Number | Structure | EC$_{50}$ Group from Table 1 |
|---|---|---|
| P-I-10 | 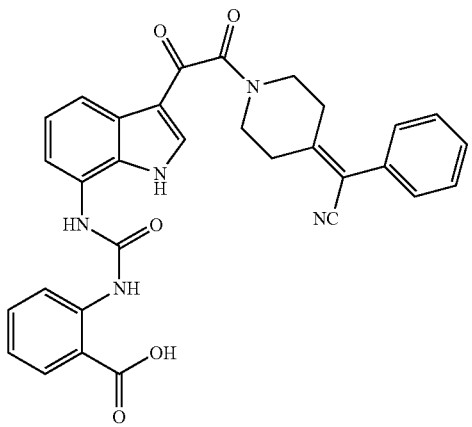 [SMILES: N#CC(=C1CCN(C(=O)C(=O)c2c[nH]c3c(NC(=O)Nc4ccccc4C(=O)O)cccc23)CC1)c1ccccc1] | A |
| P-I-11 | 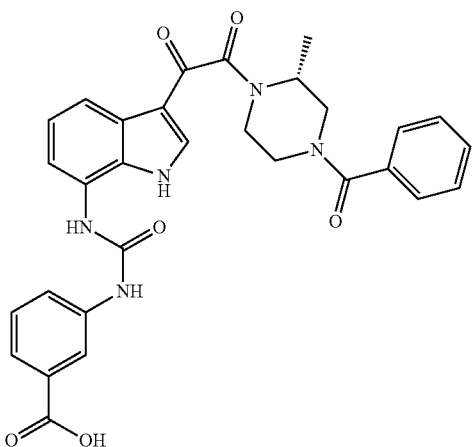 [SMILES: C[C@@H]1CN(C(=O)c2ccccc2)CCN1C(=O)C(=O)c1c[nH]c2c(NC(=O)Nc3cccc(C(=O)O)c3)cccc12] | A |
| P-I-12 | 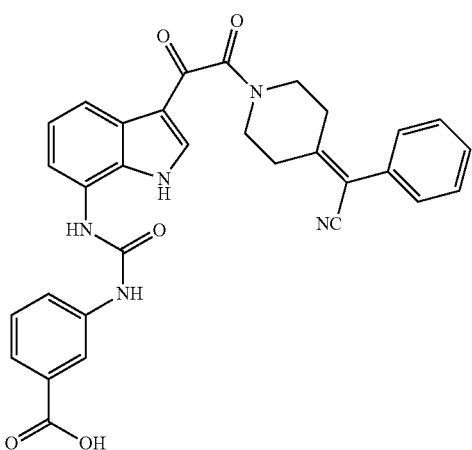 [SMILES: N#CC(=C1CCN(C(=O)C(=O)c2c[nH]c3c(NC(=O)Nc4cccc(C(=O)O)c4)cccc23)CC1)c1ccccc1] | A |

… 247 …
TABLE 2-continued
| Compd. Number | Structure | EC$_{50}$ Group from Table 1 |
| --- | --- | --- |
| P-I-13 | 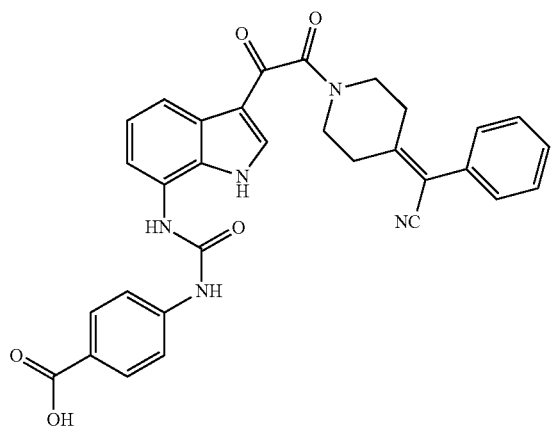 [SMILES: N#CC(=C1CCN(C(=O)C(=O)c2c[nH]c3c(NC(=O)Nc4ccc(C(=O)O)cc4)cccc23)CC1)c1ccccc1] | A |
| P-I-14 | 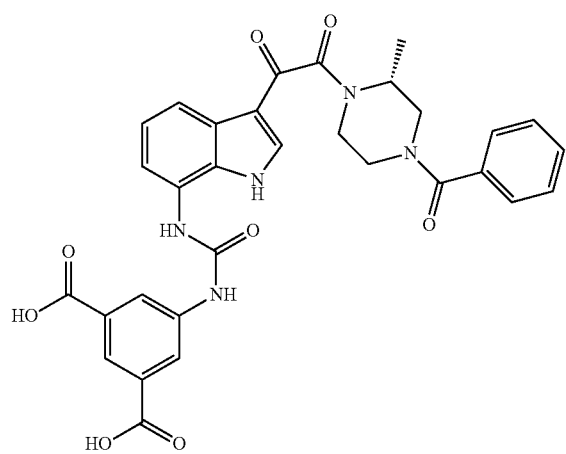 [SMILES: C[C@@H]1CN(C(=O)c2ccccc2)CCN1C(=O)C(=O)c1c[nH]c2c(NC(=O)Nc3cc(C(=O)O)cc(C(=O)O)c3)cccc12] | A |
| P-I-15 | 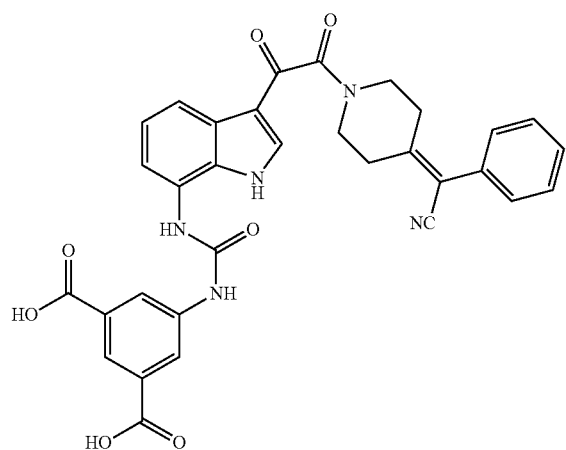 [SMILES: N#CC(=C1CCN(C(=O)C(=O)c2c[nH]c3c(NC(=O)Nc4cc(C(=O)O)cc(C(=O)O)c4)cccc23)CC1)c1ccccc1] | A |

TABLE 2-continued
| Compd. Number | Structure | EC$_{50}$ Group from Table 1 |
|---|---|---|
| P-I-16 | 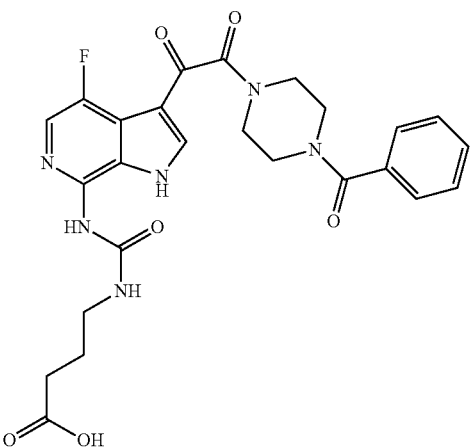 [SMILES: O=C(O)CCCNC(=O)Nc1ncc(F)c2c(C(=O)C(=O)N3CCN(C(=O)c4ccccc4)CC3)c[nH]c12] | A |
| P-I-17 | 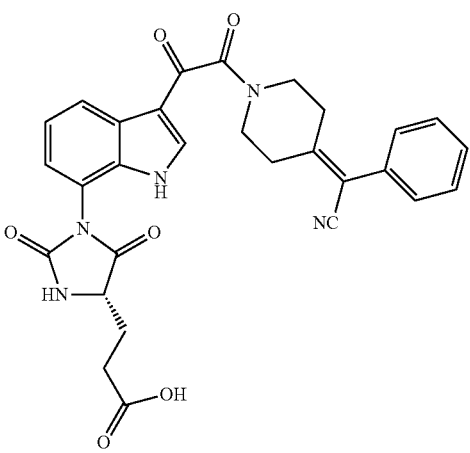 [SMILES: N#CC(=C1CCN(C(=O)C(=O)c2c[nH]c3c(N4C(=O)N[C@@H](CCC(=O)O)C4=O)cccc23)CC1)c1ccccc1] | A |
| P-A-22 | 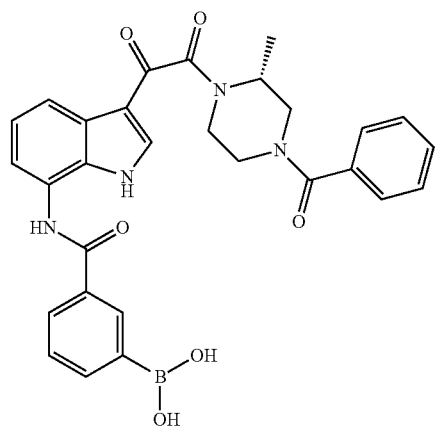 [SMILES: C[C@@H]1CN(C(=O)c2ccccc2)CCN1C(=O)C(=O)c1c[nH]c2c(NC(=O)c3cccc(B(O)O)c3)cccc12] | A |

TABLE 2-continued
| Compd. Number | Structure | EC$_{50}$ Group from Table 1 |
|---|---|---|
| P-C-205 | 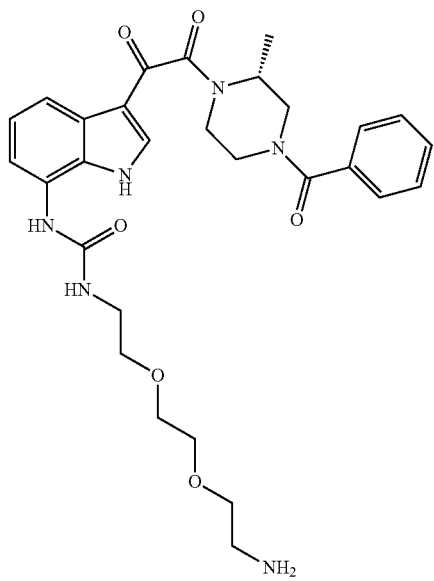 [SMILES: C[C@@H]1CN(C(=O)c2ccccc2)CCN1C(=O)C(=O)c1c[nH]c2c(NC(=O)NCCOCCOCCN)cccc12] | A |
| P-C-111 | 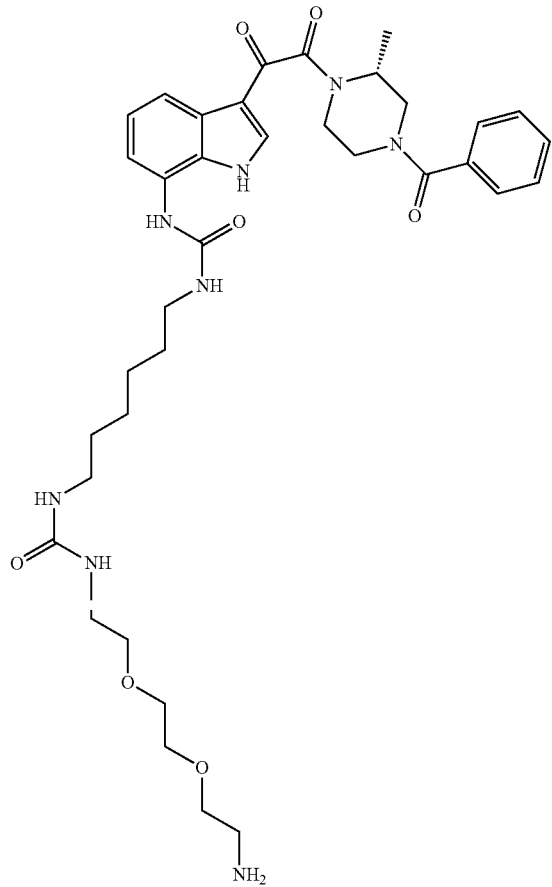 [SMILES: C[C@@H]1CN(C(=O)c2ccccc2)CCN1C(=O)C(=O)c1c[nH]c2c(NC(=O)NCCCCCCNC(=O)NCCOCCOCCN)cccc12] | A |

TABLE 2-continued

| Compd. Number | Structure | EC$_{50}$ Group from Table 1 |
|---|---|---|
| P-I-18 | 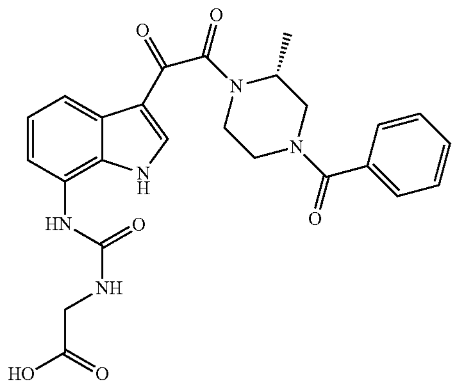 [SMILES: C[C@@H]1CN(C(=O)c2ccccc2)CCN1C(=O)C(=O)c1c[nH]c2c(NC(=O)NCC(=O)O)cccc12] | A |
| P-A-23 | 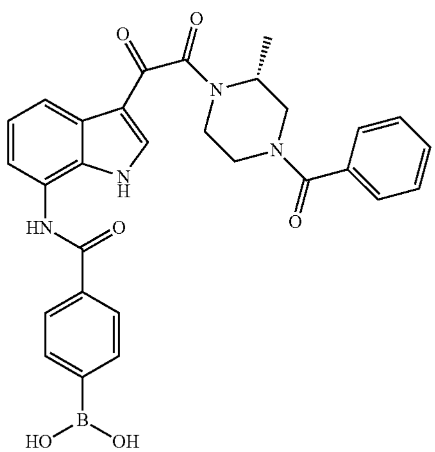 [SMILES: C[C@@H]1CN(C(=O)c2ccccc2)CCN1C(=O)C(=O)c1c[nH]c2c(NC(=O)c3ccc(B(O)O)cc3)cccc12] | A |
| P-C-402 | 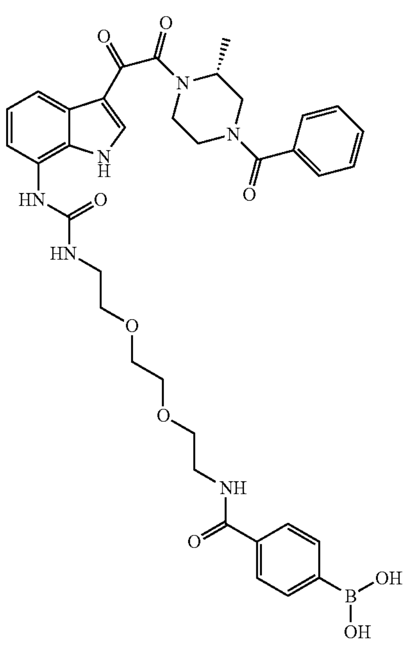 [SMILES: C[C@@H]1CN(C(=O)c2ccccc2)CCN1C(=O)C(=O)c1c[nH]c2c(NC(=O)NCCOCCOCCNC(=O)c3ccc(B(O)O)cc3)cccc12] | A |

TABLE 2-continued
| Compd. Number | Structure | EC$_{50}$ Group from Table 1 |
|---|---|---|
| P-C-112 | 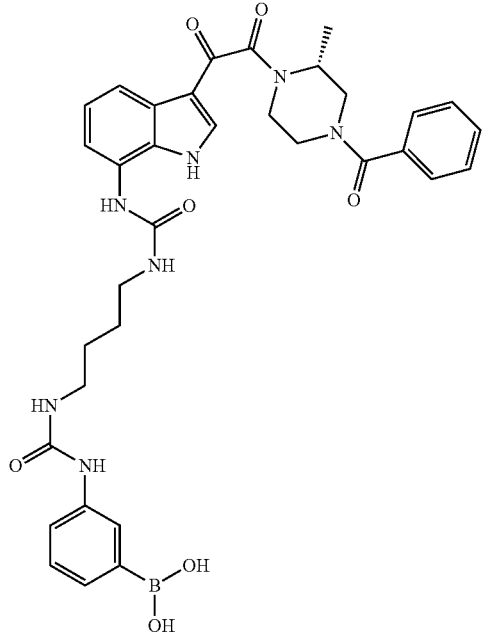 [SMILES: C[C@@H]1CN(C(=O)c2ccccc2)CCN1C(=O)C(=O)c1c[nH]c2c(NC(=O)NCCCCNC(=O)Nc3cccc(B(O)O)c3)cccc12] | A |
| P-C-113 | 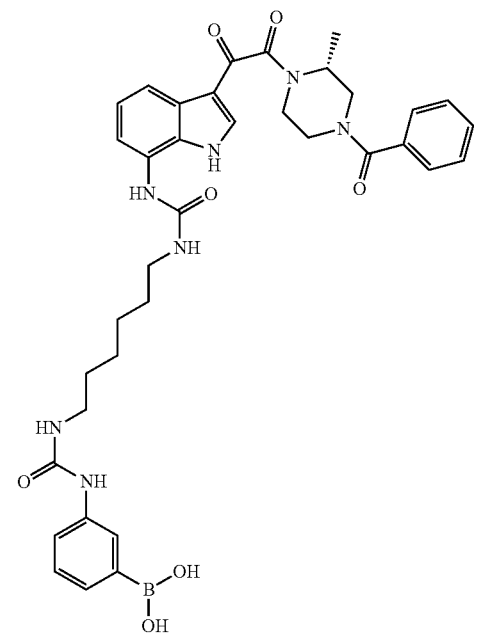 [SMILES: C[C@@H]1CN(C(=O)c2ccccc2)CCN1C(=O)C(=O)c1c[nH]c2c(NC(=O)NCCCCCCNC(=O)Nc3cccc(B(O)O)c3)cccc12] | A |

TABLE 2-continued
| Compd. Number | Structure | EC$_{50}$ Group from Table 1 |
|---|---|---|
| P-C-114 | 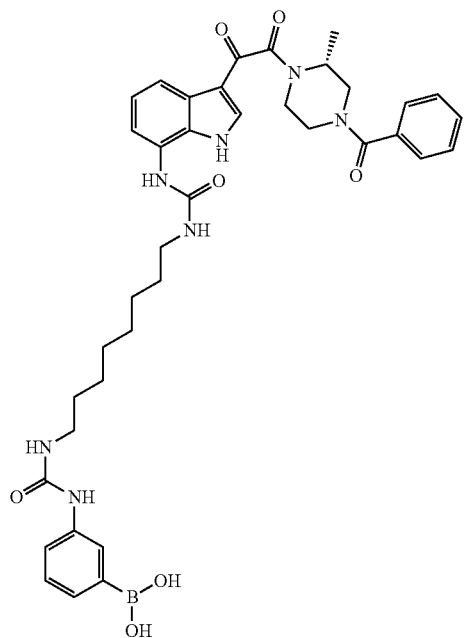 [SMILES: C[C@@H]1CN(C(=O)c2ccccc2)CCN1C(=O)C(=O)c1c[nH]c2c(NC(=O)NCCCCCCCCNC(=O)Nc3cccc(B(O)O)c3)cccc12] | A |
| P-C-115 | 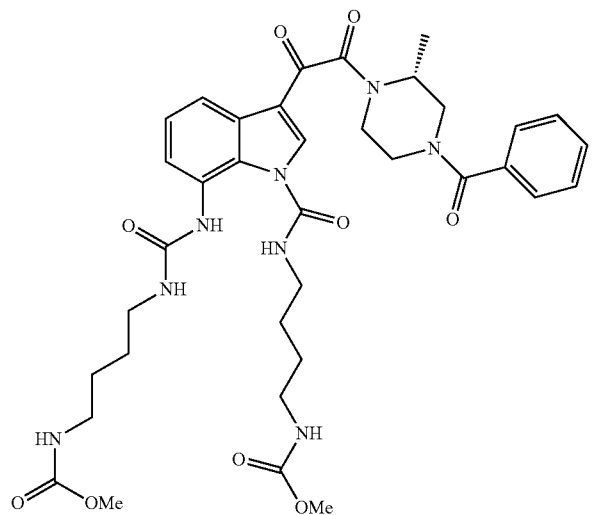 [SMILES: COC(=O)NCCCCNC(=O)Nc1cccc2c(C(=O)C(=O)N3CCN(C(=O)c4ccccc4)C[C@H]3C)cn(C(=O)NCCCCNC(=O)OC)c12] | A |

TABLE 2-continued
| Compd. Number | Structure | EC$_{50}$ Group from Table 1 |
|---|---|---|
| P-C-103 | 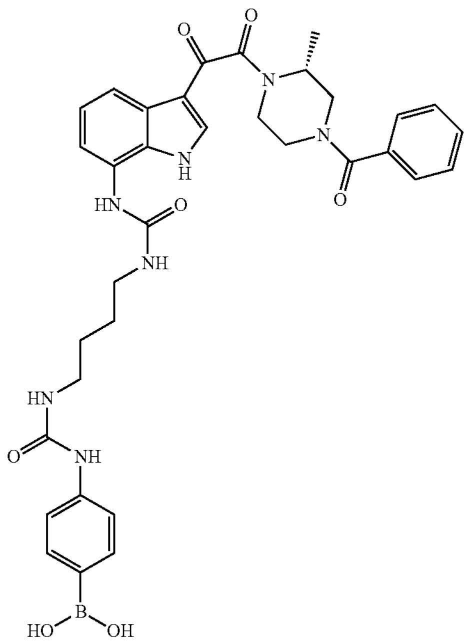 [SMILES: C[C@@H]1CN(C(=O)c2ccccc2)CCN1C(=O)C(=O)c1c[nH]c2c(NC(=O)NCCCCNC(=O)Nc3ccc(B(O)O)cc3)cccc12] | A |
| P-C-106 | 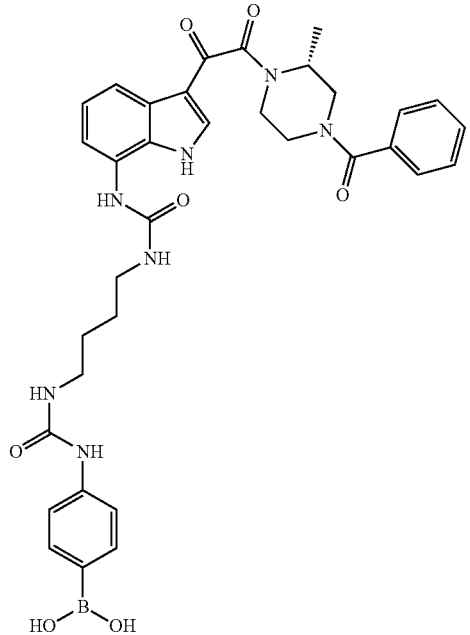 | A |

TABLE 2-continued
| Compd. Number | Structure | EC$_{50}$ Group from Table 1 |
|---|---|---|
| P-C-109 | 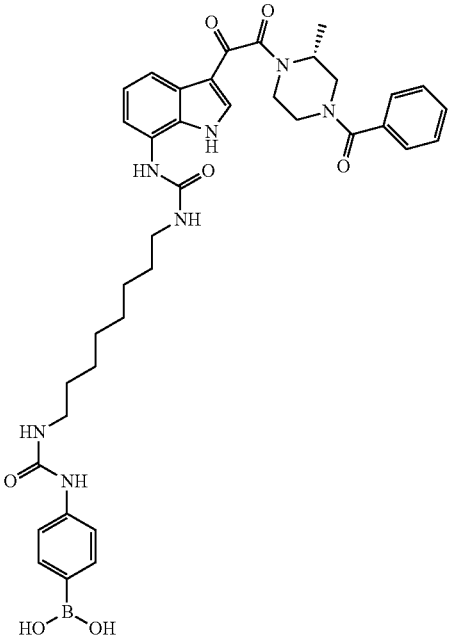 [SMILES: C[C@@H]1CN(C(=O)c2ccccc2)CCN1C(=O)C(=O)c1c[nH]c2c(NC(=O)NCCCCCCCCNC(=O)Nc3ccc(B(O)O)cc3)cccc12] | A |
| P-C-202 | 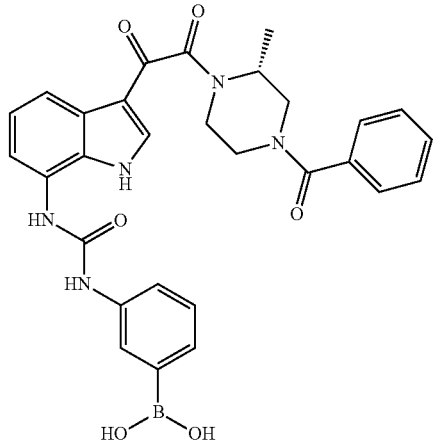 [SMILES: C[C@@H]1CN(C(=O)c2ccccc2)CCN1C(=O)C(=O)c1c[nH]c2c(NC(=O)Nc3cccc(B(O)O)c3)cccc12] | A |
| P-C-204 | 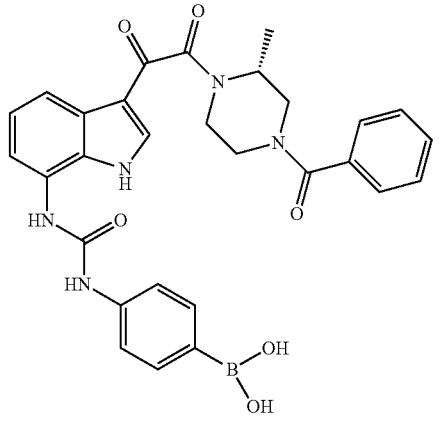 [SMILES: C[C@@H]1CN(C(=O)c2ccccc2)CCN1C(=O)C(=O)c1c[nH]c2c(NC(=O)Nc3ccc(B(O)O)cc3)cccc12] | A |

TABLE 2-continued

| Compd. Number | Structure | EC$_{50}$ Group from Table 1 |
|---|---|---|
| P-C-401 | 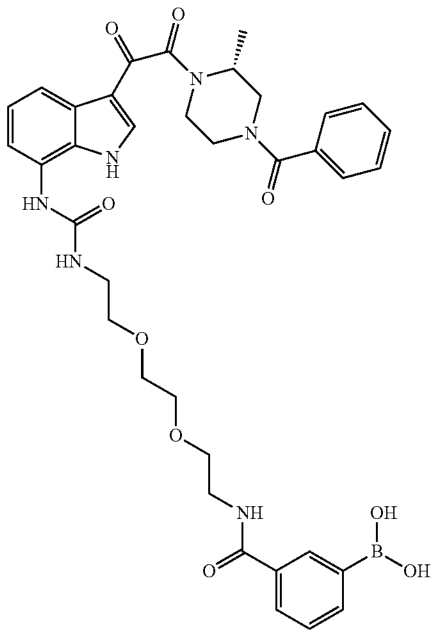 [SMILES: C[C@@H]1CN(C(=O)c2ccccc2)CCN1C(=O)C(=O)c1c[nH]c2c(NC(=O)NCCOCCOCCNC(=O)c3cccc(B(O)O)c3)cccc12] | A |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound or a pharmaceutically acceptable salt thereof selected from the group consisting of:

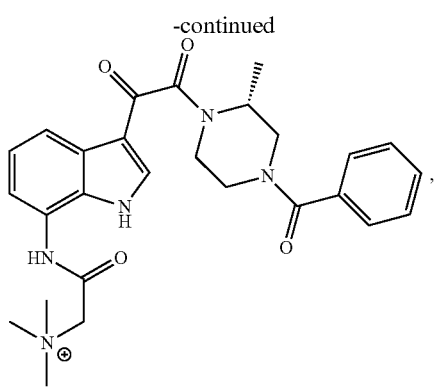

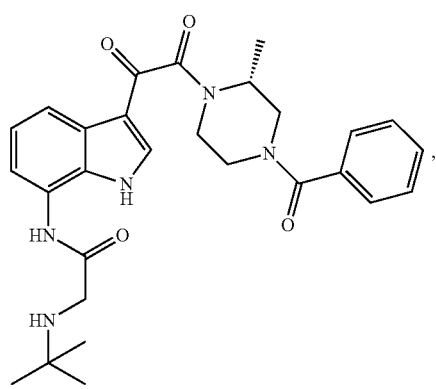

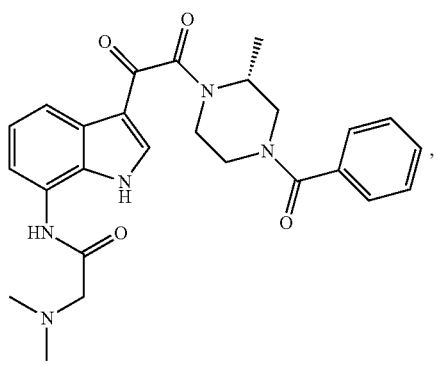

265
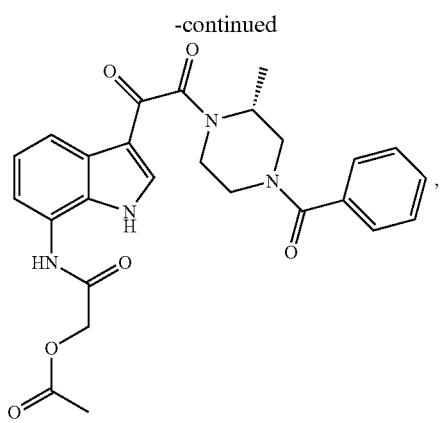
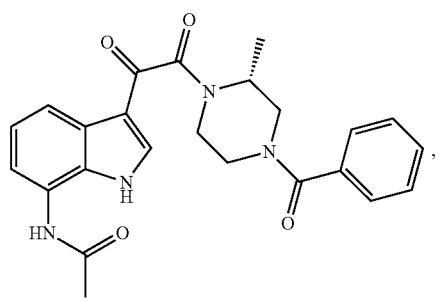
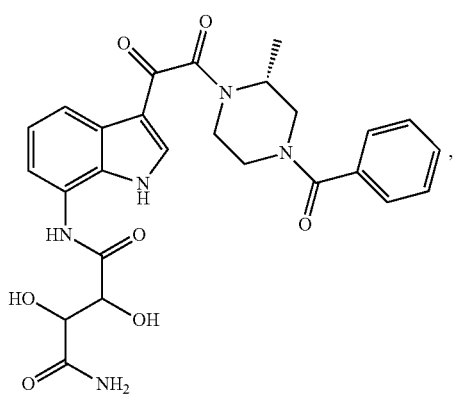
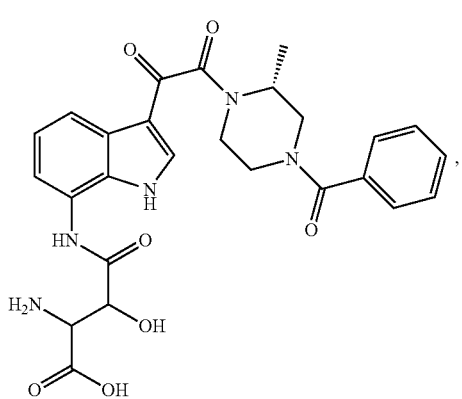
266
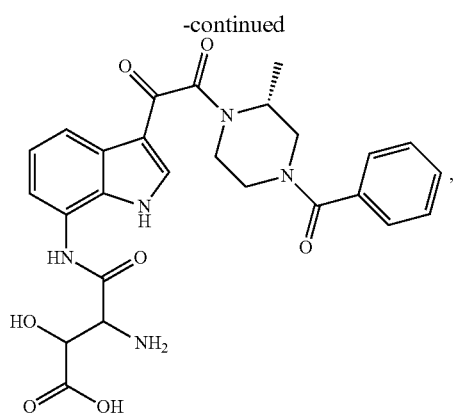
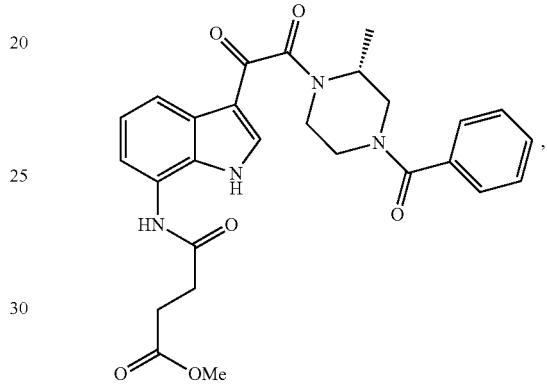
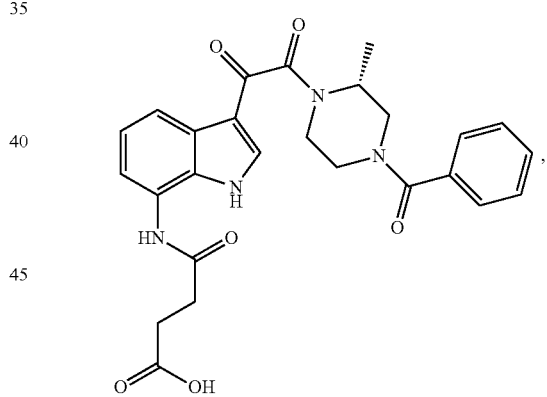
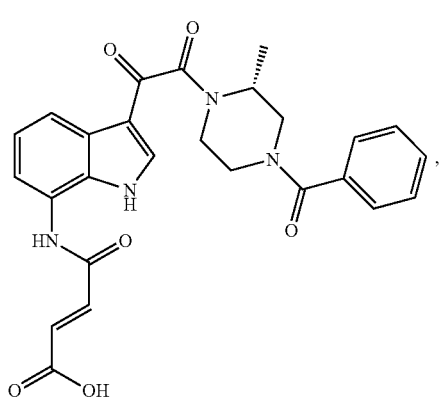

267  
-continued
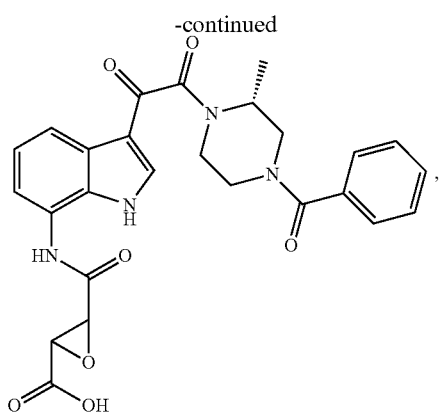
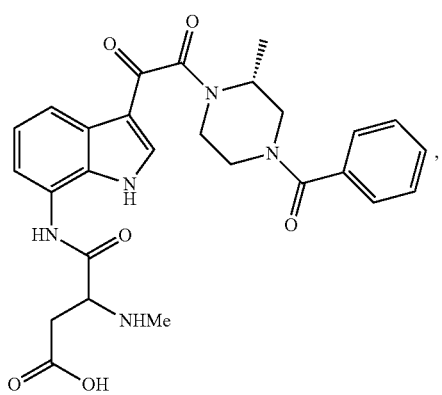
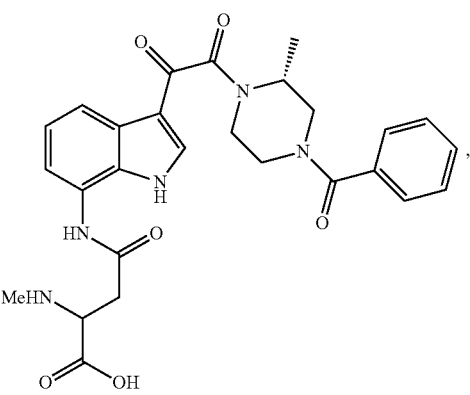
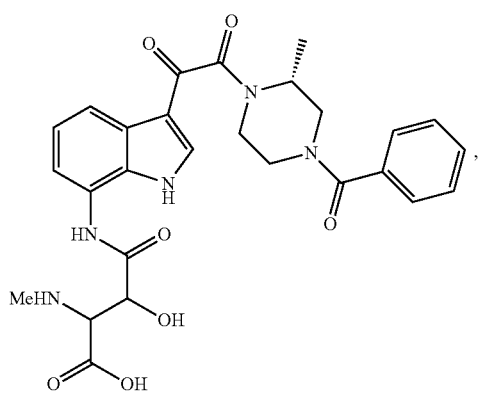
268  
-continued
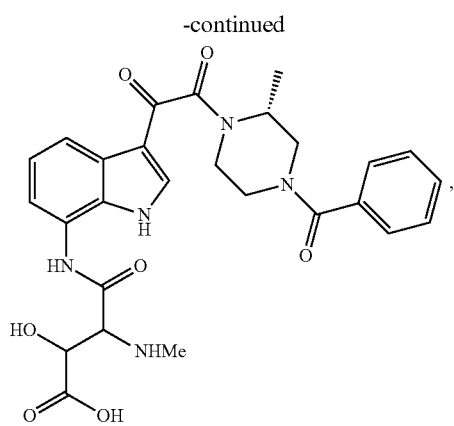
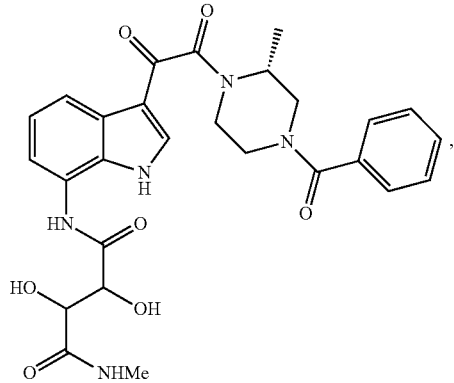
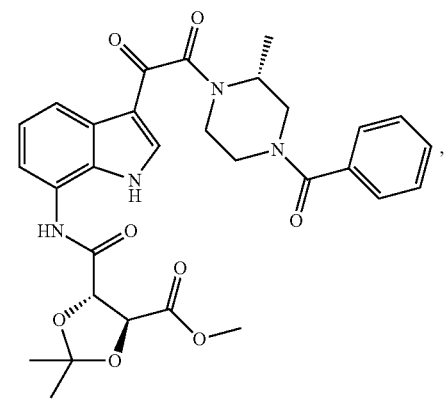
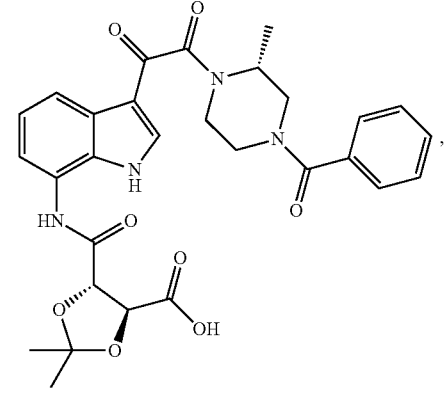

269
-continued
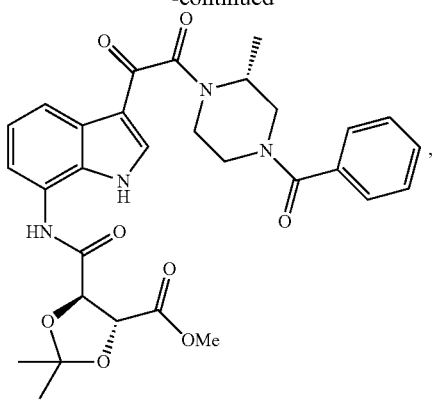
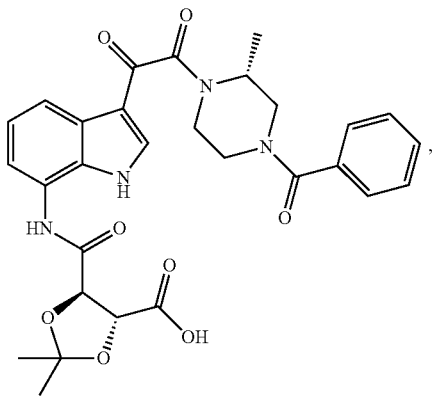
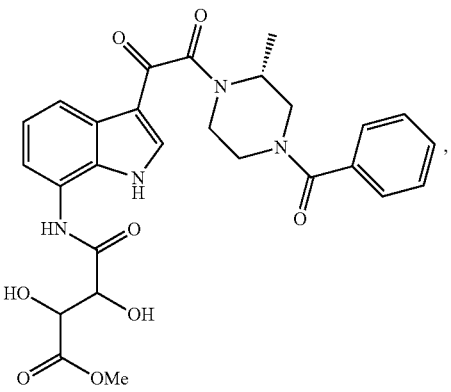
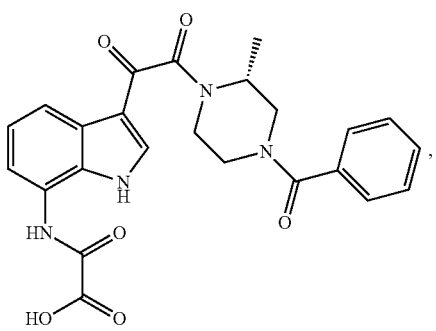
270
-continued
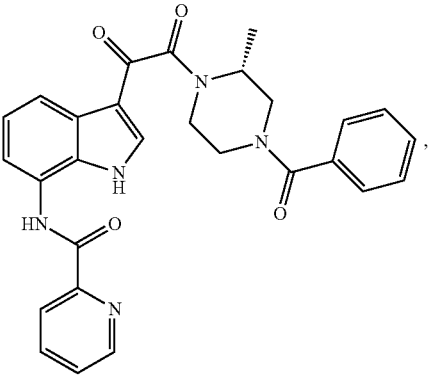
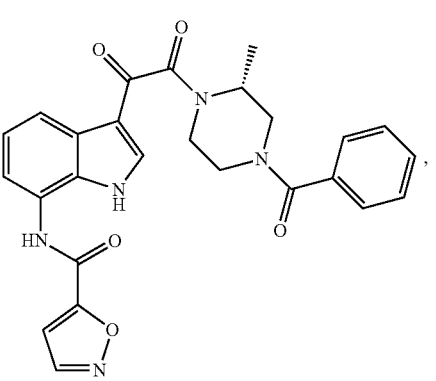
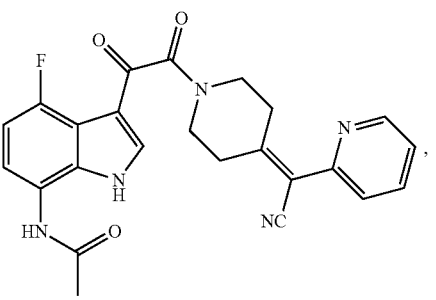
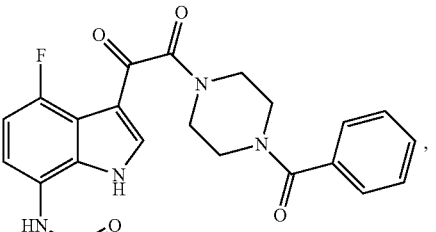
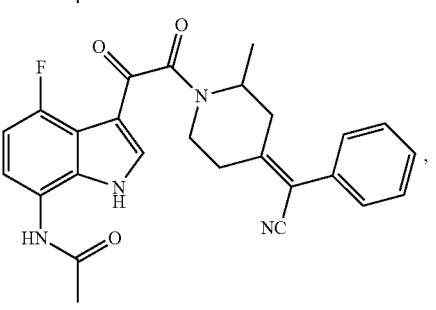

271
-continued
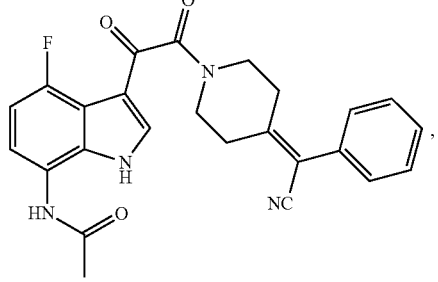
272
-continued
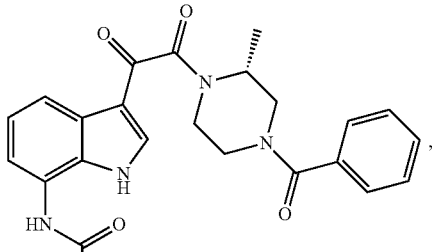
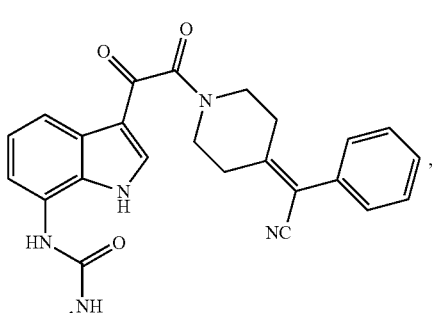
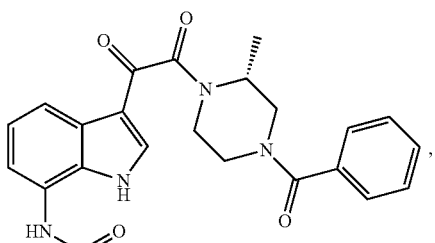
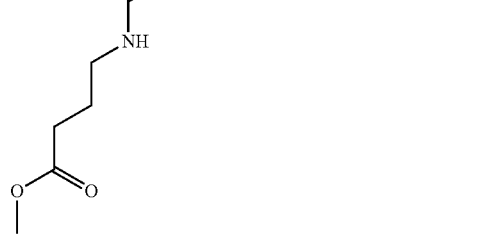

273
-continued
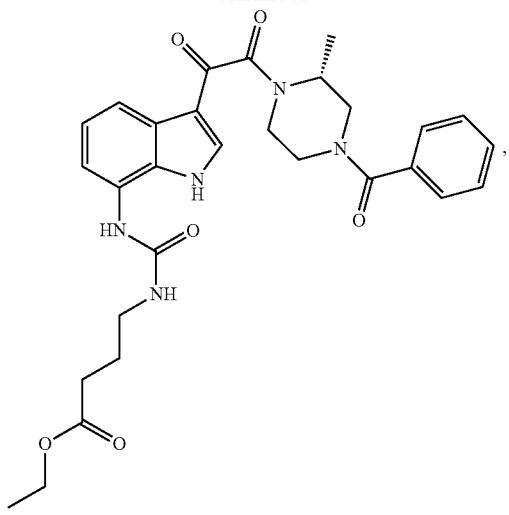
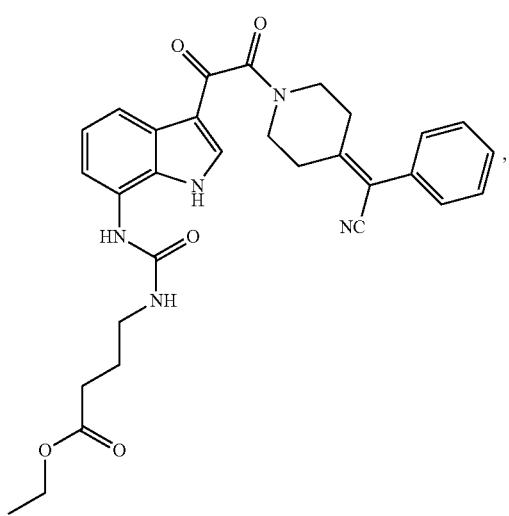
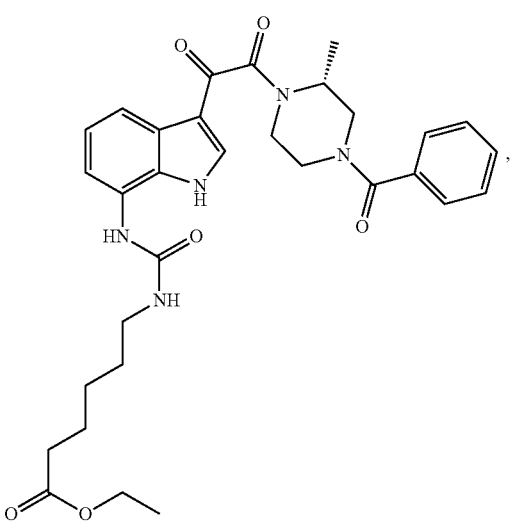
274
-continued
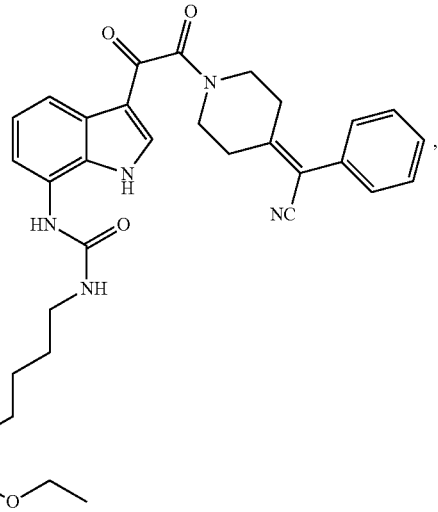
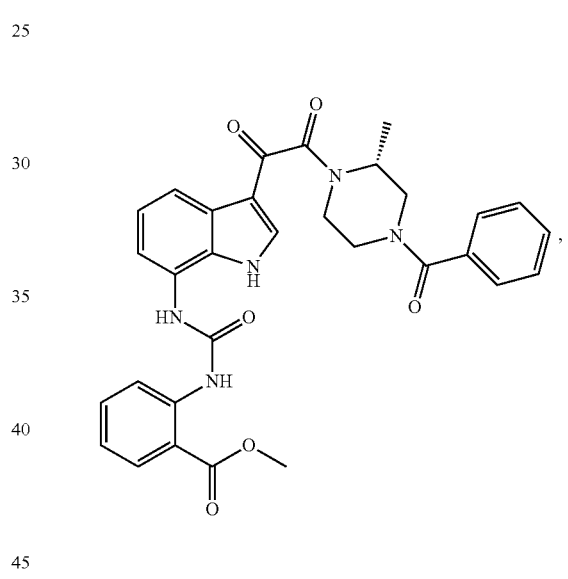
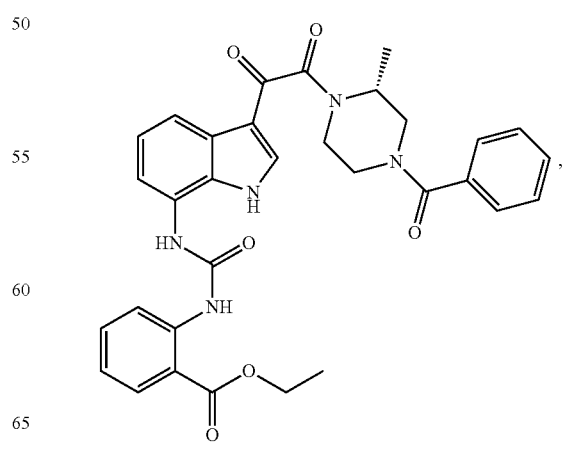

275
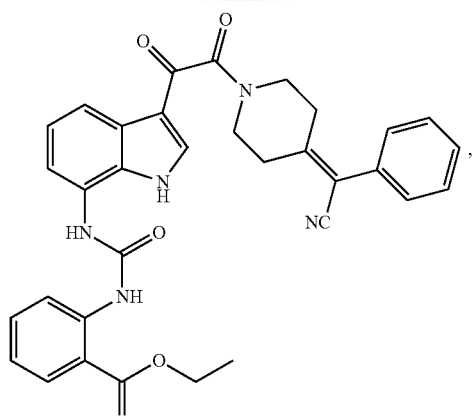
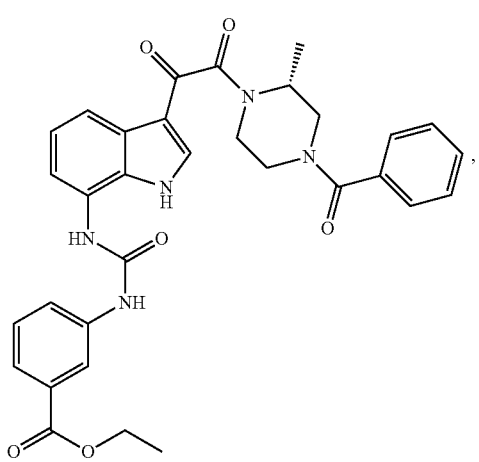
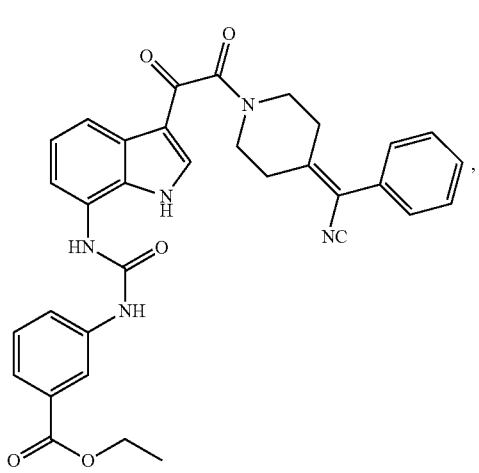
276
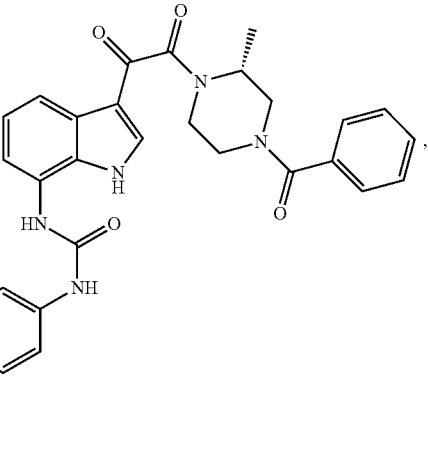
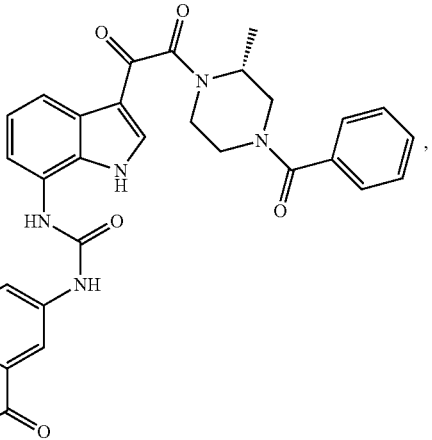

277
-continued
278
-continued
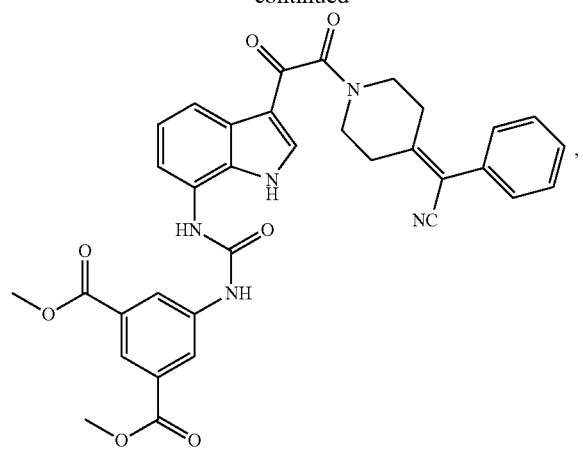
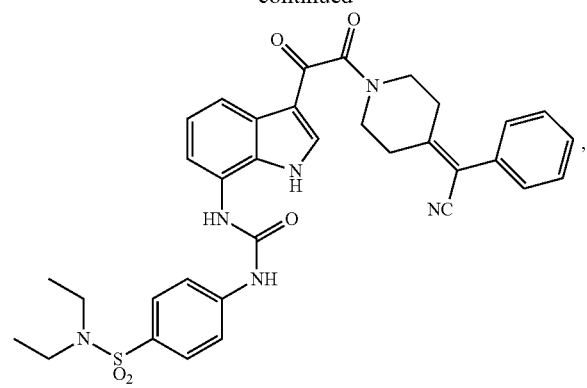

279                                    280
-continued                            -continued
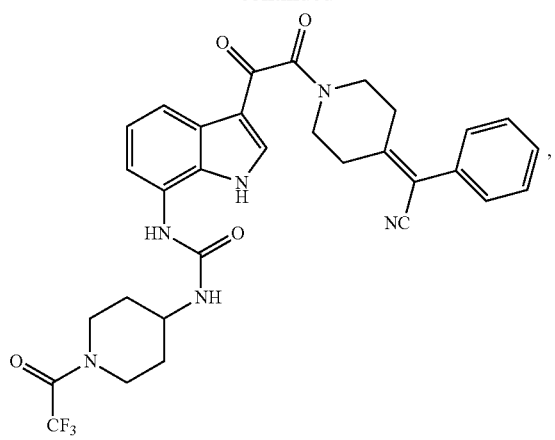 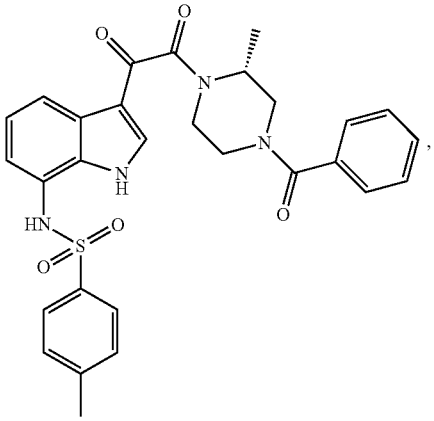
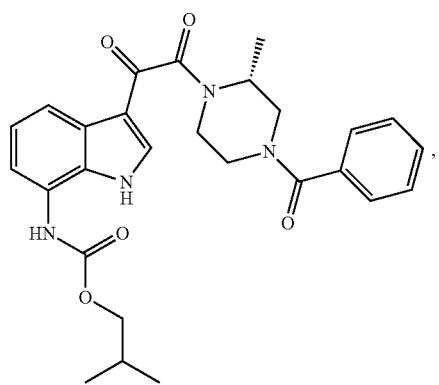 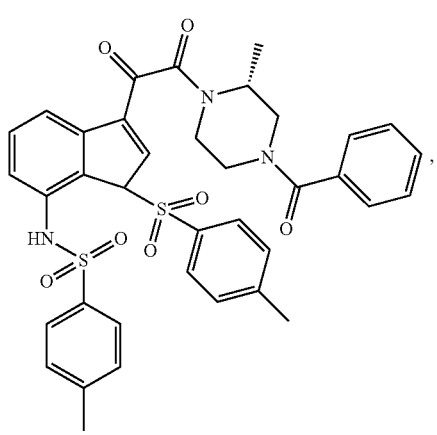
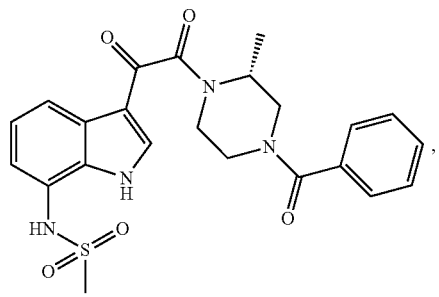 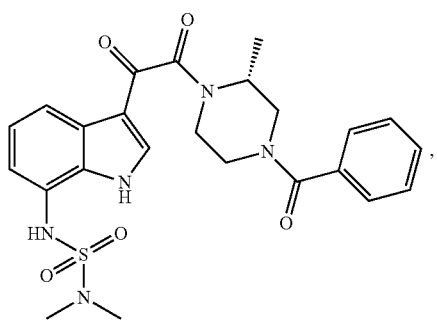
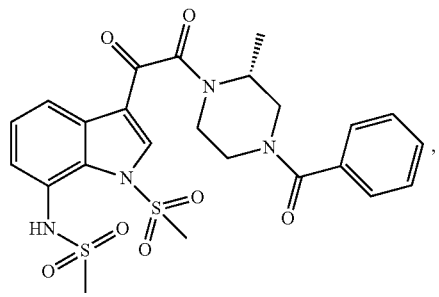 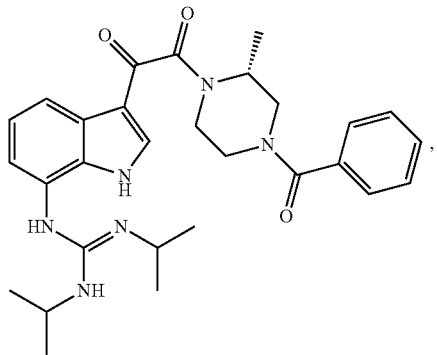

281
-continued
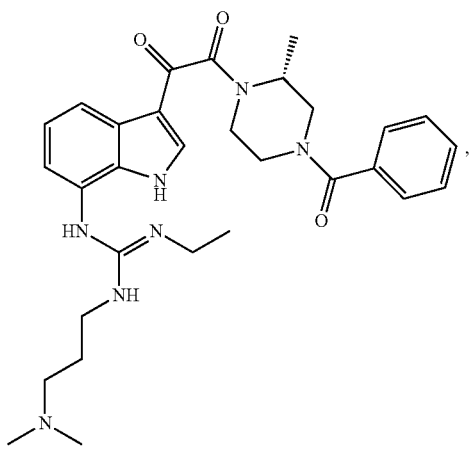
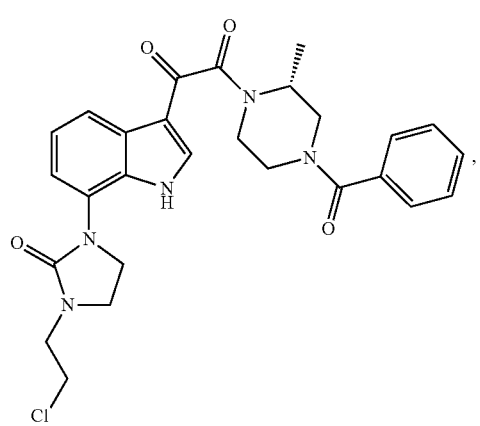
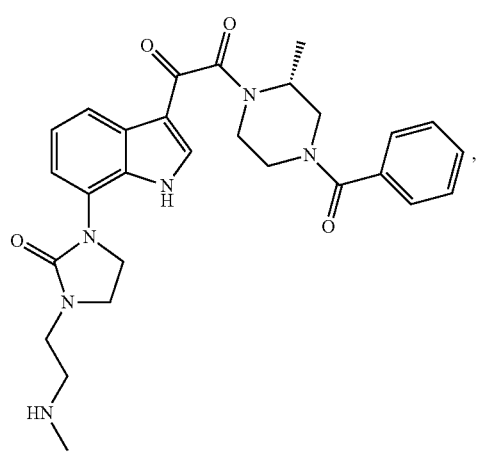
282
-continued
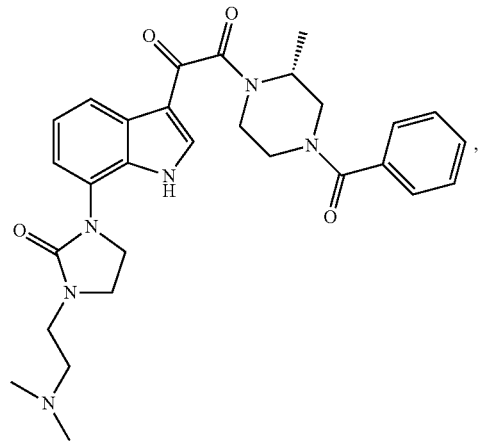
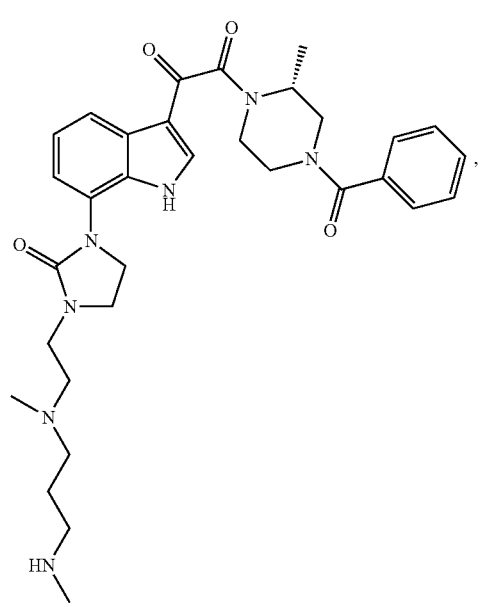
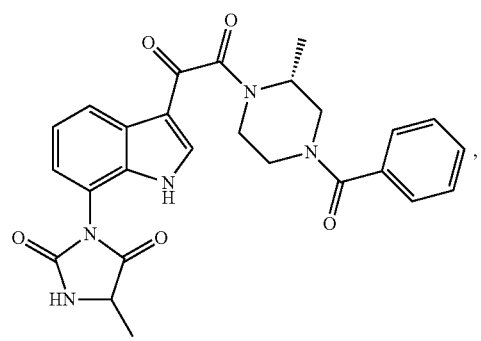

283
-continued
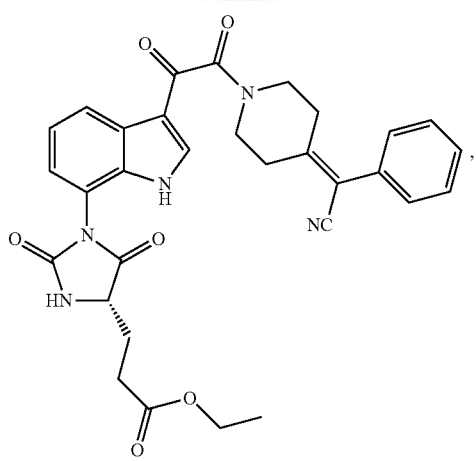
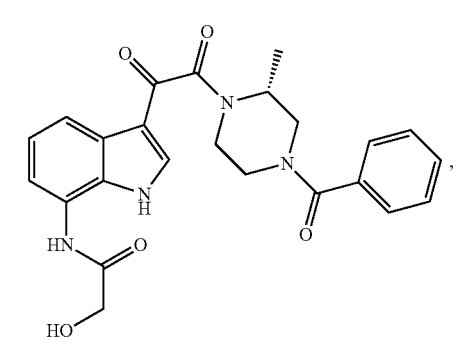
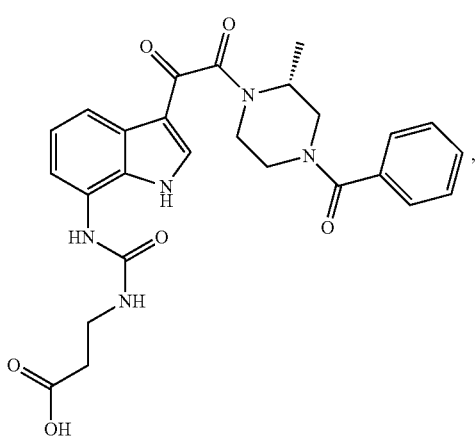
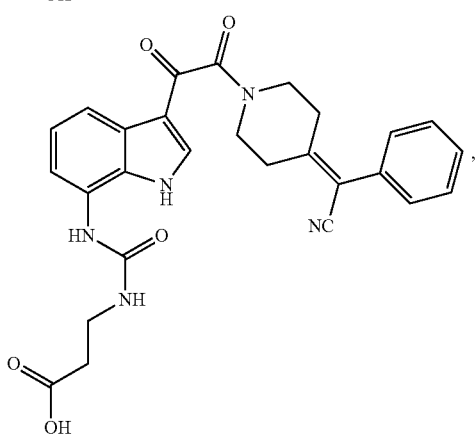
284
-continued
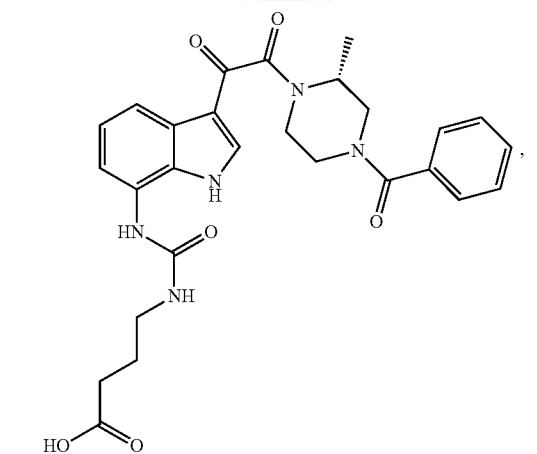
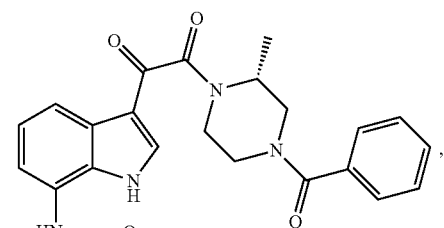
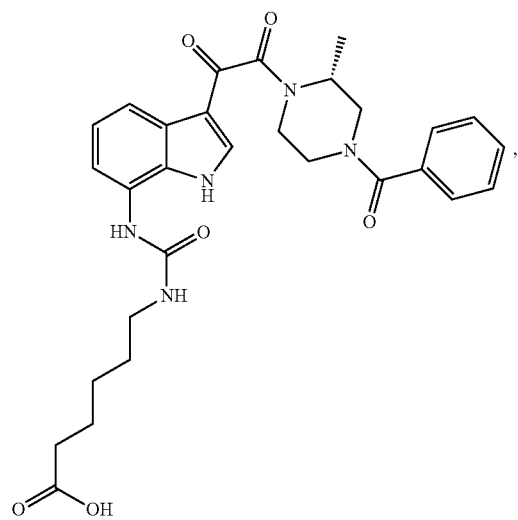

285
-continued
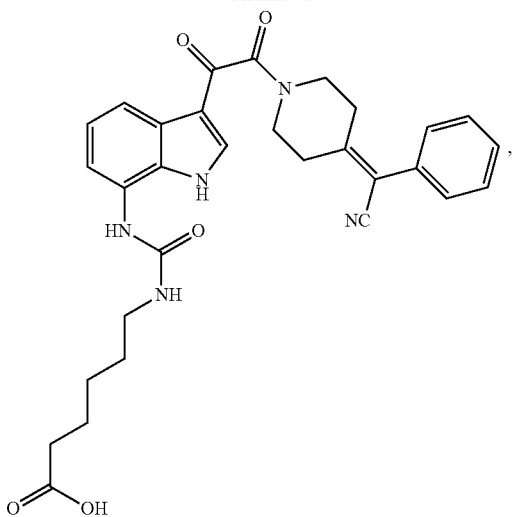
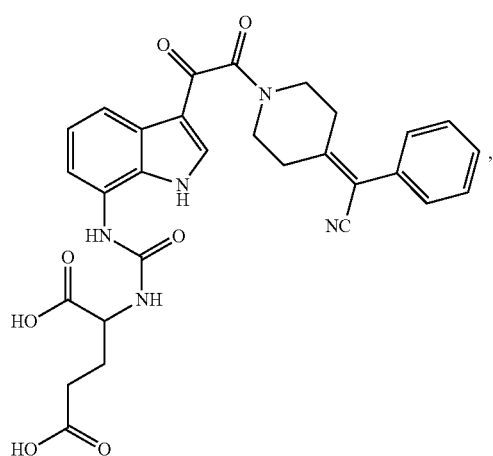
286
-continued
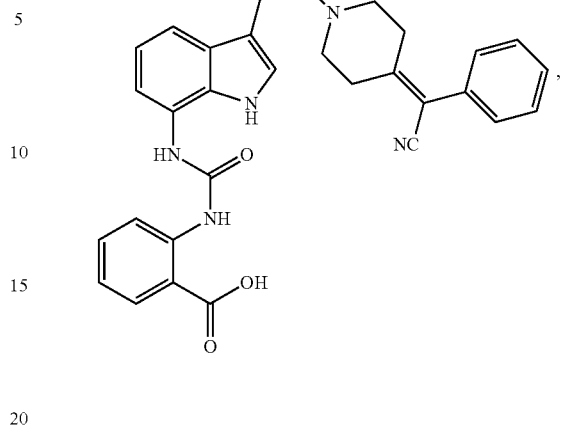
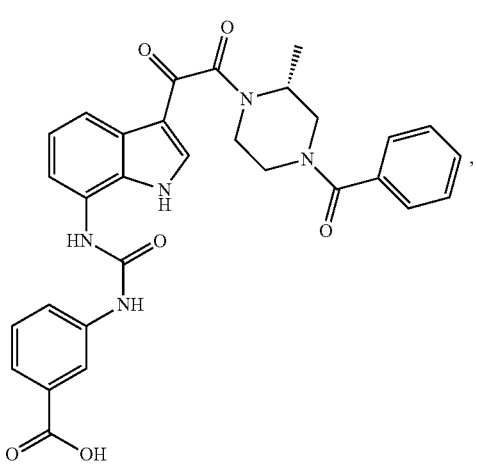
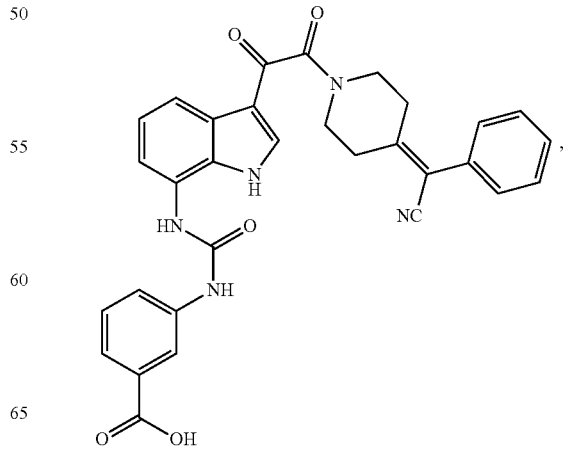

287
-continued
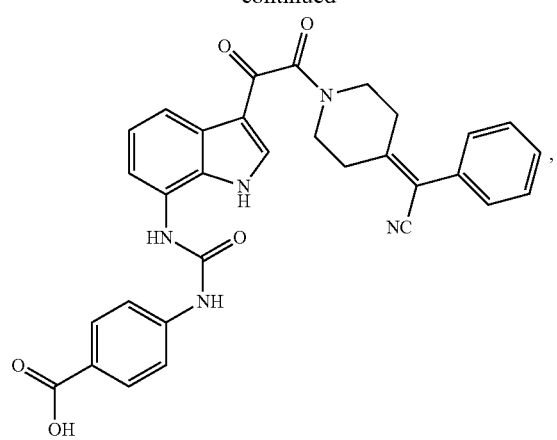
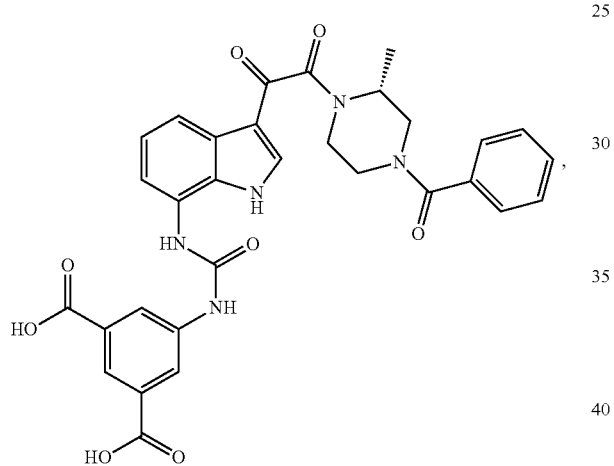
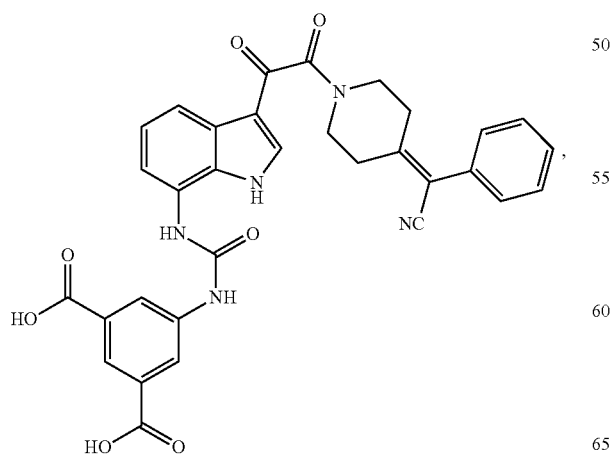
288
-continued
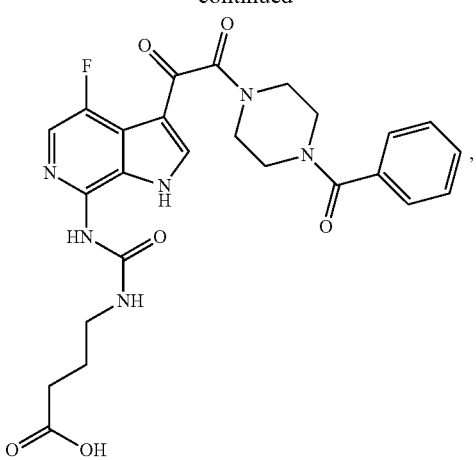
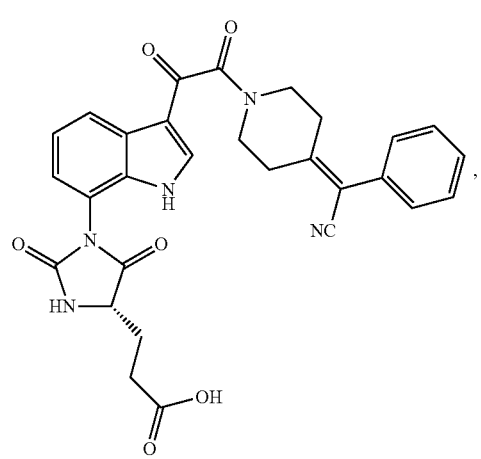
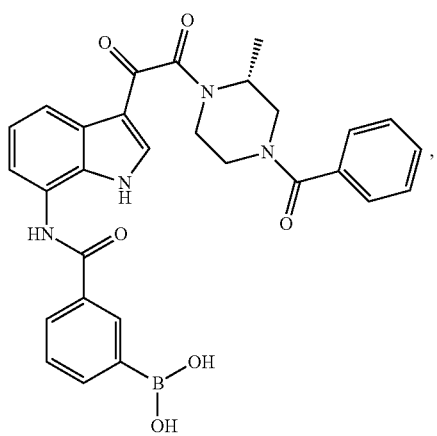

289
-continued
290
-continued
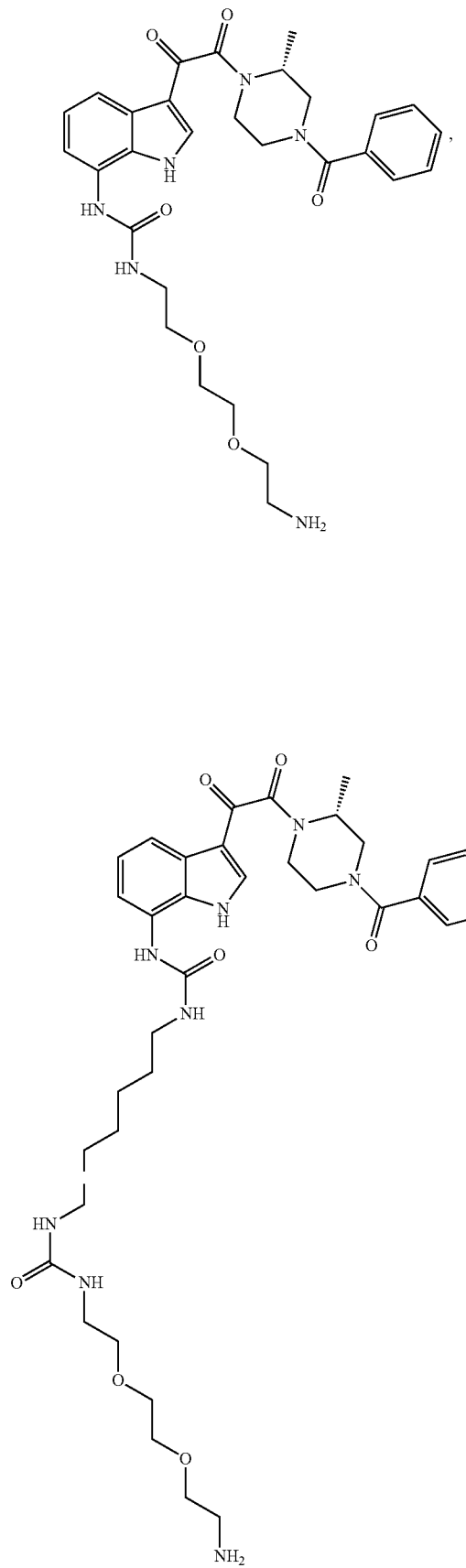
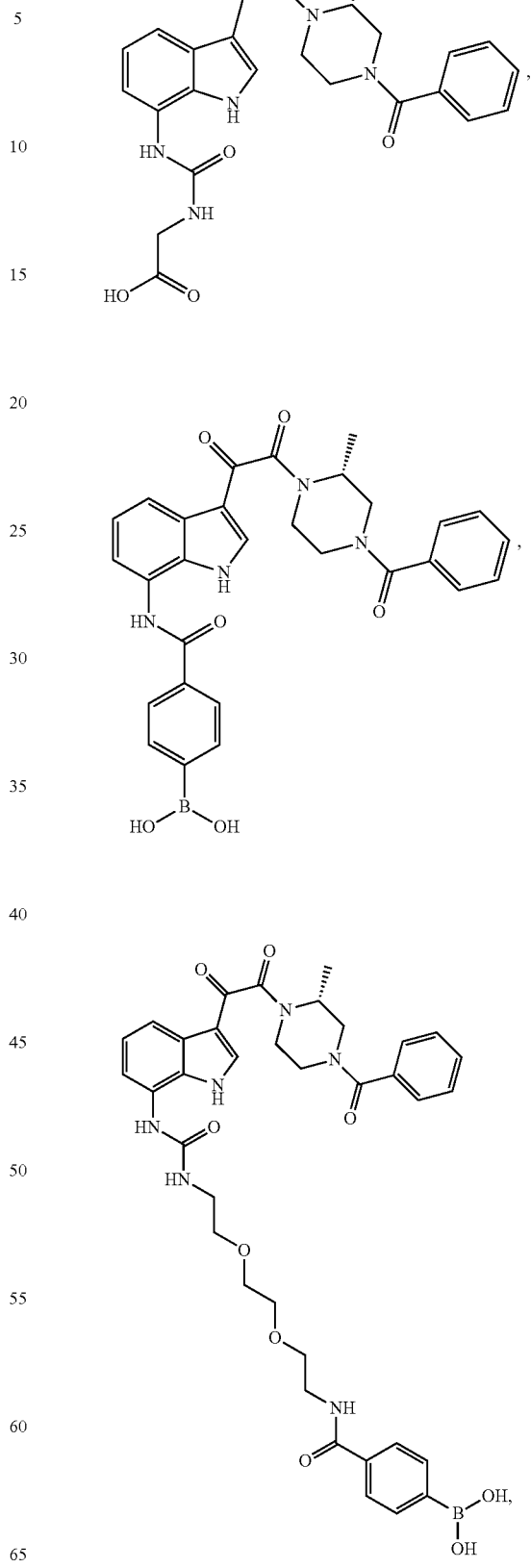

291
-continued
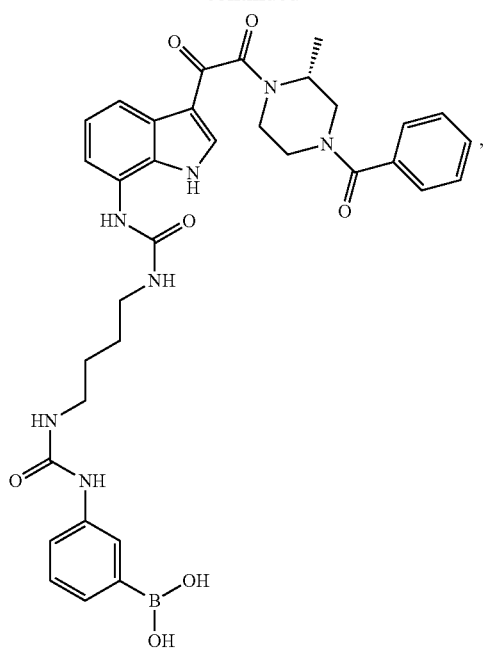
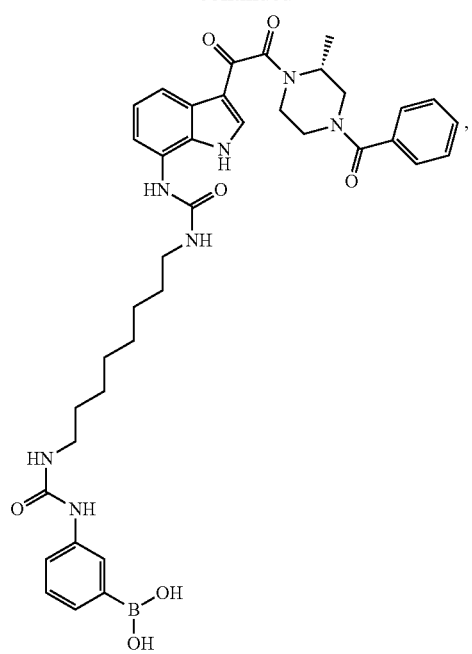
292
-continued
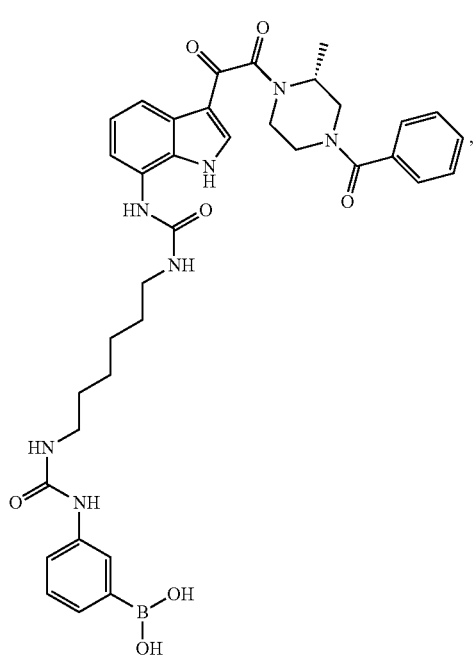
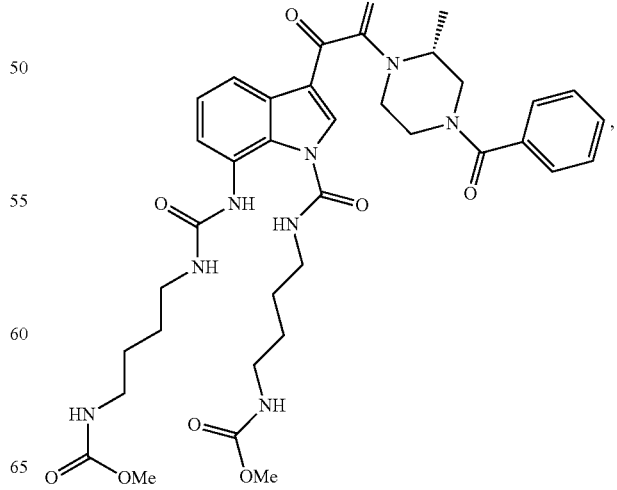

293
-continued
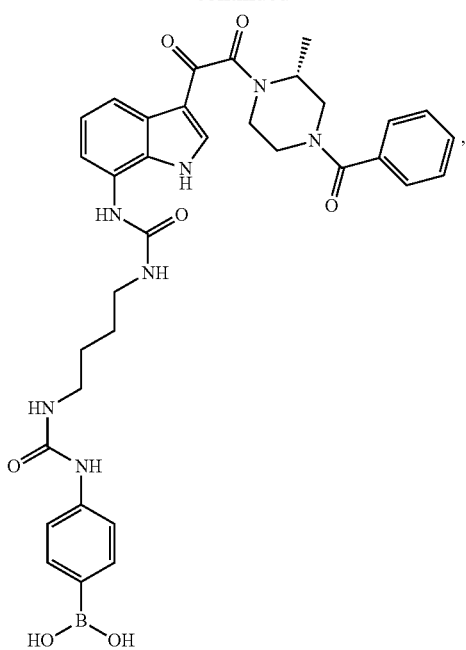
294
-continued
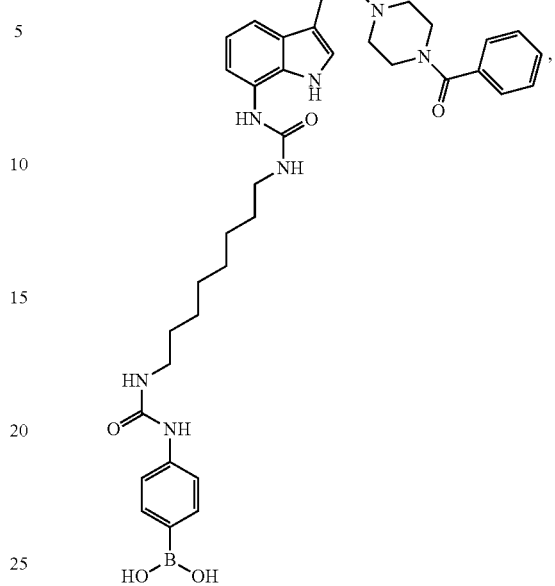
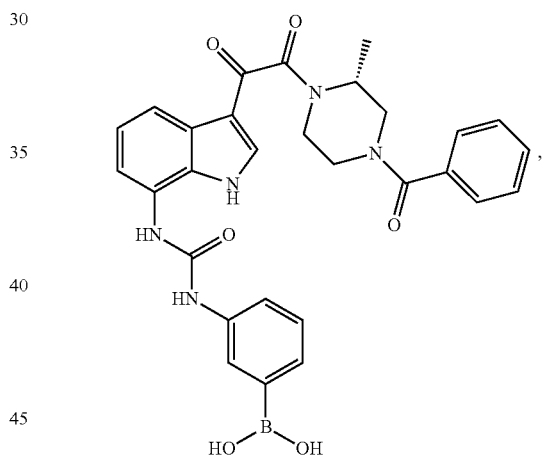
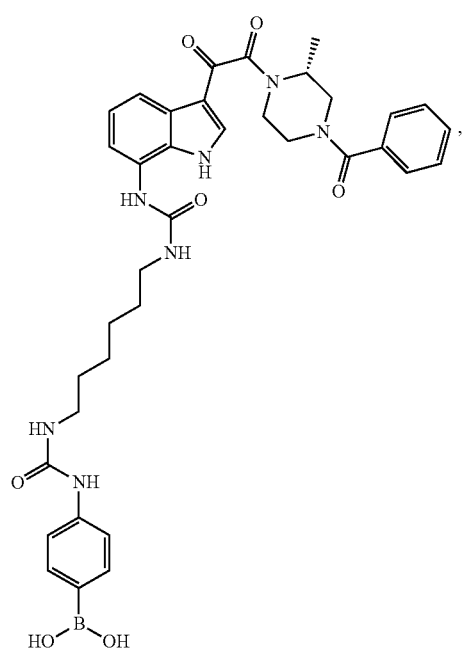
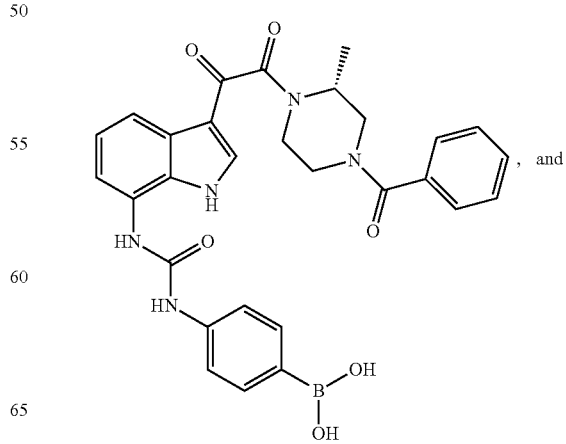, and 295
-continued
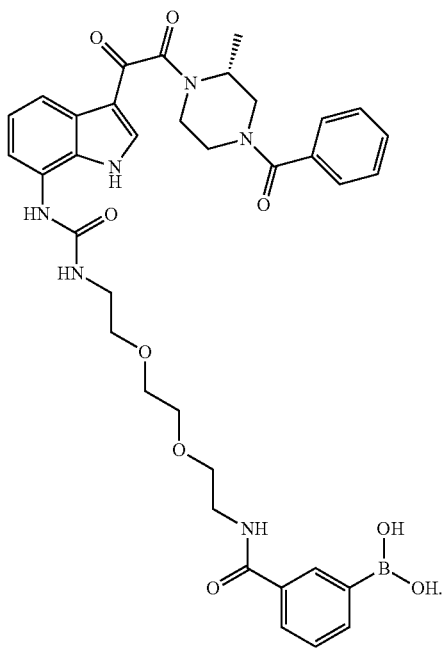 [SMILES: C[C@@H]1CN(C(=O)c2ccccc2)CCN1C(=O)C(=O)c1c[nH]c2c(NC(=O)NCCOCCOCCNC(=O)c3cccc(B(O)O)c3)cccc12]
2. A compound or a pharmaceutically acceptable salt thereof selected from the group consisting of:
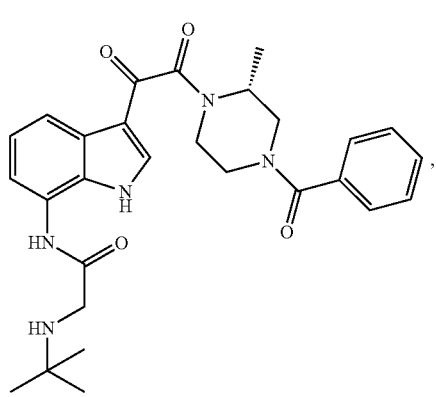
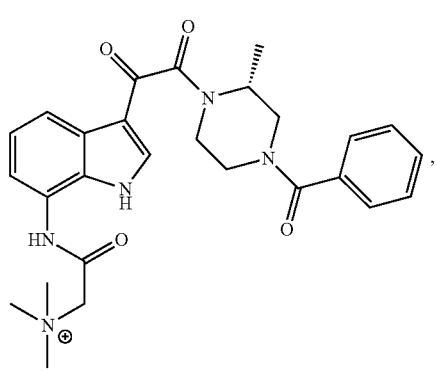
296
-continued
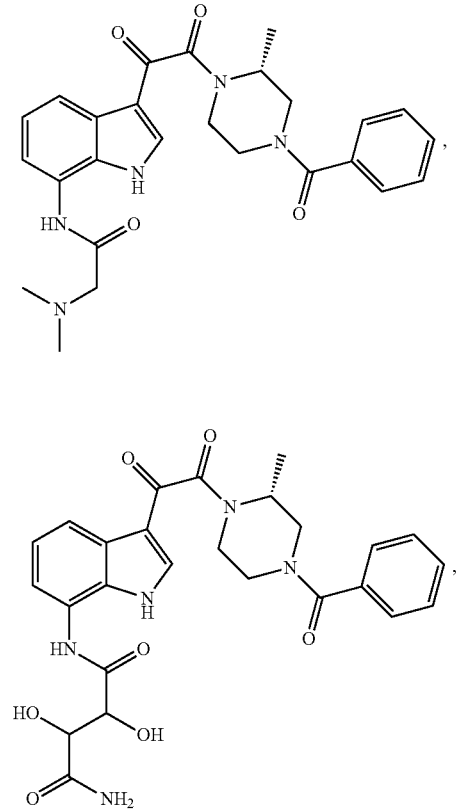
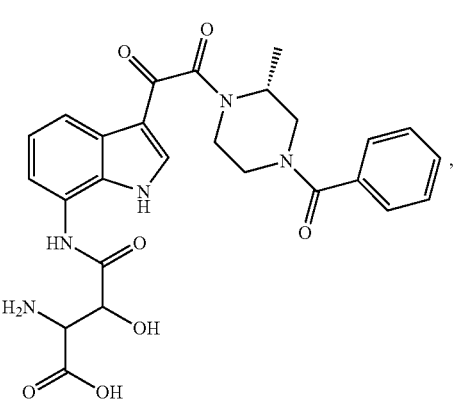
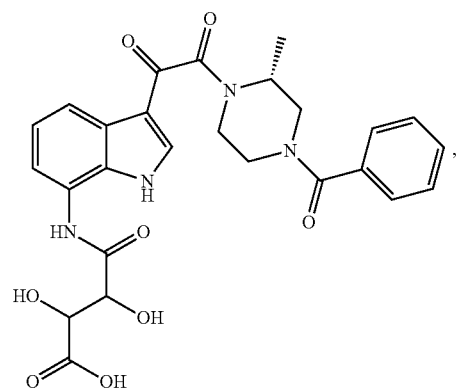

297
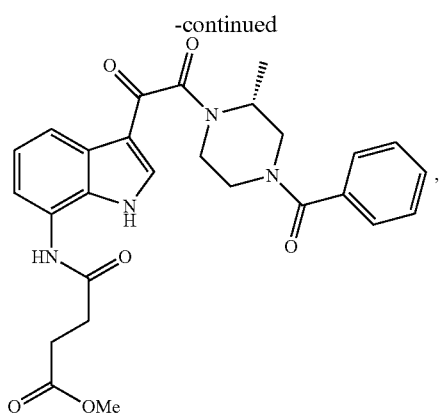
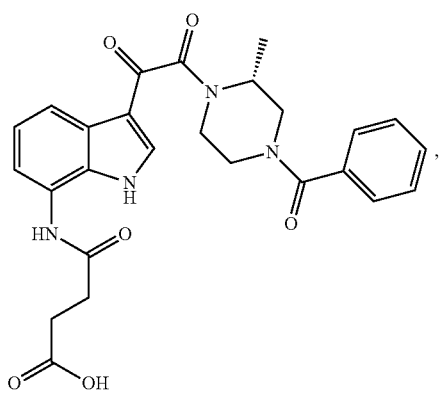
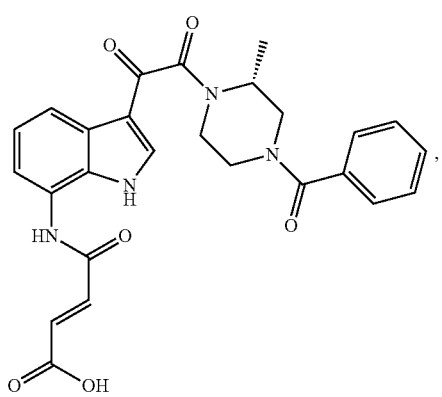
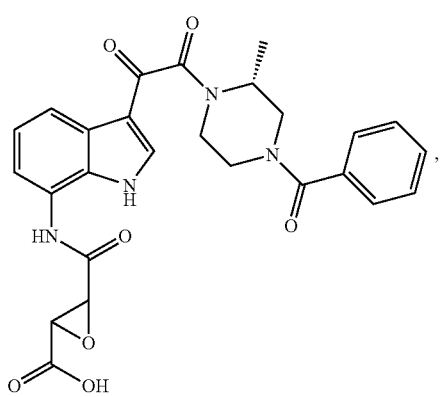
298
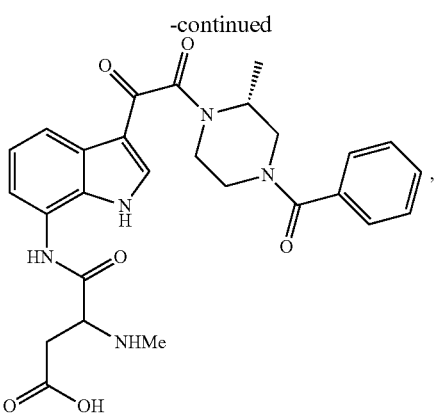
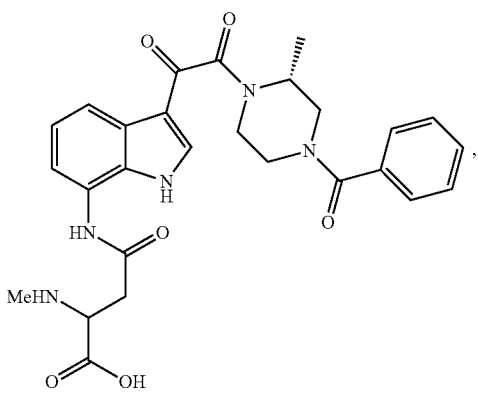
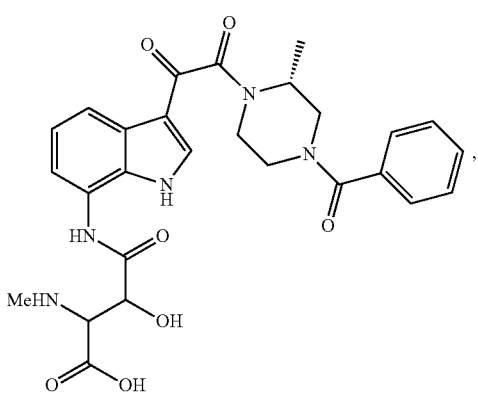
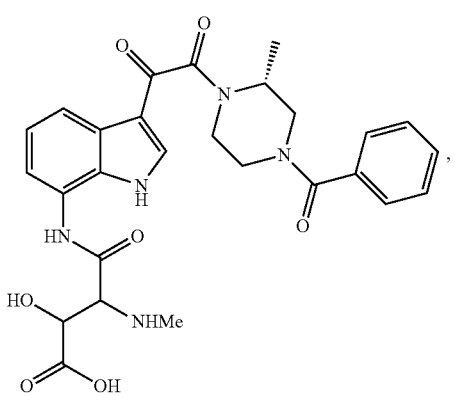

299
-continued
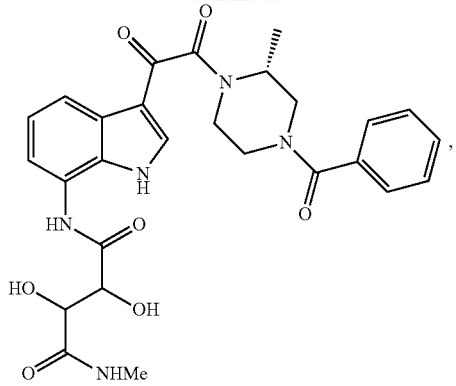
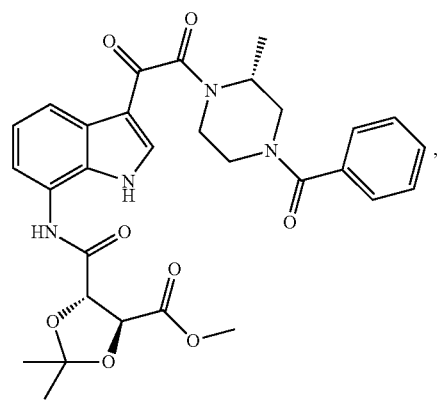
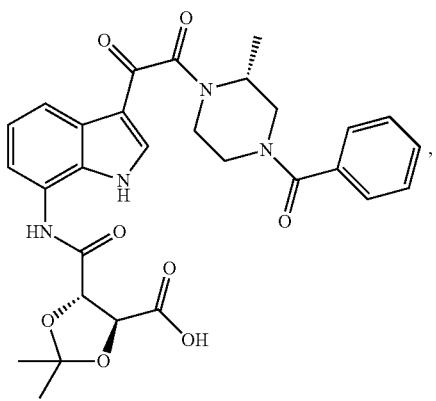
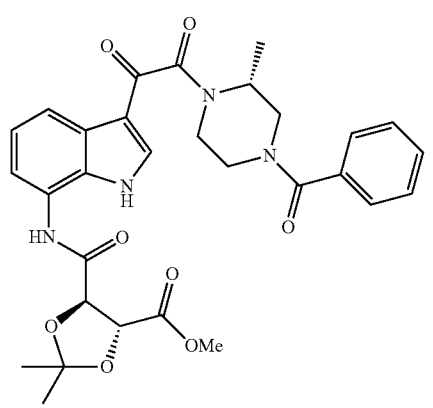
300
-continued
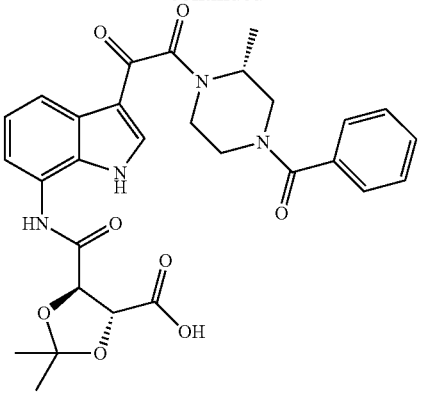
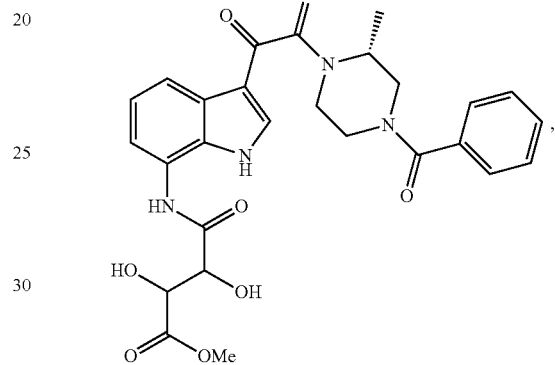
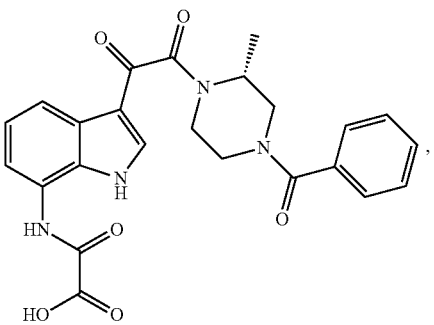
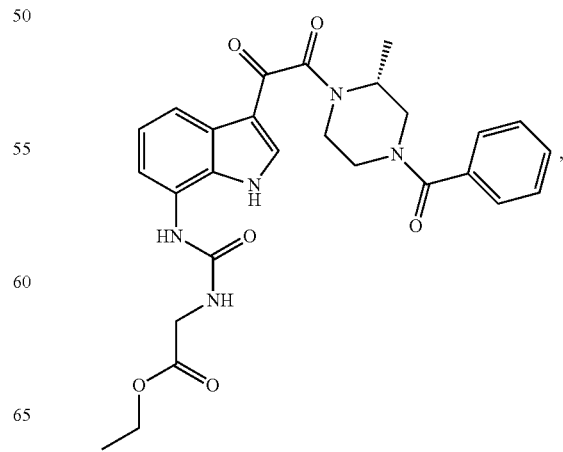

301
-continued
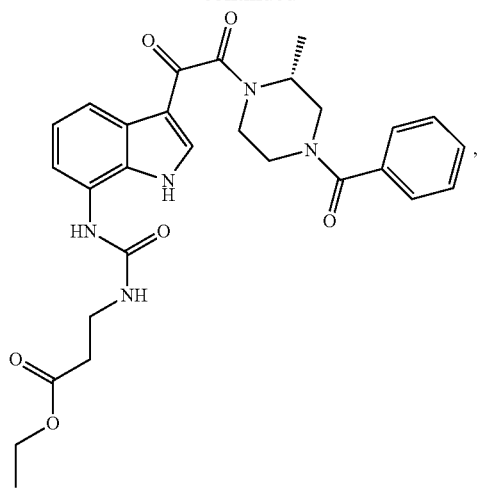
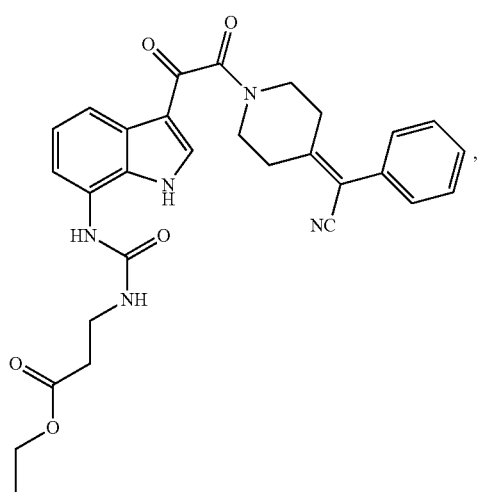
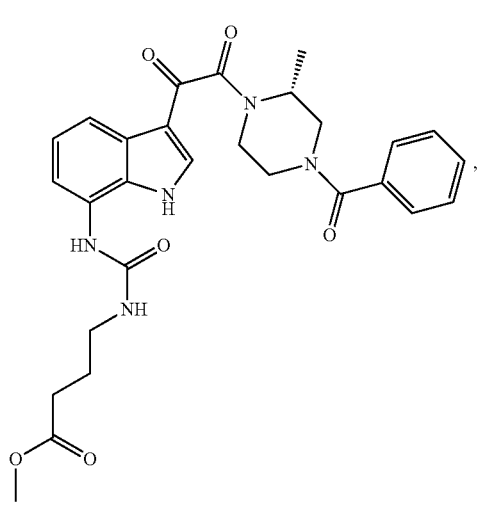
302
-continued
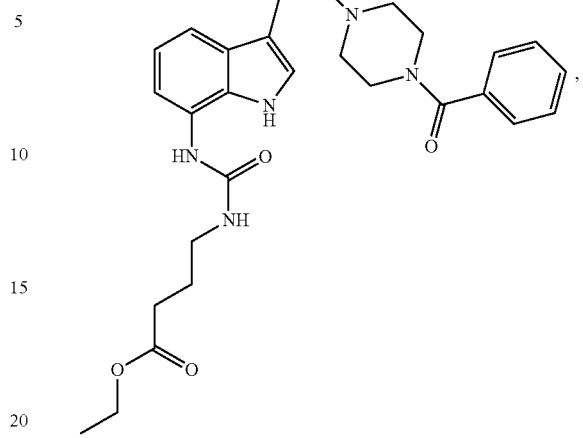
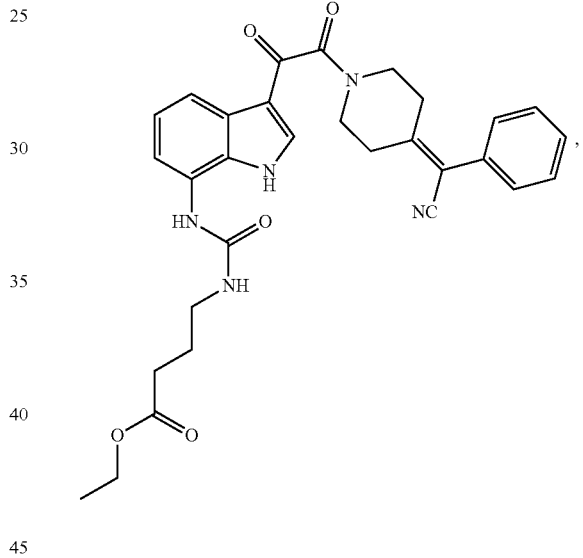
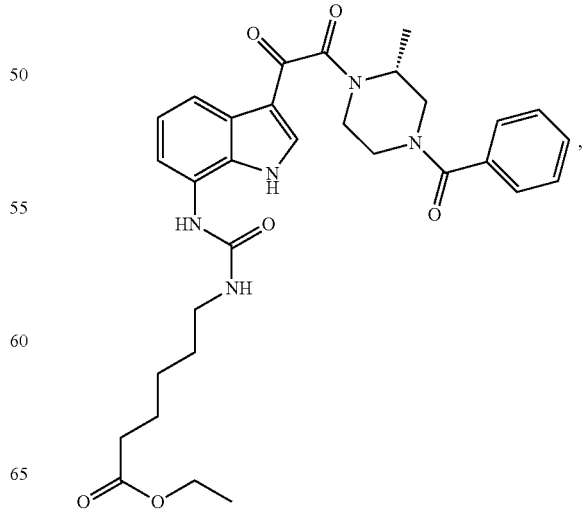

303
-continued
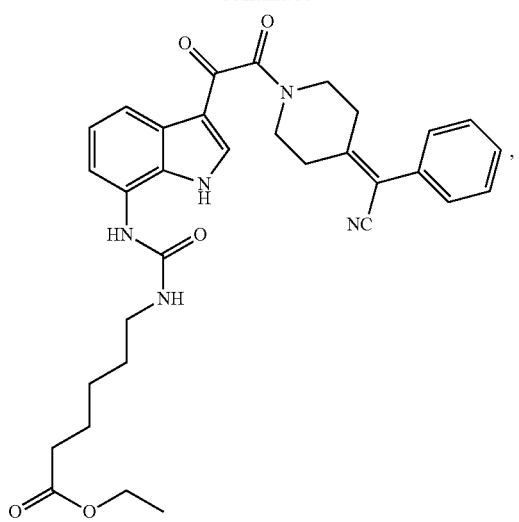
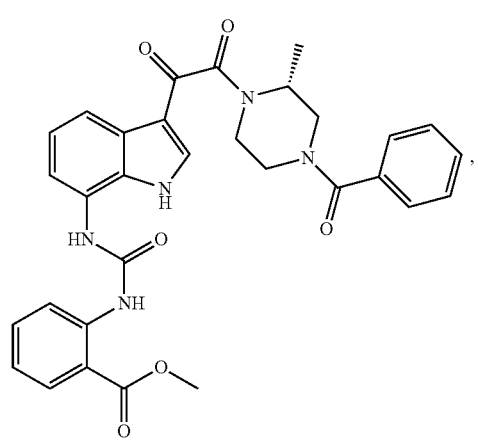
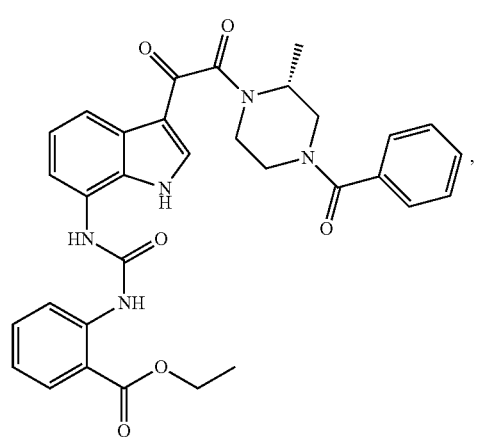
304
-continued
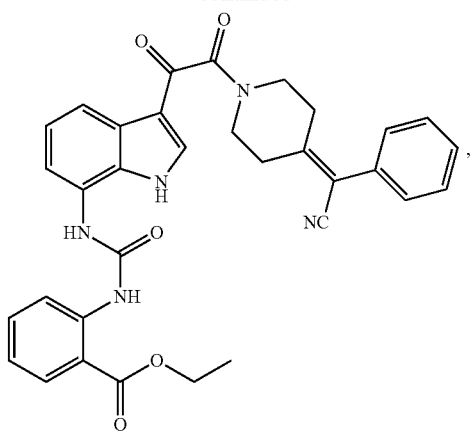
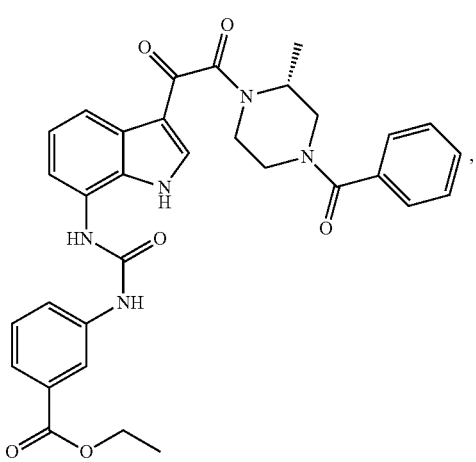
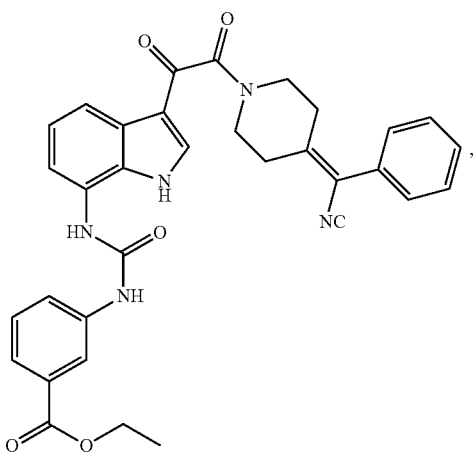

305
-continued
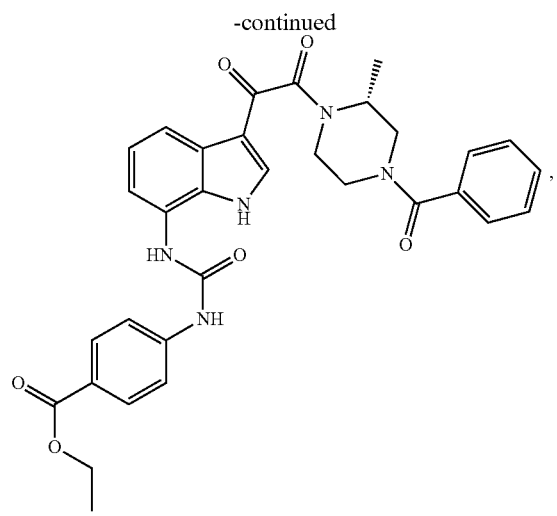
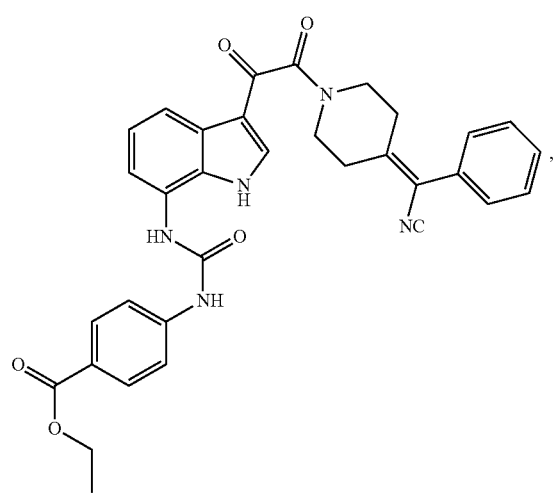
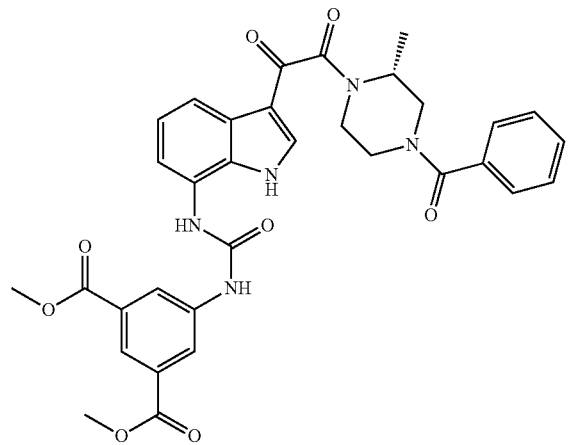
306
-continued
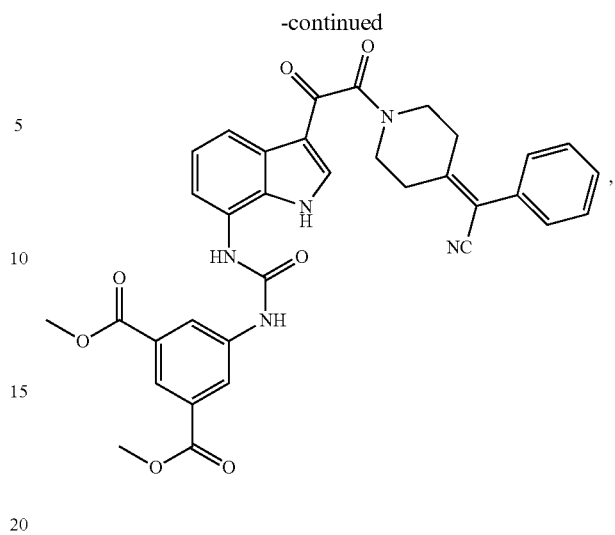
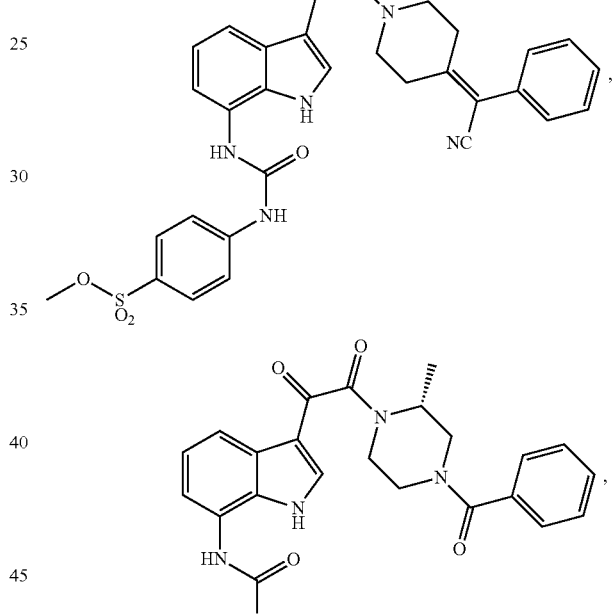
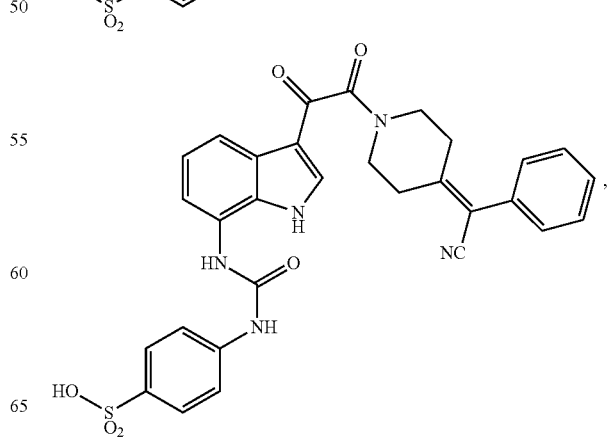

307
-continued
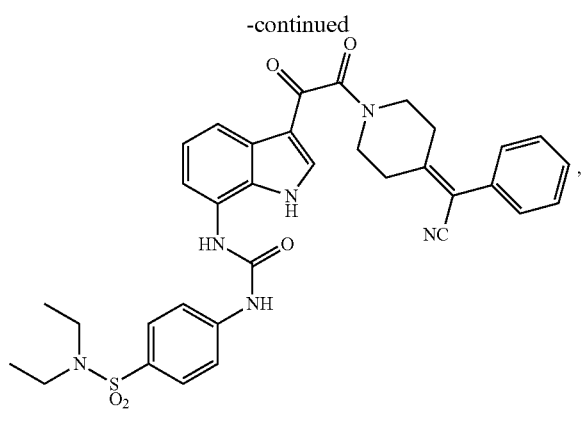
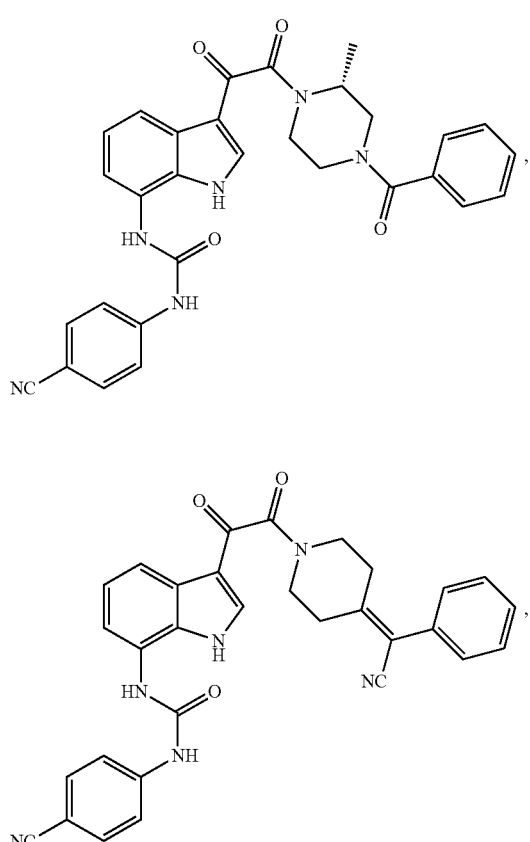
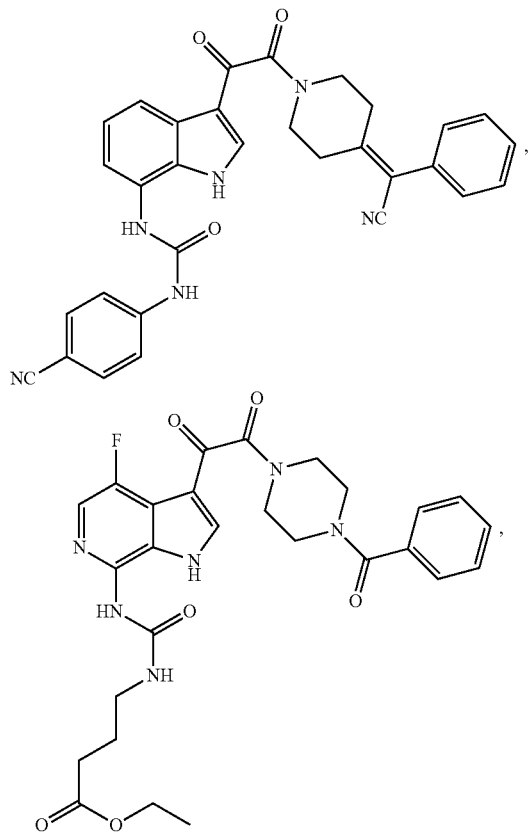
308
-continued
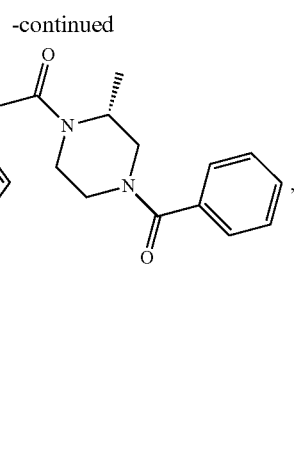
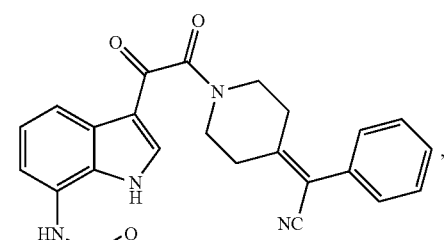
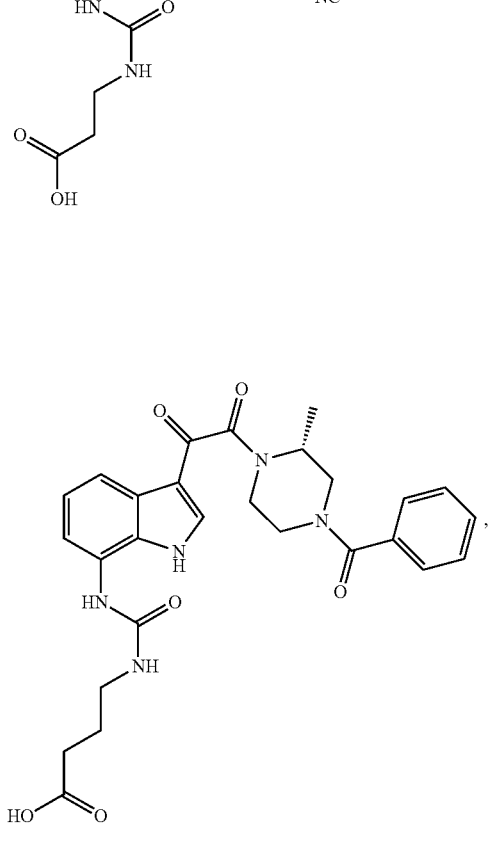

309
-continued
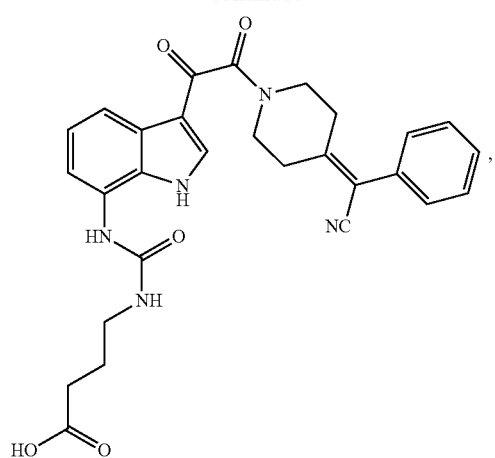
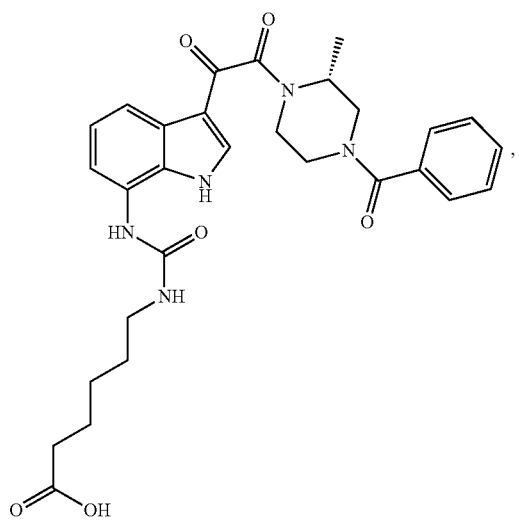
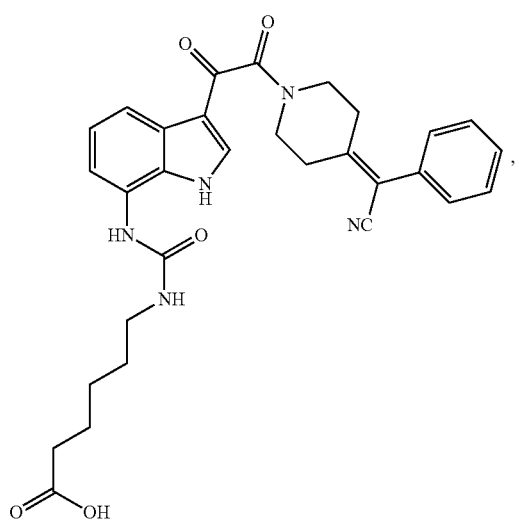
310
-continued
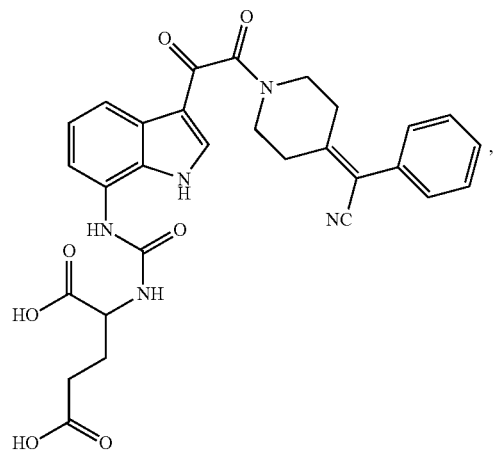
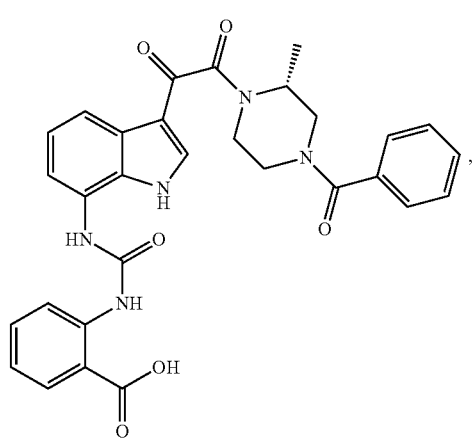
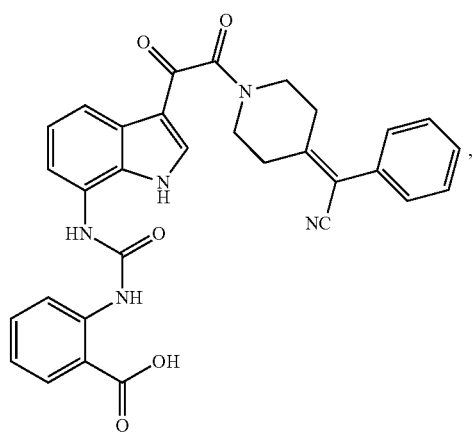

311 -continued
312 -continued
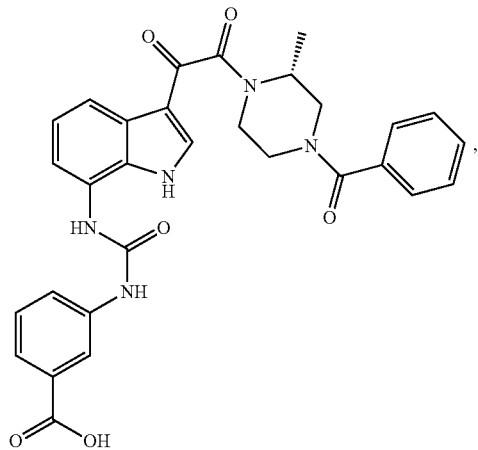
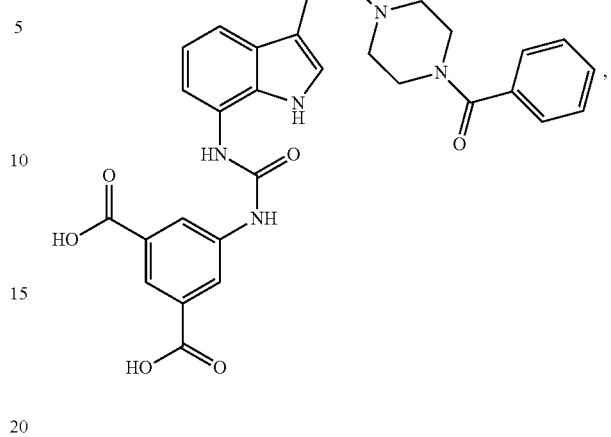
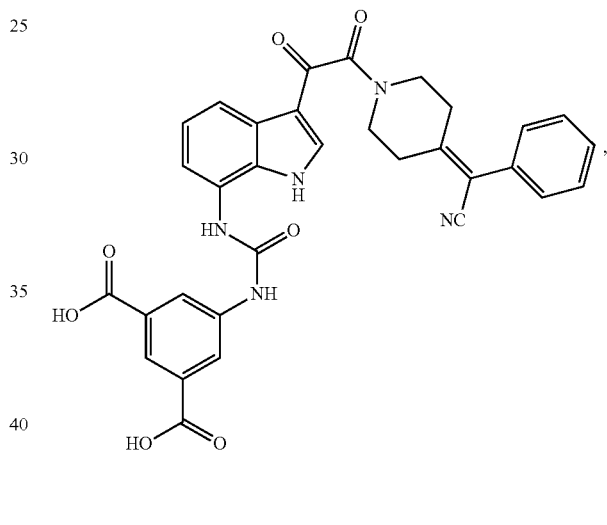
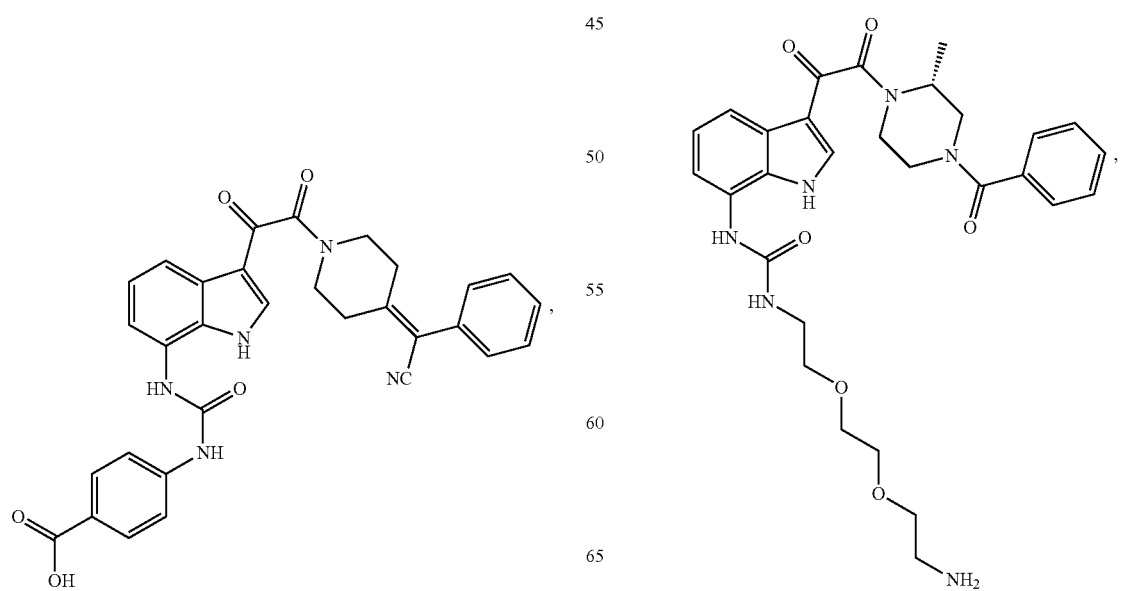

313
-continued

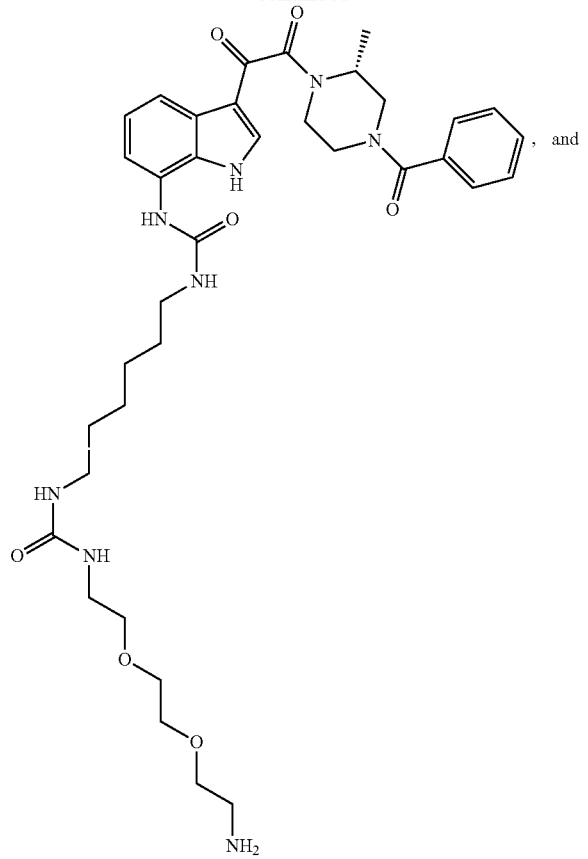

, and

314
-continued

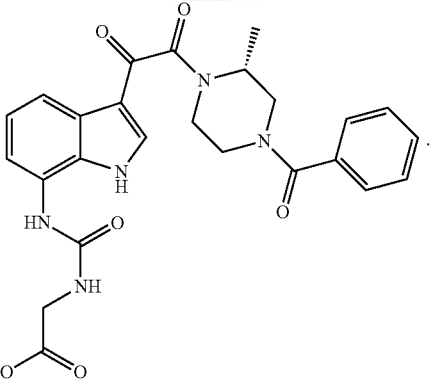

.

3. A pharmaceutical composition which comprises one or more of the compounds as claimed in claim 2, and one or more pharmaceutically acceptable carriers, excipients or diluents.

4. The pharmaceutical composition of claim 3, which additionally comprises an AIDS treatment agent selected from the group consisting of:
  (a) an AIDS antiviral agent;
  (b) an anti-infective agent;
  (c) an immunomodulator; and
  (d) another HIV entry inhibitor.

* * * * *